(12) United States Patent
Boudreaux et al.

(10) Patent No.: US 8,333,313 B2
(45) Date of Patent: Dec. 18, 2012

(54) SURGICAL STAPLING INSTRUMENT WITH A FIRING MEMBER RETURN MECHANISM

(75) Inventors: Chad P. Boudreaux, Cincinnati, OH (US); Alessandro Pastorelli, Rome (IT)

(73) Assignee: Ethicon Endo-Surgery, Inc.

( * ) Notice: Subject to any disclaimer, the term of this patent is extended or adjusted under 35 U.S.C. 154(b) by 0 days.

(21) Appl. No.: 13/152,952

(22) Filed: Jun. 3, 2011

(65) Prior Publication Data
US 2011/0233258 A1    Sep. 29, 2011

Related U.S. Application Data

(63) Continuation of application No. 12/008,266, filed on Jan. 10, 2008, now Pat. No. 7,954,684, which is a continuation-in-part of application No. 11/821,277, filed on Jun. 22, 2007, now Pat. No. 7,753,245.

(51) Int. Cl.
*A61B 17/068* (2006.01)

(52) U.S. Cl. ............... 227/175.1; 227/175.2; 227/176.1; 227/180.1; 227/19

(58) Field of Classification Search ............... 227/175.1, 227/176.1, 180.1, 19
See application file for complete search history.

(56) References Cited

U.S. PATENT DOCUMENTS

| | | | |
|---|---|---|---|
| 2,853,074 A | 9/1958 | Olson | |
| 2,959,974 A | 11/1960 | Emrick | |
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| RE28,932 E | 8/1976 | Noiles et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,475,679 A | 10/1984 | Fleury, Jr. | |
| 4,489,875 A | 12/1984 | Crawford et al. | |
| 4,500,024 A | 2/1985 | DiGiovanni et al. | |
| 4,505,273 A | 3/1985 | Braun et al. | |
| 4,505,414 A | 3/1985 | Filipi | |
| 4,506,671 A | 3/1985 | Green | |

(Continued)

FOREIGN PATENT DOCUMENTS
CA    2458946 A1    3/2003
(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Brian D Nash
*Assistant Examiner* — Michelle Lopez

(57) ABSTRACT

A surgical instrument including a firing drive configured to selectively advance a firing member and/or cutting member relative to an end effector and, in addition, a reversing drive configured to selectively retract the firing member and/or cutting member relative to the end effector.

31 Claims, 116 Drawing Sheets

U.S. PATENT DOCUMENTS

| | | |
|---|---|---|
| 4,522,327 A | 6/1985 | Korthoff et al. |
| 4,530,453 A | 7/1985 | Green |
| 4,565,109 A | 1/1986 | Tsay |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,880,015 A | 11/1989 | Nierman |
| 4,941,623 A | 7/1990 | Pruitt |
| 4,944,443 A | 7/1990 | Oddsen et al. |
| 4,973,274 A | 11/1990 | Hirukawa |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,209,747 A | 5/1993 | Knoepfler |
| 5,211,649 A | 5/1993 | Kohler et al. |
| 5,221,036 A | 6/1993 | Takase |
| 5,222,975 A | 6/1993 | Crainich |
| 5,236,440 A | 8/1993 | Hlavacek |
| 5,258,009 A | 11/1993 | Conners |
| 5,271,543 A | 12/1993 | Grant et al. |
| 5,282,806 A | 2/1994 | Haber et al. |
| 5,282,829 A | 2/1994 | Hermes |
| 5,304,204 A | 4/1994 | Bregen |
| 5,307,976 A | 5/1994 | Olson et al. |
| 5,312,024 A | 5/1994 | Grant et al. |
| 5,318,221 A | 6/1994 | Green et al. |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,383,888 A | 1/1995 | Zvenyatsky et al. |
| 5,397,324 A | 3/1995 | Carroll et al. |
| 5,405,072 A | 4/1995 | Zlock et al. |
| 5,413,268 A | 5/1995 | Green et al. |
| 5,413,272 A | 5/1995 | Green et al. |
| 5,417,203 A | 5/1995 | Tovey et al. |
| 5,417,361 A | 5/1995 | Williamson, IV |
| 5,425,745 A | 6/1995 | Green et al. |
| 5,431,654 A | 7/1995 | Nic |
| 5,437,681 A | 8/1995 | Meade et al. |
| 5,456,401 A | 10/1995 | Green et al. |
| 5,465,894 A | 11/1995 | Clark et al. |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,505,363 A | 4/1996 | Green et al. |
| 5,509,596 A | 4/1996 | Green et al. |
| 5,514,157 A | 5/1996 | Nicholas et al. |
| 5,520,700 A | 5/1996 | Beyar et al. |
| 5,529,235 A | 6/1996 | Boiarski et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,547,117 A | 8/1996 | Hamblin et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,609,601 A | 3/1997 | Kolesa et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,527 A | 9/1997 | Cook |
| 5,669,544 A | 9/1997 | Schulze et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,690,269 A | 11/1997 | Bolanos et al. |
| 5,692,668 A | 12/1997 | Schulze et al. |
| 5,697,543 A | 12/1997 | Burdorff |
| 5,702,408 A | 12/1997 | Wales et al. |
| 5,704,534 A | 1/1998 | Huitema et al. |
| 5,706,997 A | 1/1998 | Green et al. |
| 5,706,998 A | 1/1998 | Plyley et al. |
| 5,709,334 A | 1/1998 | Sorrentino et al. |

| Patent | Kind | Date | Inventor |
|---|---|---|---|
| 5,711,472 | A | 1/1998 | Bryan |
| 5,713,505 | A | 2/1998 | Huitema |
| 5,715,987 | A | 2/1998 | Kelley et al. |
| 5,715,988 | A | 2/1998 | Palmer |
| 5,716,366 | A | 2/1998 | Yates |
| 5,718,359 | A | 2/1998 | Palmer et al. |
| 5,718,360 | A | 2/1998 | Green et al. |
| 5,725,536 | A | 3/1998 | Oberlin et al. |
| 5,725,554 | A | 3/1998 | Simon et al. |
| 5,730,758 | A | 3/1998 | Allgeyer |
| 5,732,821 | A | 3/1998 | Stone et al. |
| 5,732,871 | A | 3/1998 | Clark et al. |
| 5,732,872 | A | 3/1998 | Bolduc et al. |
| 5,735,445 | A | 4/1998 | Vidal et al. |
| 5,743,456 | A | 4/1998 | Jones et al. |
| 5,752,644 | A | 5/1998 | Bolanos et al. |
| 5,758,814 | A | 6/1998 | Gallagher et al. |
| 5,762,255 | A | 6/1998 | Chrisman et al. |
| 5,762,256 | A | 6/1998 | Mastri et al. |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,785,232 | A | 7/1998 | Vidal et al. |
| 5,794,834 | A | 8/1998 | Hamblin et al. |
| 5,797,536 | A | 8/1998 | Smith et al. |
| 5,797,537 | A | 8/1998 | Oberlin et al. |
| 5,797,538 | A | 8/1998 | Heaton et al. |
| 5,799,857 | A | 9/1998 | Robertson et al. |
| 5,820,009 | A | 10/1998 | Melling et al. |
| 5,826,776 | A | 10/1998 | Schulze et al. |
| 5,829,662 | A | 11/1998 | Allen et al. |
| 5,833,695 | A | 11/1998 | Yoon |
| 5,836,503 | A | 11/1998 | Ehrenfels et al. |
| 5,836,960 | A | 11/1998 | Kolesa et al. |
| 5,839,639 | A | 11/1998 | Sauer et al. |
| 5,855,311 | A | 1/1999 | Hamblin et al. |
| 5,865,361 | A | 2/1999 | Milliman et al. |
| 5,868,760 | A | 2/1999 | McGuckin, Jr. |
| 5,871,135 | A | 2/1999 | Williamson IV et al. |
| 5,878,937 | A | 3/1999 | Green et al. |
| 5,878,938 | A | 3/1999 | Bittner et al. |
| 5,893,506 | A | 4/1999 | Powell |
| 5,894,979 | A | 4/1999 | Powell |
| 5,897,562 | A | 4/1999 | Bolanos et al. |
| 5,901,895 | A | 5/1999 | Heaton et al. |
| 5,904,693 | A | 5/1999 | Dicesare et al. |
| 5,908,427 | A | 6/1999 | McKean et al. |
| 5,911,353 | A | 6/1999 | Bolanos et al. |
| 5,915,616 | A | 6/1999 | Viola et al. |
| 5,918,791 | A | 7/1999 | Sorrentino et al. |
| 5,919,198 | A | 7/1999 | Graves, Jr. et al. |
| 5,937,951 | A | 8/1999 | Izuchukwu et al. |
| 5,941,442 | A | 8/1999 | Geiste et al. |
| 5,954,259 | A | 9/1999 | Viola et al. |
| 5,988,479 | A | 11/1999 | Palmer |
| 6,010,054 | A | 1/2000 | Johnson et al. |
| 6,032,849 | A | 3/2000 | Mastri et al. |
| 6,045,560 | A | 4/2000 | McKean et al. |
| 6,047,861 | A | 4/2000 | Vidal et al. |
| 6,050,472 | A | 4/2000 | Shibata |
| 6,053,390 | A | 4/2000 | Green et al. |
| 6,062,360 | A | 5/2000 | Shields |
| 6,079,606 | A | 6/2000 | Milliman et al. |
| 6,083,242 | A | 7/2000 | Cook |
| 6,086,600 | A | 7/2000 | Kortenbach |
| 6,099,551 | A | 8/2000 | Gabbay |
| 6,102,271 | A | 8/2000 | Longo et al. |
| 6,109,500 | A | 8/2000 | Alli et al. |
| 6,119,913 | A | 9/2000 | Adams et al. |
| 6,126,058 | A | 10/2000 | Adams et al. |
| 6,131,789 | A | 10/2000 | Schulze et al. |
| 6,155,473 | A | 12/2000 | Tompkins et al. |
| 6,171,330 | B1 | 1/2001 | Benchetrit |
| 6,193,129 | B1 | 2/2001 | Bittner et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,273,897 | B1 | 8/2001 | Dalessandro et al. |
| 6,302,311 | B1 | 10/2001 | Adams et al. |
| 6,315,184 | B1 | 11/2001 | Whitman |
| 6,330,965 | B1 | 12/2001 | Milliman et al. |
| 6,370,981 | B1 | 4/2002 | Watarai |
| 6,387,113 | B1 | 5/2002 | Hawkins et al. |
| RE37,814 | E | 8/2002 | Allgeyer |
| 6,436,107 | B1 | 8/2002 | Wang et al. |
| 6,439,439 | B1 | 8/2002 | Rickard et al. |
| 6,439,446 | B1 | 8/2002 | Perry et al. |
| 6,443,973 | B1 | 9/2002 | Whitman |
| 6,488,196 | B1 | 12/2002 | Fenton, Jr. |
| 6,488,197 | B1 | 12/2002 | Whitman |
| 6,491,201 | B1 | 12/2002 | Whitman |
| 6,505,768 | B2 | 1/2003 | Whitman |
| 6,517,565 | B1 | 2/2003 | Whitman et al. |
| 6,569,171 | B2 | 5/2003 | DeGuillebon et al. |
| 6,578,751 | B2 | 6/2003 | Hartwick |
| 6,588,643 | B2 | 7/2003 | Bolduc et al. |
| 6,601,749 | B2 | 8/2003 | Sullivan et al. |
| 6,616,686 | B2 | 9/2003 | Coleman et al. |
| 6,619,529 | B2 | 9/2003 | Green et al. |
| 6,629,630 | B2 | 10/2003 | Adams |
| 6,629,988 | B2 | 10/2003 | Weadock |
| 6,644,532 | B2 | 11/2003 | Green et al. |
| 6,669,073 | B2 | 12/2003 | Milliman et al. |
| 6,681,978 | B2 | 1/2004 | Geiste et al. |
| 6,681,979 | B2 | 1/2004 | Whitman |
| 6,695,199 | B2 | 2/2004 | Whitman |
| 6,698,643 | B2 | 3/2004 | Whitman |
| 6,716,233 | B1 | 4/2004 | Whitman |
| 6,755,338 | B2 | 6/2004 | Hahnen et al. |
| 6,769,594 | B2 | 8/2004 | Orban, III |
| 6,773,438 | B1 | 8/2004 | Knodel et al. |
| 6,786,382 | B1 | 9/2004 | Hoffman |
| 6,805,273 | B2 | 10/2004 | Bilotti et al. |
| 6,817,508 | B1 | 11/2004 | Racenet et al. |
| 6,817,509 | B2 | 11/2004 | Geiste et al. |
| 6,817,974 | B2 | 11/2004 | Cooper et al. |
| 6,830,174 | B2 | 12/2004 | Hillstead et al. |
| 6,843,403 | B2 | 1/2005 | Whitman |
| RE38,708 | E | 3/2005 | Bolanos et al. |
| 6,866,178 | B2 | 3/2005 | Adams et al. |
| 6,874,669 | B2 | 4/2005 | Adams et al. |
| 6,877,647 | B2 | 4/2005 | Green et al. |
| 6,905,057 | B2 | 6/2005 | Swayze et al. |
| 6,945,444 | B2 | 9/2005 | Gresham et al. |
| 6,953,138 | B1 | 10/2005 | Dworak et al. |
| 6,953,139 | B2 | 10/2005 | Milliman et al. |
| 6,959,851 | B2 | 11/2005 | Heinrich |
| 6,959,852 | B2 | 11/2005 | Shelton, IV et al. |
| 6,960,107 | B1 | 11/2005 | Schaub et al. |
| 6,964,363 | B2 | 11/2005 | Wales et al. |
| 6,978,921 | B2 | 12/2005 | Shelton, IV et al. |
| 6,978,922 | B2 | 12/2005 | Bilotti et al. |
| 6,981,628 | B2 | 1/2006 | Wales |
| 6,986,451 | B1 | 1/2006 | Mastri et al. |
| 6,988,649 | B2 | 1/2006 | Shelton, IV et al. |
| 6,988,650 | B2 | 1/2006 | Schwemberger et al. |
| 6,997,931 | B2 | 2/2006 | Sauer et al. |
| 7,000,818 | B2 | 2/2006 | Shelton, IV et al. |
| 7,000,819 | B2 | 2/2006 | Swayze et al. |
| 7,008,435 | B2 | 3/2006 | Cummins |
| 7,032,798 | B2 | 4/2006 | Whitman et al. |
| 7,032,799 | B2 | 4/2006 | Viola et al. |
| 7,044,352 | B2 | 5/2006 | Shelton, IV et al. |
| 7,044,353 | B2 | 5/2006 | Mastri et al. |
| 7,055,730 | B2 | 6/2006 | Ehrenfels et al. |
| 7,055,731 | B2 | 6/2006 | Shelton, IV et al. |
| 7,056,330 | B2 | 6/2006 | Gayton |
| 7,059,508 | B2 | 6/2006 | Shelton, IV et al. |
| 7,070,083 | B2 | 7/2006 | Jankowski |
| 7,077,856 | B2 | 7/2006 | Whitman |
| 7,080,769 | B2 | 7/2006 | Vresh et al. |
| 7,083,075 | B2 | 8/2006 | Swayze et al. |
| 7,090,684 | B2 | 8/2006 | McGuckin, Jr. et al. |
| 7,097,089 | B2 | 8/2006 | Marczyk |

| Patent No. | Date | Inventor |
|---|---|---|
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,156,863 B2 | 1/2007 | Sonnenschein et al. |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,237,708 B1 | 7/2007 | Guy et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,297,149 B2 | 11/2007 | Vitali et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,343,920 B2 | 3/2008 | Toby et al. |
| 7,354,447 B2 | 4/2008 | Shelton, IV et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,481,347 B2 | 1/2009 | Roy |
| 7,481,349 B2 | 1/2009 | Holsten et al. |
| 7,481,824 B2 | 1/2009 | Boudreaux et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,559,450 B2 | 7/2009 | Wales et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,624,902 B2 | 12/2009 | Marczyk et al. |
| 7,631,793 B2 | 12/2009 | Rethy et al. |
| 7,641,092 B2 | 1/2010 | Kruszynski et al. |
| 7,641,093 B2 | 1/2010 | Doll et al. |
| 7,644,848 B2 | 1/2010 | Swayze et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,699,204 B2 | 4/2010 | Viola |
| 7,717,312 B2 | 5/2010 | Beetel |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shelton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,780,054 B2 | 8/2010 | Wales |
| 7,780,055 B2 | 8/2010 | Scirica et al. |
| 7,784,662 B2 * | 8/2010 | Wales et al. ............... 227/175.1 |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,080 B2 | 11/2010 | Schwemberger |
| 7,845,533 B2 | 12/2010 | Marczyk et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |

| | | |
|---|---|---|
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,221 B2 | 3/2011 | Viola et al. |
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,934,630 B2 | 5/2011 | Shelton, IV et al. |
| 7,942,303 B2 | 5/2011 | Shah |
| 7,950,560 B2 | 5/2011 | Zemlok et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,966,799 B2 | 6/2011 | Morgan et al. |
| 7,967,180 B2 | 6/2011 | Scirica |
| 7,980,443 B2 | 7/2011 | Scheib et al. |
| 8,002,795 B2 | 8/2011 | Beetel |
| 8,011,551 B2 | 9/2011 | Marczyk et al. |
| 8,020,743 B2 | 9/2011 | Shelton, IV |
| D650,074 S | 12/2011 | Hunt et al. |
| 2002/0117534 A1 | 8/2002 | Green et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0243176 A1 | 12/2004 | Hahnen et al. |
| 2004/0254608 A1 | 12/2004 | Huitema et al. |
| 2004/0267310 A1 | 12/2004 | Racenet et al. |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0145675 A1 | 7/2005 | Hartwick et al. |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0167471 A1 | 7/2006 | Phillips |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0034668 A1 | 2/2007 | Holsten et al. |
| 2007/0073341 A1 | 3/2007 | Smith |
| 2007/0084897 A1 | 4/2007 | Shelton, IV et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0246505 A1 | 10/2007 | Pace-Floridia et al. |
| 2007/0288044 A1 | 12/2007 | Jinno et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0183193 A1 | 7/2008 | Omori et al. |
| 2008/0197167 A1 | 8/2008 | Viola et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |

| Publication No. | Date | Inventor(s) |
|---|---|---|
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0308907 A1 | 12/2009 | Nalagatla et al. |
| 2010/0001036 A1 | 1/2010 | Marczyk et al. |
| 2010/0012704 A1 | 1/2010 | Tarinelli Racenet et al. |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0072254 A1 | 3/2010 | Aranyi et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0226837 A1 | 9/2011 | Baxter, III et al. |
| 2011/0253766 A1 | 10/2011 | Baxter, III et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0061448 A1 | 3/2012 | Zingman |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080334 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |

FOREIGN PATENT DOCUMENTS

| | | | |
|---|---|---|---|
| CA | 2512960 | A1 | 1/2006 |
| CA | 2514274 | A1 | 1/2006 |
| CN | 1868411 | A | 11/2006 |
| CN | 1915180 | A | 2/2007 |
| CN | 101095621 | A | 1/2008 |
| DE | 273689 | C | 5/1914 |
| DE | 3036217 | A1 | 4/1982 |
| DE | 9412228 | U | 9/1994 |
| DE | 19509116 | A1 | 9/1996 |
| DE | 19851291 | A1 | 1/2000 |
| DE | 19924311 | A1 | 11/2000 |
| DE | 69328576 | T2 | 1/2001 |
| DE | 10052679 | A1 | 5/2001 |
| DE | 20112837 | U1 | 10/2001 |
| DE | 20121753 | U1 | 4/2003 |
| DE | 10314072 | A1 | 10/2004 |
| EP | 0122046 | A1 | 10/1984 |
| EP | 0070230 | B1 | 10/1985 |
| EP | 0387980 | B1 | 10/1985 |
| EP | 0033548 | B1 | 5/1986 |
| EP | 0276104 | A2 | 7/1988 |
| EP | 0248844 | B1 | 1/1993 |
| EP | 0545029 | A1 | 6/1993 |
| EP | 0277959 | B1 | 10/1993 |
| EP | 0233940 | B1 | 11/1993 |
| EP | 0261230 | B1 | 11/1993 |
| EP | 0639349 | A2 | 2/1994 |
| EP | 0324636 | B1 | 3/1994 |
| EP | 0593920 | A1 | 4/1994 |
| EP | 0427949 | B1 | 6/1994 |
| EP | 0523174 | B1 | 6/1994 |
| EP | 0600182 | A2 | 6/1994 |
| EP | 0310431 | B1 | 11/1994 |
| EP | 0375302 | B1 | 11/1994 |
| EP | 0376562 | B1 | 11/1994 |
| EP | 0630612 | A1 | 12/1994 |
| EP | 0634144 | A1 | 1/1995 |
| EP | 0646356 | A2 | 4/1995 |
| EP | 0646357 | A1 | 4/1995 |
| EP | 0653189 | A2 | 5/1995 |
| EP | 0669104 | A1 | 8/1995 |
| EP | 0511470 | B1 | 10/1995 |
| EP | 0679367 | A2 | 11/1995 |
| EP | 0392547 | B1 | 12/1995 |
| EP | 0685204 | A1 | 12/1995 |
| EP | 0364216 | B1 | 1/1996 |
| EP | 0699418 | A1 | 3/1996 |
| EP | 0702937 | A1 | 3/1996 |
| EP | 0705571 | A1 | 4/1996 |
| EP | 0711611 | A2 | 5/1996 |
| EP | 0484677 | B2 | 6/1996 |
| EP | 0541987 | B1 | 7/1996 |
| EP | 0667119 | B1 | 7/1996 |
| EP | 0708618 | B1 | 3/1997 |
| EP | 0770355 | A1 | 5/1997 |
| EP | 0503662 | B1 | 6/1997 |
| EP | 0447121 | B1 | 7/1997 |
| EP | 0625077 | B1 | 7/1997 |
| EP | 0633749 | B1 | 8/1997 |
| EP | 0710090 | B1 | 8/1997 |
| EP | 0578425 | B1 | 9/1997 |
| EP | 0625335 | B1 | 11/1997 |
| EP | 0552423 | B1 | 1/1998 |
| EP | 0592244 | B1 | 1/1998 |
| EP | 0648476 | B1 | 1/1998 |
| EP | 0649290 | B1 | 3/1998 |
| EP | 0598618 | B1 | 9/1998 |
| EP | 0676173 | B1 | 9/1998 |
| EP | 0678007 | B1 | 9/1998 |
| EP | 0603472 | B1 | 11/1998 |
| EP | 0605351 | B1 | 11/1998 |
| EP | 0878169 | A1 | 11/1998 |
| EP | 0879742 | A1 | 11/1998 |
| EP | 0695144 | B1 | 12/1998 |
| EP | 0722296 | B1 | 12/1998 |
| EP | 0760230 | B1 | 2/1999 |
| EP | 0623316 | B1 | 3/1999 |
| EP | 0650701 | B1 | 3/1999 |
| EP | 0537572 | B1 | 6/1999 |
| EP | 0923907 | A1 | 6/1999 |
| EP | 0843906 | B1 | 3/2000 |
| EP | 0552050 | B1 | 5/2000 |
| EP | 0833592 | B1 | 5/2000 |
| EP | 0830094 | B1 | 9/2000 |
| EP | 1034747 | A1 | 9/2000 |
| EP | 1034748 | A1 | 9/2000 |
| EP | 0694290 | B1 | 11/2000 |
| EP | 1050278 | A1 | 11/2000 |
| EP | 1053719 | A1 | 11/2000 |
| EP | 1053720 | A1 | 11/2000 |
| EP | 1055399 | A1 | 11/2000 |
| EP | 1055400 | A1 | 11/2000 |
| EP | 1080694 | A1 | 3/2001 |
| EP | 1095627 | A1 | 5/2001 |
| EP | 1256318 | B1 | 5/2001 |
| EP | 0806914 | B1 | 9/2001 |
| EP | 0768840 | B1 | 12/2001 |
| EP | 0908152 | B1 | 1/2002 |
| EP | 0872213 | B1 | 5/2002 |
| EP | 0862386 | B1 | 6/2002 |
| EP | 1238634 | A2 | 9/2002 |
| EP | 0858295 | B1 | 12/2002 |
| EP | 0656188 | B1 | 1/2003 |
| EP | 1284120 | A1 | 2/2003 |
| EP | 1287788 | A1 | 3/2003 |
| EP | 0717966 | B1 | 4/2003 |
| EP | 0869742 | B1 | 5/2003 |
| EP | 0829235 | B1 | 6/2003 |
| EP | 0887046 | B1 | 7/2003 |
| EP | 0852480 | B1 | 8/2003 |
| EP | 0891154 | B1 | 9/2003 |
| EP | 0813843 | B1 | 10/2003 |
| EP | 0856326 | B1 | 11/2003 |
| EP | 1374786 | A1 | 1/2004 |
| EP | 0741996 | B1 | 2/2004 |
| EP | 0814712 | B1 | 2/2004 |
| EP | 1402837 | A1 | 3/2004 |
| EP | 0705570 | B1 | 4/2004 |
| EP | 0959784 | B1 | 4/2004 |
| EP | 1407719 | A2 | 4/2004 |
| EP | 1086713 | B1 | 5/2004 |
| EP | 0996378 | B1 | 6/2004 |
| EP | 1426012 | A1 | 6/2004 |
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1459695 | A1 | 9/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1520521 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621145 | A2 | 2/2006 |
| EP | 1621151 | A2 | 2/2006 |

| | | | | | | |
|---|---|---|---|---|---|---|
| EP | 1034746 | B1 | 3/2006 | GB | 1210522 | A | 10/1970 |
| EP | 1632191 | A2 | 3/2006 | GB | 1217159 | A | 12/1970 |
| EP | 1065981 | B1 | 5/2006 | GB | 1339394 | A | 12/1973 |
| EP | 1082944 | B1 | 5/2006 | GB | 2109241 | A | 6/1983 |
| EP | 1652481 | A2 | 5/2006 | GB | 2272159 | A | 5/1994 |
| EP | 1382303 | B1 | 6/2006 | GB | 2284242 | A | 5/1995 |
| EP | 1253866 | B1 | 7/2006 | GB | 2336214 | A | 10/1999 |
| EP | 1032318 | B1 | 8/2006 | GB | 2425903 | A | 11/2006 |
| EP | 1045672 | B1 | 8/2006 | JP | 6007357 | A | 1/1994 |
| EP | 1593337 | B1 | 8/2006 | JP | 7051273 | A | 2/1995 |
| EP | 1617768 | B1 | 8/2006 | JP | 8033641 | A | 2/1996 |
| EP | 1693015 | A2 | 8/2006 | JP | 8229050 | A | 9/1996 |
| EP | 1400214 | B1 | 9/2006 | JP | 2000033071 | A | 2/2000 |
| EP | 1702567 | A2 | 9/2006 | JP | 2000171730 | A | 6/2000 |
| EP | 1129665 | B1 | 11/2006 | JP | 2000287987 | A | 10/2000 |
| EP | 1400206 | B1 | 11/2006 | JP | 2000325303 | A | 11/2000 |
| EP | 1721568 | A1 | 11/2006 | JP | 2001286477 | A | 10/2001 |
| EP | 1256317 | B1 | 12/2006 | JP | 2002143078 | A | 5/2002 |
| EP | 1728473 | A1 | 12/2006 | JP | 2002369820 | A | 12/2002 |
| EP | 1728475 | A2 | 12/2006 | JP | 2005-028149 | A | 2/2005 |
| EP | 1479346 | B1 | 1/2007 | JP | 2005505322 | T | 2/2005 |
| EP | 1484024 | B1 | 1/2007 | JP | 2005103293 | A | 4/2005 |
| EP | 1754445 | A2 | 2/2007 | JP | 2005131163 | A | 5/2005 |
| EP | 1759812 | A1 | 3/2007 | JP | 2005131164 | A | 5/2005 |
| EP | 1767163 | A1 | 3/2007 | JP | 2005131173 | A | 5/2005 |
| EP | 1769756 | A1 | 4/2007 | JP | 2005131211 | A | 5/2005 |
| EP | 1769758 | A1 | 4/2007 | JP | 2005131212 | A | 5/2005 |
| EP | 1581128 | B1 | 5/2007 | JP | 2005137423 | A | 6/2005 |
| EP | 1785097 | A2 | 5/2007 | JP | 2005152416 | A | 6/2005 |
| EP | 1790293 | A2 | 5/2007 | JP | 2005524474 | A | 8/2005 |
| EP | 1800610 | A1 | 6/2007 | JP | 2006-281405 | A | 10/2006 |
| EP | 1300117 | B1 | 8/2007 | RU | 2008830 | C1 | 3/1994 |
| EP | 1813199 | A1 | 8/2007 | RU | 2187249 | C2 | 8/2002 |
| EP | 1813201 | A1 | 8/2007 | RU | 2225170 | C2 | 3/2004 |
| EP | 1813203 | A2 | 8/2007 | SU | 189517 | A | 1/1967 |
| EP | 1813207 | A1 | 8/2007 | SU | 328636 | A | 9/1972 |
| EP | 1813209 | A1 | 8/2007 | SU | 886900 | A1 | 12/1981 |
| EP | 1487359 | B1 | 10/2007 | SU | 1009439 | A | 4/1983 |
| EP | 1599146 | B1 | 10/2007 | SU | 1377053 | A | 2/1988 |
| EP | 1839596 | A1 | 10/2007 | SU | 1561964 | A1 | 5/1990 |
| EP | 1402821 | B1 | 12/2007 | SU | 1722476 | A1 | 3/1992 |
| EP | 1872727 | A1 | 1/2008 | WO | WO 91/15157 | A1 | 10/1991 |
| EP | 1897502 | A1 | 3/2008 | WO | WO 92/20295 | A1 | 11/1992 |
| EP | 1330201 | B1 | 6/2008 | WO | WO 92/21300 | A1 | 12/1992 |
| EP | 1702568 | B1 | 7/2008 | WO | WO 93/08755 | A1 | 5/1993 |
| EP | 1943957 | A2 | 7/2008 | WO | WO 93/13718 | A1 | 7/1993 |
| EP | 1943976 | A2 | 7/2008 | WO | WO 93/14690 | A1 | 8/1993 |
| EP | 1970014 | A1 | 9/2008 | WO | WO 93/15648 | A1 | 8/1993 |
| EP | 1980213 | A2 | 10/2008 | WO | WO 93/15850 | A1 | 8/1993 |
| EP | 1759645 | B1 | 11/2008 | WO | WO 93/19681 | A1 | 10/1993 |
| EP | 1990014 | A2 | 11/2008 | WO | WO 94/00060 | A1 | 1/1994 |
| EP | 1693008 | B1 | 12/2008 | WO | WO 94/11057 | A1 | 5/1994 |
| EP | 1759640 | B1 | 12/2008 | WO | WO 94/12108 | A1 | 6/1994 |
| EP | 2000102 | A2 | 12/2008 | WO | WO 94/18893 | A1 | 9/1994 |
| EP | 1736104 | B1 | 3/2009 | WO | WO 94/22378 | A1 | 10/1994 |
| EP | 1749486 | B1 | 3/2009 | WO | WO 94/23659 | A1 | 10/1994 |
| EP | 2039316 | A2 | 3/2009 | WO | WO 95/02369 | A1 | 1/1995 |
| EP | 1721576 | B1 | 4/2009 | WO | WO 95/03743 | A1 | 2/1995 |
| EP | 1733686 | B1 | 4/2009 | WO | WO 95/06817 | A1 | 3/1995 |
| EP | 2044890 | A1 | 4/2009 | WO | WO 95/09576 | A1 | 4/1995 |
| EP | 1745748 | B1 | 8/2009 | WO | WO 95/09577 | A1 | 4/1995 |
| EP | 2090256 | A2 | 8/2009 | WO | WO 95/14436 | A1 | 6/1995 |
| EP | 1813208 | B1 | 11/2009 | WO | WO 95/16383 | A1 | 7/1995 |
| EP | 1607050 | B1 | 12/2009 | WO | WO 95/17855 | A1 | 7/1995 |
| EP | 1566150 | B1 | 4/2010 | WO | WO 95/18572 | A1 | 7/1995 |
| EP | 1813206 | B1 | 4/2010 | WO | WO 95/19739 | A1 | 7/1995 |
| EP | 1769754 | B1 | 6/2010 | WO | WO 95/20360 | A1 | 8/1995 |
| EP | 1535565 | B1 | 10/2010 | WO | WO 95/23557 | A1 | 9/1995 |
| EP | 1702570 | B1 | 10/2010 | WO | WO 95/24865 | A1 | 9/1995 |
| EP | 1785098 | B1 | 10/2010 | WO | WO 95/25471 | A3 | 9/1995 |
| EP | 1627605 | B1 | 12/2010 | WO | WO 95/26562 | A1 | 10/1995 |
| EP | 1090592 | A1 | 4/2011 | WO | WO 95/29639 | A1 | 11/1995 |
| EP | 1813205 | B1 | 6/2011 | WO | WO 96/04858 | A1 | 2/1996 |
| EP | 1785102 | B1 | 1/2012 | WO | WO 96/19151 | A1 | 6/1996 |
| ER | 0949886 | B1 | 9/2002 | WO | WO 96/19152 | A1 | 6/1996 |
| ER | 0873089 | B1 | 10/2003 | WO | WO 96/20652 | A1 | 7/1996 |
| FR | 1112936 | A | 3/1956 | WO | WO 96/21119 | A1 | 7/1996 |
| FR | 2765794 | A | 1/1999 | WO | WO 96/22055 | A1 | 7/1996 |
| GB | 939929 | A | 10/1963 | WO | WO 96/23448 | A1 | 8/1996 |

| | | | | | | | |
|---|---|---|---|---|---|---|---|
| WO | WO 96/24301 | A1 | 8/1996 | WO | WO 03/000138 | A2 | 1/2003 |
| WO | WO 96/27337 | A1 | 9/1996 | WO | WO 03/001329 | A2 | 1/2003 |
| WO | WO 96/31155 | A1 | 10/1996 | WO | WO 03/013363 | A1 | 2/2003 |
| WO | WO 96/35464 | A1 | 11/1996 | WO | WO 03/015604 | A2 | 2/2003 |
| WO | WO 96/39085 | A1 | 12/1996 | WO | WO 03/020106 | A2 | 3/2003 |
| WO | WO 96/39086 | A1 | 12/1996 | WO | WO 03/020139 | A2 | 3/2003 |
| WO | WO 96/39087 | A1 | 12/1996 | WO | WO 03/024339 | A1 | 3/2003 |
| WO | WO 96/39088 | A1 | 12/1996 | WO | WO 03/079909 | A3 | 3/2003 |
| WO | WO 96/39089 | A1 | 12/1996 | WO | WO 03/030743 | A2 | 4/2003 |
| WO | WO 97/00646 | A1 | 1/1997 | WO | WO 03/037193 | A1 | 5/2003 |
| WO | WO 97/00647 | A1 | 1/1997 | WO | WO 03/047436 | A3 | 6/2003 |
| WO | WO 97/06582 | A1 | 2/1997 | WO | WO 03/055402 | A1 | 7/2003 |
| WO | WO 97/10763 | A1 | 3/1997 | WO | WO 03/057048 | A1 | 7/2003 |
| WO | WO 97/10764 | A1 | 3/1997 | WO | WO 03/057058 | A1 | 7/2003 |
| WO | WO 97/11648 | A1 | 4/1997 | WO | WO 03/063694 | A1 | 8/2003 |
| WO | WO 97/11649 | A1 | 4/1997 | WO | WO 03/077769 | A1 | 9/2003 |
| WO | WO 97/15237 | A1 | 5/1997 | WO | WO 03/062126 | A1 | 10/2003 |
| WO | WO 97/24073 | A1 | 7/1997 | WO | WO 03/079911 | A1 | 10/2003 |
| WO | WO 97/24993 | A1 | 7/1997 | WO | WO 03/088845 | A2 | 10/2003 |
| WO | WO 97/30644 | A1 | 8/1997 | WO | WO 03/090630 | A2 | 11/2003 |
| WO | WO 97/34533 | A1 | 9/1997 | WO | WO 03/094743 | A1 | 11/2003 |
| WO | WO 97/37598 | A1 | 10/1997 | WO | WO 03/094745 | A1 | 11/2003 |
| WO | WO 97/39688 | A2 | 10/1997 | WO | WO 03/094746 | A1 | 11/2003 |
| WO | WO 98/17180 | A1 | 4/1998 | WO | WO 03/094747 | A1 | 11/2003 |
| WO | WO 98/27880 | A1 | 7/1998 | WO | WO 03/101313 | A1 | 12/2003 |
| WO | WO 98/30153 | A1 | 7/1998 | WO | WO 03/105698 | A2 | 12/2003 |
| WO | WO 98/47436 | A1 | 10/1998 | WO | WO 03/105702 | A2 | 12/2003 |
| WO | WO 99/03407 | A1 | 1/1999 | WO | WO 2004/006980 | A2 | 1/2004 |
| WO | WO 99/03408 | A1 | 1/1999 | WO | WO 2004/019769 | A1 | 3/2004 |
| WO | WO 99/03409 | A1 | 1/1999 | WO | WO 2004/021868 | A2 | 3/2004 |
| WO | WO 99/12483 | A1 | 3/1999 | WO | WO 2004/028585 | A2 | 4/2004 |
| WO | WO 99/12487 | A1 | 3/1999 | WO | WO 2004/032754 | A2 | 4/2004 |
| WO | WO 99/12488 | A1 | 3/1999 | WO | WO 2004/032760 | A2 | 4/2004 |
| WO | WO 99/15086 | A1 | 4/1999 | WO | WO 2004/032762 | A1 | 4/2004 |
| WO | WO 99/15091 | A1 | 4/1999 | WO | WO 2004/032763 | A2 | 4/2004 |
| WO | WO 99/23933 | A1 | 5/1999 | WO | WO 2004/034875 | A2 | 4/2004 |
| WO | WO 99/23959 | A1 | 5/1999 | WO | WO 2004/047626 | A1 | 6/2004 |
| WO | WO 99/25261 | A1 | 5/1999 | WO | WO 2004/047653 | A2 | 6/2004 |
| WO | WO 99/29244 | A1 | 6/1999 | WO | WO 2004/049956 | A2 | 6/2004 |
| WO | WO 99/34744 | A1 | 7/1999 | WO | WO 2004/052426 | A2 | 6/2004 |
| WO | WO 99/45849 | A1 | 9/1999 | WO | WO 2004/056276 | A1 | 7/2004 |
| WO | WO 99/48430 | A1 | 9/1999 | WO | WO 2004/056277 | A1 | 7/2004 |
| WO | WO 99/51158 | A1 | 10/1999 | WO | WO 2004/062516 | A1 | 7/2004 |
| WO | WO 00/24322 | A1 | 5/2000 | WO | WO 2004/078050 | A2 | 9/2004 |
| WO | WO 00/24330 | A1 | 5/2000 | WO | WO 2004/078051 | A2 | 9/2004 |
| WO | WO 00/41638 | A1 | 7/2000 | WO | WO 2004/086987 | A1 | 10/2004 |
| WO | WO 00/48506 | A1 | 8/2000 | WO | WO 2004/096015 | A2 | 11/2004 |
| WO | WO 00/53112 | A2 | 9/2000 | WO | WO 2004/096057 | A1 | 11/2004 |
| WO | WO 00/54653 | A1 | 9/2000 | WO | WO 2004/103157 | A2 | 12/2004 |
| WO | WO 00/57796 | A1 | 10/2000 | WO | WO 2004/105593 | A1 | 12/2004 |
| WO | WO 00/64365 | A1 | 11/2000 | WO | WO 2004/105621 | A1 | 12/2004 |
| WO | WO 00/72762 | A1 | 12/2000 | WO | WO 2004/112618 | A2 | 12/2004 |
| WO | WO 00/72765 | A1 | 12/2000 | WO | WO 2004/112652 | A2 | 12/2004 |
| WO | WO 01/03587 | A1 | 1/2001 | WO | WO 2005/027983 | A2 | 3/2005 |
| WO | WO 01/05702 | A1 | 1/2001 | WO | WO 2005/037329 | A2 | 4/2005 |
| WO | WO 01/10482 | A1 | 2/2001 | WO | WO 2005/044078 | A2 | 5/2005 |
| WO | WO 01/35845 | A1 | 5/2001 | WO | WO 2005/055846 | A1 | 6/2005 |
| WO | WO 01/54594 | A1 | 8/2001 | WO | WO 2005/072634 | A2 | 8/2005 |
| WO | WO 01/58371 | A1 | 8/2001 | WO | WO 2005/078892 | A1 | 8/2005 |
| WO | WO 01/62158 | A2 | 8/2001 | WO | WO 2005/096954 | A2 | 10/2005 |
| WO | WO 01/62161 | A1 | 8/2001 | WO | WO 2005/112806 | A2 | 12/2005 |
| WO | WO 01/62162 | A1 | 8/2001 | WO | WO 2005/112808 | A1 | 12/2005 |
| WO | WO 01/62164 | A2 | 8/2001 | WO | WO 2005/115251 | A2 | 12/2005 |
| WO | WO 01/62169 | A2 | 8/2001 | WO | WO 2005/117735 | A1 | 12/2005 |
| WO | WO 01/78605 | A2 | 10/2001 | WO | WO 2005/122936 | A1 | 12/2005 |
| WO | WO 01/91646 | A1 | 12/2001 | WO | WO 2006/027014 | A1 | 3/2006 |
| WO | WO 02/07608 | A2 | 1/2002 | WO | WO 2006/044490 | A2 | 4/2006 |
| WO | WO 02/07618 | A1 | 1/2002 | WO | WO 2006/044581 | A2 | 4/2006 |
| WO | WO 02/17799 | A1 | 3/2002 | WO | WO 2006/044810 | A2 | 4/2006 |
| WO | WO 02/19920 | A1 | 3/2002 | WO | WO 2006/051252 | A1 | 5/2006 |
| WO | WO 02/19932 | A1 | 3/2002 | WO | WO 2006/059067 | A1 | 6/2006 |
| WO | WO 02/30297 | A2 | 4/2002 | WO | WO 2006/083748 | A1 | 8/2006 |
| WO | WO 02/32322 | A2 | 4/2002 | WO | WO 2006/092563 | A1 | 9/2006 |
| WO | WO 02/36028 | A1 | 5/2002 | WO | WO 2006/092565 | A1 | 9/2006 |
| WO | WO 02/43571 | A2 | 6/2002 | WO | WO 2006/115958 | A1 | 11/2006 |
| WO | WO 02/058568 | A1 | 8/2002 | WO | WO 2006/125940 | A1 | 11/2006 |
| WO | WO 02/060328 | A1 | 8/2002 | WO | WO 2006/132992 | A1 | 12/2006 |
| WO | WO 02/067785 | A2 | 9/2002 | WO | WO 2007/002180 | A2 | 1/2007 |
| WO | WO 02/098302 | A1 | 12/2002 | WO | WO 2007/016290 | A2 | 2/2007 |

| | | |
|---|---|---|
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/089404 A2 | 7/2008 |
| WO | WO 2008/109125 A1 | 9/2008 |
| WO | WO 2010/063795 A1 | 6/2010 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs." Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online]accessed: Sep. 22, 2008 (2 pages).

The Sodem Aseptic Battery Transfer Kit, Sodem Systems, 2000, 3 pages.

"Biomedical Coatings," Fort Wayne Metals. Research Products Corporation, obtained online at www.fwmetals.com Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get The Lowdown On Ultracapacitors," Nov. 15, 2007; [online] URL: http://electronicdesign.com/Articles/Print.cfm?ArticleID=17165, accessed Jan. 15, 2008, 5 pages.

Datasheet for Panasonic TK Relays Ultra Low Profile 2 A Polarized Relay, Copyright Matsushita Electric Works, Ltd. (Known of a least as early as Aug. 17, 2010), 5 pages.

Partial European Search Report, Application No. 08252151.9, dated Mar. 17, 2009 (4 pages).

European Search Report, Application No. 09250057.8, dated May 8, 2009 (7 pages).

European Search Report, Application No. 09250061.0, dated May 7, 2009 (7 pages).

Partial European Search Report, Application 11163523.1, dated Aug. 4, 2011 (2 pages).

Partial European Search Report, Application 11163532.2, dated Aug. 4, 2011 (5 pages).

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

\* cited by examiner

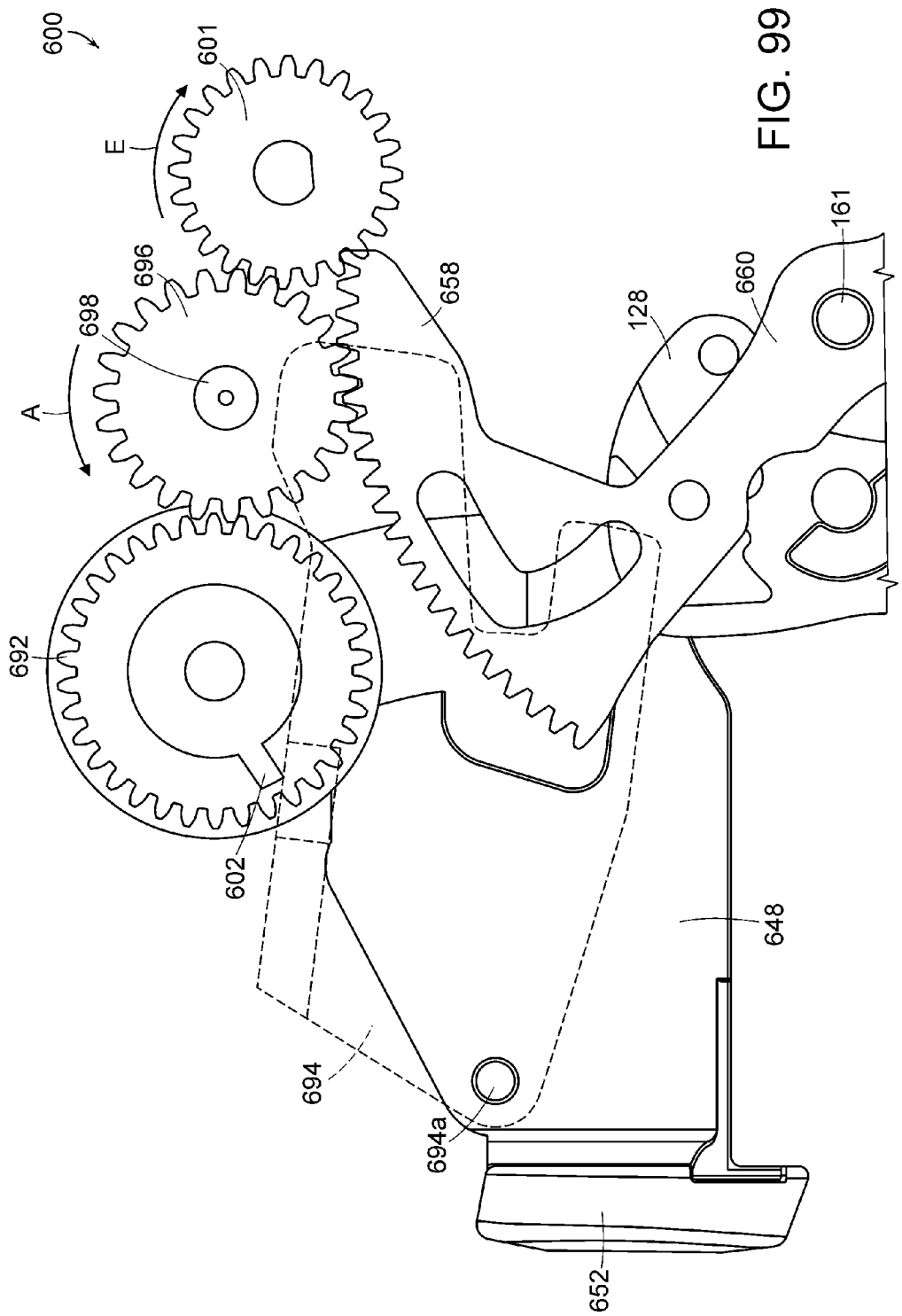

SURGICAL STAPLING INSTRUMENT WITH A FIRING MEMBER RETURN MECHANISM

CROSS REFERENCE TO RELATED APPLICATIONS

The present application is a continuation application claiming the benefit under 35 U.S.C. §120 of co-pending U.S. patent application Ser. No. 12/008,266, entitled SURGICAL STAPLING INSTRUMENT WITH A FIRING MEMBER RETURN MECHANISM, filed on Jan. 10, 2008, now U.S. Pat. No. 7,954,684 the entire disclosure of which is hereby incorporated by reference herein, which is a continuation-in-part application claiming the benefit under 35 U.S.C. §120 of co-pending U.S. patent application Ser. No. 11/821,277, entitled SURGICAL STAPLING INSTRUMENTS, filed on Jun. 22, 2007, now U.S. Pat. No. 7,753,245, the entire disclosure of which is hereby incorporated by reference herein.

BACKGROUND

1. Field of the Invention

The present invention generally relates to surgical stapling instruments and, more particularly, to surgical staplers having a closing system for closing an end effector and a firing system for deploying staples.

2. Description of the Related Art

As known in the art, surgical staplers are often used to deploy staples into soft tissue in order to reduce or eliminate bleeding from the soft tissue, especially as the tissue is being transected, for example. Surgical staplers, such as an endocutter, for example, can comprise an end effector which can be moved, or articulated, with respect to an elongate shaft assembly. End effectors are often configured to secure soft tissue between first and second jaw members where the first jaw member often includes a staple cartridge which is configured to removably store staples therein and the second jaw member often includes an anvil. Such surgical staplers can include a closing system for pivoting the anvil relative to the staple cartridge. These closing systems, however, do not prevent the end effector from being articulated relative to the shaft assembly after the jaw members have been closed. As a result, when the end effector is articulated, the end effector may apply a shear force to the soft tissue captured between the jaw members.

Surgical staplers, as outlined above, can be configured to pivot the anvil of the end effector relative to the staple cartridge in order to capture soft tissue therebetween. In various circumstances, the anvil can be configured to apply a clamping force to the soft tissue in order to hold the soft tissue tightly between the anvil and the staple cartridge. If a surgeon is unsatisfied with the position of the end effector, however, the surgeon must typically activate a release mechanism on the surgical stapler to pivot the anvil into an open position and then reposition the end effector. Thereafter, staples are typically deployed from the staple cartridge by a driver which traverses a channel in the staple cartridge and causes the staples to be deformed against the anvil and secure layers of the soft tissue together. Often, as known in the art, the staples are deployed in several staple lines, or rows, in order to more reliably secure the layers of tissue together. The end effector may also include a cutting member, such as a knife, for example, which is advanced between two rows of the staples to resect the soft tissue after the layers of the soft tissue have been stapled together.

After the driver and the cutting member have been advanced within the end effector, it is often necessary to retract the driver and/or cutting member to their starting positions. Previous surgical staplers have included a return spring which retracts the cutting member relative to the staple cartridge after a release button or toggle switch on the surgical stapler has been actuated by the surgeon, for example. In various embodiments, a first end of the return spring can be connected to the housing of the surgical instrument and a second end of the spring can be connected to the cutting member. Such staplers, however, are often difficult to use as the force required to extend the return spring as the cutting member is advanced is often significant. Furthermore, such return springs often apply a biasing force to the cutting member as it is advanced which can, in various circumstances, prematurely return the cutting member, especially in embodiments where multiple strokes of a trigger are required to completely advance the cutting member. What is needed is an improvement over the foregoing.

SUMMARY

In at least one form, a surgical instrument can comprise an end effector, a firing member, a trigger, a firing drive selectively engageable with the firing member, wherein the firing drive comprises a rack. The rack can comprise a first drive portion, wherein the firing drive is configured to engage the first drive portion and advance the firing member relative to the end effector upon a first actuation of the trigger, a second drive portion, wherein the firing drive is configured to engage the second drive portion and advance the firing member relative to the end effector upon a second actuation of the trigger, and a rotatable portion configured to be rotated a first amount during the first actuation of the trigger and a second amount during the second actuation of the trigger, wherein the rotatable portion comprises a key positionable in an initial position, and wherein the rotatable portion may be configurable in an activated configuration and a deactivated configuration. The surgical instrument can further comprise a reversing drive selectively engageable with the rack, wherein the reversing drive is configured to retract the rack and the firing member relative to the end effector upon a subsequent actuation of the trigger, and wherein the subsequent actuation is subsequent to the second actuation. The surgical instrument can comprise an indexing member comprising a first stop, wherein the key is configured to rotate past the first stop into a first position during the first actuation of the trigger, and wherein the first stop is configured to prevent the key from returning to its initial position when the rotatable portion is in its activated configuration, and a second stop, wherein the key is configured to rotate past the second stop into a second position during the second actuation of the trigger, wherein the second stop is configured to prevent the key from returning to the first position when the rotatable portion is in the activated configuration, and wherein the key is configured to rotate past the second stop and the first stop when the rotatable portion is in its deactivated configuration and the key is returned to its initial position.

In at least one form, a surgical instrument can comprise an end effector, a firing member movable between an initial position, a first fired position, and a second fired position, a trigger, and a firing drive selectively engageable with the firing member, wherein the firing drive comprises a rack. The rack can comprise a first drive portion, wherein the firing drive is configured to engage the first drive portion and advance the firing member relative to the end effector upon a first actuation of the trigger, and a second drive portion, wherein the firing drive is configured to engage the second drive portion and advance the firing member relative to the end effector upon a second actuation of the trigger. The surgical instrument can further comprise a reversing drive selectively engageable with the rack, wherein the reversing drive is configured to retract the rack and the firing member relative to the end effector upon a subsequent actuation of the trigger, and wherein the subsequent actuation is subsequent to the second actuation. The surgical instrument can further comprise holding means for holding the firing drive in the first position after the first actuation and before the second actuation and for holding the firing drive in the second position after the second actuation and before the subsequent actuation.

In at least one form, a surgical instrument can comprise a shaft comprising a distal end, a firing member, a trigger, and a firing drive selectively engageable with the firing member, wherein the firing drive comprises a first drive portion, wherein the firing drive is configured to engage the first drive portion and advance the firing member relative to the distal end upon a first actuation of the trigger, and a second drive portion, wherein the firing drive is configured to engage the second drive portion and advance the firing member relative to the distal end upon a second actuation of the trigger, and a rotatable portion configured to be rotated a first amount during the first actuation of the trigger and a second amount during the second actuation of the trigger, wherein the rotatable portion comprises a key positionable in an initial position. The surgical instrument can comprise a reversing drive selectively engageable with the firing member, wherein the reversing drive is configured to retract the firing member relative to the distal end upon a subsequent actuation of the trigger, and wherein the subsequent actuation is subsequent to the second actuation. The surgical instrument can further comprise a holding member comprising a first backstop, wherein the key is configured to rotate past the first backstop into a first position during the first actuation of the trigger, wherein the first backstop is configured to prevent the key from returning to its initial position prior to the reversing drive being engaged with the firing member, and a second backstop, wherein the key is configured to rotate past the second backstop into a second position during the second actuation of the trigger, wherein the second backstop is configured to prevent the key from returning to its first position prior to the reversing drive being engaged with the firing member, and wherein the reversing drive is configured to disengage the key from the holding member when the reversing drive is engaged with the firing member.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 99 is an elevational view of the reversing mechanism of FIG. 95 illustrating the return carriage in an actuated position;

FIG. 113 is a cross-sectional view of the indexing element of FIG. 112;

FIG. 114 is a perspective view of an indexing element in accordance with another alternative embodiment of the present invention;

FIG. 115 is a partial perspective view of a surgical instrument including an anti-backup mechanism in accordance with an alternative embodiment of the present invention with some components of the surgical instrument removed;

FIG. 116 is a cross-sectional view of the anti-backup mechanism of FIG. 115;

FIG. 117 is a perspective view of the surgical instrument of FIG. 115 illustrating a return carriage of a reversing mechanism in an actuated position;

FIG. 118 is a cross-sectional view of the anti-backup mechanism of FIG. 115 when the return carriage of FIG. 117 is in its actuated position;

FIG. 119 is a perspective view of a surgical instrument in accordance with an alternative embodiment of the present invention with some components of the surgical instrument removed to illustrate a switch for actuating a reversing drive of the surgical instrument;

FIG. 120 is a partial elevational view of a surgical instrument in accordance with another alternative embodiment of the present invention with some components of the surgical instrument removed to illustrate a switch for actuating a reversing drive of the surgical instrument;

FIG. 121 is a partial elevational view of the surgical instrument of FIG. 120 illustrating a first portion of the switch in an actuated position; and FIG. 122 is a partial elevational view of the surgical instrument of FIG. 120 illustrating a second portion of the switch utilized to position the first portion of the switch in its actuated position.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Figure 3:
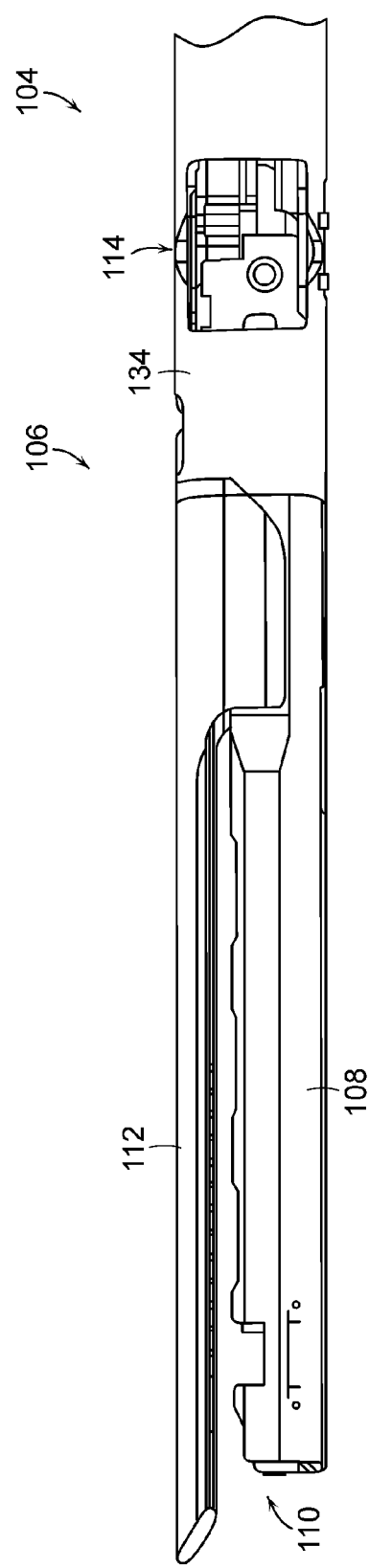
FIG. 3 is an elevational view of an end effector of the surgical instrument of FIG. 1.
Figure 4:
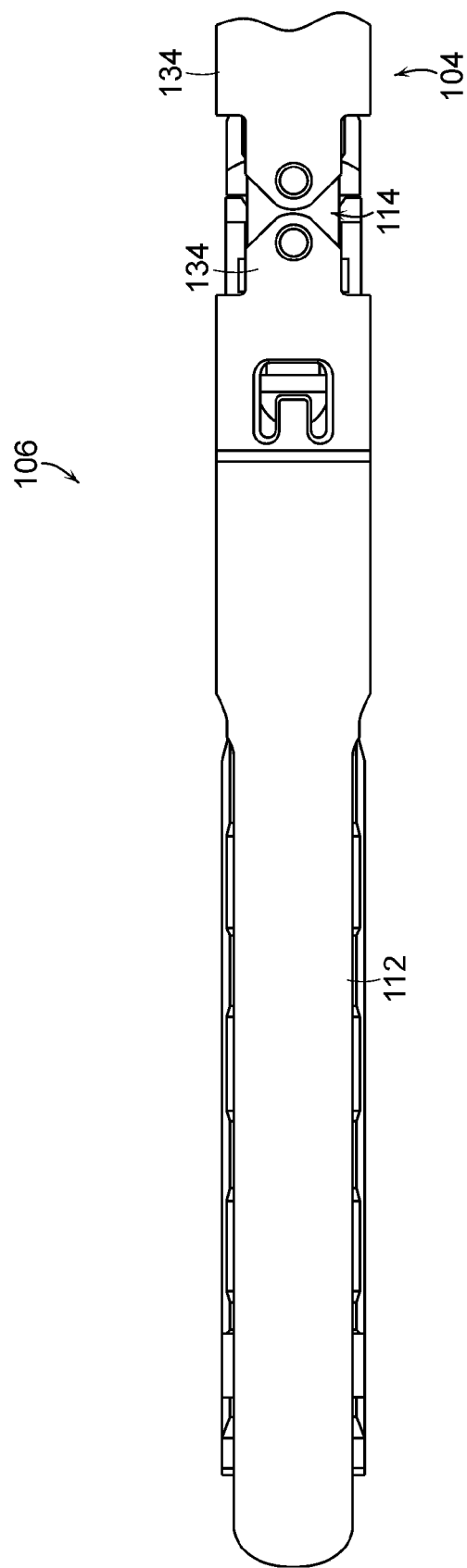
FIG. 4 is a top view of the end effector of FIG. 3.

In various embodiments, a surgical instrument in accordance with the present invention can be configured to insert surgical staples into soft tissue, for example. In at least one embodiment, referring to FIGS. 1-4, surgical instrument 100 can include handle portion 102, elongate shaft assembly 104, and end effector 106. In various embodiments, referring to FIGS. 3 and 4, end effector 106 can include staple cartridge channel 108 and staple cartridge 110, where staple cartridge 110 can be configured to removably store staples therein. In at least one embodiment, end effector 106 can further include anvil 112 which can be pivotably connected to staple cartridge channel 108 and can be pivoted between open and closed positions by an end effector closure system. In order to deploy the staples from staple cartridge 110, surgical instrument 100 can further include a staple driver configured to traverse staple cartridge 110 and a firing drive configured to advance the staple driver within the staple cartridge. In various embodiments, anvil 112 can be configured to deform at least a portion of the staples as they are deployed from the staple cartridge. Although various embodiments of an end effector closure system and a firing drive are described in further detail below, several embodiments of end effector closure systems and firing drives are disclosed in U.S. Pat. No. 6,905,057, entitled SURGICAL STAPLING INSTRUMENT INCORPORATING A FIRING MECHANISM HAVING A LINKED RACK TRANSMISSION, which issued on Jun. 14, 2005, and U.S. Pat. No. 7,044,352, entitled SURGICAL STAPLING INSTRUMENT HAVING A SINGLE LOCKOUT MECHANISM FOR PREVENTION OF FIRING, which issued on May 16, 2006, the entire disclosures of which are hereby incorporated by reference herein.

In various embodiments, a surgical instrument in accordance with the present invention can include a system for moving, or articulating, an end effector relative to an elongate shaft assembly of the surgical instrument. In at least one embodiment, referring to FIGS. 3-7, surgical instrument 100 can include articulation joint 114 which can movably connect end effector 106 and elongate shaft assembly 104. In various embodiments, articulation joint 114 can permit end effector 106 to be moved relative to shaft assembly 104 in a single plane or, alternatively, multiple planes. In either event, articulation joint 114 can include one or more pivot axes 116 (FIG. 5) about which end effector 106 can be articulated. In various embodiments, referring to FIGS. 5 and 6, surgical instrument 100 can further include locking mechanism 118 which can fix, or lock, the relative relationship between end effector 106 and elongate shaft assembly 104. In at least one embodiment, locking mechanism 118 can include lock member 120 which can be slid relative to end effector 106 and engage end effector 106 in order to prevent, or at least partially inhibit, relative movement between end effector 106 and shaft assembly 104. In at least one embodiment, lock member 120 can be configured to engage at least one of teeth 312 (FIGS. 5 and 6) of end effector 106 such that the interaction between lock member 120 and teeth 312 can prevent, or at least partially inhibit, end effector 106 from rotating about axis 116 as described in greater detail further below.

Figure 6:
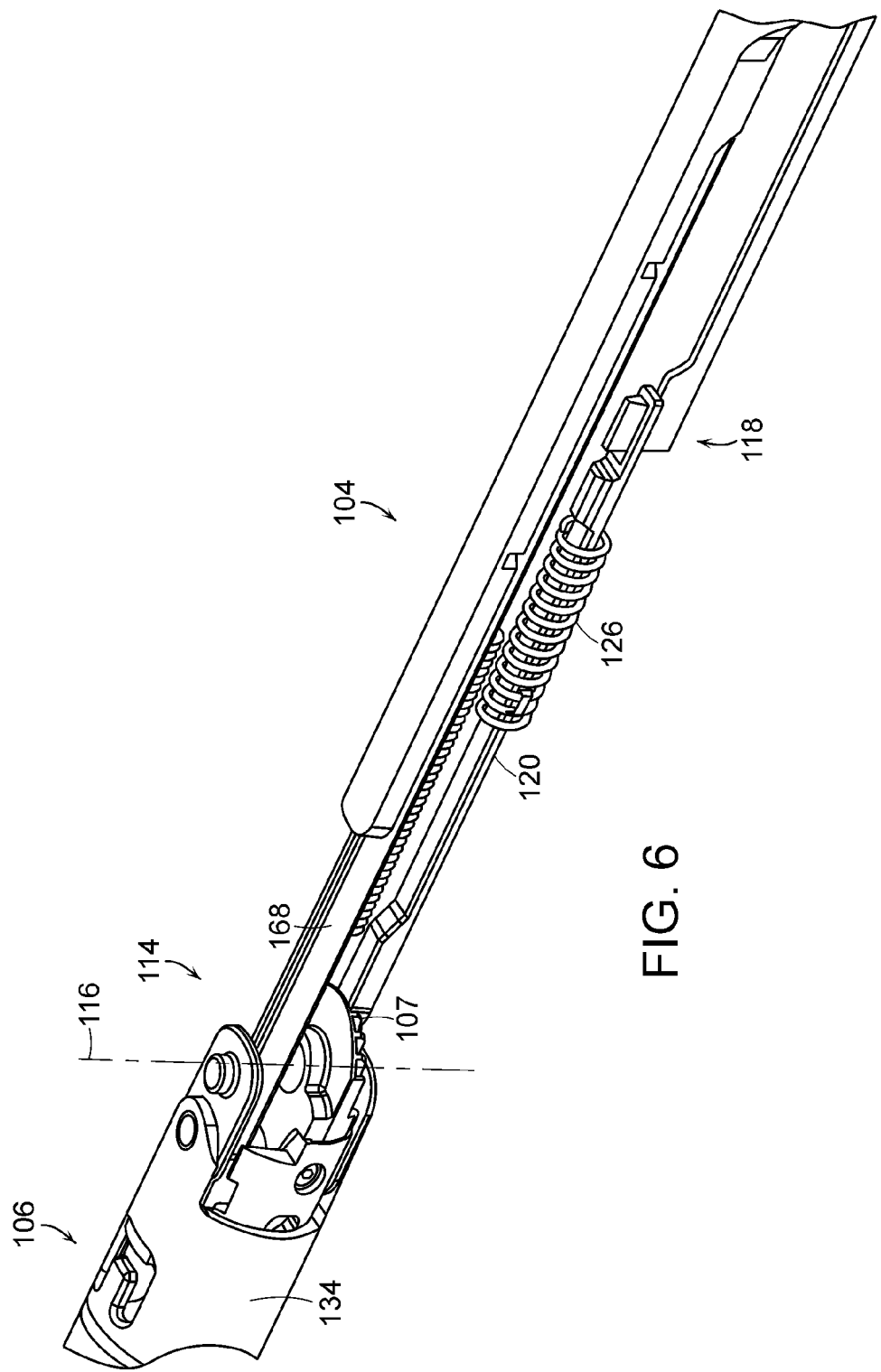
FIG. 6 is a perspective view of an elongate shaft assembly and the articulation joint of the surgical instrument of FIG. 1 with some components of the surgical instrument removed.
Figure 7:
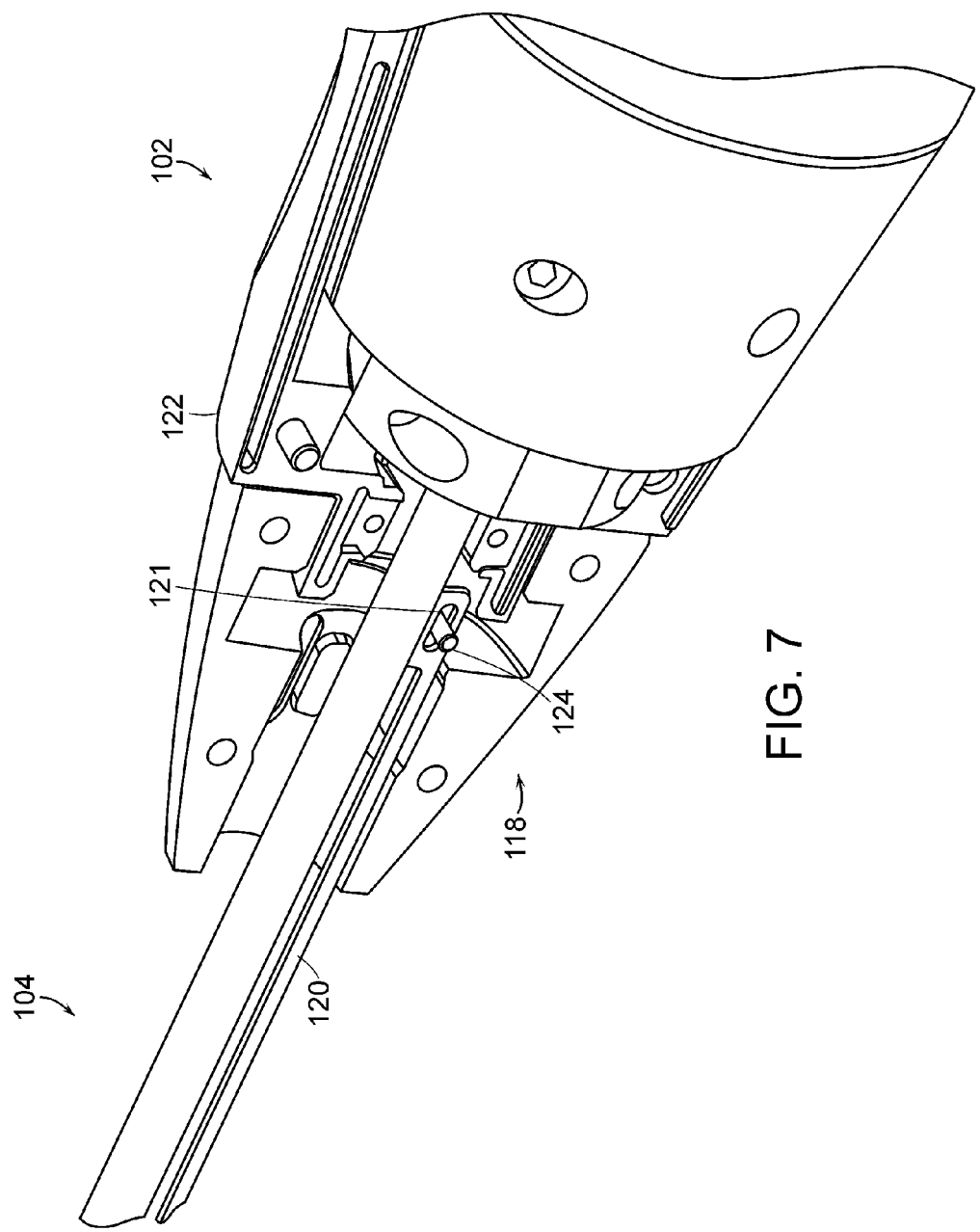
FIG. 7 is a partial perspective view of the handle portion and the elongate shaft assembly of the surgical instrument of FIG. 1 with some components of the surgical instrument removed.
Figure 8:
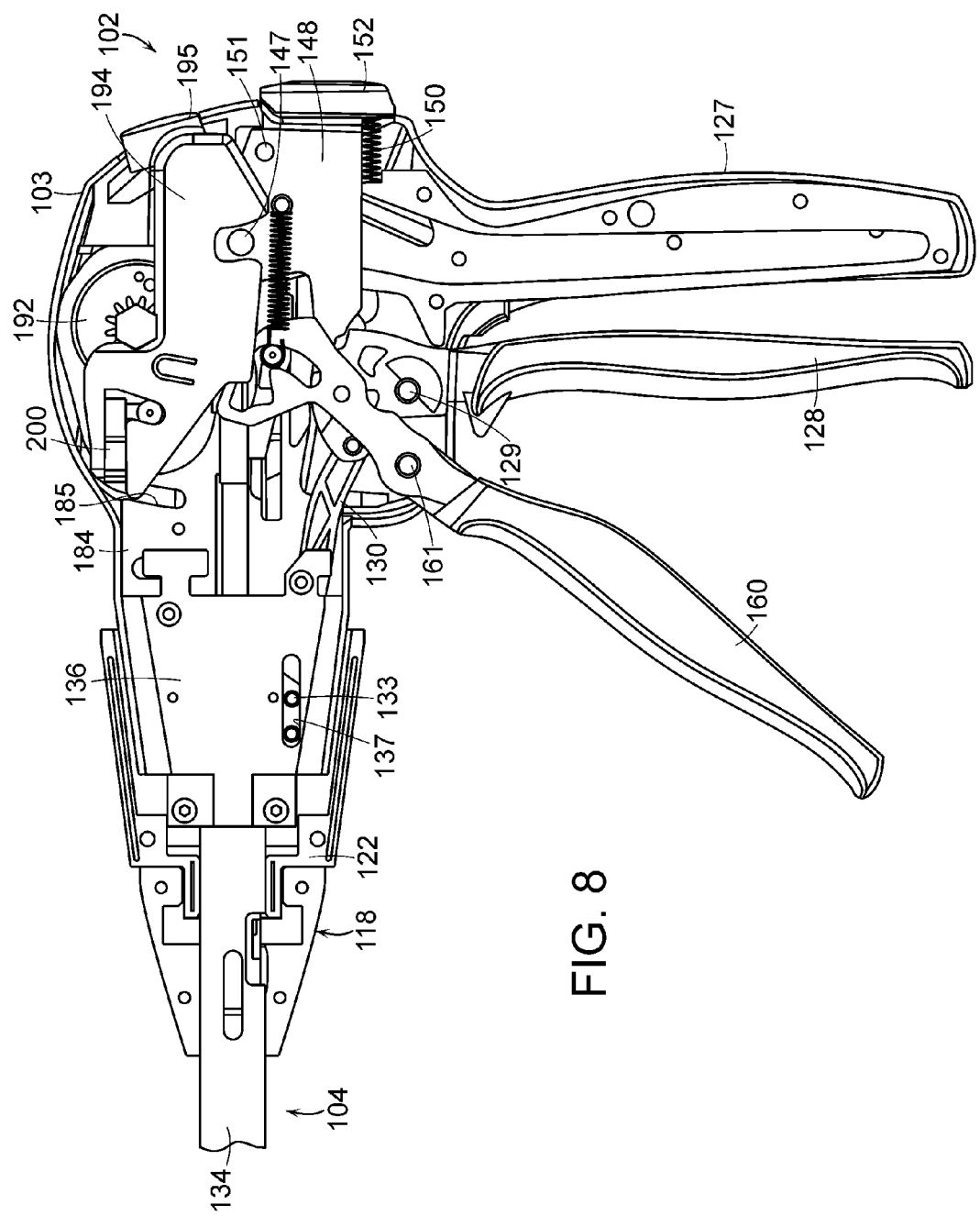
FIG. 8 is an elevational view of the handle portion of FIG. 2 with some components of the surgical instrument removed.
Figure 9:
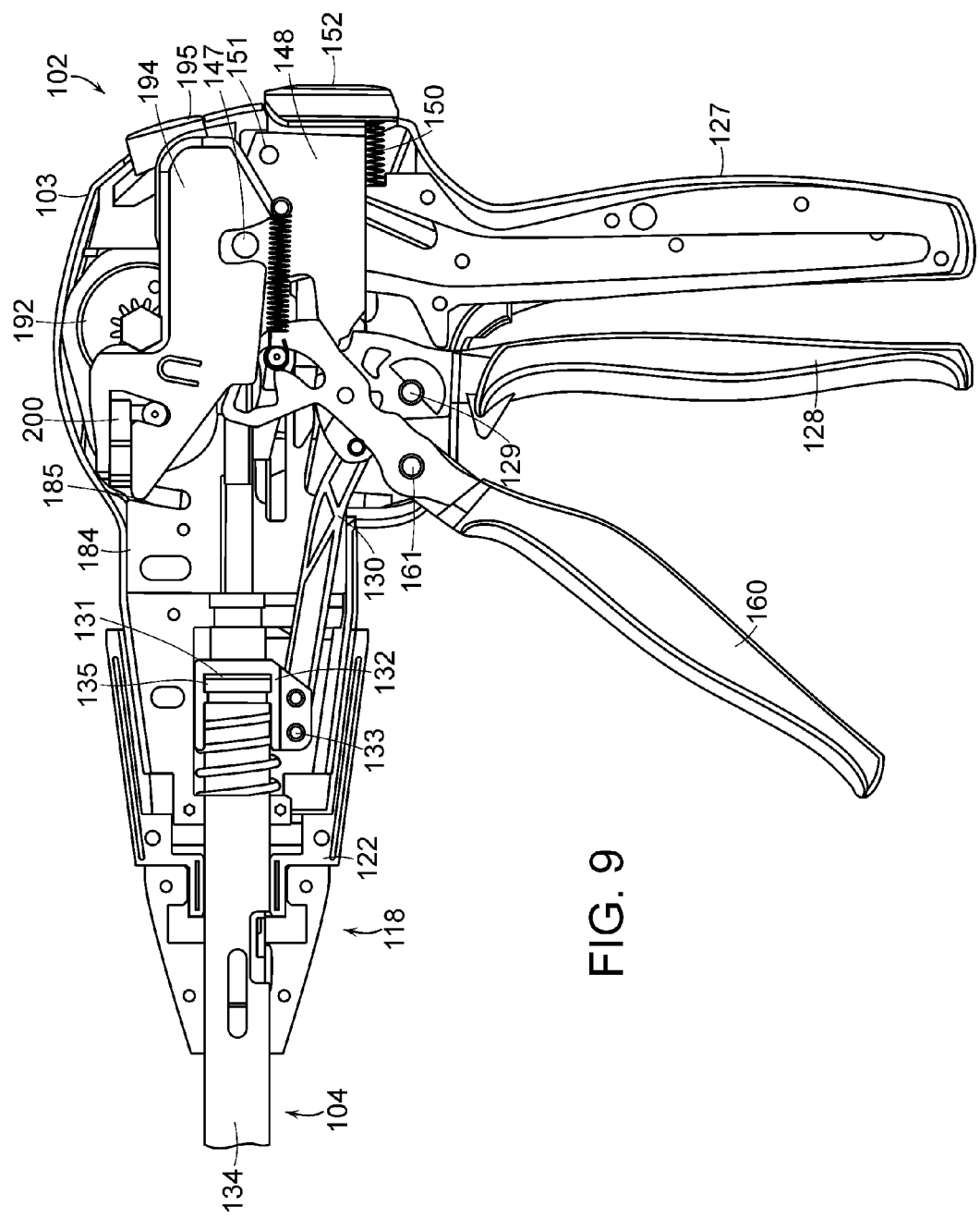
FIG. 9 is an elevational view of the handle portion of FIG. 2 with additional components of the surgical instrument removed.

In various embodiments, referring to FIGS. 7-9, locking mechanism 118 can further include actuator 122 which can be operably connected to lock member 120. In at least one embodiment, actuator 122 can include pin 124 which can be received within slot 121 in lock member 120 such that, when actuator 122 is slid relative to handle portion 102, pin 124 can abut a side wall of slot 121 and motivate lock member 120 relative to end effector 106. In at least one embodiment, actuator 122 can be pulled away from end effector 106, i.e., proximally, to disengage lock member 120 from end effector 106. Although not illustrated, other embodiments are envisioned where actuator 122 can be moved distally, or even rotated, in order to disengage lock member 120 from end effector 106. In either event, locking mechanism 118 can further include return spring 126 (FIG. 6) which can be configured to move lock member 120 toward end effector 106, i.e., distally, to engage lock member 120 with end effector 106 after actuator 122 has been released. Other locking mechanisms are disclosed in U.S. patent application Ser. No. 11/100,772, entitled SURGICAL INSTRUMENT WITH ARTICULATING SHAFT WITH SINGLE PIVOT CLOSURE AND DOUBLE PIVOT FRAME GROUND, which was filed on Apr. 7, 2005, U.S. patent application Ser. No. 11/238,358, entitled SURGICAL INSTRUMENT WITH ARTICULATING SHAFT WITH RIGID FIRING BAR SUPPORTS, which was filed on Sep. 29, 2005, and U.S. patent application Ser. No. 11/491,626, entitled SURGICAL STAPLING AND CUTTING DEVICE AND METHOD FOR USING THE DEVICE, which was filed on Jul. 24, 2006, the entire disclosures of which are hereby incorporated by reference herein.

Figure 1:
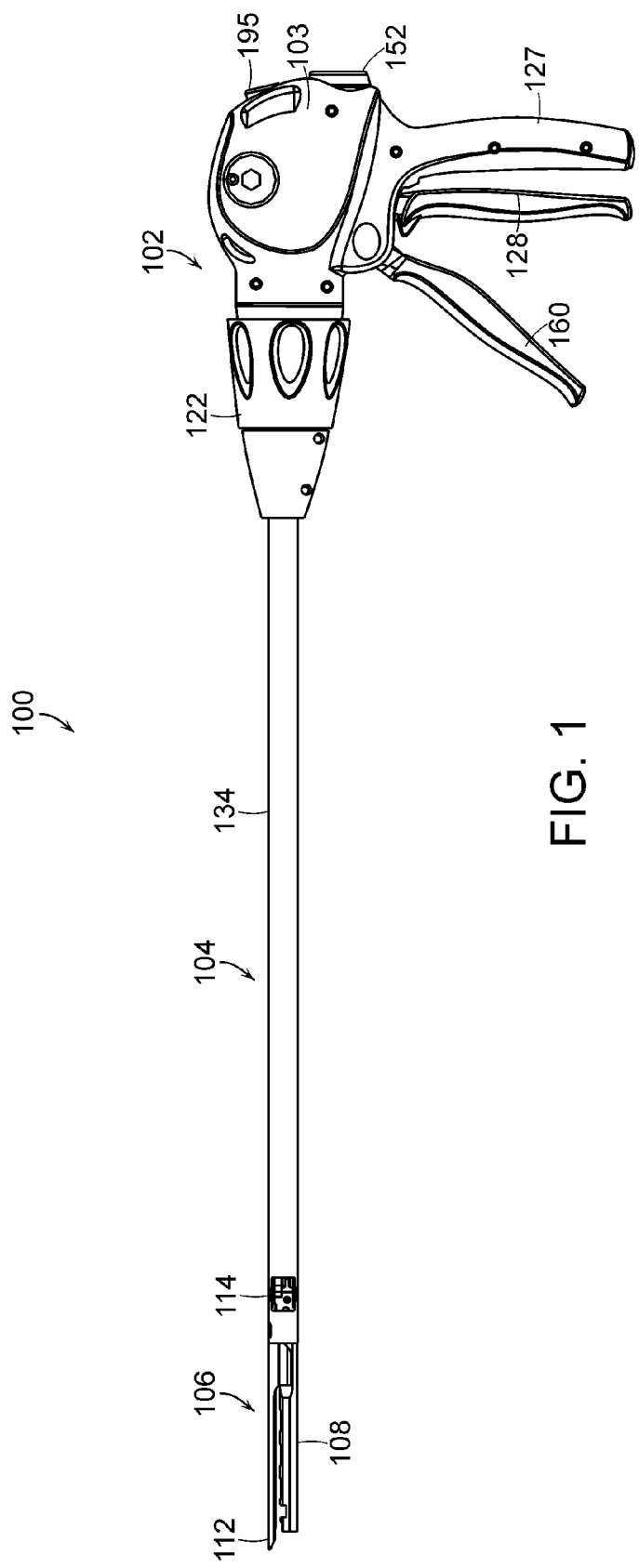
FIG. 1 is an elevational view of a surgical instrument in accordance with an embodiment of the present invention.
Figure 2:
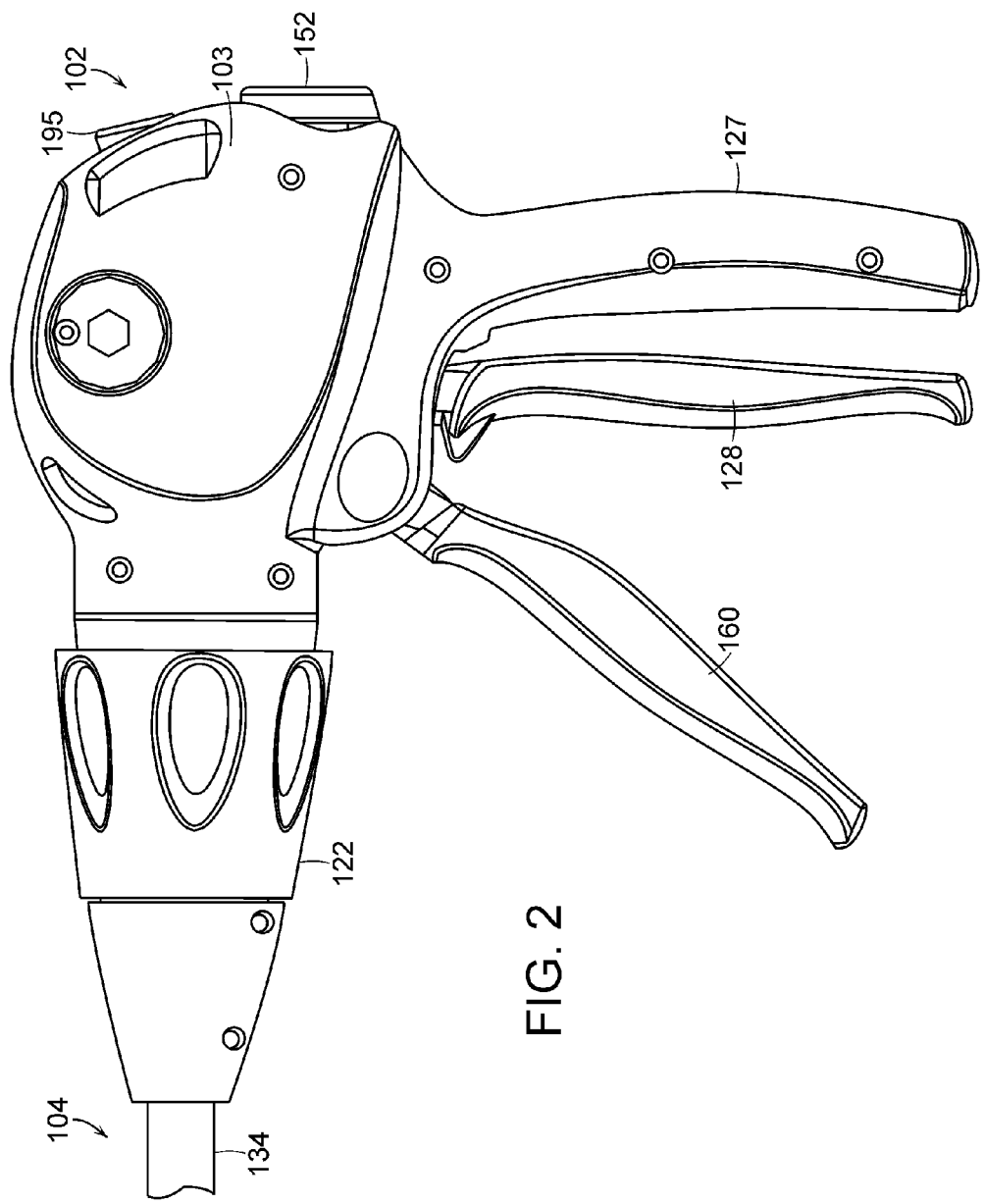
FIG. 2 is an elevational view of a handle portion of the surgical instrument of FIG. 1.

In various embodiments, referring to FIGS. 1 and 2, actuator 122 can be contoured such that a surgeon can grasp the outer surface of actuator 122 and pull actuator 122 proximally as described above. To move actuator 122, in at least one embodiment, a surgeon may place one hand on handle grip 127, for example, and place their other hand on actuator 122 so that the surgeon can move actuator 122 relative to handle grip 127. In other various embodiments, referring to FIGS. 10-13, actuator 122' can be configured such that a surgeon may only need one hand to operate the surgical instrument. More particularly, in at least one embodiment, actuator 122' can include hooks, or projections, 115 extending therefrom which can allow the surgeon to hold handle grip 127 with one hand and extend at least one finger from that hand distally to grip at least one projection 115 and pull actuator 122' proximally as described above. While actuator 122' is described herein as having projections 115, actuator 122, or any other suitable actuator, can also include projections 115 and/or any other suitable features that can assist a surgeon in operating surgical instrument 100 with one hand. In at least one embodiment, projections 115 can be at least partially comprised of and/or coated with an elastic or 'soft-touch' material which can improve the surgeon's grip on projections 115 and can provide other ergonomic benefits to the surgeon. In various embodiments, actuator 122', for example, can be operably engaged with shaft assembly 104 such that end effector 106 and shaft assembly 104 can be rotated about a longitudinal axis by actuator 122'. In such embodiments, a surgeon can orient end effector 106 in a surgical site by articulating end effector 106 as described above and/or rotating end effector 106 into position. In at least one embodiment, the surgeon can rotate actuator 122' by positioning a finger against one of projections 115 and applying a force thereto. In various embodiments, the surgeon can hold actuator 122' in position by placing a finger against a projection 115 and resisting any undesired motion of actuator 122' and, correspondingly, end effector 106.

Figure 5:
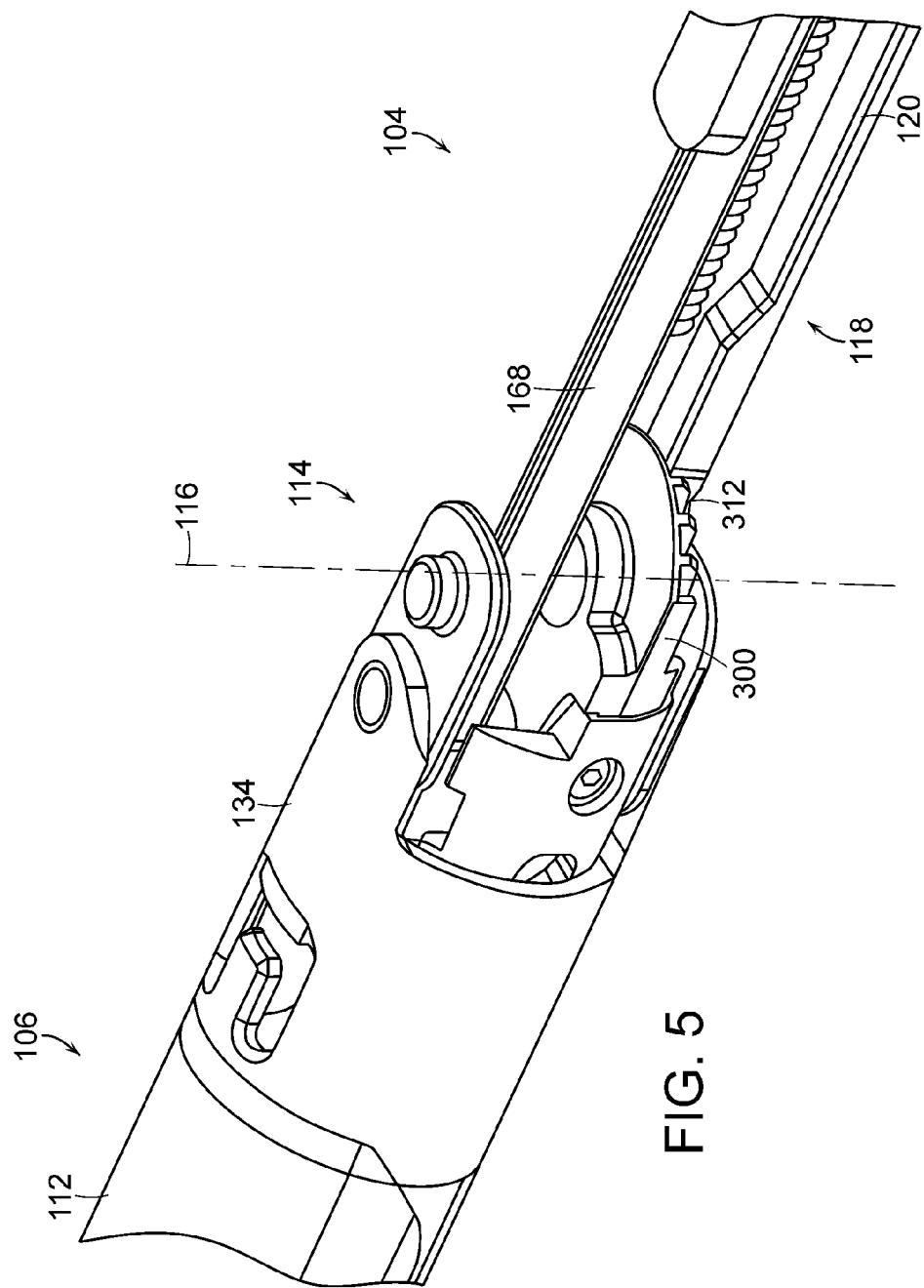
FIG. 5 is a perspective view of an articulation joint of the surgical instrument of FIG. 1 with some components of the surgical instrument removed.

In various embodiments, a surgical instrument in accordance with the present invention can include a system for closing, or clamping, an end effector onto soft tissue, for example. In at least one embodiment, referring to FIGS. 2, 5, 8 and 9, surgical instrument 100 can include closure trigger 128, drive link 130, driver 132, and closure tube 134. In various embodiments, upon an actuation of closure trigger 128, closure trigger 128 can be configured to displace drive link 130, driver 132, and closure tube 134 distally. More particularly, in at least one embodiment, drive link 130 can include a first end pivotably connected to trigger 128 and a second end pivotably connected to driver 132 such that the rotation of trigger 128 toward handle grip 127 can drive link 130 forward and slide driver 132 along an axis defined by driver guide 136 (FIG. 8). In various embodiments, driver 132 can include projections 133 extending therefrom which can be slidably received within slots 135 in driver guide 136 such that slots 135 can define a path for driver 132 as it is moved. In various embodiments, closure tube 134 can be operably engaged with driver 132 such that, when driver 132 is moved distally as described above, closure tube 134 can engage anvil 112 and pivot anvil 112 downwardly. Referring primarily to FIG. 5, closure tube 134 can be configured to slide over articulation joint 114 and pivot anvil 112 relative to staple cartridge 110. In at least one embodiment, as illustrated in FIG. 9, closure tube 134 can include a proximal end having projection 135 extending therefrom which can be received in slot 131 in driver 132 such that the displacement of driver 132 is transmitted to closure tube 134.

Figure 10:
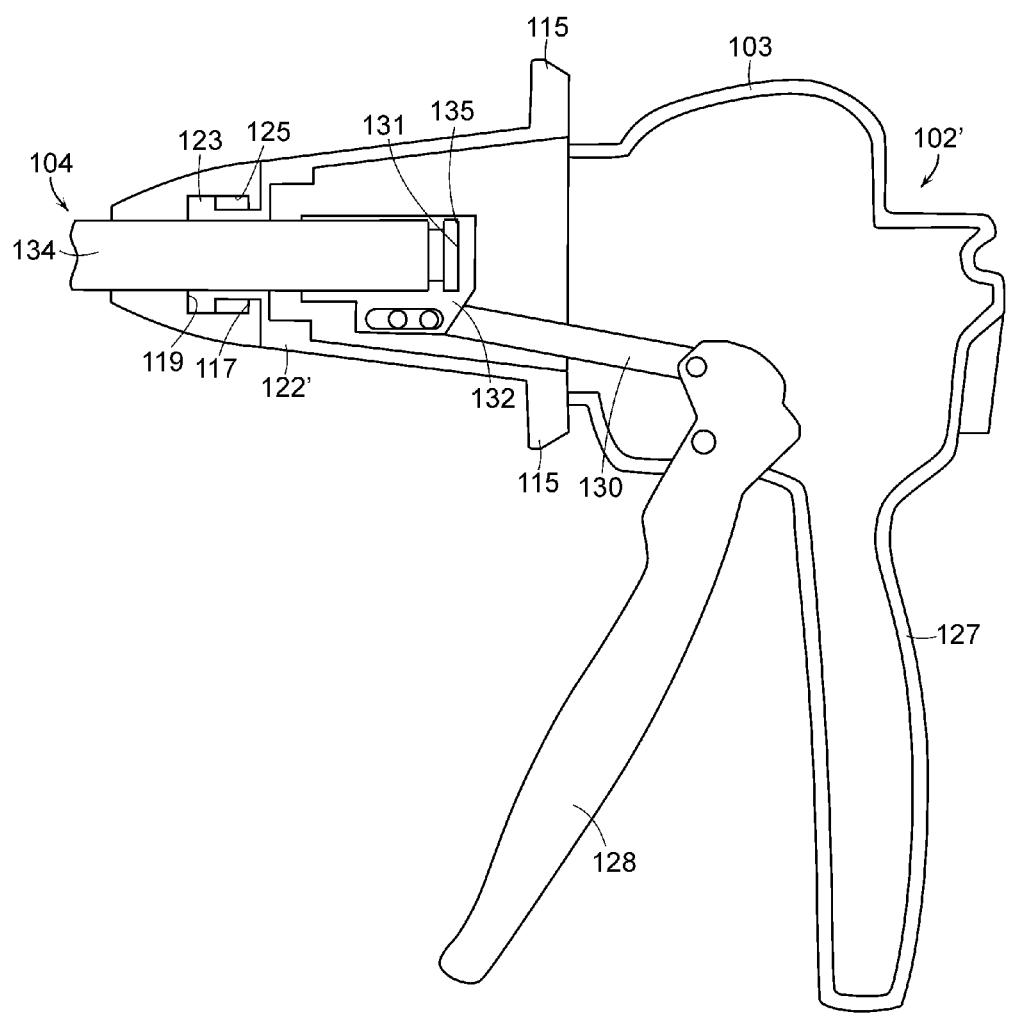
FIG. 10 is an elevational view of an actuator of an articulation locking mechanism and an end effector closure system of a surgical instrument in accordance with an alternative embodiment of the present invention with some components of the surgical instrument removed.
Figure 11:
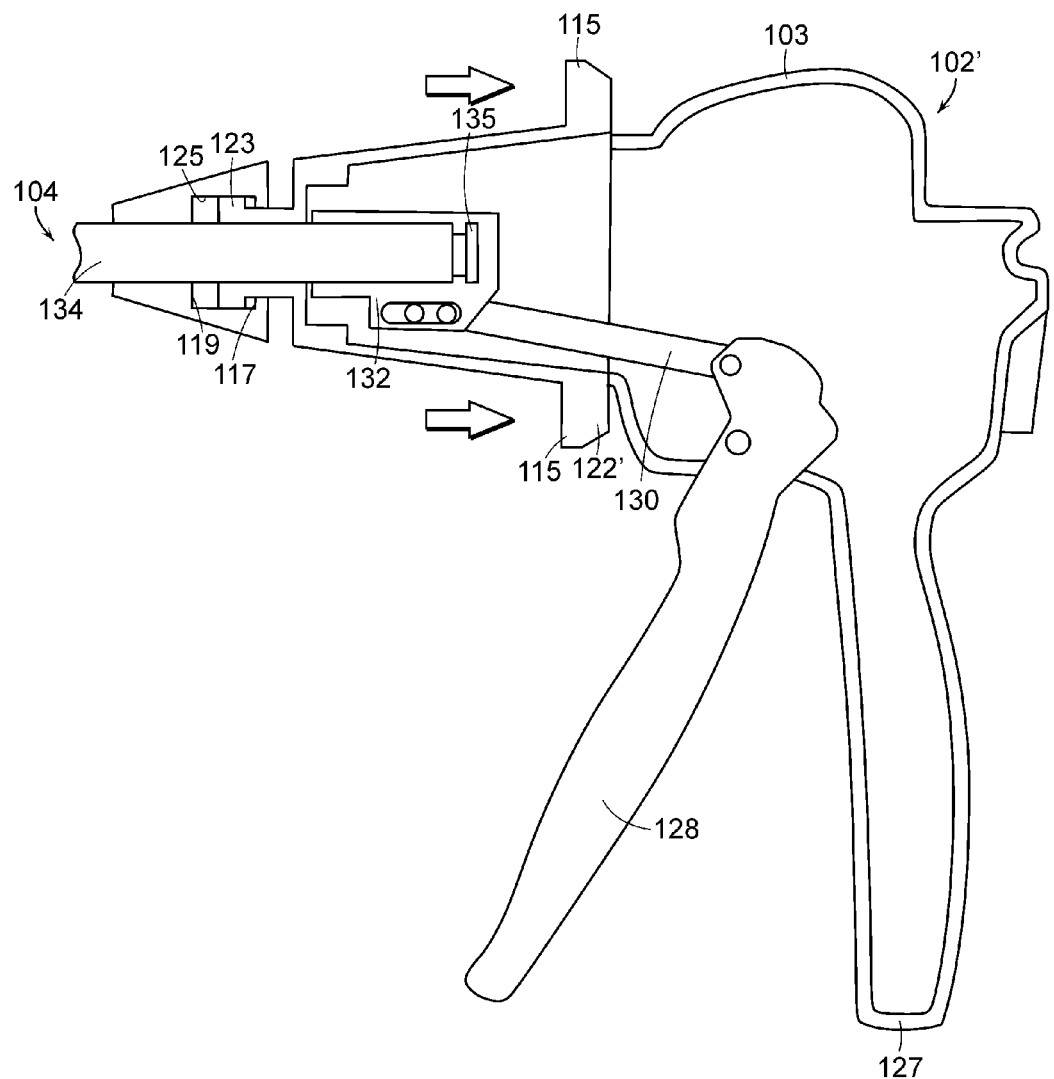
FIG. 11 is an elevational view of the surgical instrument of FIG. 10 illustrating the articulation locking mechanism actuator in an unlocked position and the end effector closure system in an open configuration.
Figure 12:
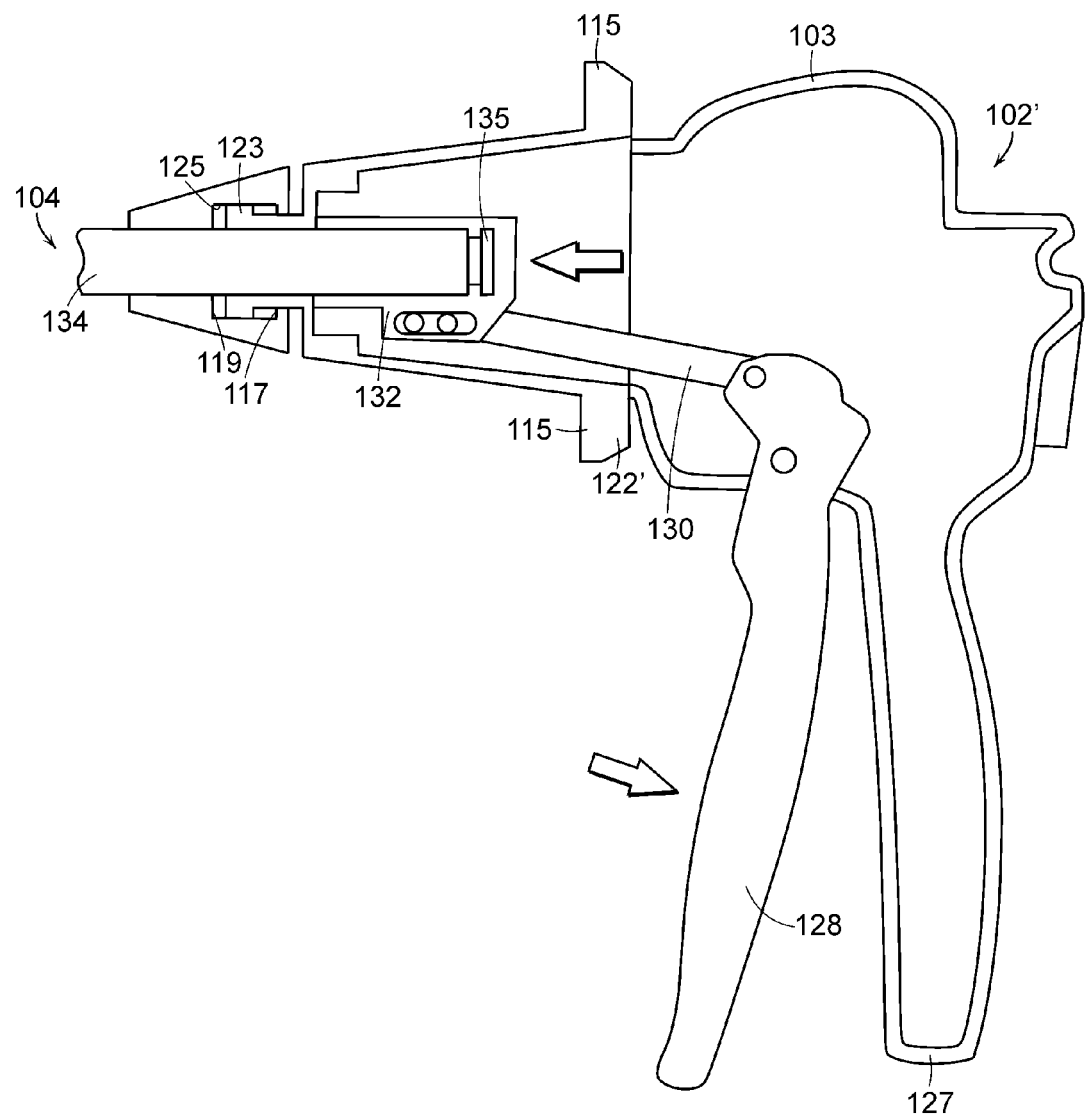
FIG. 12 is an elevational view of the surgical instrument of FIG. 10 illustrating the articulation locking mechanism actuator in an unlocked position and the end effector closure system in a partially closed configuration.

In various embodiments, as described above, locking mechanism 118 can prevent, or at least partially inhibit, relative movement between end effector 106 and shaft assembly 104. In circumstances where soft tissue is clamped between anvil 112 and staple cartridge 110, for example, relative movement between end effector 106 and shaft assembly 104 can apply a shear force to the soft tissue clamped therebetween which may damage it. In various embodiments, referring to FIGS. 10-13, in order to prevent, or at least reduce, relative movement between end effector 106 and shaft assembly 104 when end effector 106 is closed, the end effector closure system can be configured to engage locking mechanism 118 to prevent actuator 122' from being moved into its unlocked position. In effect, in at least one embodiment, the actuation of closure trigger 128 can not only close end effector 106, but it can also prevent locking mechanism 118 from being unlocked. In various embodiments, referring to FIGS. 10-13, surgical instrument 100' can include driver 132 which can be configured to abut, or be positioned closely adjacent to, actuator 122' when driver 132 is moved distally by trigger 128 and thereby prevent actuator 122' from being moved proximally as described above with respect to actuator 122. More particularly, before trigger 132 is actuated, as illustrated in FIGS. 10 and 11, actuator 122' can be slid proximally in order to slide lock member 120 relative to end effector 106 and unlock articulation joint 114. Upon an actuation of trigger of 132, however, referring to FIG. 13, driver 132 can be configured to abut, or be positioned adjacent to, actuator 122' such that actuator 122' cannot be moved proximally to disengage lock member 120 from end effector 106. As a result, the end effector closure system can prevent end effector 106 from being articulated after it has been closed, thereby reducing the possibility that a shear force will be transmitted to the soft tissue clamped therein.

Further to the above, the end effector closure system can provide feedback to the surgeon that the end effector has been closed and, in order for the surgeon to unlock and articulate the end effector, the surgeon must first at least partially re-open the end effector before the end effector can be articulated. More particularly, owing to the interaction between driver 132 and actuator 122' when end effector 106 is closed, when a surgeon attempts to pull actuator 122' proximally to unlock articulation joint 114, driver 132 can substantially prevent actuator 122' from moving thereby signaling to the surgeon that end effector 106 is closed and end effector 106 must first be opened before actuator 122' can be moved and the articulation joint can be unlocked. In various embodiments, such an end effector closure system can prevent the surgeon from damaging the surgical instrument and/or tissue captured within, or surrounding, the end effector. More particularly, in at least one embodiment, when closure tube 134 has been advanced to close anvil 112 as described above, closure tube 134 may apply a force to anvil 112 to maintain anvil 112 in a closed position and, in various circumstances, this force can create friction forces within articulation joint 114 which can inhibit, if not prevent, end effector 106 from rotating about articulation joint 114. In embodiments without the end effector closure system described above, if a surgeon attempts to overcome these friction forces without first at least partially opening the end effector, the surgeon may bend or break one or more components of the surgical instrument, for example. In various embodiments of the present invention, however, driver 132, for example, may prevent the surgeon from releasing articulation lock 120 as described above and, as a result, the surgeon may not be afforded the opportunity to unlock articulation joint 114 let alone articulate end effector 106.

In various embodiments, a surgical instrument in accordance with the present invention can include an end effector closure system which can position anvil 112, for example, in an open position, a closed position, and a partially closed position. In at least one embodiment, a surgeon can move an anvil 112 into a partially closed position and evaluate whether the end effector should be repositioned or articulated before anvil 112 is moved into its closed position. In such embodiments, anvil 112 can be moved relative to soft tissue positioned intermediate anvil 112 and staple cartridge 110 without applying a shear force, or at least a substantial shear force, to the soft tissue before anvil 112 is completely closed. In at least one embodiment, anvil 112 can be configured such that it does not clamp the soft tissue positioned between anvil 112 and staple cartridge 110 when it is in its partially closed position. Alternatively, anvil 112 can be configured to apply a light clamping force to the soft tissue when anvil 112 is in its partially closed position before applying a larger clamping force when it is moved into its closed position. In at least one such embodiment, the surgical instrument can include a trigger which can be moved between a first position (FIG. 11) which corresponds to the open position of anvil 112, a second position (FIG. 12) which corresponds with its partially closed position, and a third position (FIG. 13) which corresponds with its closed position. In various embodiments, referring to FIGS. 8 and 9, trigger 128 can be pivotably mounted to housing 103 of handle portion 102 such that trigger 128 can be rotated about pin 129 between its first, second, and third positions. In various embodiments, referring to FIGS. 8, 9, 17 and 18, surgical instrument 100 can further include trigger lock 148 which can be configured to engage trigger 128 and selectively lock trigger 128 in at least one of its first, second, and third positions described above. In at least one embodiment, trigger 128 can include pivot end 138 comprising cam surface 140, first notch 142, and second notch 144 where trigger lock 148 can be configured to engage first notch 142 and second notch 144. More particularly, surgical instrument 100 can further include, referring to FIGS. 8 and 9, trigger lock spring 150 which can be configured to bias follower portion 149 of trigger lock 148 against cam surface 140 such that when either first notch 142 or second notch 144 is aligned with follower portion 149, trigger lock spring 150 can push follower portion 149 into first notch 142 or second notch 144, respectively. In at least one embodiment, referring primarily to FIGS. 8 and 9, trigger lock 148 can be pivotably mounted to housing 103 of handle portion 102 via pin 151. In various embodiments, trigger lock spring 150 can be compressed intermediate button portion 152 of trigger lock 148 and housing 103 such that trigger lock spring 150 can rotate trigger lock 148 about pin 151 and bias trigger lock 148 downwardly against cam surface 140 of trigger 128.

Further to the above, in at least one embodiment, first notch 142 can be aligned with follower portion 149 when trigger 132 is moved into its second position and anvil 112 is moved into its partially closed position. In various embodiments, follower portion 149 can be securely retained within first notch 142 such that trigger lock 148 may need to be manually disengaged from trigger 132 before trigger 132 can be moved into its third position and/or returned to its first position. In at least one embodiment, referring to FIGS. 8 and 9, a surgeon can depress button portion 152 of lock member 148 such that lock member 148 is rotated about pin 151 and follower portion 149 is lifted upwardly and out of engagement with trigger 128. In other various embodiments, first notch 142 can be configured such that follower portion 149 can slide out of first notch 142 upon an application of force to trigger 132. In either event, after follower portion 149 has been disengaged from first notch 142, a surgeon can selectively move trigger 132 into its third position or release trigger 132 and allow a trigger spring, for example, to return trigger 132 to its first position. In at least one alternative embodiment, first notch 142 and follower portion 149 can be configured such that, after trigger 132 has been moved into its second position, trigger 132 must be moved into its third position before it can be returned into its first position. In either event, in at least one embodiment, second notch 144 of trigger 132 can be aligned with follower portion 149 when trigger 132 is moved into its third position and anvil 112 is moved into its closed position. Similar to first notch 142, second notch 144 can be configured to retain follower portion 149 therein until lock member 148 is disengaged from trigger 132 and/or a sufficient force is applied to trigger 132 to dislodge follower portion 149 from second notch 144. Thereafter, in various embodiments, a trigger spring can move trigger 132 from its third position into its second position where the surgeon may be required to, similar to the above, disengage follower portion 149 from first notch 142. In at least one alternative embodiment, first notch 142 can be configured such that follower portion 149 can slide past first notch 142 and allow trigger 132 to be moved from its third position to its first position without requiring the surgeon to dislodge follower portion 149 from first notch 142.

Further to the above, although not illustrated, button portion 152 of lock member 148 can be recessed, for example, within surgical instrument housing 103 when closure trigger 128 is in its first position. In alternative embodiments, button portion 152 can be positioned flushly with housing 103 or it can extend slightly from housing 103. In either event, in at least one embodiment, button portion 152 can move outwardly relative to housing 103 when closure trigger 128 is moved into its second position. Such movement can provide visual feedback to the surgeon that the anvil of the surgical instrument is in its partially closed position. In addition, the movement of button portion 152 can also be accompanied by audio and/or tactile feedback. In either event, a surgeon can access button portion 152 after it has been moved outwardly such that lock member 148 can be disengaged from trigger 128 as described above. In various embodiments, button portion 152 can move outwardly even further when trigger 128 is moved from its second position to its third position. Similar to the above, such movement can provide a visual cue to the surgeon that the anvil is now in its closed position and can be accompanied by audio and/or tactile feedback, as described above. Although button 152 is described above as moving outwardly as trigger 128 is progressed between its first and third positions, the invention is not so limited. On the contrary, button 152, or any other suitable indicator, can be provide feedback to the surgeon in any suitable manner.

In alternative embodiments, although not illustrated, anvil 112 can be held, or retained, in more than the three positions described above, i.e., its open, closed, and partially-closed positions. In at least one embodiment, anvil 112 can be retained in open, closed, and two or more intermediate positions. In such embodiments, anvil 112 could be progressed through these intermediate positions and apply an increasingly greater force to the soft tissue captured in end effector 106 as anvil 112 is moved toward its closed position. In at least one embodiment, similar to the above, trigger 132 could include a plurality of notches which could correspond with the various intermediate positions of anvil 112. In various alternative embodiments, although not illustrated, the end effector closure system could include a ratchet assembly which could allow trigger 132 and, correspondingly, anvil 112 to be held in a plurality of positions. In such embodiments, anvil 112 and trigger 132 could be held in place by a pawl pivotably engaged with a ratchet wheel operably engaged with trigger 132.

Figure 13:
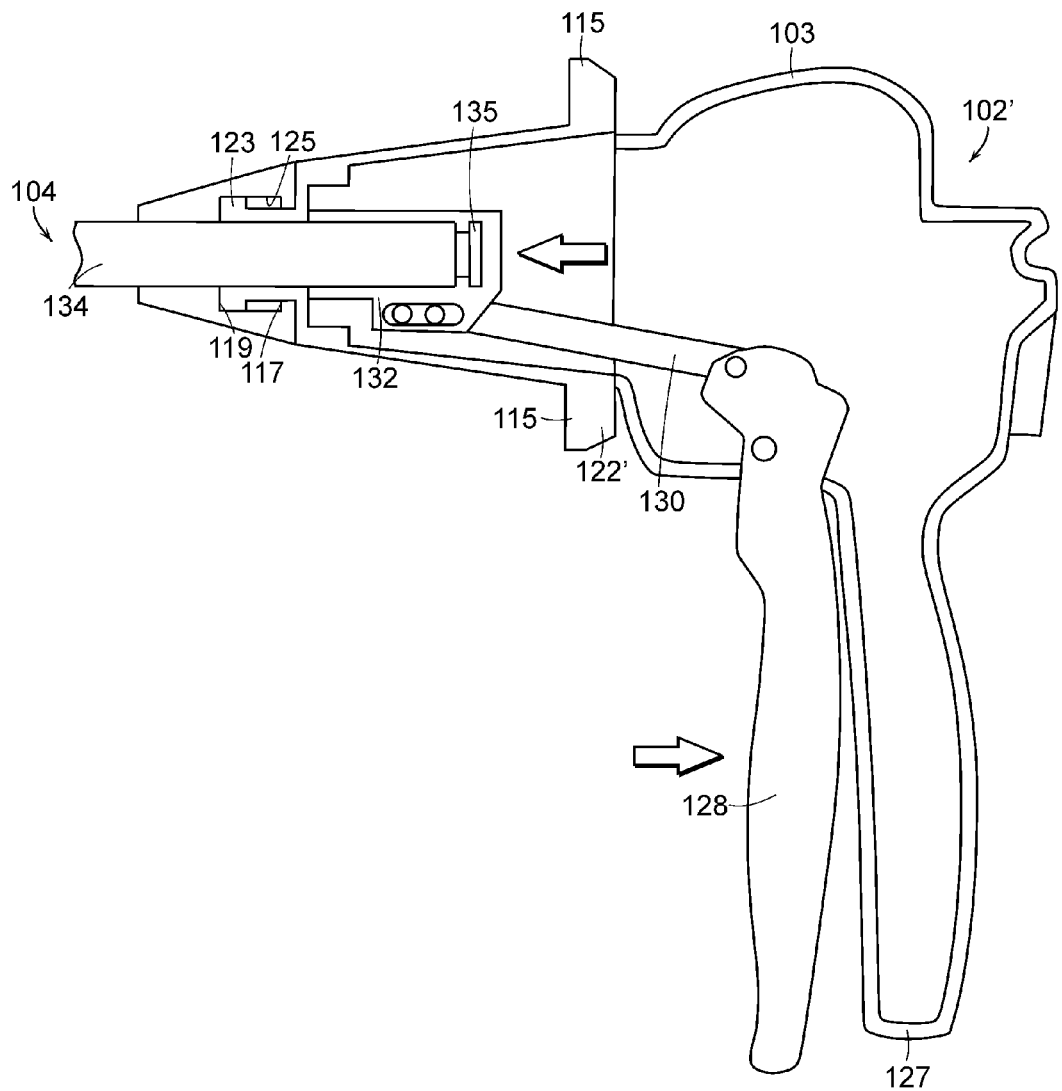
FIG. 13 is an elevational view of the surgical instrument of FIG. 10 illustrating the articulation locking mechanism actuator in a locked position and the end effector closure system in a closed configuration.
Figure 14:
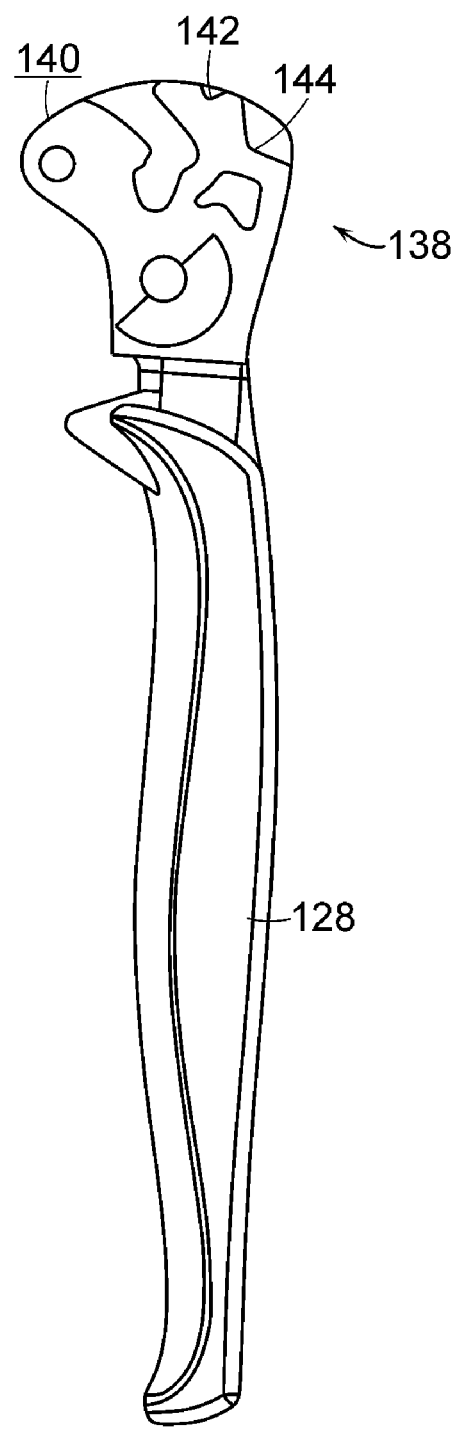
FIG. 14 is an elevational view of a closure trigger of an end effector closure system of the surgical instrument of FIG. 1.
Figure 15:
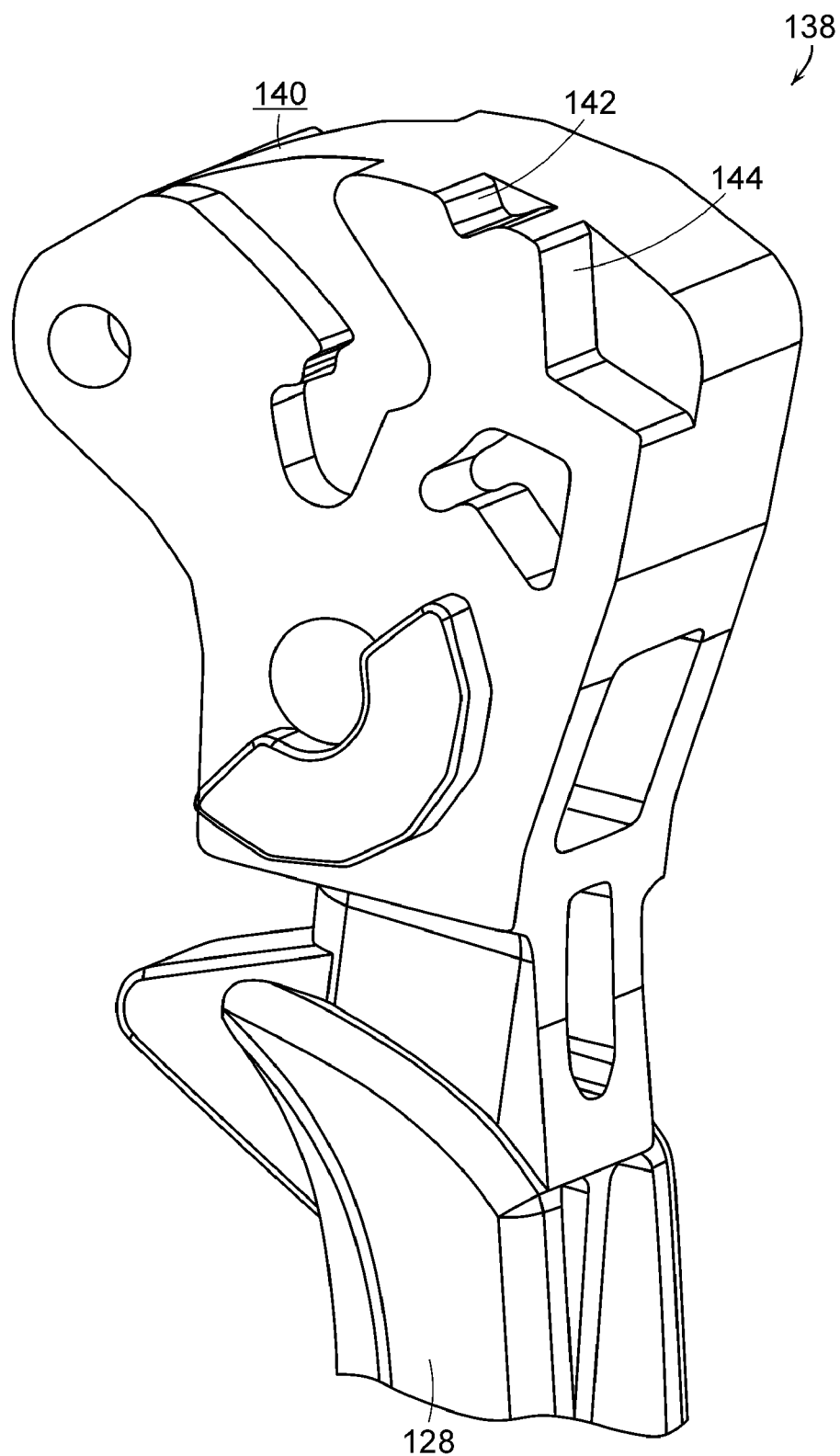
FIG. 15 is a partial perspective view of the closure trigger of FIG. 15.
Figure 16:
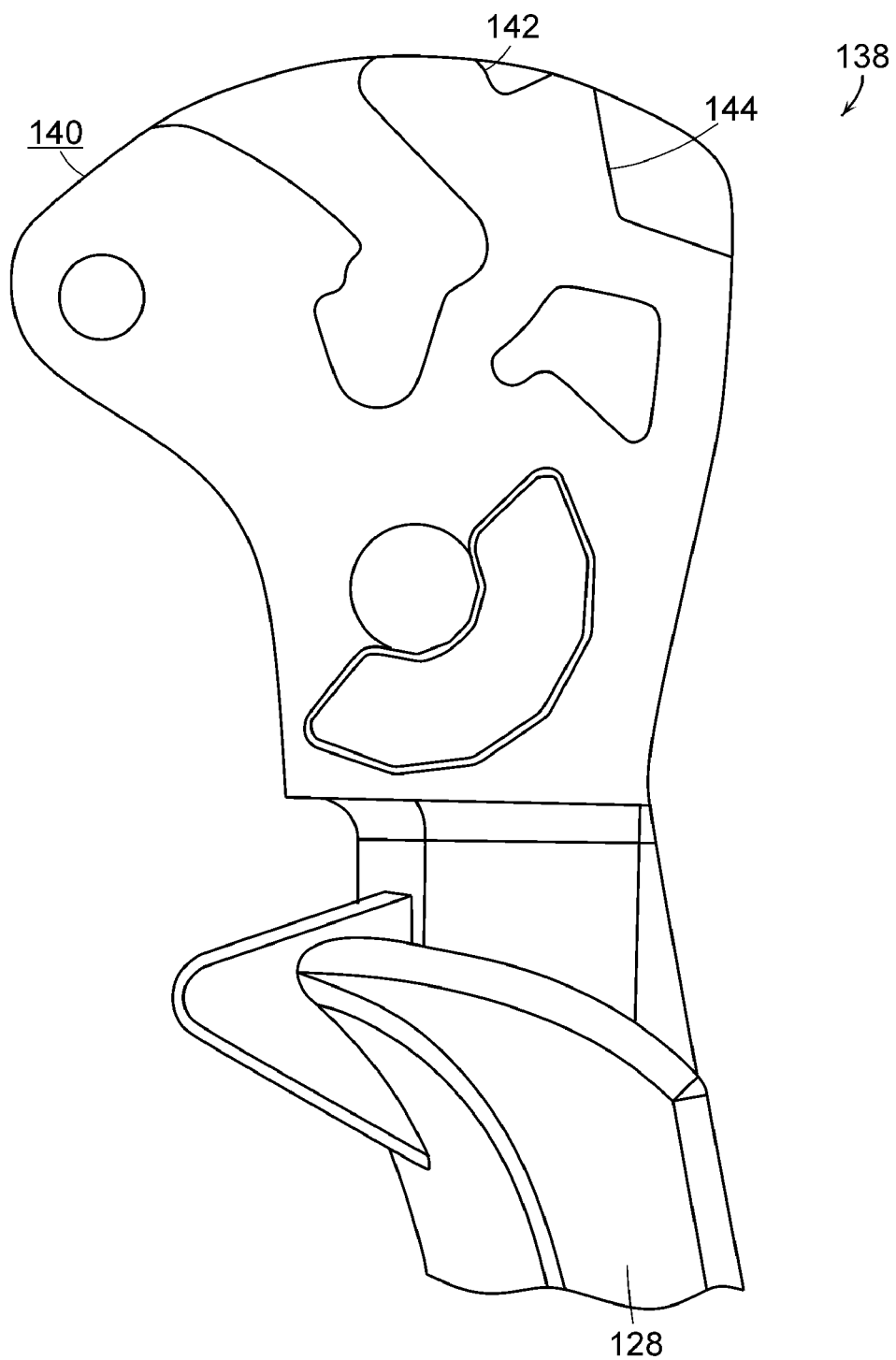
FIG. 16 is a partial elevational view of the closure trigger of FIG. 15.
Figure 17:
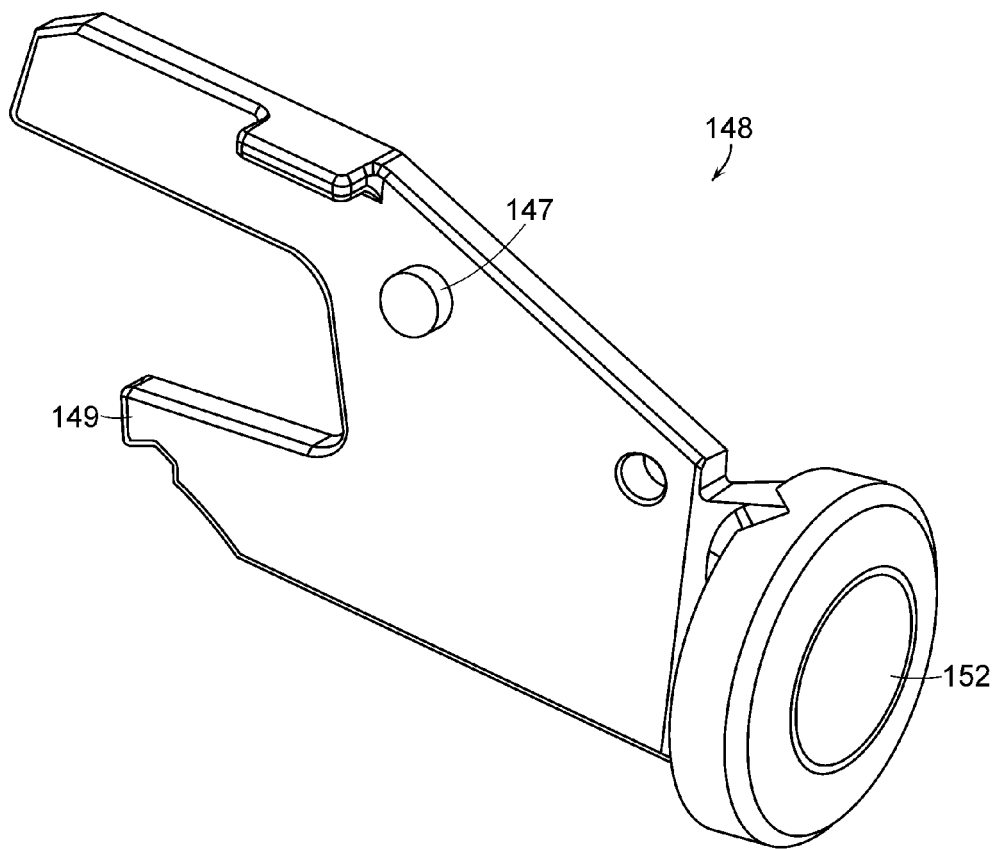
FIG. 17 is a perspective view of a trigger lock of the surgical instrument of FIG. 1.
Figure 18:
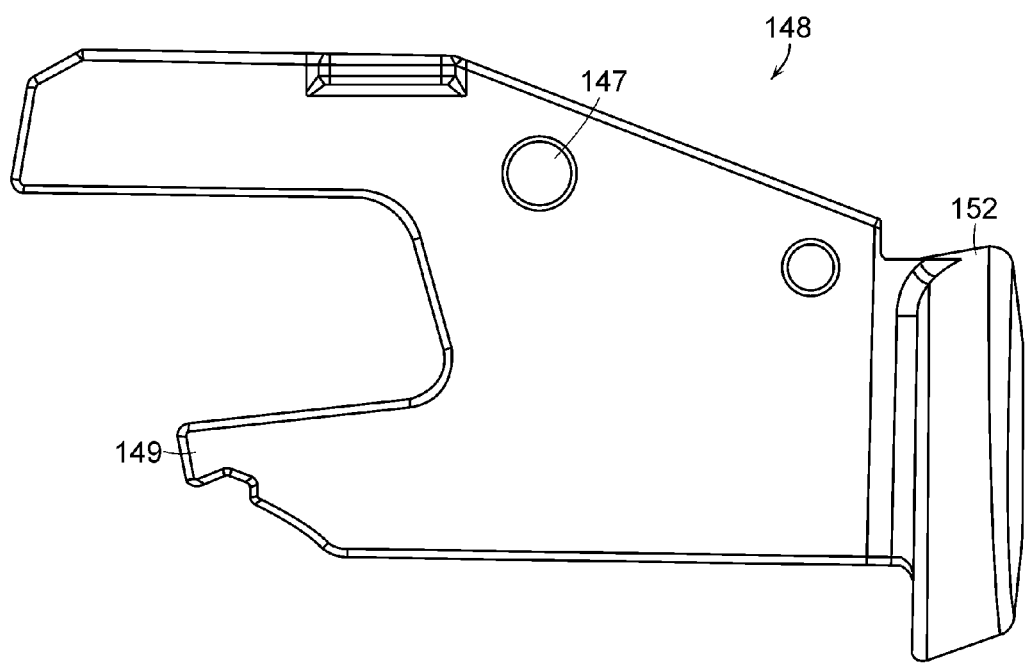
FIG. 18 is an elevational view of the trigger lock of FIG. 17.

In various embodiments, referring to FIGS. 10-13, the relative movement between actuator 122' and handle portion 102', as described above, can be limited in order to control the range through which lock member 120 can be displaced. More particularly, referring to FIGS. 10 and 11, the distal portion of actuator 122' can include projection 123 extending therefrom which can be received in cavity 125 where the displacement of actuator 122' can be limited by proximal wall 117 and distal wall 119 of cavity 125. In at least one embodiment, when trigger 128 is in its first position, as illustrated in FIGS. 10 and 11, actuator 122 can be moved from a distal position in which projection 123 can abut distal wall 119, as illustrated in FIG. 10, into a more proximal position in which projection 123 does not abut distal wall 119, as illustrated in FIG. 11. In this more distal position, as described above, lock member 120 can be disengaged from end effector 106 and end effector 106 can be rotated relative to shaft assembly 104. When trigger 128 is in its second position, referring to FIG. 12, driver 132 can limit the range of motion of actuator 122' such that projection 123 cannot be positioned against proximal wall 117. In at least one embodiment, however, actuator 122' can be moved proximally a sufficient distance to disengage lock member 120 from end effector 106. In these circumstances, a surgeon can reposition end effector 106 although anvil 112 may be partially closed onto the soft tissue, for example. When trigger 128 is in its third position, as illustrated in FIG. 13, driver 132 can force actuator 122' distally such that projection 132 abuts, or is positioned adjacent to, distal wall 119 and actuator 122' cannot be moved sufficiently to unlock articulation joint 114.

In various embodiments, a surgical instrument in accordance with the present invention can include a firing drive configured to advance a cutting member and/or staple driver within an end effector as described above. In at least one embodiment, referring to FIGS. 8, 9 and 19-25, the firing drive of surgical instrument 100 can include firing trigger 160, first firing link 162, second firing link 164, and firing member 166. In various embodiments, firing trigger 160 can be operably engaged with at least one of firing member 166 and firing links 162 and 164 in order to advance knife bar 168 within elongate shaft assembly 104. In at least one embodiment, knife bar 168 can be operably engaged with a cutting member (not illustrated) and a staple driver (not illustrated) in end effector 106 where the cutting member can be configured to incise tissue, for example, and the staple driver can be configured to deploy staples from staple cartridge 110. Cutting members and staple drivers are well disclosed in U.S. Pat. Nos. 6,905,057 and 7,044,352, which have been previously incorporated by reference into the present application, and, as a result, these devices are not described in greater detail herein. Other cutting members and staple drivers are disclosed in U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, which was filed on Sep. 29, 2006, and U.S. patent application Ser. No. 11/652,169, entitled SURGICAL STAPLING DEVICE WITH A CURVED CUTTING MEMBER, which was filed on Jan. 11, 2007, the entire disclosures of which are hereby incorporated by reference herein.

Figure 19:
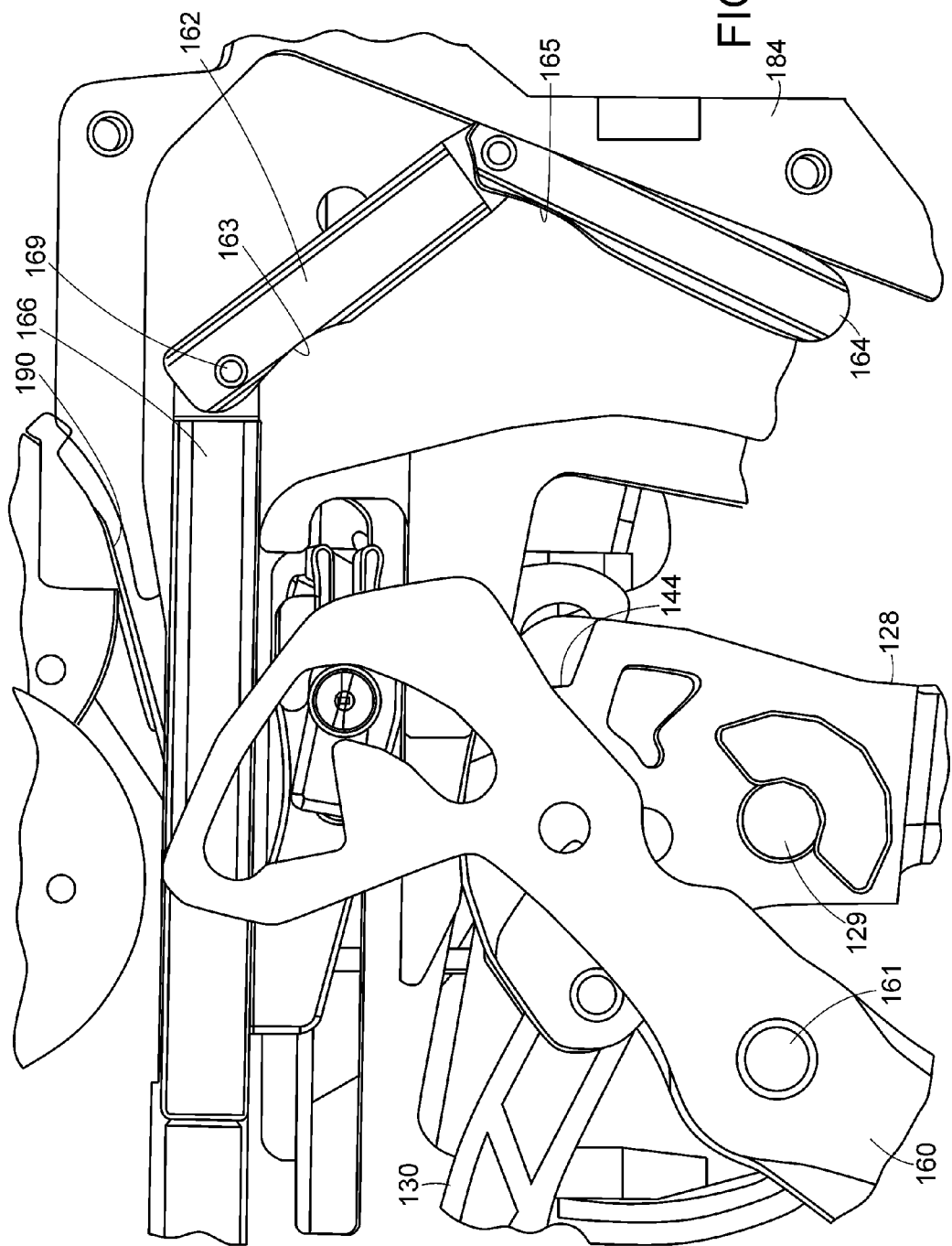
FIG. 19 is a detail view of a firing drive of the surgical instrument of FIG. 1 with some components of the surgical instrument removed.
Figure 20:
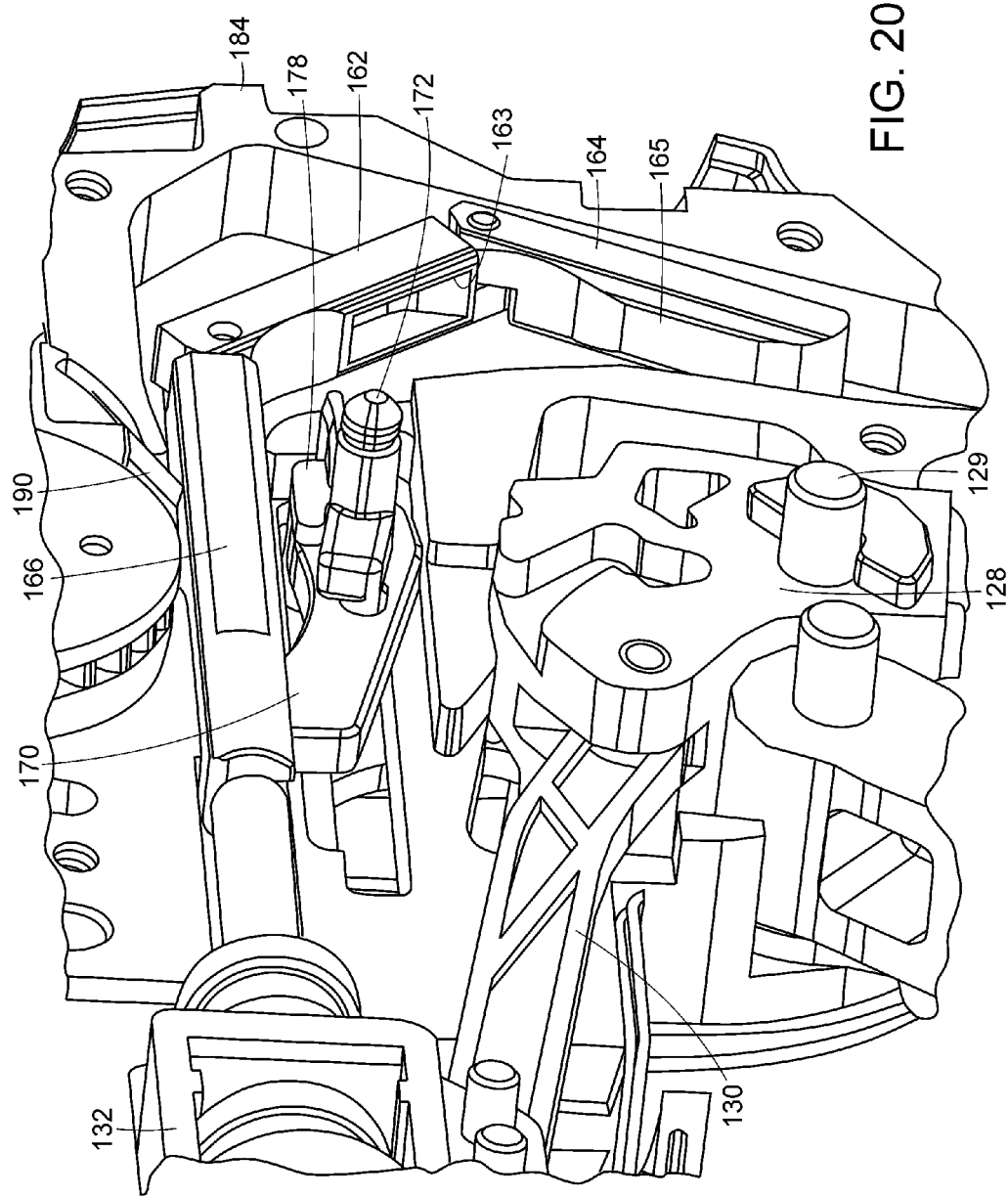
FIG. 20 is a perspective view of the firing drive of FIG. 19.
Figure 21:
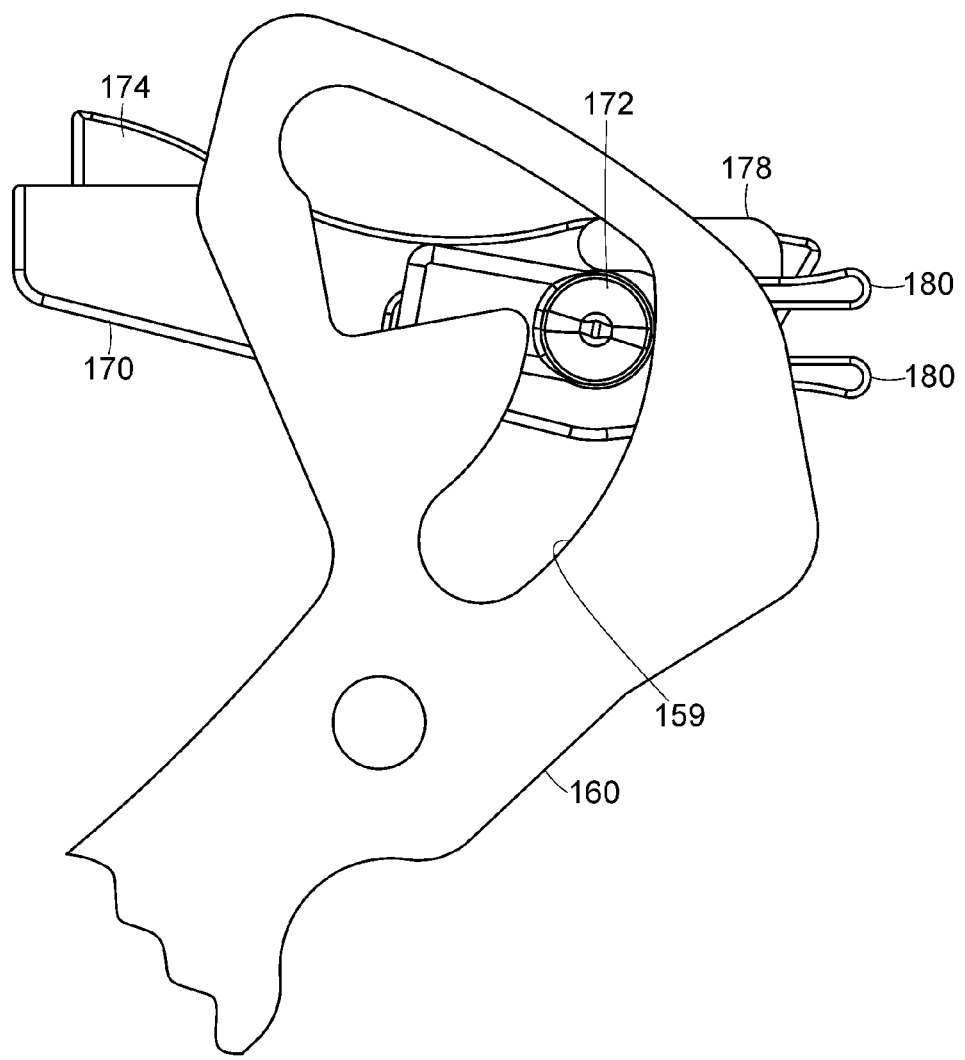
FIG. 21 is a partial detail view of a firing trigger, pawl, and tilter mechanism of the firing drive of FIG. 19.
Figure 22:
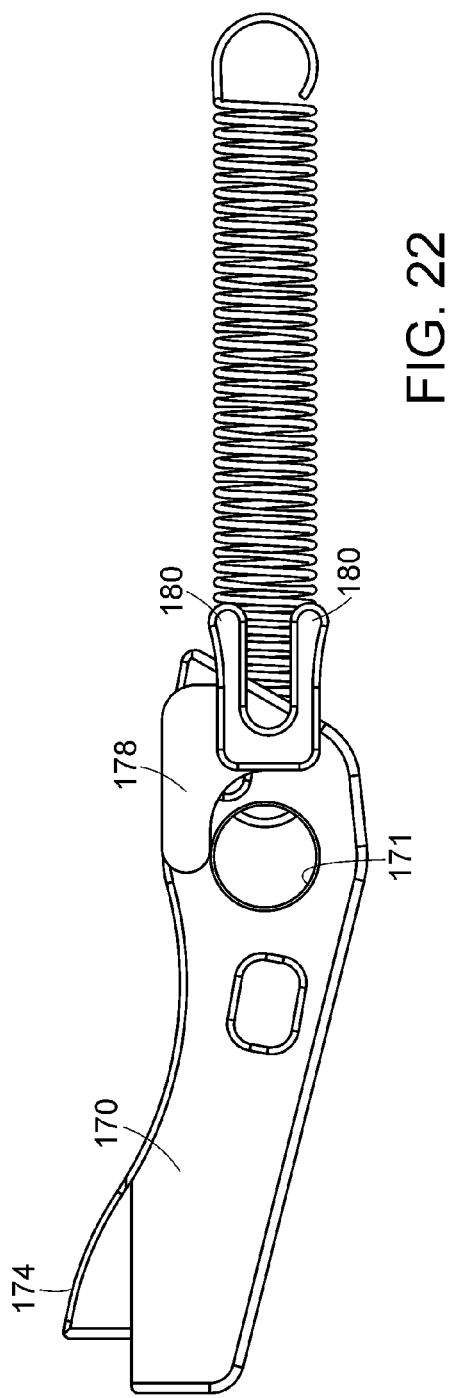
FIG. 22 is an elevational view of the pawl, tilter mechanism, and a pawl return spring of the firing drive of FIG. 19.
Figure 23:
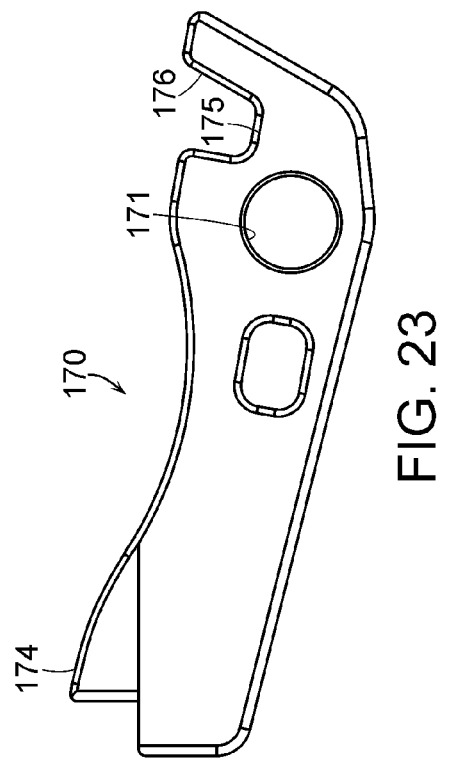
FIG. 23 is an elevational view of the pawl of FIG. 22.

In various embodiments, referring primarily to FIGS. 19 and 20, firing trigger 160 can be pivotably connected to surgical instrument housing 103 (FIGS. 8 and 9) by pin 161. In use, in at least one embodiment, firing trigger 160 can be pivoted about pin 161 in order to advance firing member 166 and firing links 162 and 164 distally. In various embodiments, firing trigger 160 can include slots 159, where slots 159 can be configured to receive firing pin 172. In various embodiments, when firing trigger 160 is actuated, or rotated, from its position illustrated in FIG. 2 to a position adjacent handle grip 127, the side walls of slots 159 can be configured to engage and advance firing pin 172 distally. In at least one embodiment, referring to FIG. 23, the firing drive can further include pawl 170, where pawl 170 can include aperture 171. In various embodiments, aperture 171 can be configured to receive at least a portion of firing pin 172 such that, when firing pin 172 is advanced distally by trigger 160, firing pin 172 can advance pawl 170 distally as well. In various embodiments, referring to FIG. 24, pawl 170 can include tooth 174 and firing member 166 can include recess 167, where recess 167 can be configured to receive tooth 174. In use, when pawl 170 is advanced distally by firing pin 172 and tooth 174 is engaged with a side wall of recess 167, pawl 170 can advance firing member 166 distally as well. In various embodiments, pawl 170 can be advanced distally by firing pin 172 along a substantially linear path. In such embodiments, slots 159 can include arcuate profiles which can, in cooperation with firing pin 172, convert the rotational motion of firing trigger 160 into translational motion of pawl 170. In at least one embodiment, the force applied to pawl 170 can be substantially, if not entirely, directed in the distal direction. In such embodiments, as a result, the possibility of pawl 170 becoming bound or stuck against stapler frame 184 can be reduced.

In various embodiments, pawl 170 can be pivoted between a first position in which pawl 170 is operably disengaged from firing member 166 and a second position, referring to FIGS. 19 and 20, in which pawl 170 is operably engaged with firing member 166. Referring primarily to FIGS. 21-25, the firing drive can further include tilter mechanism 178 which can be configured to pivot pawl 170 between its first and second positions. In use, when firing trigger 160 is actuated, pawl 170 can be moved, at least initially, relative to tilter mechanism 178 such that at least a portion of pawl 170 can abut tilter mechanism 178 and pivot pawl 170 upwardly and into operative engagement with firing member 166. In at least one embodiment, pawl 170 can include, referring primarily to FIG. 23, groove 175 which can be configured to receive projection 179 (FIG. 25) extending from the center portion of tilter mechanism 178. In at least one embodiment, as pawl 170 is advanced distally, proximal wall 176 of groove 175 can contact a cam surface on projection 179 and, owing to the force applied to pawl 170 by pivot pin 172, pawl 170 can be pivoted, or rotated, upwardly such that tooth 174 can be positioned in recess 167 of firing member 166 as described above. After pawl 170 has been pivoted, pawl 170 can drag tilter mechanism 178 distally as pawl 170 is advanced toward end effector 106. More particularly, in at least one embodiment, tilter mechanism 178 can include deformable members 180 which can be received within slots 182 in stapler frame 184 such that the interaction between deformable members 180 and stapler frame 184 at least partially inhibits the movement of tilter mechanism 178 relative to stapler frame 184. Stated another way, owing to static friction forces between deformable members 180 and the side walls of slots 182, a force sufficient to overcome these friction forces must be applied to tilter mechanism 178 before tilter mechanism 178 can be 'dragged' relative to stapler frame 184.

Figure 24:
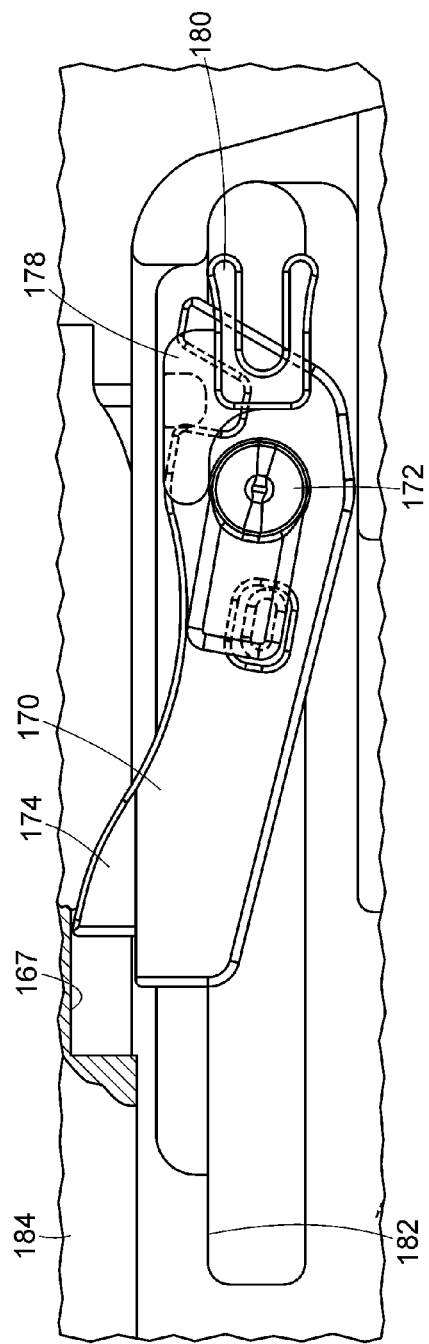
FIG. 24 is a detail view of the firing drive of FIG. 19 illustrating the pawl pivoted into a position to engage a firing link of the firing drive.
Figure 25:
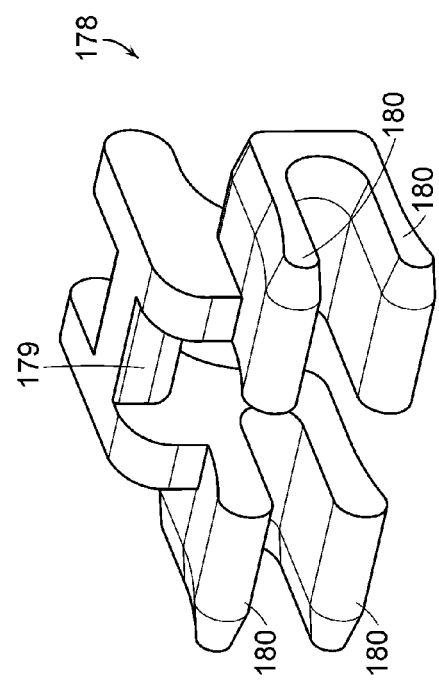
FIG. 25 is a perspective view of the tilter mechanism of FIG. 22.
Figure 26:
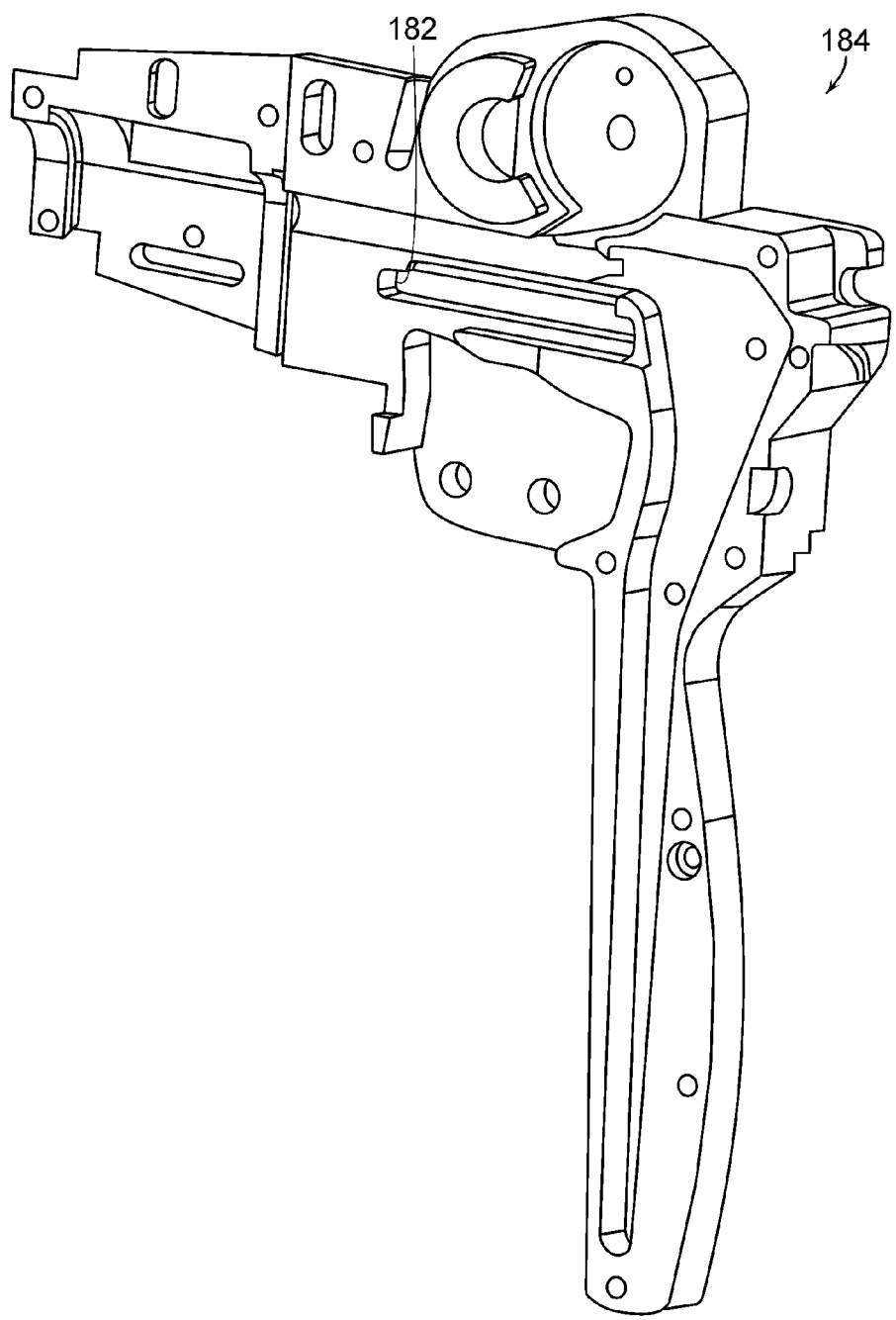
FIG. 26 is a perspective view of a frame of the surgical instrument of FIG. 1.

After firing trigger 160 has been actuated and firing member 166 has been advanced, trigger 160 can be released and returned to its unactuated position illustrated in FIG. 2 and pawl 170 can be disengaged from firing member 166 and retracted to its starting position illustrated in FIG. 19. More particularly, in at least one embodiment, surgical instrument 100 can further include a trigger spring (not illustrated) operably engaged with trigger 160 and housing 103, for example, where the trigger spring can be configured to rotate trigger 160 about pin 161 and drive firing pin 172 proximally after pawl 170 has been disengaged from firing member 166. In various embodiments, pawl 170 can be disengaged from firing member 166 when it is pivoted from its second position, as illustrated in FIG. 24, into its first position, as described above, by tilter mechanism 178. In such embodiments, pawl 170 can be moved, at least initially, relative to tilter mechanism 178 such that distal wall 177 of groove 175 can contact a second cam surface on projection 179 and can, owing to a force applied to firing pin 172 by trigger 160 or return spring 186, rotate pawl 170 downwardly such that tooth 174 of pawl 170 can be disengaged from recess 167 in firing member 166. Thereafter, trigger 160 and/or return spring 186 can pull, or retract, pawl 170 relative to firing member 166. In various embodiments, similar to the above, pawl 170 can be configured to drag tilter mechanism 178 proximally within slot 182. As a result of the above, pawl 170 does not need to be biased into its first or second positions. In various circumstances, pawl 170 can be rotated freely between its first and second positions without having to overcome a force applied thereto by a biasing spring. In effect, in various embodiments, the force to move pawl 170 between its first and second positions need only overcome the gravitational weight of pawl 170 and any frictional forces between pawl 170 and the surrounding components of the surgical instrument.

Once pawl 170 has been returned to its original position, in at least one embodiment, tooth 174 of pawl 170 may no longer be aligned with recess 167 in firing member 166. On the contrary, referring generally to FIGS. 19 and 20, tooth 174 of pawl 170 can be aligned with recess 163 in first firing link 162. More particularly, first firing link 162 can be pivotably connected to firing member 166 such that, when firing member 166 is advanced distally, as described above, firing member 166 can pull first firing link 162 into the position that firing member 166 previously occupied. As a result, upon a second actuation firing trigger 160, pawl 170 can be pivoted from its first position into its second position such that tooth 174 is operably engaged with recess 163 and pawl 170 can advance firing link 162 distally. In at least one embodiment, firing link 162 can push firing member 166 and knife bar 168 distally and, correspondingly, advance the cutting member and the staple driver distally within end effector 106. Thereafter, pawl 170 can once again be pivoted from its second position to its first position and can be retracted relative to first firing link 162. Once pawl 170 is returned to its original position for the second time, tooth 174 of pawl 170 may no longer be aligned with recess 163 of first firing link 162. On the contrary, similar to the above, tooth 174 can be aligned with recess 165 in second firing link 164 and the process described above can be repeated.

Although not illustrated, a surgical instrument in accordance with the present invention can include more than two, or less than two, firing links in order to advance the cutting member and staple driver to their desired positions within end effector 106. In various embodiments, as described in greater detail below, firing member 166 can include more than one recess 167 such that pawl 170 can directly advance firing member 166 toward end effector 106 more than once. In at least one such embodiment, pawl 170 can be retracted after advancing firing member 166 distally, as described above, such that, when pawl 170 is once again tilted upwardly, pawl 170 can engage another recess 167 in firing member 166 and advance firing member 166 toward end effector 106 once again. As a result, in at least one embodiment, firing links 162 and 164 may not be required.

Figure 27:
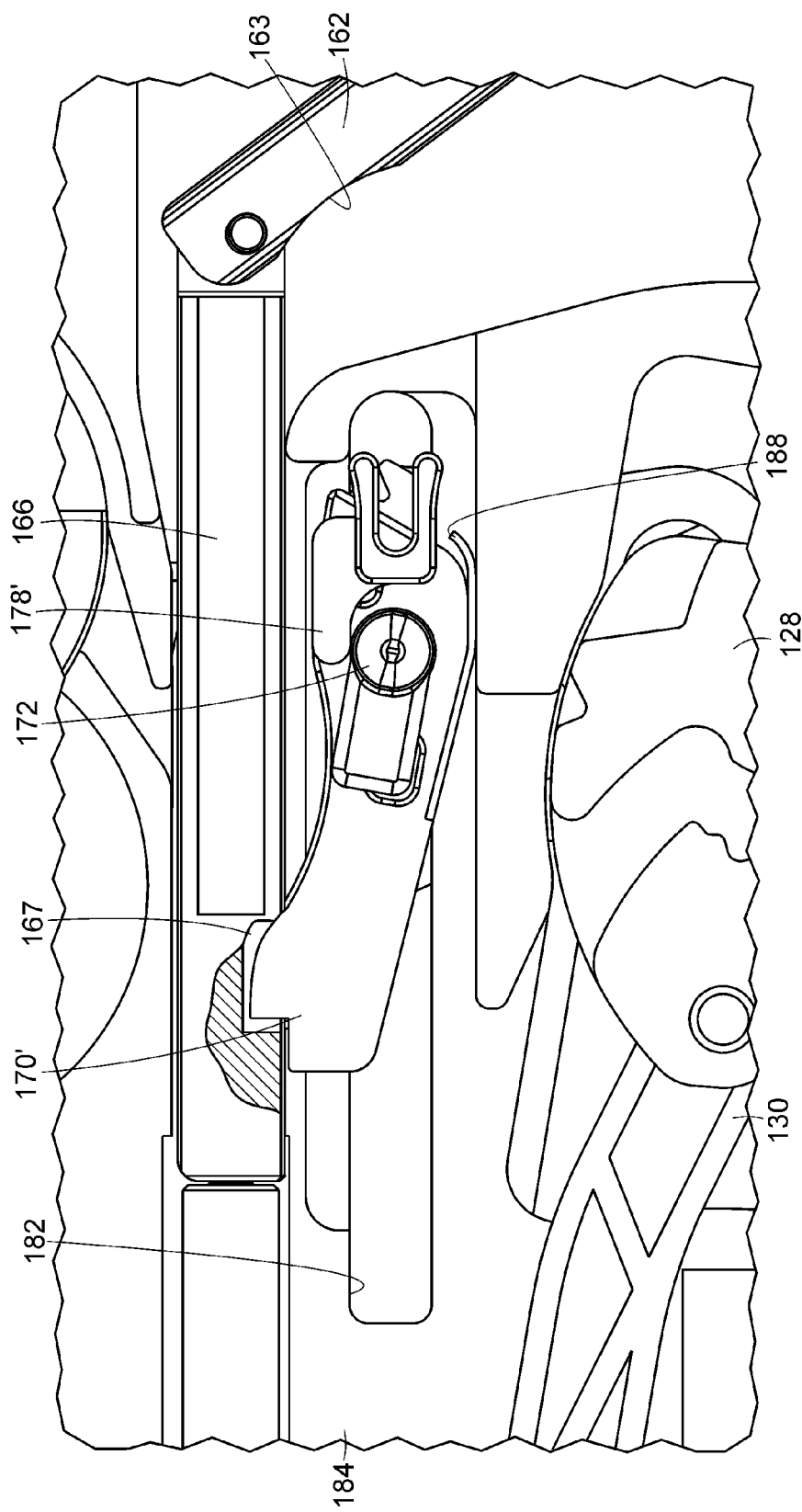
FIG. 27 is a detail view of a firing drive of a surgical instrument in accordance with an alternative embodiment of the present invention with some components of the surgical instrument removed.
Figure 28:
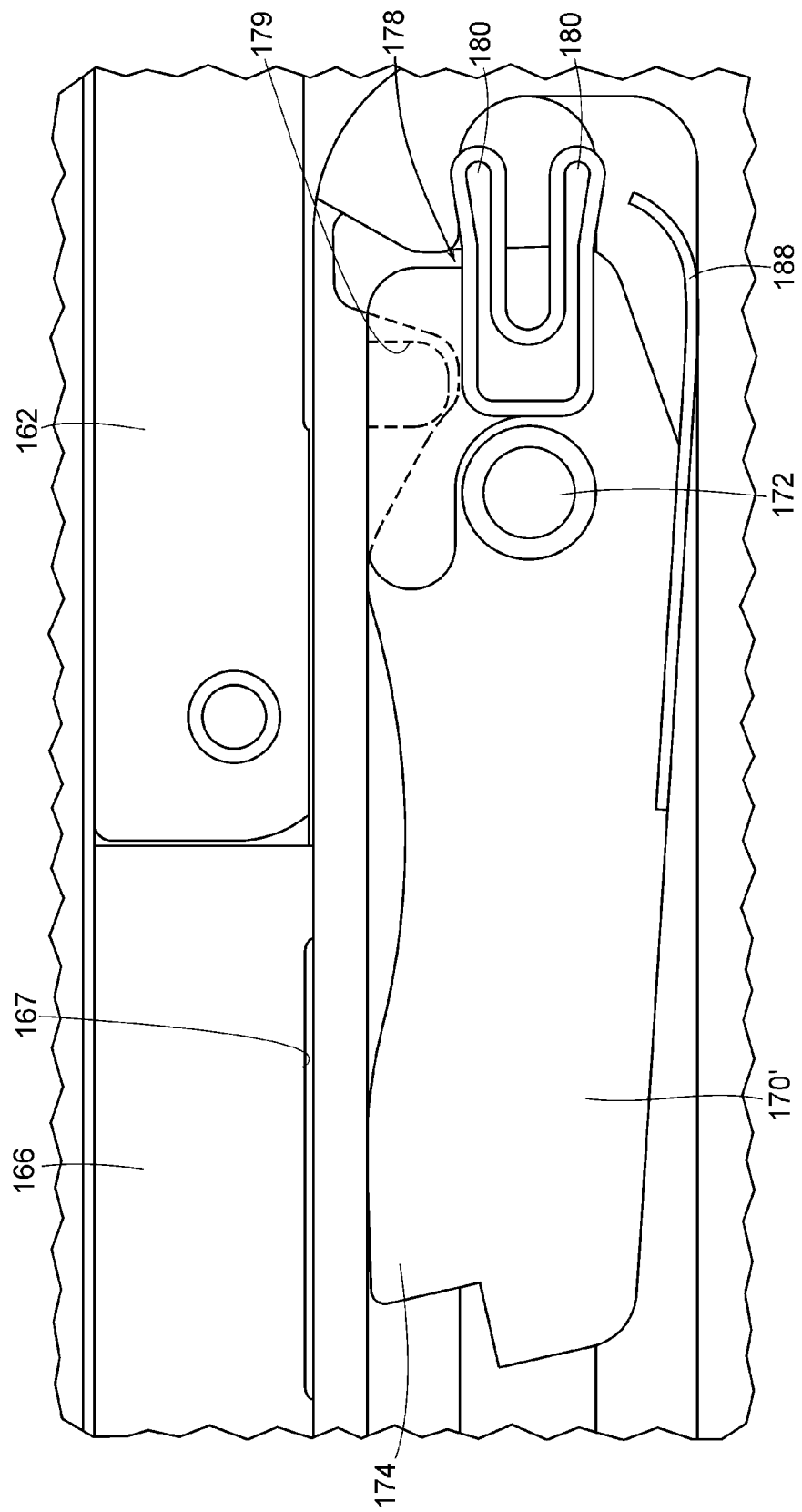
FIG. 28 is a detail view of the firing drive of FIG. 27 illustrating a pawl of the firing drive disengaged from a firing link.

In various embodiments, a surgical instrument can include one or more spring members configured to move pawl 170 into at least one of its first and second positions. In at least one embodiment, referring to FIGS. 27 and 28, the firing drive can include pawl 170', firing pin 172, and tilter mechanism 178' where, similar to the above, tilter mechanism 178' can be configured to pivot pawl 170' upwardly when pawl 170' is advanced distally. The firing drive can further include pivot spring 188 which can be operably connected to pawl 170' such that, when pawl 170' is pivoted upwardly into its second position as illustrated in FIG. 27, pawl 170' can flex, or resiliently bend, pivot spring 188. After pawl 170' has been advanced, pawl 170' can be pivoted downwardly into its first position by pivot spring 188 as illustrated in FIG. 28. More particularly, owing to potential energy stored in pivot spring 188 when it is flexed, spring 188 can move pawl 170' downwardly once pawl 170' is no longer held in its second position by tilter mechanism 178' and firing pin 172. Thereafter, as described above, pawl 170' can be retracted relative to firing member 166 and/or firing links 162 and 164. In various embodiments, tilter mechanism 178' may not include a second cam surface for pivoting pawl 170 into its first position. In such embodiments, pawl 170' can be retracted by a force applied to firing pin 172 as described above. In various alternative embodiments, although not illustrated, tilter mechanism 178' and pawl 170' can also include co-operating features for pivoting pawl 170' downwardly into its first position.

In various embodiments, referring to FIGS. 19 and 20, surgical instrument 100 can further include band 190 which can be configured to move firing member 166 and firing links 162 and 164 relative to end effector 106. In at least one embodiment, a first end of band 190 can be connected to firing member 166, for example, such that, when firing member 166 is advanced distally, band 190 can be pulled distally as well. In various alternative embodiments, band 190 can be connected to first firing link 162 and/or second firing link 164. In at least one embodiment, band 190 can be positioned around at least a portion of reel, or spool, 192 such that when band 190 is pulled by firing member 166, band 190 can be deployed, or unwound, from reel 192. In at least one embodiment, a second end of band 190 can be connected to reel 192 such that band 190 cannot be readily disengaged from reel 192 under the normal operating conditions of surgical instrument 100. In either event, when band 190 is pulled by firing member 166, reel 192 can be rotated in one of a clockwise or counter-clockwise direction, depending on the manner in which band 190 is positioned around reel 192. In order to retract firing member 166, reel 192 can be rotated in an opposite direction to move firing member 166, and firing links 162 and 164, proximally and wind band 190 around reel 192.

In various embodiments, band 190 can be wound around reel 192 such that band 190 is wrapped around a substantially cylindrical surface on reel 192. In at least one embodiment, the distance between an axis of rotation of reel 192 and the cylindrical surface can be substantially equidistant around the perimeter of reel 192. In these embodiments, the mechanical advantage of reel 192 can remain substantially constant as band 190 is pulled proximally as described above and the capacity for reel 192 to apply a pulling force to band 190 can remain substantially the same. In alternative embodiments, however, reel 192 can be configured to provide a variable mechanical advantage. In at least one embodiment, reel 192 can include a non-cylindrical surface on which band 190 can be wrapped such that the distance between the axis of rotation of reel 192 and the non-cylindrical surface is not equidistant around the perimeter of reel 192. In these embodiments, as a result, the capacity for reel 192 to apply a pulling force to band 190 can change as band 190 is wound around reel 192. In at least one embodiment, reel 192 can act as a cam and can include a shape which can be optimized to provide additional force to band 190 when it is initially retracted, i.e., when the force to retract the cutting member, for example, can be at its highest.

Figure 29:
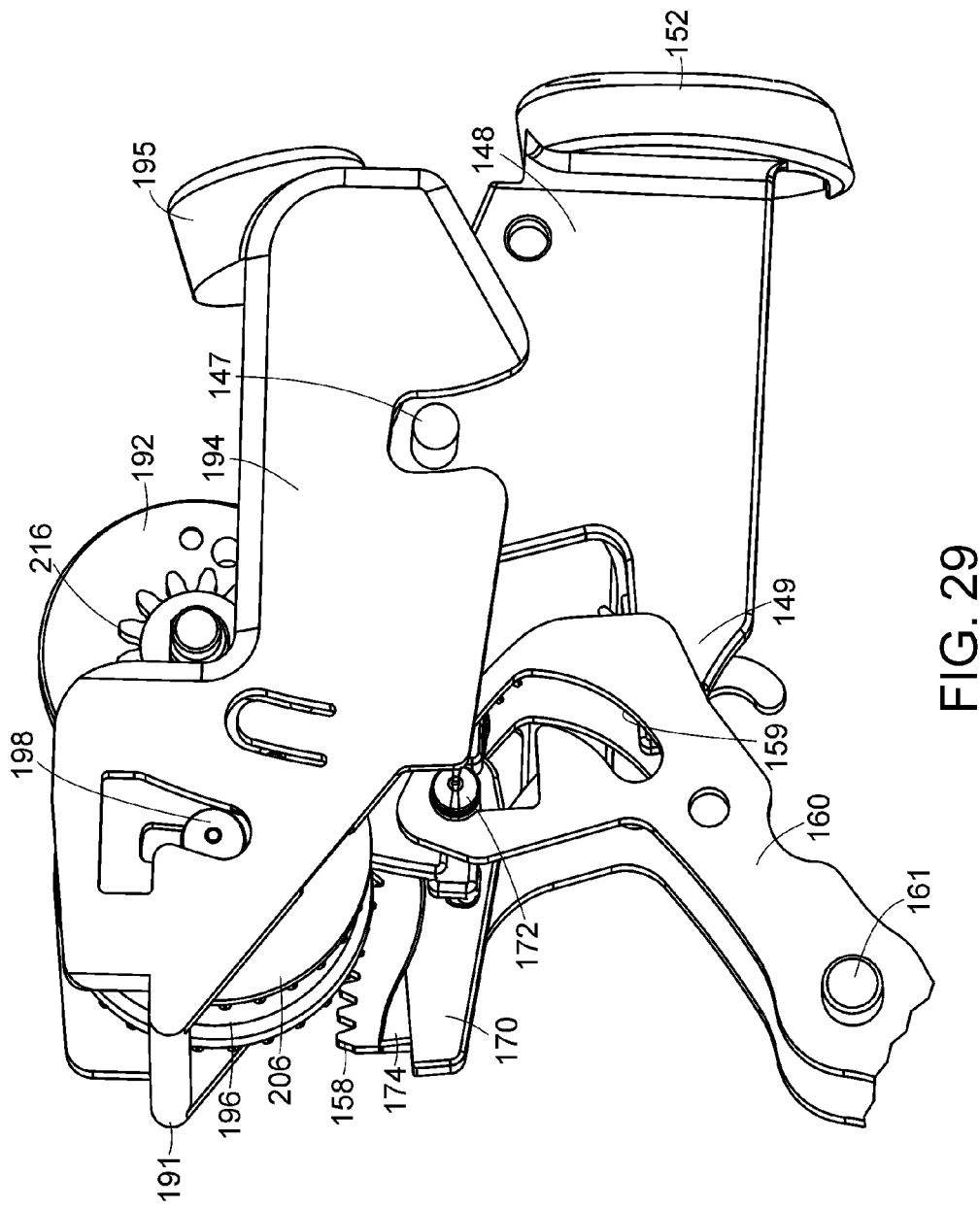
FIG. 29 is a perspective view of a return mechanism of the surgical instrument of Claim 1 illustrating the firing trigger in an unactuated position with some components of the surgical instrument removed.

In various embodiments, referring to FIGS. 29-42, firing trigger 160 can be selectively engaged with a return mechanism of surgical instrument 100. In at least one embodiment, when firing trigger 160 is operably engaged with firing member 166 via pawl 170, as described above, an actuation of firing trigger 160 can advance firing member 166 distally and, when firing trigger 160 is operably engaged with firing member 166 via band 190, an actuation of firing trigger 160 can retract firing member 166 proximally. In various embodiments, the return mechanism can be manually actuated to disengage firing trigger 160 from firing member 166 and to operably engage firing trigger 160 with reel 192. In at least one embodiment, the return mechanism can include return carriage 194 which can be pivotably mounted in surgical instrument housing 103 such that return carriage 194 can be pivoted between a first, or unactuated, position as illustrated in FIG. 29 and a second, or actuated, position as illustrated in FIG. 32. In at least one such embodiment, return carriage 194 can include push button portion 195 which, when a force is applied thereto, can be configured to move return carriage 194 from its unactuated position to its actuated position.

Figure 30:
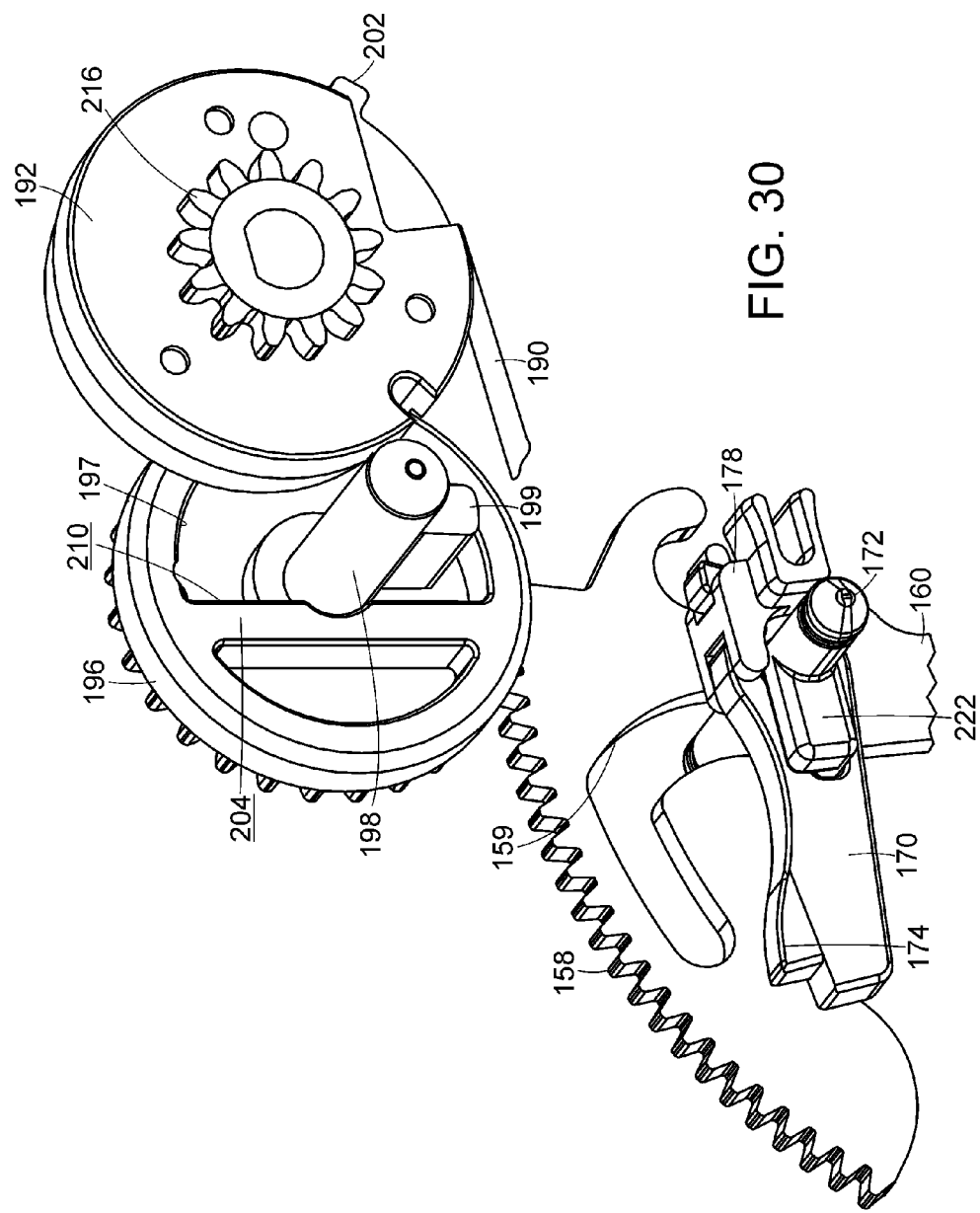
FIG. 30 is a partial perspective view of the return mechanism of FIG. 29 illustrating the firing trigger in an actuated position with some components of the return mechanism removed.
Figure 31:
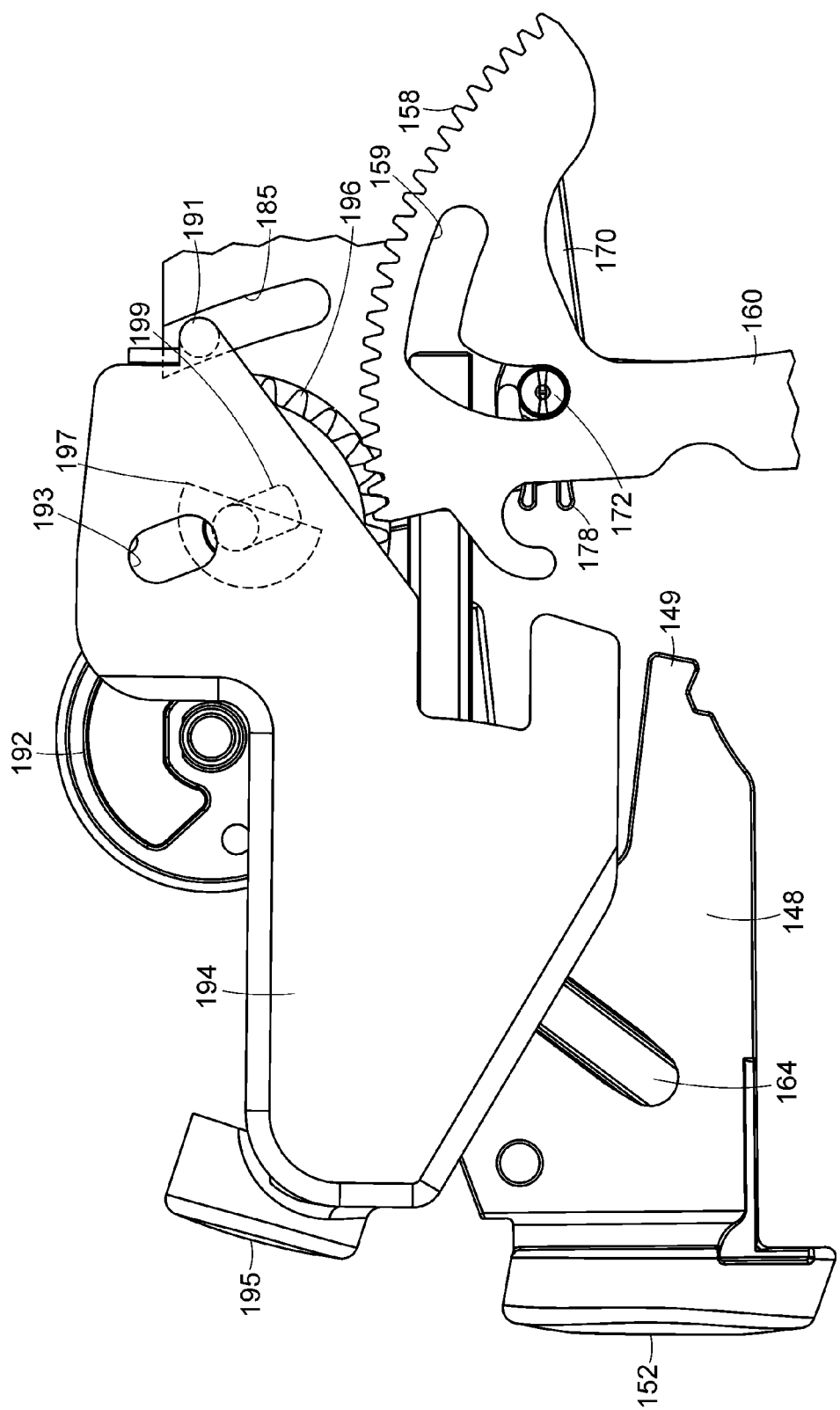
FIG. 31 is an elevational view of the return mechanism of FIG. 29 arranged in the configuration illustrated in FIG. 30.
Figure 32:
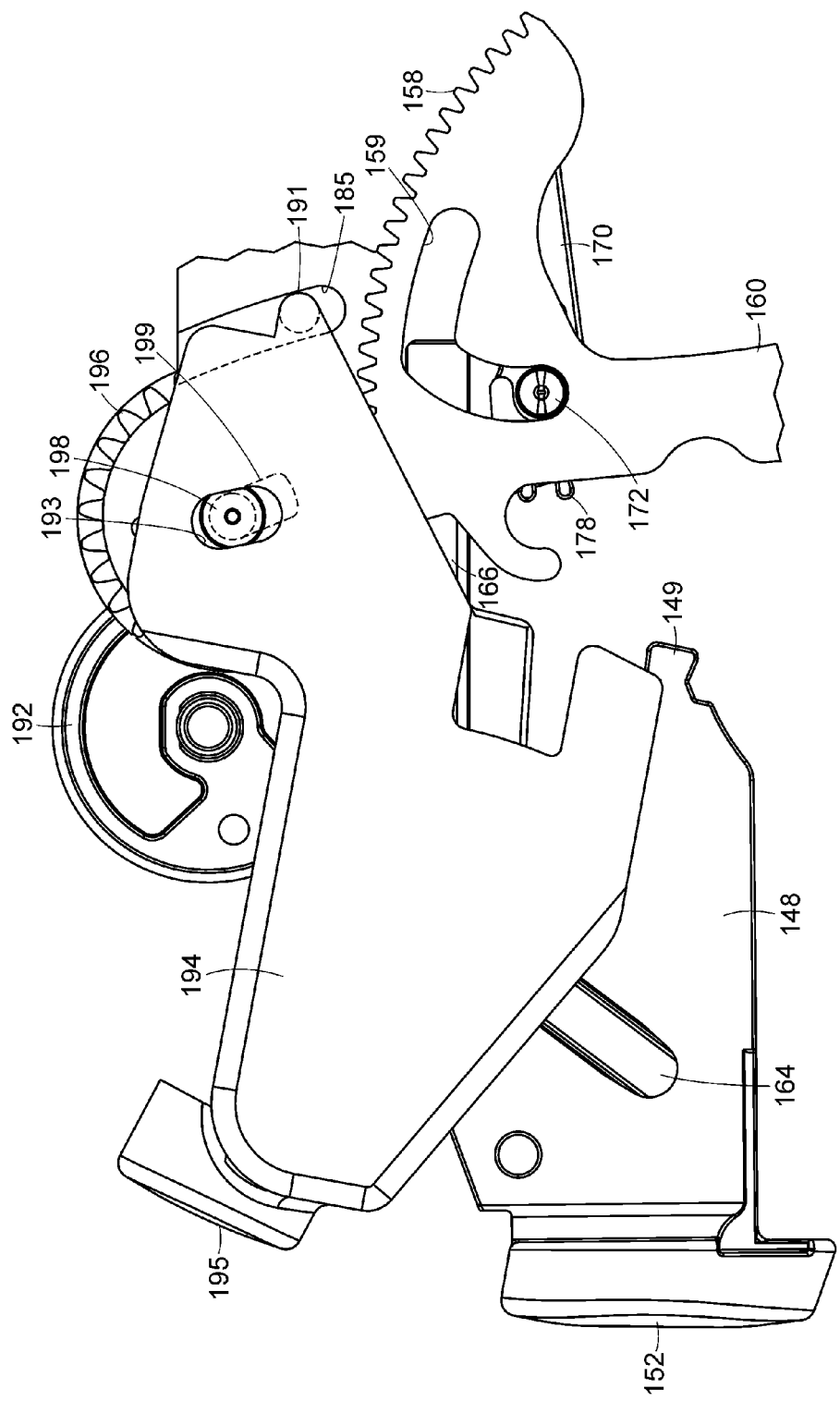
FIG. 32 is an elevational view of the return mechanism of FIG. 29 illustrating a return carriage of the return mechanism in an actuated position.
Figure 33:
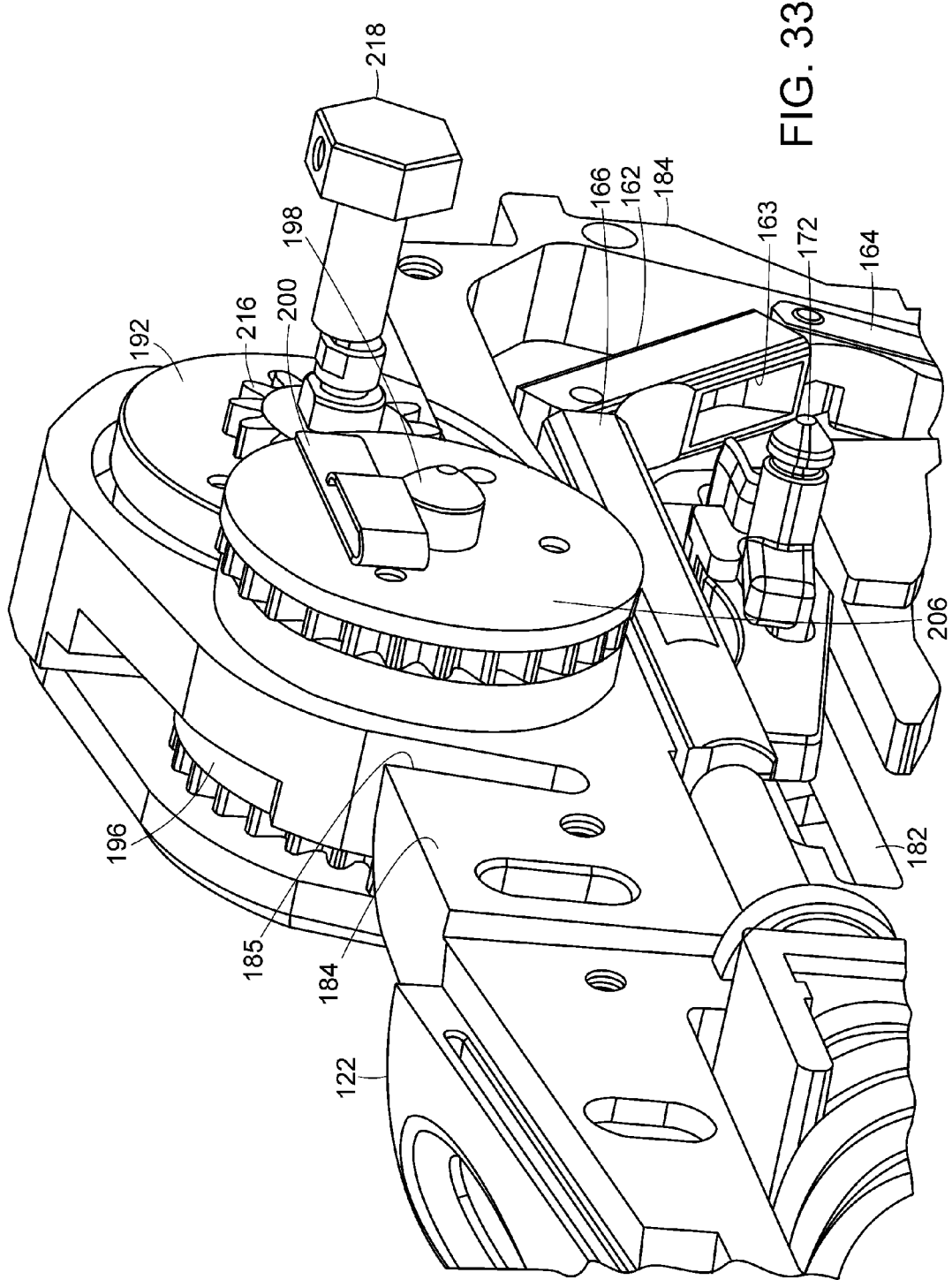
FIG. 33 is a partial perspective view of the return mechanism of FIG. 29 with some components of the return mechanism removed.
Figure 34:
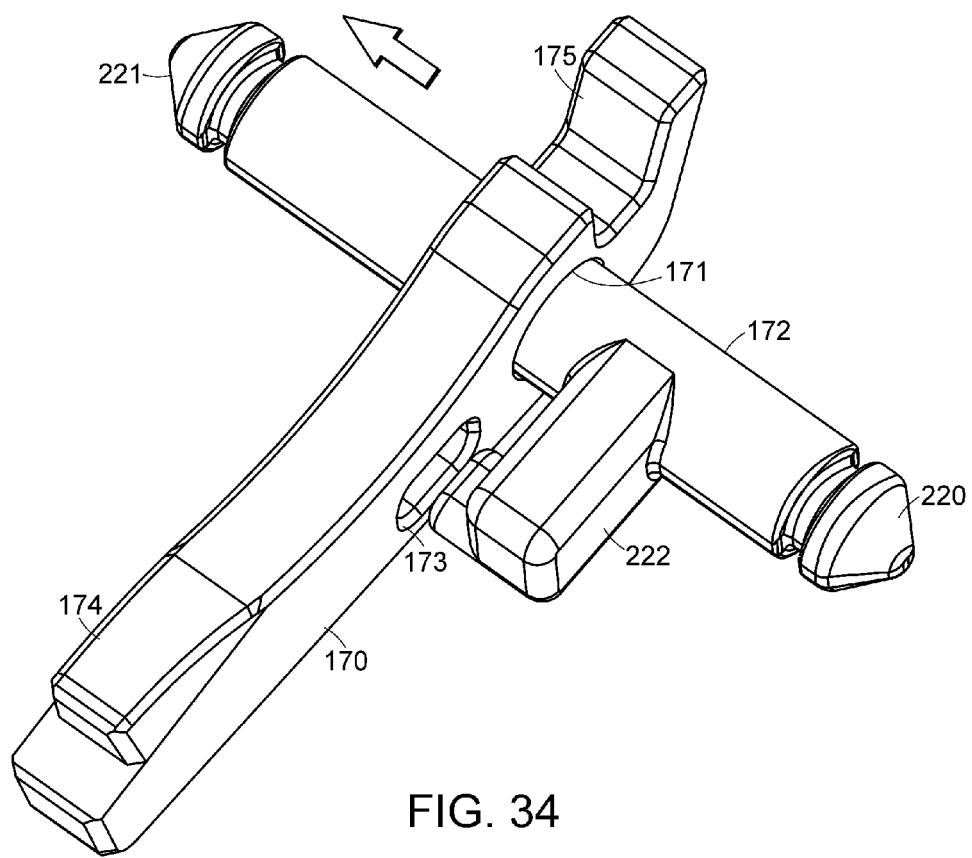
FIG. 34 is a perspective view of the pawl and firing pin of the firing drive of FIG. 19.
Figure 35:
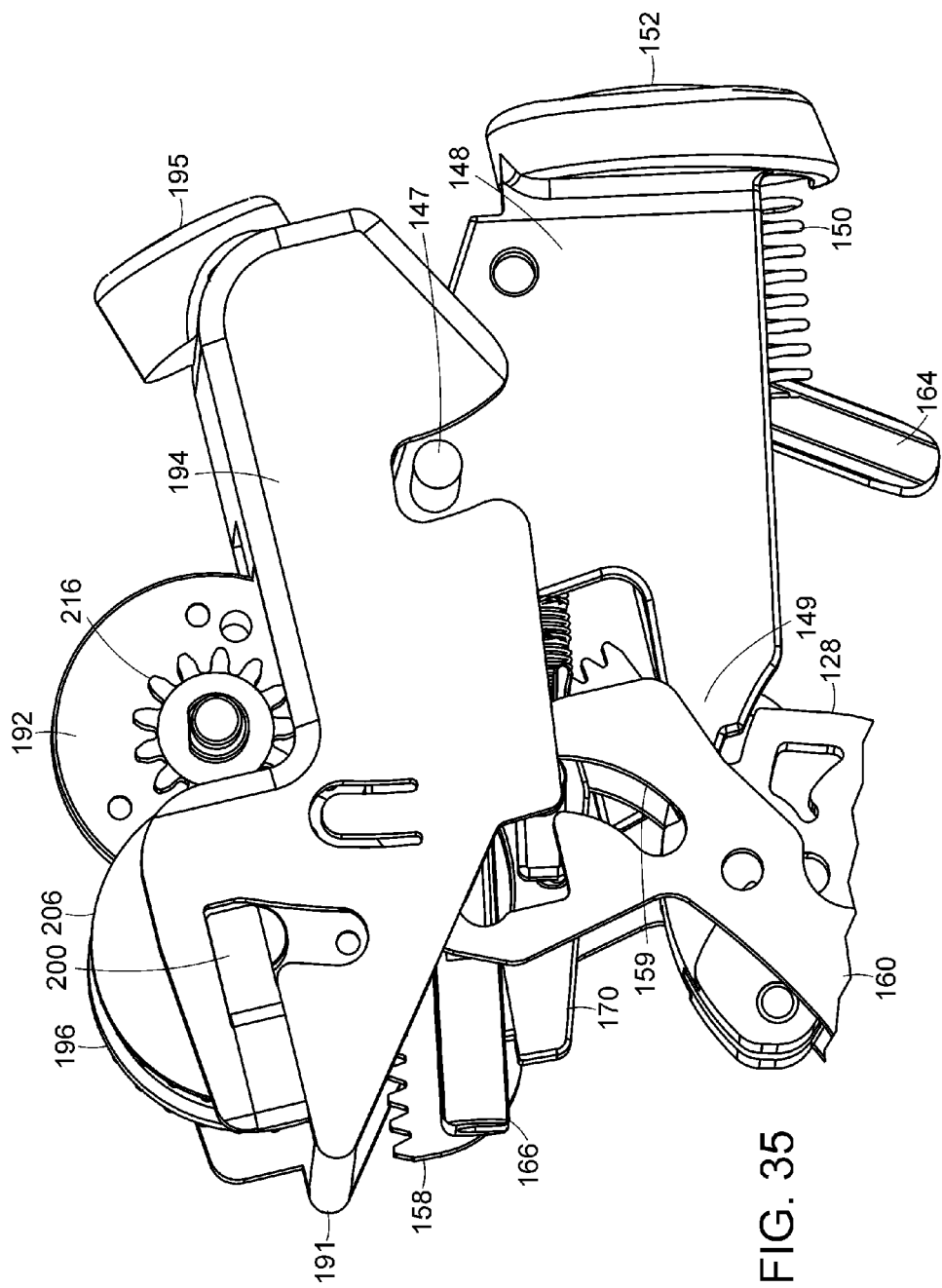
FIG. 35 is a perspective view of the return mechanism of FIG. 29 illustrating the return carriage in an actuated position and the firing trigger returned to its unactuated position.

When return carriage 194 is positioned in its unactuated position illustrated in FIGS. 29-31, firing trigger 160 can be configured to advance firing member 166 as described above and gear portion 158 of trigger 160 can be operatively engaged with trigger gear 196. In various embodiments, gear portion 158 and trigger gear 196 can be operably engaged such that a rotation of trigger 160 about pin 161 can drive trigger gear 196 about an axis defined by return pin 198. In at least one embodiment, when return carriage 194 is in its unactuated position, trigger gear 196 can be configured to rotate freely about return pin 198 such that the rotation of trigger gear 196 is not transmitted, or at least not substantially transmitted, to return pin 198. More particularly, referring to FIG. 30, key 199 of return pin 198 can be biased out of engagement with trigger gear 196 such that the rotation of trigger gear 196 is not transmitted to key gear 206 and reel 192. As a result, an actuation of trigger gear 196 does not rotate, or at least substantially rotate, reel 192 when return carriage 194 is in its unactuated position.

After the cutting member and the staple driver have been advanced within end effector 106, return carriage 194 can be moved into its actuated position. In various embodiments, referring to FIG. 30, reel 192 can include cam member 202 extending therefrom which can contact return carriage 194 and rotate return carriage 194 downwardly. In at least one embodiment, cam member 202 can contact return carriage 194 during the final actuation of trigger 160 which advances the cutting member and staple driver within end effector 106. In at least one such embodiment, cam member 202 can contact return carriage 194 after the third actuation of firing trigger 160. In various embodiments, referring to FIGS. 32-35, when gear carriage 194 is moved into its actuated position, return carriage 194 can be configured to operably engage trigger gear 196 with reel 192. In at least one embodiment, referring to FIGS. 33 and 35, return carriage 194 can include biasing spring 200 where, when return carriage 194 is in its unactuated position, spring 200 can be located in the position illustrated in FIG. 33 and, when return carriage 194 is moved into its actuated position illustrated in FIG. 35, spring 200 can contact return pin 198 and bias return pin 198 toward trigger gear 196. In at least one embodiment, referring to FIG. 31, trigger gear 196 can include D-shaped cavity 197 therein which can, under certain circumstances explained below, receive key 199 extending from return pin 198 and operably engage trigger gear 196 with key gear 206 and reel 192. In various embodiments, the movement of return carriage 194 into its actuated position can be accompanied by an audio and/or tactile feedback to inform the surgeon that the return mechanism of the surgical instrument has been engaged with trigger 160.

Figure 36:
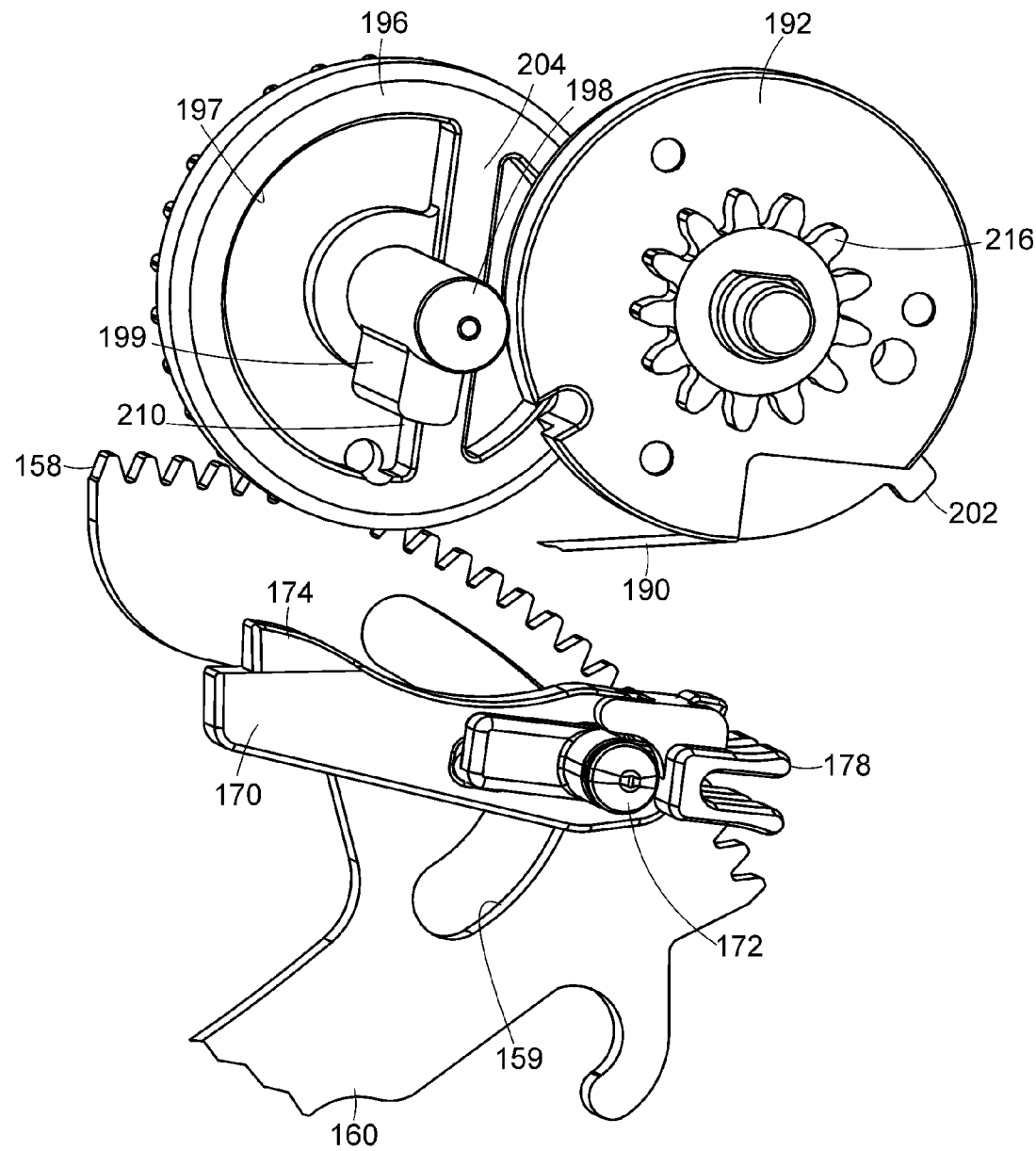
FIG. 36 is a partial perspective view of the return mechanism of FIG. 29 arranged in the configuration illustrated in FIG. 35 illustrating a return pin of the return mechanism operably engaged with the firing trigger.
Figure 37:
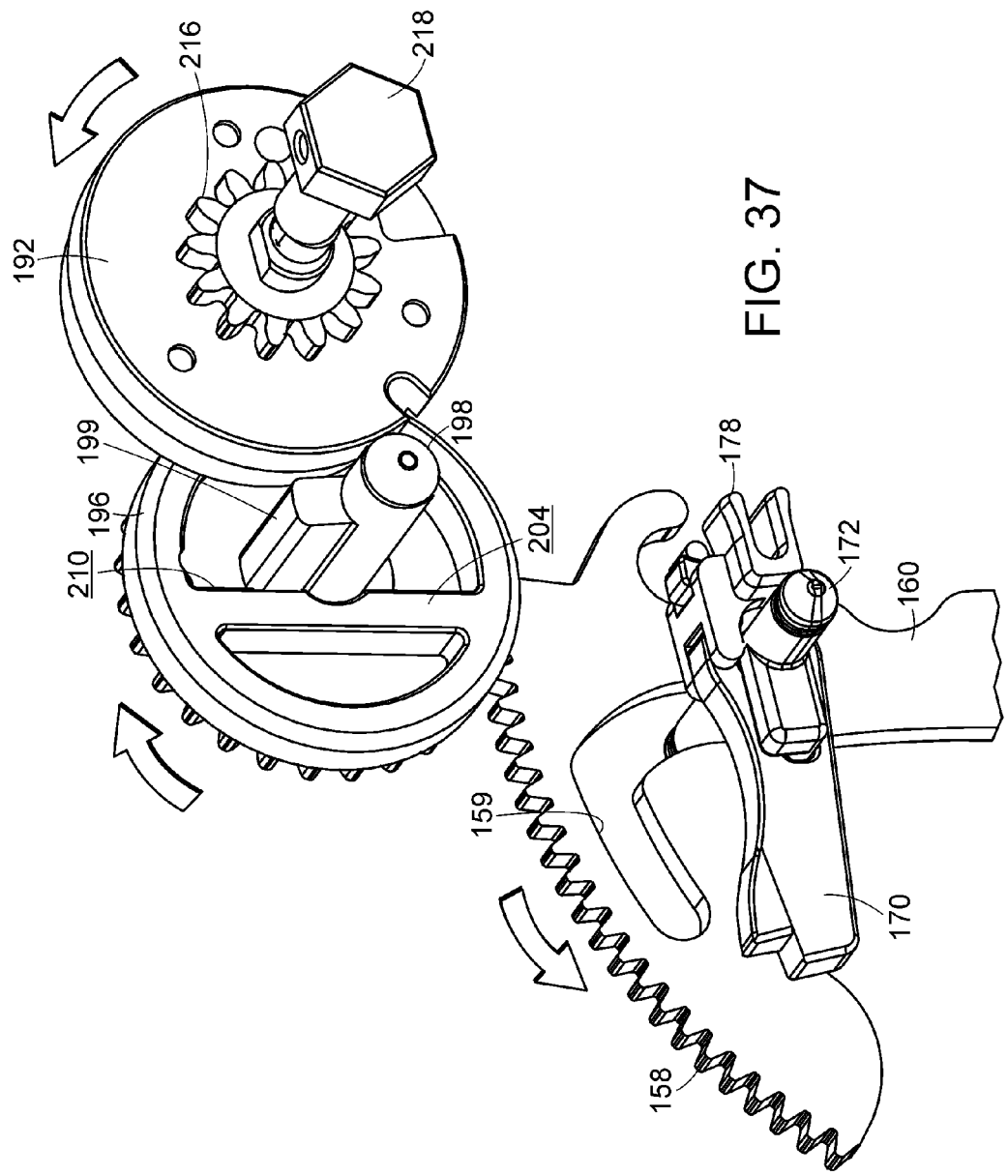
FIG. 37 is a partial perspective view of the return mechanism of FIG. 29 illustrating the firing trigger in an actuated position after rotating the return pin.
Figure 39:
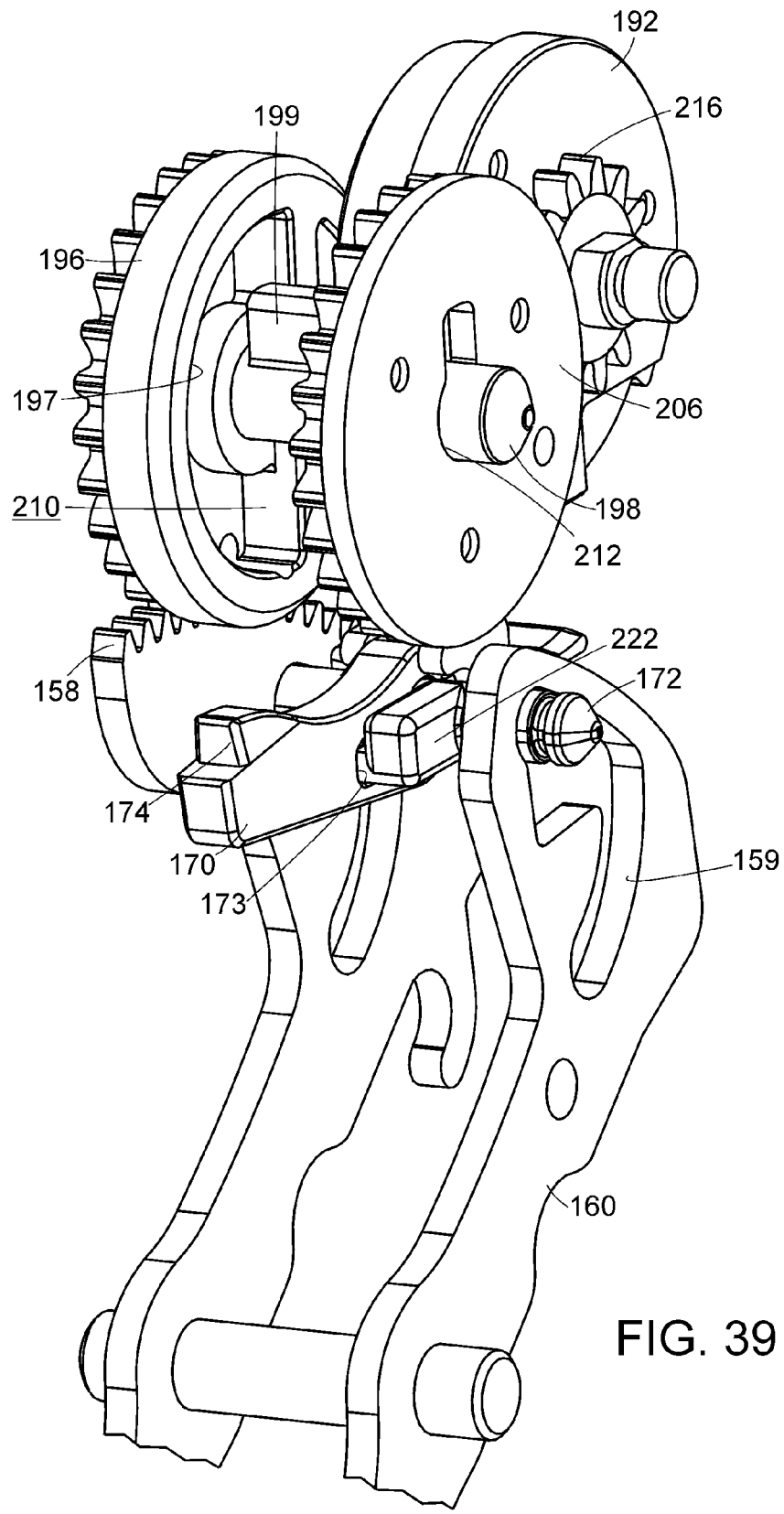
FIG. 39 is a partial perspective view of the return mechanism of FIG. 29 illustrating the firing trigger returned to its unactuated position.
Figure 40:
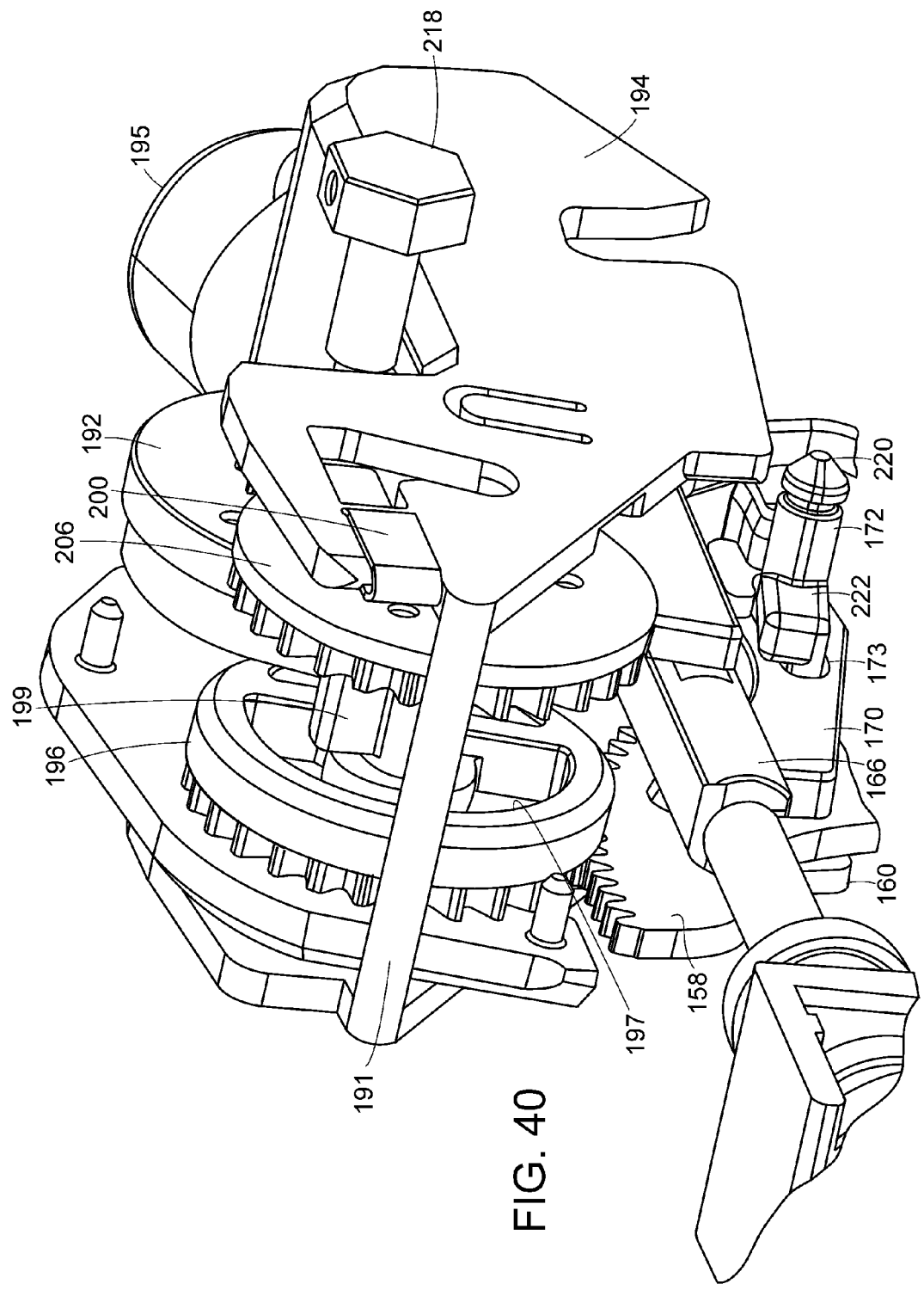
FIG. 40 is a perspective view of the return mechanism of FIG. 29 illustrating the return carriage returned to its unactuated position.
Figure 41:
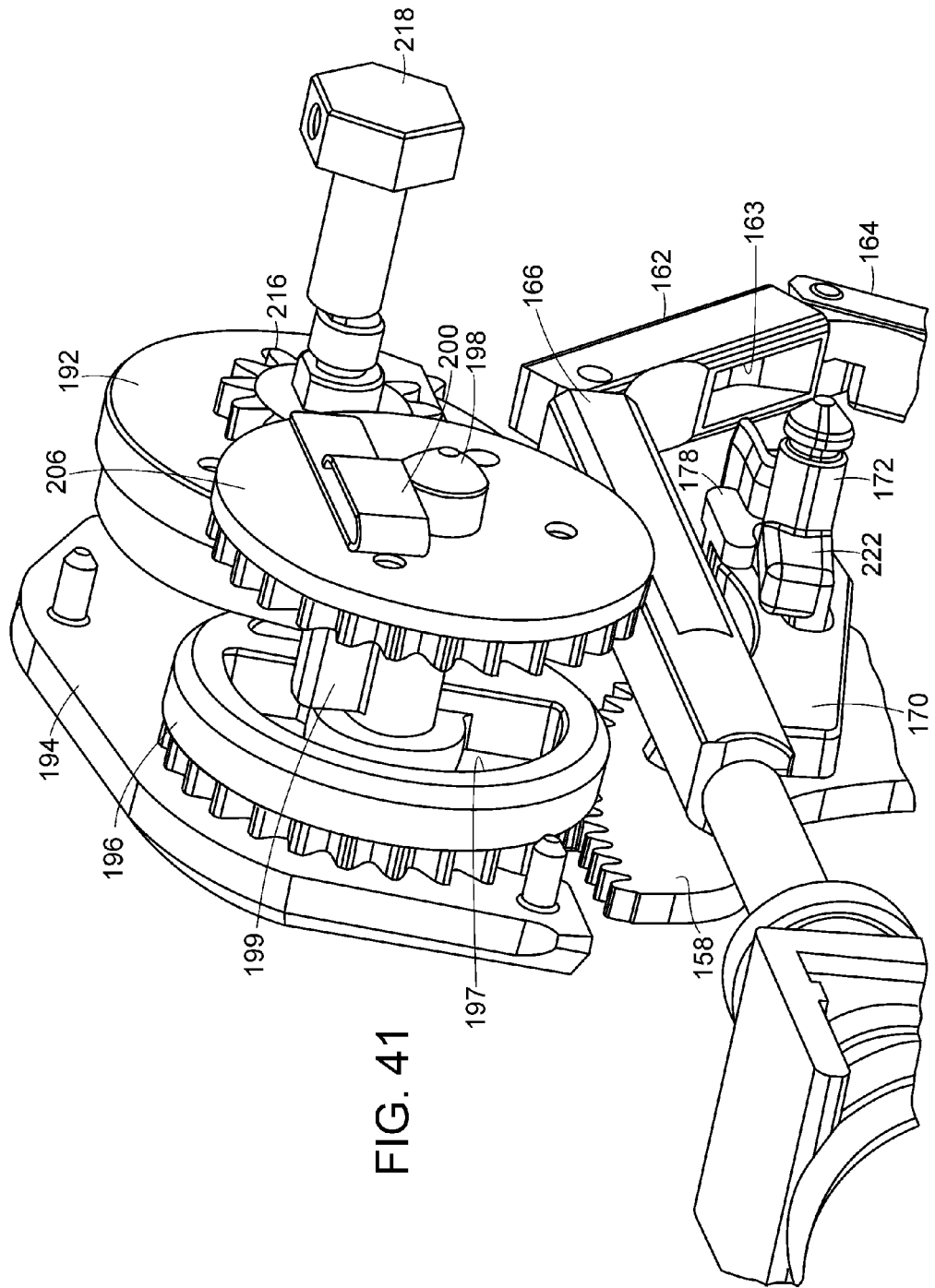
FIG. 41 is a perspective view of the return mechanism of FIG. 29 arranged in the configuration of FIG. 40 illustrating the relative relationship between a biasing spring and the return pin of the return mechanism with some components of the return mechanism removed.
Figure 42:
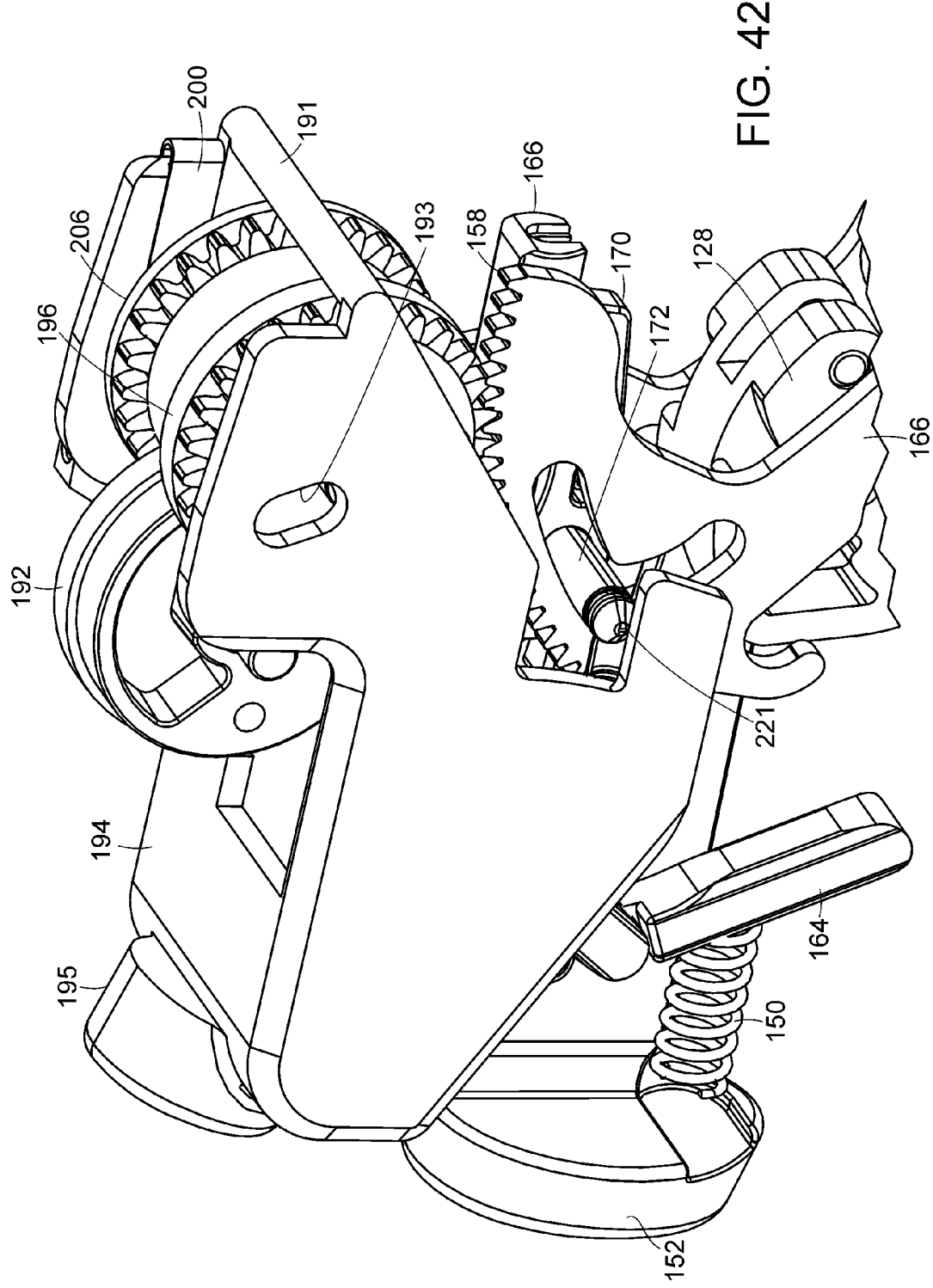
FIG. 42 is a perspective view of the return mechanism of FIG. 29 arranged in the configuration of FIG. 40 illustrating the return carriage operably engaged with the firing pin of the firing drive and the return pin of the return mechanism in order to reset the firing drive and the return mechanism to the their initial configurations.

Further to the above, when return pin 198 is slid toward trigger gear 196, D-shaped cavity 197 can be positioned such that key 199 does not immediately enter cavity 197. On the contrary, referring to FIG. 31, spring 200 can bias return pin 198 such that key 199 initially abuts face 204 of trigger gear 196. After trigger 160 is released and is returned to its unactuated position, however, D-shaped cavity 197 can be rotated and aligned with key 199 such that spring 200 can bias key 199 into cavity 197 as illustrated in FIG. 36. In at least one embodiment, referring to FIG. 31, when return pin 198 is slid toward trigger gear 196, an end of return pin 198 can be received in slot 193 in return carriage 194 as illustrated in FIG. 32. After key 199 has been inserted into cavity 197, a subsequent actuation of trigger 160 can cause drive surface 210 of D-shaped cavity 197 to abut key 199 and rotate return pin 198 to a position illustrated in FIGS. 37 and 38. In effect, an actuation of trigger 160, in at least one embodiment, can rotate key 199 approximately half a revolution such that key 199, which is initially extending substantially downwardly (FIG. 36), can be rotated such that key 199 is extending substantially upwardly (FIG. 37). Thereafter, trigger 160 can be released and trigger gear 194 can be rotated relative to key 199 where key 199 can remain oriented in a substantially upward direction as illustrated in FIGS. 39-41.

Figure 38:
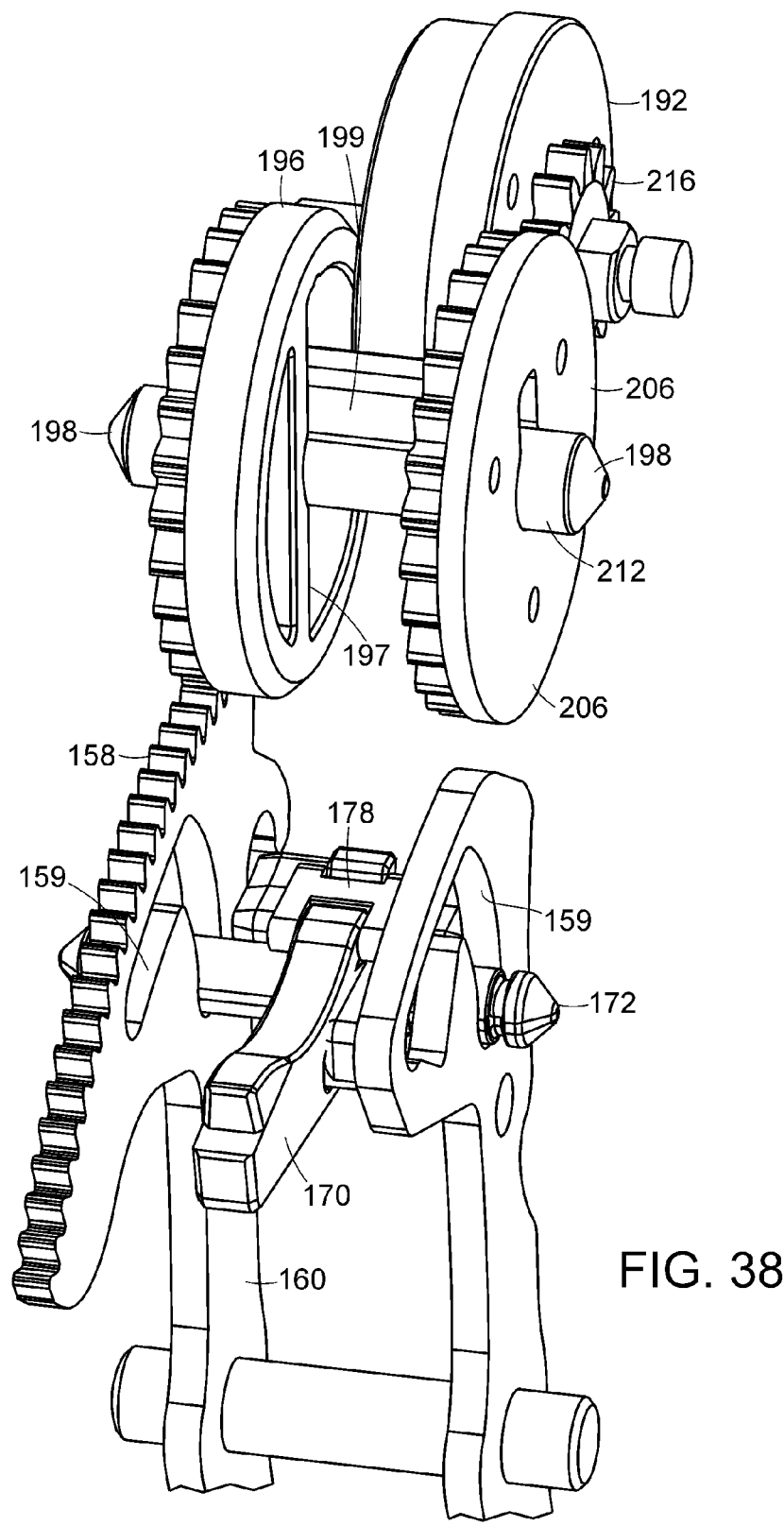
FIG. 38 is an additional perspective view of the return mechanism of FIG. 29 arranged in the configuration illustrated in FIG. 37.

In various embodiments, referring primarily to FIG. 38, key gear 206 can be operably engaged with return pin 198 such that the rotation of return pin 198 can be transmitted to key gear 206. In at least one embodiment, key gear 206 can include key-shaped aperture 212 which can be configured to slidably receive key 199 of return pin 198. In at least one such embodiment, key 199 can be operably engaged with both recess 197 of trigger gear 196 and aperture 212 of key gear 206 when return pin 198 is engaged with trigger gear 196. In various alternative embodiments, key gear 206 can be fixedly mounted to return pin 198. In such embodiments, when return pin 198 is slid relative to trigger gear 196, key gear 206 can also be slid relative to trigger gear 196. In various embodiments, referring generally to FIG. 38, reel 192 can include spur gear 216 mounted thereto, where spur gear 216 can be operatively engaged with key gear 206 such that the rotation of key gear 206 can be transmitted to reel 192. In at least one embodiment, key gear 206, when it is slid toward trigger gear 196 as described above, can be slid into operative engagement with reel 192. In alternative embodiments, spur gear 216 can be configured such that key gear 206 is in operative engagement therewith regardless of whether key gear 206 has been biased toward trigger gear 196.

As a result of the above, when return carriage 194 is positioned in its actuated position illustrated in FIG. 32, an actuation of trigger 160 can rotate reel 192 and wind band 190 around at least a portion thereof. In the event that key 199 cannot be operably engaged with trigger gear 196 when return carriage 194 is actuated, reel 192 can be rotated manually to retract band 190. In at least one such embodiment, referring to FIGS. 33 and 37, bolt, or fastener, 218 can be operatively engaged with reel 192 such that the rotation of bolt 218 can effect rotation of reel 192. In various embodiments, a surgeon can insert bolt 218 through an opening in surgical instrument housing 103 and engage bolt 218 with reel 192. In at least one embodiment, surgical instrument 100 can further include a counting mechanism (not illustrated) which can count the actuations of trigger 160 and, in at least one such embodiment, bolt 218, for example, can be operably engaged with the counting mechanism to rotate reel 192. In various embodiments, as a result, the surgical instrument can include a first, or primary, actuator for winding reel 192 and a second actuator which can be configured to wind reel 192 in lieu of the first actuator.

In various embodiments, as described above, reel 192 can be configured to pull band 190 and retract firing member 166 and firing links 162 and 164 proximally. More particularly, as described above, firing member 166 and firing links 162 and 164 can be retracted relative to pawl 170 in order to reposition firing member 166 and firing links 162 and 164 in their starting positions. In such embodiments, especially in embodiments where pawl 170 is pivotable as described above, the return mechanism of surgical instrument 100 can be further configured to hold pawl 170 out of operative engagement with firing member 166 and firing links 162 and 164 while they are moved relative to pawl 170. More particularly, when return carriage 194 is moved into its actuated position illustrated in FIG. 35, return carriage 194 can be configured to contact an end of firing pin 172 and slide firing pin 172 toward pawl 170 such that firing pin 172 engages pawl 170 and prevents pawl 170 from pivoting upwardly. More particularly, referring to FIG. 34, firing pin 172 can include first end 220 which can include a beveled and/or rounded surface, for example, where, when return carriage 194 contacts first end 220, return carriage 194 can push firing pin 172 toward pawl 170. In at least one embodiment, pawl 170 can include recess 173 which can be configured to receive key 222 extending from firing pin 172 when firing pin 172 is moved toward pawl 170. When key 222 and recess 173 are operatively engaged, firing pin 172 can prevent pawl 170 from pivoting upwardly into engagement with firing member 166 and firing links 162 and 164.

After firing member 166 and firing links 162 and 164 have been retracted, a new staple cartridge 110 can be secured in end effector 106 and surgical instrument 100 can be reset such that it can be used to incise and staple soft tissue once again. In various embodiments, referring to FIGS. 39-42, return carriage 194 can be moved from its actuated position illustrated in FIG. 32 to its unactuated position illustrated in FIG. 40. In at least one embodiment, return carriage 194 can be rotated, or pivoted, upwardly when a force is applied to button portion 195. Alternatively, return carriage 194 can be moved upwardly when, referring to FIG. 29, trigger lock 148 is rotated upwardly to disengage follower portion 149 from closure trigger 128 in order to reopen end effector 106 as described above. More particularly, when a force is applied to button portion 152 of trigger lock 148, trigger lock 148 can be rotated upwardly such that projection 147 extending therefrom can contact return carriage 194 and move return carriage 194 upwardly as well. In either event, referring to FIG. 42, when return carriage 194 is moved upwardly into is unactuated position, return carriage 194 can disengage firing pin 172 from pawl 170 and, in addition, disengage return pin 198 from trigger gear 196. More particularly, return carriage 194 can be configured to abut beveled, or rounded, end 221 of firing pin 172 such that, when return carriage 194 is rotated upwardly, return carriage 194 can slide return pin 172 away from pawl 170 and disengage key 222 from recess 173. Similarly, when return carriage 194 is moved upwardly, a side wall of slot 193 can be configured to contact an end of return pin 198 and slide return pin 198 away from trigger gear 196 to disengage key 199 from D-shaped recess 197. In short, in at least the illustrated embodiment, when button portion 152 of lock member 148 is depressed and return carriage 194 is moved upwardly, the surgical instrument can be reset and can be reused once again.

Although the surgical instruments described above can be reset after the cutting member and staple driver have been completely advanced within end effector 106, button portion 195 of return carriage 194, for example, can be depressed after the cutting member and staple driver have been only partially advanced within end effector 106. In various embodiments, return carriage 194 can further include guide pin 191 extending between opposite sides of return carriage 194. In at least one such embodiment, guide pin 191 can be slidably received within guide slot 185 (FIG. 31) in frame 184 such that slot 185 and pin 191 can define a path for return carriage 194. In various embodiments, guide pin 191 and guide slot 185 can be configured to assure that return carriage 194 engages firing pin 172 and return pin 198 and resets the surgical instrument when return carriage 194 is moved from its actuated position to its unactuated position as described above.

Figure 43:
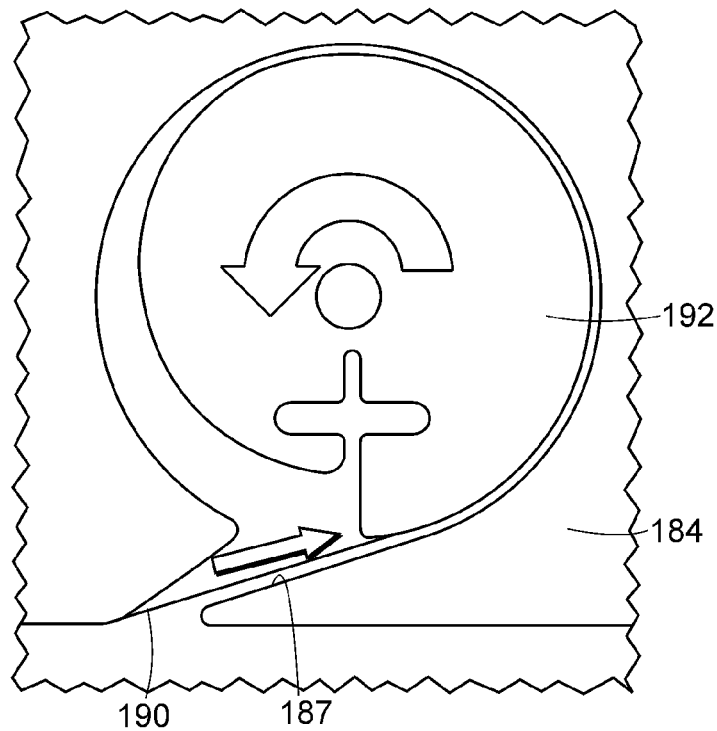
FIG. 43 is a detail view of a reel of the return mechanism of FIG. 29 illustrating the relative relationship between a return band of the return mechanism and the stapler frame of FIG. 26.
Figure 44:
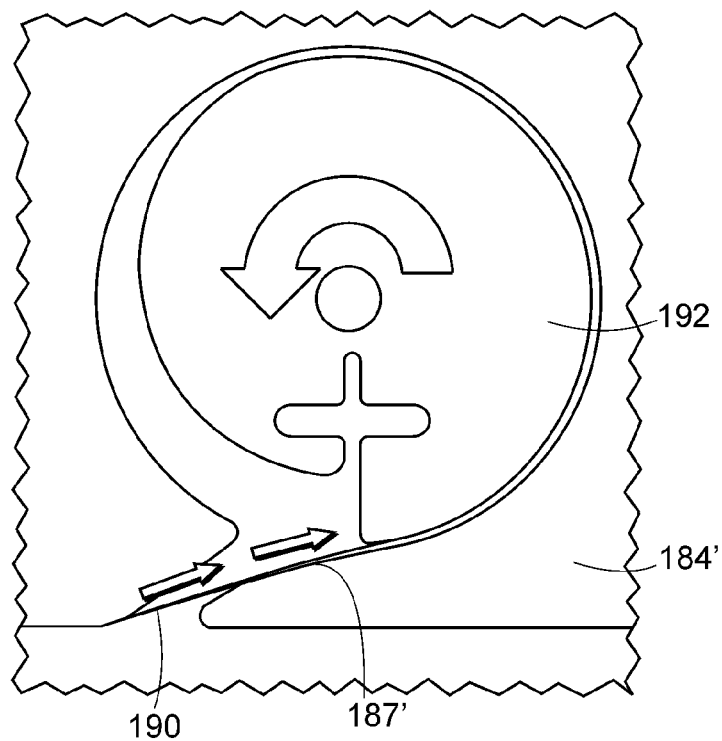
FIG. 44 is a detail view of the reel of FIG. 43 illustrating the relative relationship between the return band and an alternative embodiment of the stapler frame of FIG. 26.
Figure 45:
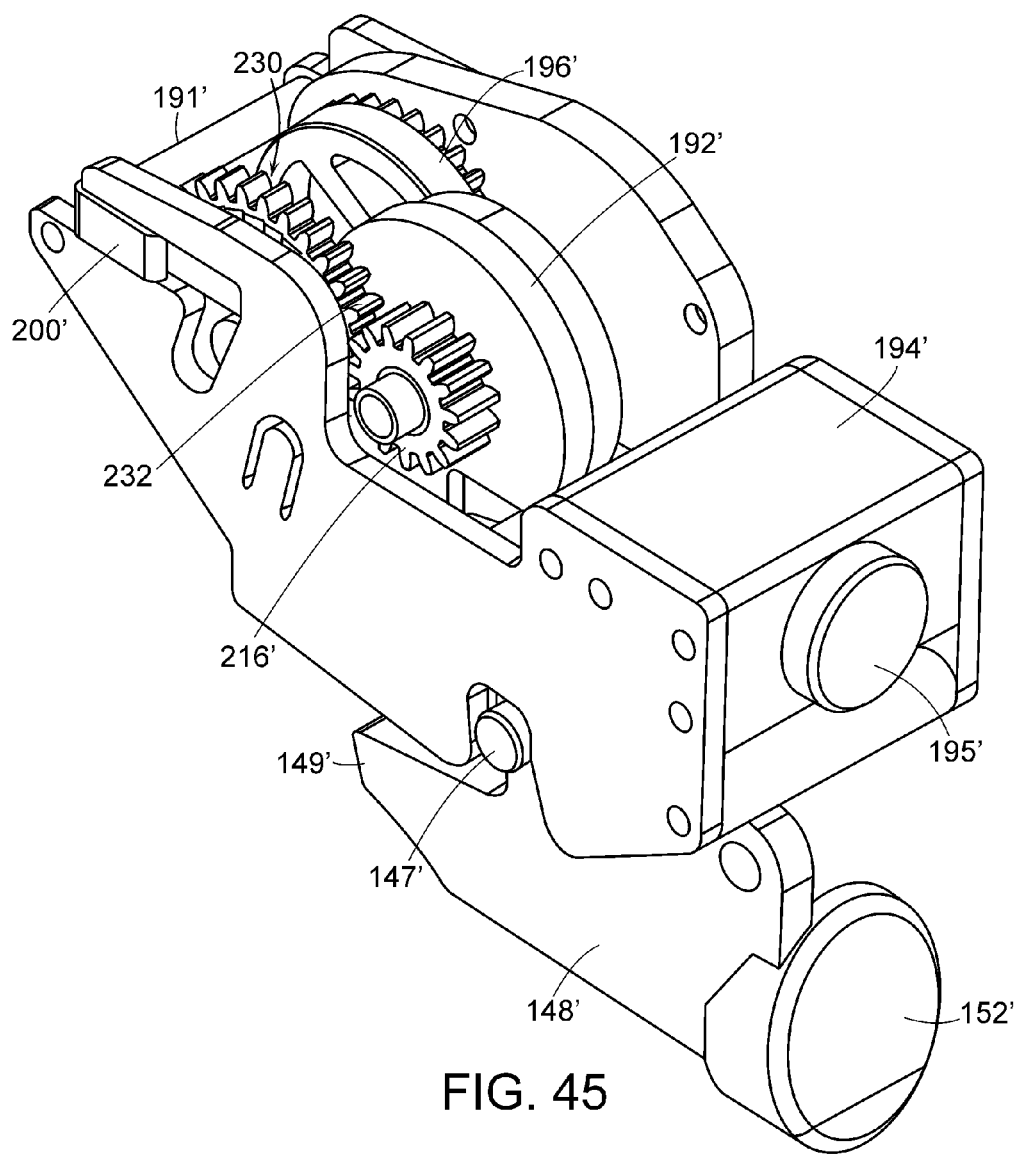
FIG. 45 is a perspective view of a return mechanism of a surgical instrument in accordance with an alternative embodiment of the present invention having an anti-back-up ratchet mechanism.
Figure 46:
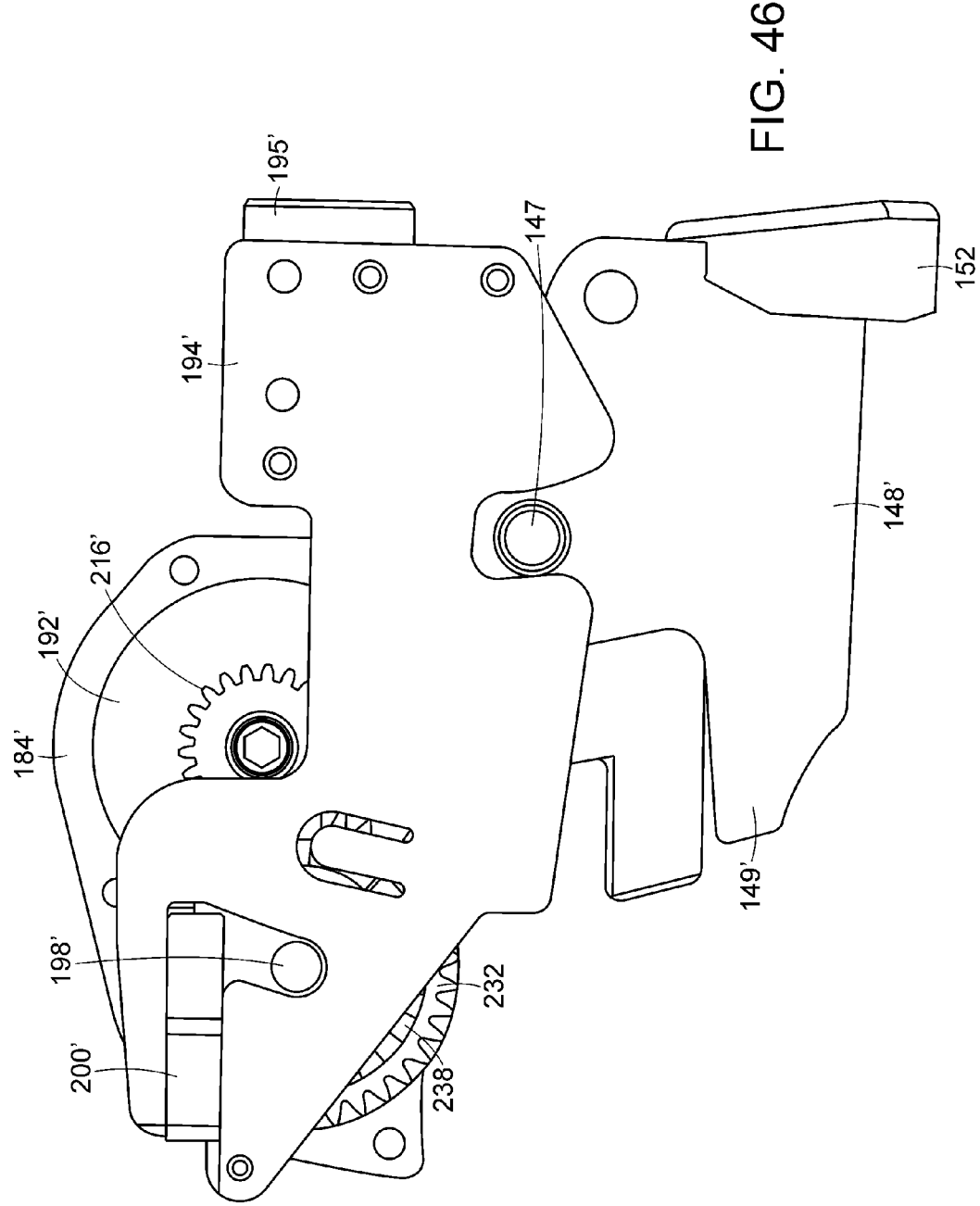
FIG. 46 is an elevational view of the return mechanism of FIG. 45 having a return carriage in an unactuated position.

In various embodiments, surgical instrument 100 can further include a brake for preventing, or at least partially inhibiting, the firing drive from advancing and/or retracting the cutting member and staple driver, for example, within end effector 106. In at least one embodiment, referring to FIG. 43, frame 184 can include brake surface 187 where brake surface 187 can be configured to apply a braking force to band 190. More particularly, when band 190 is pulled proximally and/or distally as described above, frame 184 can be configured such that band 190 slides over brake surface 187 and a friction force is created therebetween. In various embodiments, referring to FIG. 44, brake surface 187' can be configured such that the path of band 190 between firing member 166 and reel 192 is interrupted by brake surface 187' and a significant normal force can be applied to band 190.

In at least one embodiment, band 190 can be engaged with brake surface 187' when band 190 is at rest such that a static friction force between band 190 and brake surface 187' can prevent, at least initially, band 190 from moving relative to brake surface 187' when a pulling force is applied to band 190. When the pulling force applied to band 190 exceeds the static friction force, band 190 can be moved relative to brake surface 187'. Such embodiments may be particularly useful when trigger 160 is actuated more than one time to advance the cutting member and/or staple driver within end effector 106. More particularly, after an actuation of trigger 160, pawl 170 can be retracted relative to firing member 166 as described above and, in various embodiments, the friction force between band 190 and brake surface 187' can prevent, or at least partially inhibit, firing member 166 and/or firing links 162 and 164 from moving proximally, and/or distally, as pawl 170 is retracted. As a result of the above, the alignment between tooth 174 of pawl 170 and the recesses in firing member 166 and firing links 162 and 164 can be maintained when pawl 170 is moved relative thereto.

Similarly, in at least one embodiment, the stiffness of band 190 can also assist in holding firing member 166 and firing links 162 and 164 in position. More particularly, in order for firing member 166 to 'back up', or move proximally, firing member 166 would have to push band 190 proximally and, in effect, wind band 190 around reel 192. In various embodiments, the stiffness of band 190 can be such that a significant force to wind band 190 around reel 192 is required and, as a result, firing member 166 can be held in place. To further increase the force required to wind band 190 around reel 192, referring to FIG. 44, the path of band 190 can be controlled such that is not wound onto reel 192 in a tangential direction. More particularly, if the path of band 190 is such that it is wound onto reel 192 in a non-tangential direction, a portion of the force transmitted through band 190 will be lost thus resulting in a poor mechanical advantage for winding reel 192.

In various embodiments, surgical instrument 100 can include a brake which can be engaged with reel 192, or any other suitable component of the firing drive, to prevent firing member 166 and/or firing links 162 and 164 from being retracted unintentionally, for example. In at least one embodiment, although not illustrated, the brake can be moved between a first position and a second position, where, when the brake is in the first position, the brake can apply a first braking force to band 190, for example. In at least one such embodiment, the brake can apply, when it is in the second position, a second braking force to band 190, for example, which can be greater than or less than the first braking force. In various alternative embodiments, the brake may not be engaged with band 190 or any other portion of the firing drive when the brake is in the second position. In various embodiments, although not illustrated, surgical instrument 100 can include a detent mechanism which can apply a braking force to reel 192 and/or band 190. In at least one such embodiment, the detent mechanism can include a ball detent and a spring member for biasingly engaging the ball detent against reel 192 and/or band 190.

Figure 47:
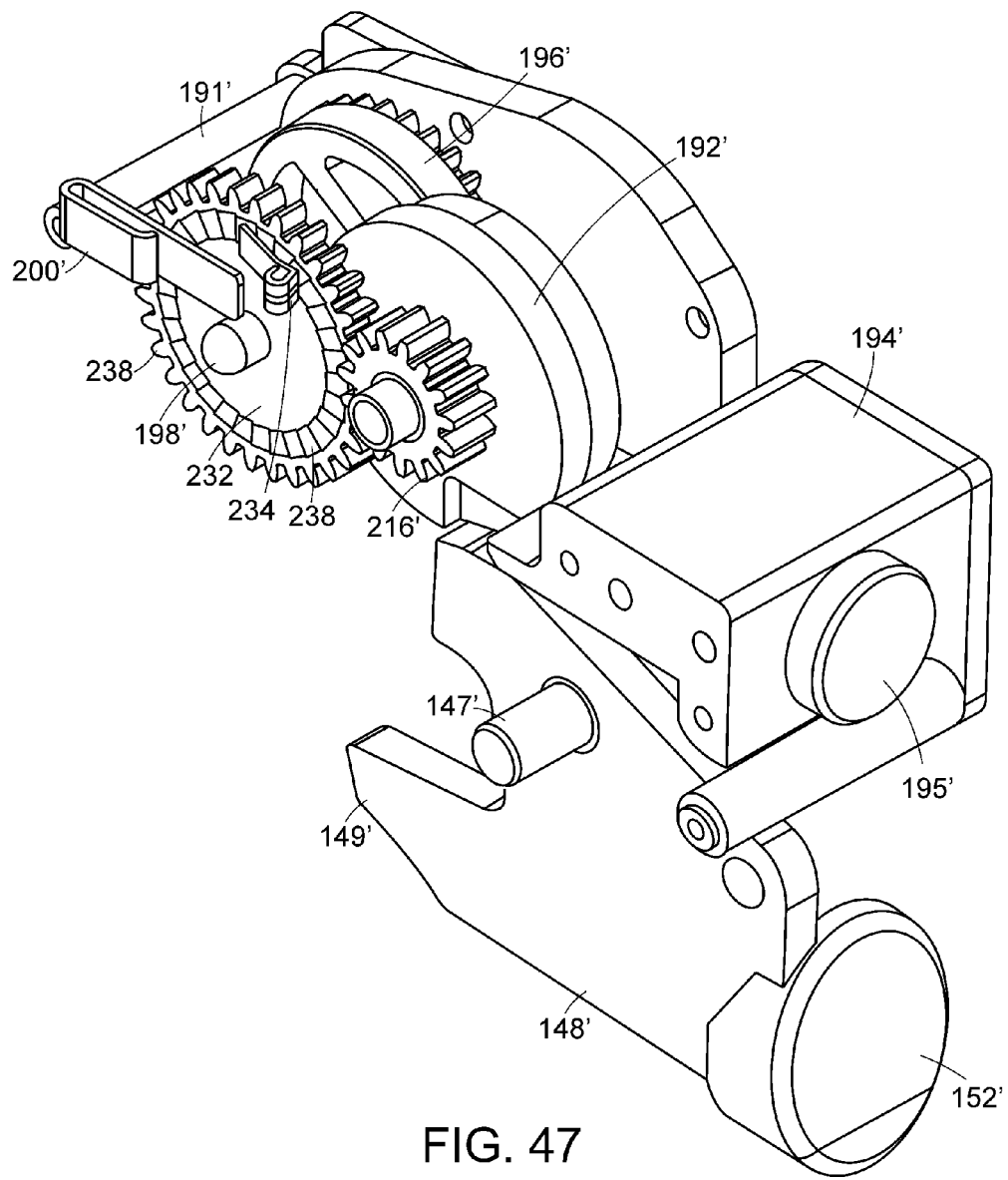
FIG. 47 is a perspective view of the return mechanism of FIG. 45 with some components of the surgical instrument removed.
Figure 48:
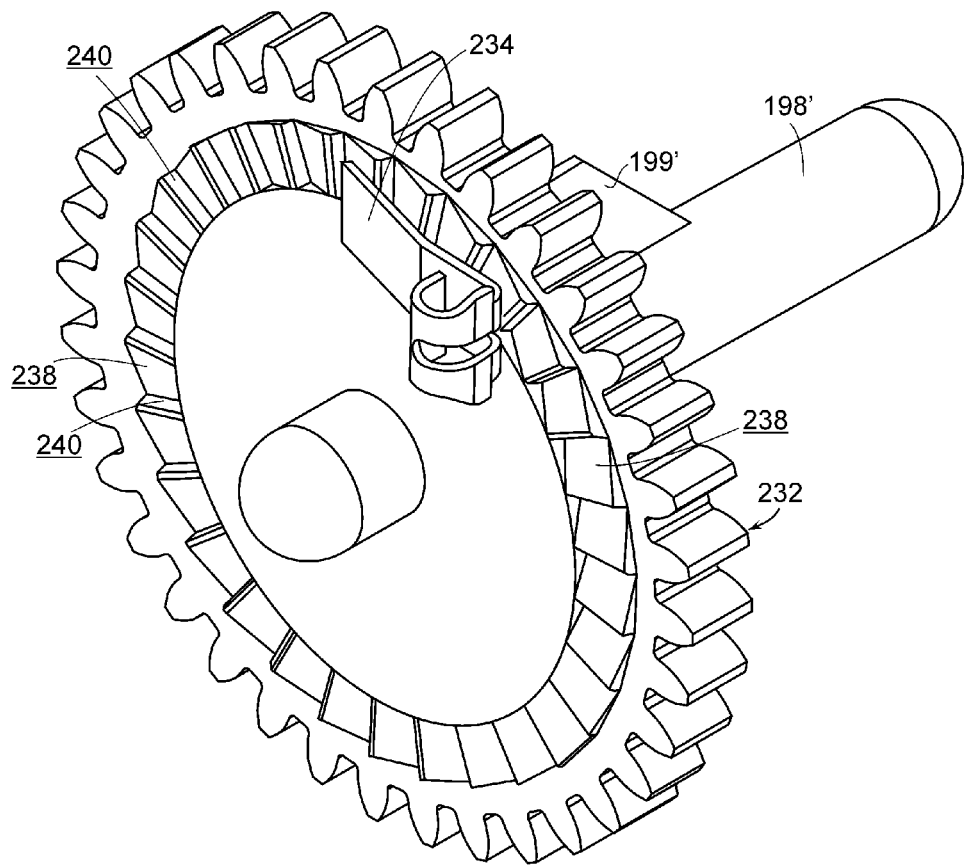
FIG. 48 is a perspective view of a return gear, return pin, and anti-back-up pawl of the ratchet mechanism of FIG. 45.
Figure 49:
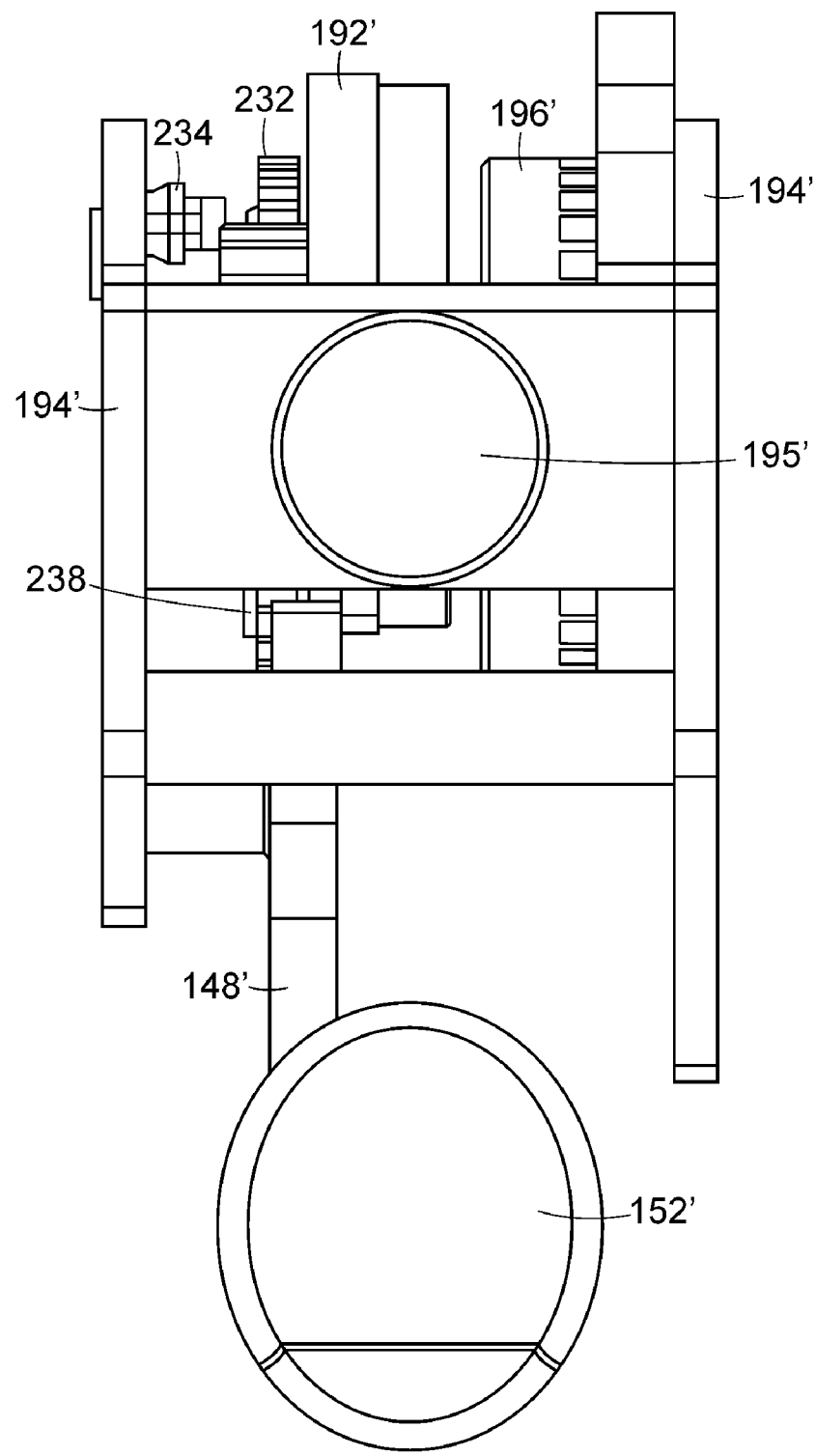
FIG. 49 is another elevational view of the return mechanism of FIG. 45.

In various embodiments, surgical instrument 100 can include a ratchet which can allow reel 192 to turn in a first direction but can, in various circumstances, prevent reel 192 from turning in a direction opposite the first direction. In at least one embodiment, referring to FIGS. 45-49, surgical instrument 100 can include ratchet assembly 230, where ratchet assembly 230 can include ratchet wheel 232 and ratchet pawl 234. In various embodiments, ratchet wheel 232 can operate in substantially the same way as key gear 206 described above except that, referring primarily to FIGS. 47 and 48, ratchet wheel 232 can include ratchet teeth 236 which can, owing to a ratcheting engagement with ratchet pawl 234, prevent ratchet wheel 232 from being turned in a clockwise direction, for example, when return carriage 194' is in its unactuated position (FIG. 47). More particularly, each ratchet tooth 236 can include a flat surface 240 where, referring to FIG. 48, at least one of flat surfaces 240 can abut edge 235 of pawl 234 and thereby prevent ratchet wheel 232 from being rotated in a clockwise direction.

Each ratchet tooth 236 can further include an inclined surface 238, where inclined surfaces 238 can be configured to slide underneath pawl 234 when ratchet wheel 232 is turned in a counter-clockwise direction. As a result of the above, ratchet assembly 230 can allow band 190 to be pulled distally by firing member 166, for example, but prevent, or at least substantially inhibit, band 190 from being moved proximally, at least when return carriage 194' is in its unactuated position. When return carriage 194' is pivoted downwardly into its actuated position, as described above with regard to return carriage 194, ratchet wheel 232 can be slid toward trigger gear 196' and out of operative engagement with ratchet pawl 234. Thereafter, as a result, ratchet wheel 232 can be rotated in either a clockwise or counter-clockwise direction without interference, or at least substantial interference, from ratchet pawl 234. In various alternative embodiments where ratchet wheel 232 is not slid toward trigger gear 196', ratchet pawl 234 can be moved downwardly and out of operative engagement with ratchet teeth 236 when return carriage 194' is moved into its actuated position. In either event, when return carriage 194' is in its actuated position, trigger gear 196' and return pin 198' can rotate ratchet wheel 232 and cam 192' to retract band 190 and firing member 166.

Figure 68:
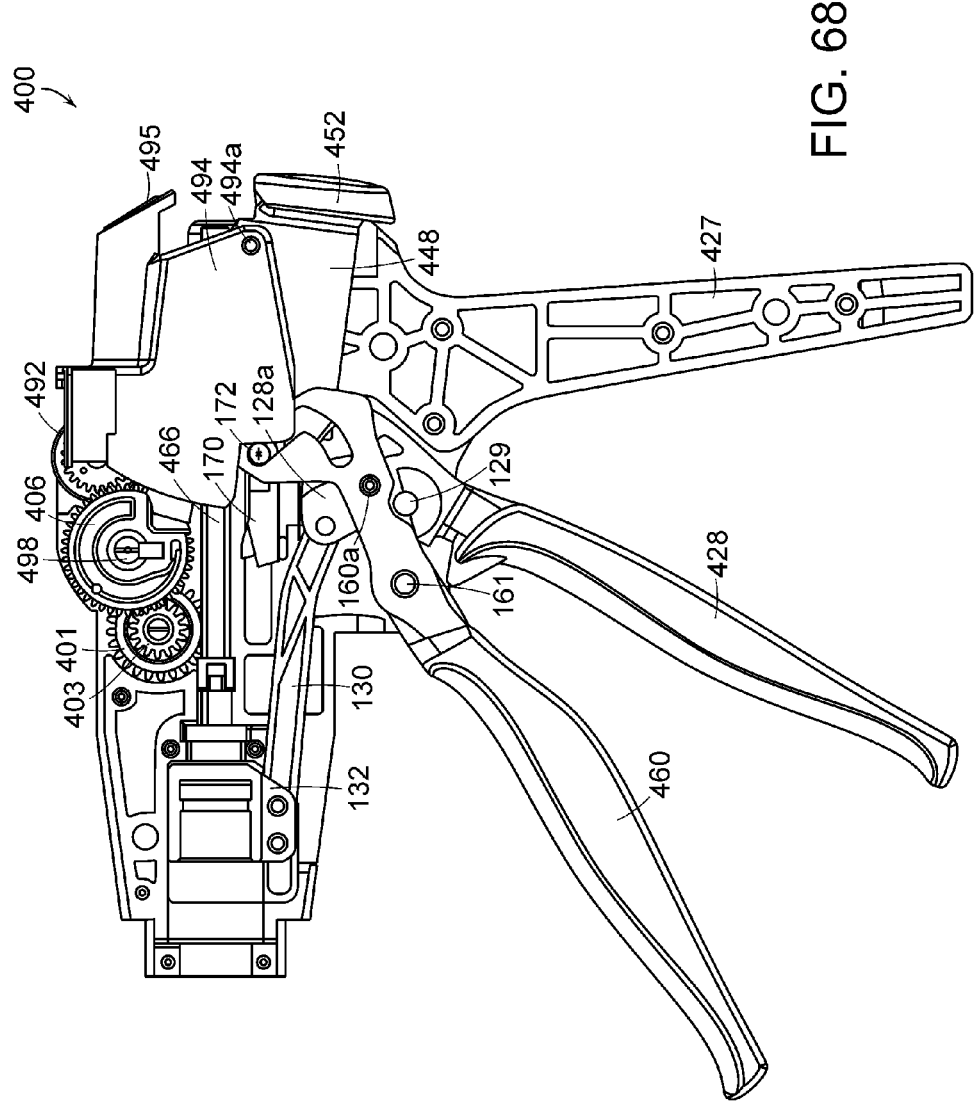
FIG. 68 is an elevational view of a surgical instrument in accordance with an embodiment of the present invention with some components of the surgical instrument removed.
Figure 69:
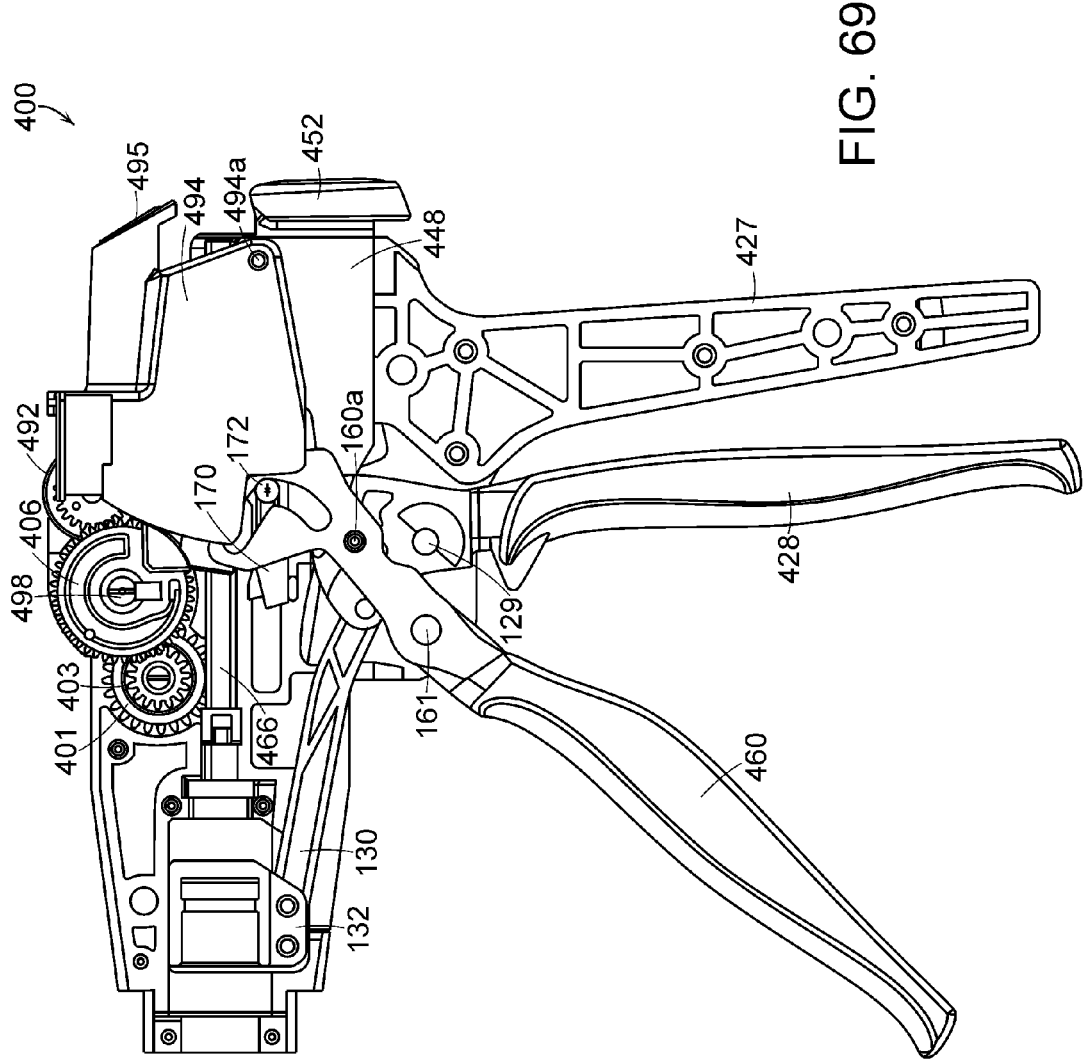
FIG. 69 is an elevational view of the surgical instrument of FIG. 68 illustrating a closure trigger in an actuated position.
Figure 70:
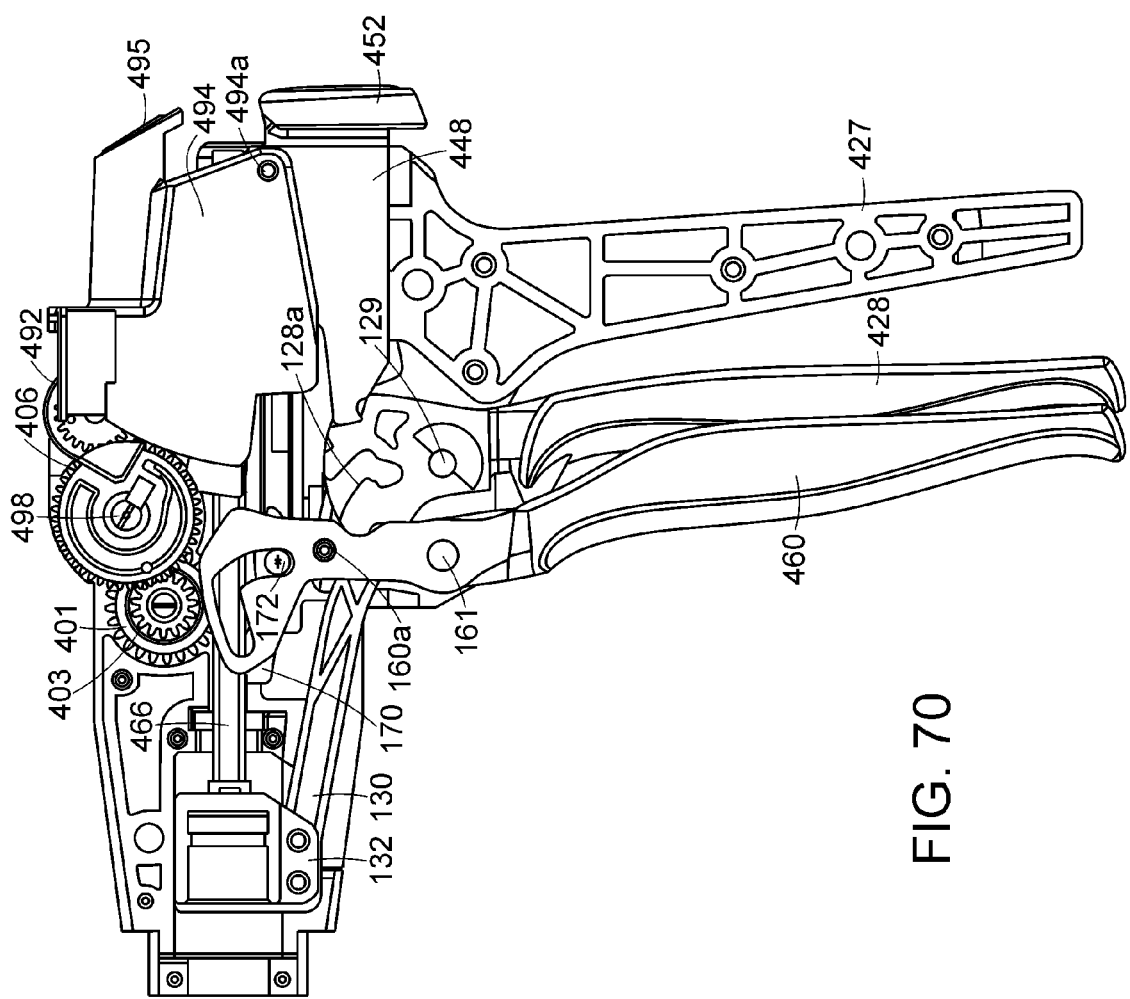
FIG. 70 is an elevational view of the surgical instrument of FIG. 68 illustrating a firing trigger in an actuated position after a first actuation of the firing trigger.

In various embodiments, referring to FIGS. 68-86, surgical instrument 400 can include a closure system for closing the anvil of an end effector, a firing drive for advancing a firing rod, cutting member, and/or staple driver within the end effector, and a gear-driven reversing drive for retracting at least one of the firing rod, cutting member, and/or staple driver relative to the end effector. In at least one embodiment, referring to FIG. 68, the closure system can include closure trigger 428, drive link 130, and driver 132 where, similar to the above, closure trigger 428 can be configured to displace drive link 130 and driver 132 when closure trigger 428 is moved from its unactuated position illustrated in FIG. 68 to its actuated position illustrated in FIG. 69. In various embodiments, the actuation of closure trigger 428 can unlock the firing drive. In at least one embodiment, the firing drive can include firing trigger 460 which, when closure trigger 428 is rotated toward handle 427, can be moved between a locked position illustrated in FIG. 68 and an unlocked position illustrated in FIG. 69. In at least one such embodiment, closure trigger 428 can include slot, or groove, 128a which can receive pin, or projection, 160a extending from firing trigger 460, wherein a sidewall of slot 128a can be configured to prevent pin 160a, and firing trigger 460, from moving, or at least substantially moving, relative to closure trigger 428 when closure trigger 428 is in its unactuated position (FIG. 68). When closure trigger 428 is actuated, or closed, the side wall of slot 128a can abut pin 160a and move firing trigger 460 between its locked position illustrated in FIG. 68 and its unlocked position illustrated in FIG. 69. In such an unlocked position, slot 128a can be oriented to permit pin 160a to move within slot 128a thereby allowing firing trigger 460 to move relative to closure trigger 428 and advance the firing drive as described in greater detail below.

In various embodiments, referring to FIG. 68, the firing drive can comprise firing trigger 460, firing pin 172, and pawl 170, wherein firing trigger 460 can be operably engaged with firing rod, or member, 466 via pawl 170 and firing pin 172 in order to advance the cutting member and the staple driver within the end effector. In at least one such embodiment, similar to the above, pawl 170 can be pivoted upwardly into engagement with firing member 466 such that, when firing trigger 460 is actuated, referring to FIG. 70, firing trigger 460 can advance firing pin 172, pawl 170, and firing member 466 distally. Thereafter, referring to FIG. 101, pawl 170 can be pivoted downwardly out of engagement with firing member 466 such that pawl 170 can be retracted proximally relative to firing member 466 when firing trigger 460 is released or returned to its unactuated, and unlocked, position illustrated in FIG. 72. Upon comparing FIGS. 69 and 72, it is readily apparent that a first cycle of the firing drive has moved firing member 466 distally and has also repositioned pawl 170, firing pin 172, and firing trigger 460 such that firing trigger 460 can be actuated a second time to further advance firing member 466. In such circumstances, referring to FIG. 102, pawl 170 can be pivoted upwardly into operative engagement with firing member 466 and advanced distally by actuating firing trigger 460 once again.

Figure 73:
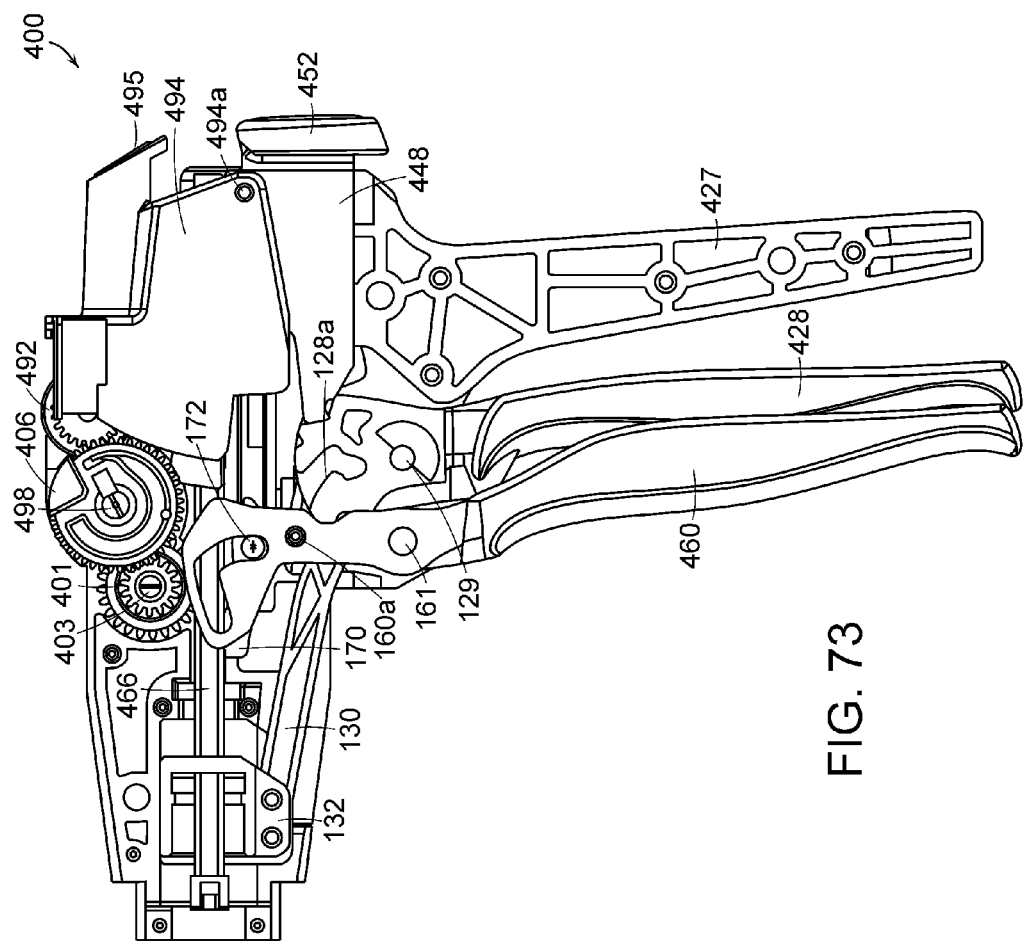
FIG. 73 is an elevational view of the surgical instrument of FIG. 68 illustrating the firing trigger in an actuated position after a second actuation of the firing trigger.
Figure 74:
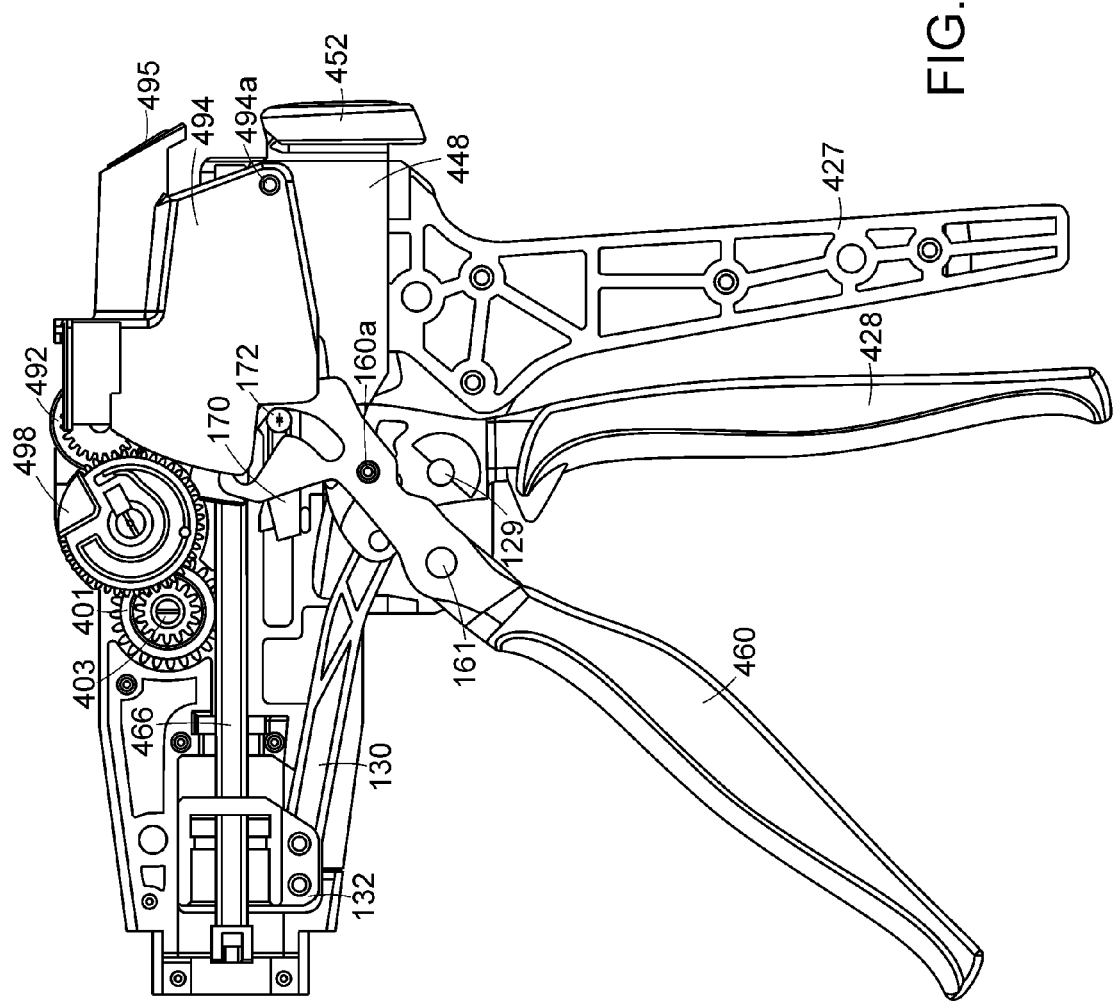
FIG. 74 is an elevational view of the surgical instrument of FIG. 68 illustrating the firing trigger in an unactuated position after it has been released from its second actuation.
Figure 75:
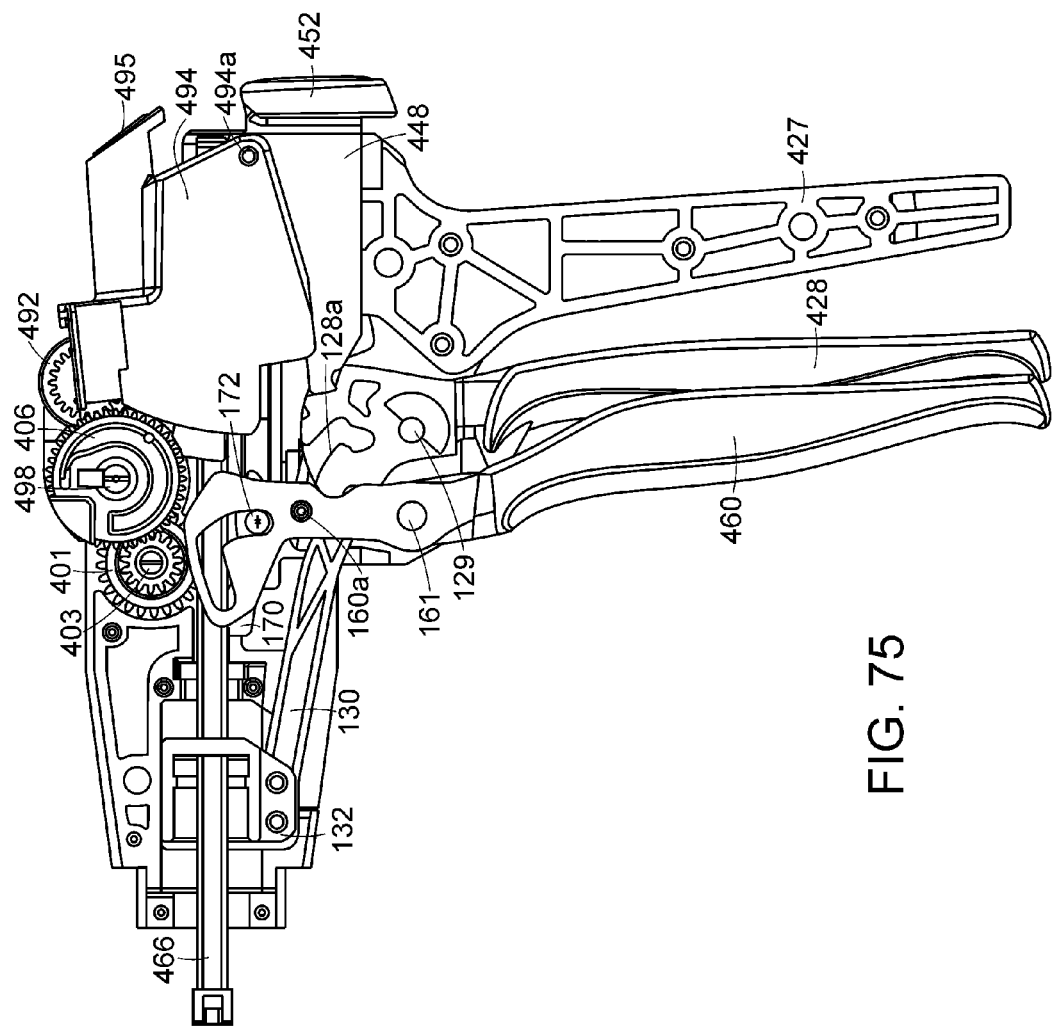
FIG. 75 is an elevational view of the surgical instrument of FIG. 68 illustrating the firing trigger in an actuated position after a third actuation of the firing trigger.
Figure 82:
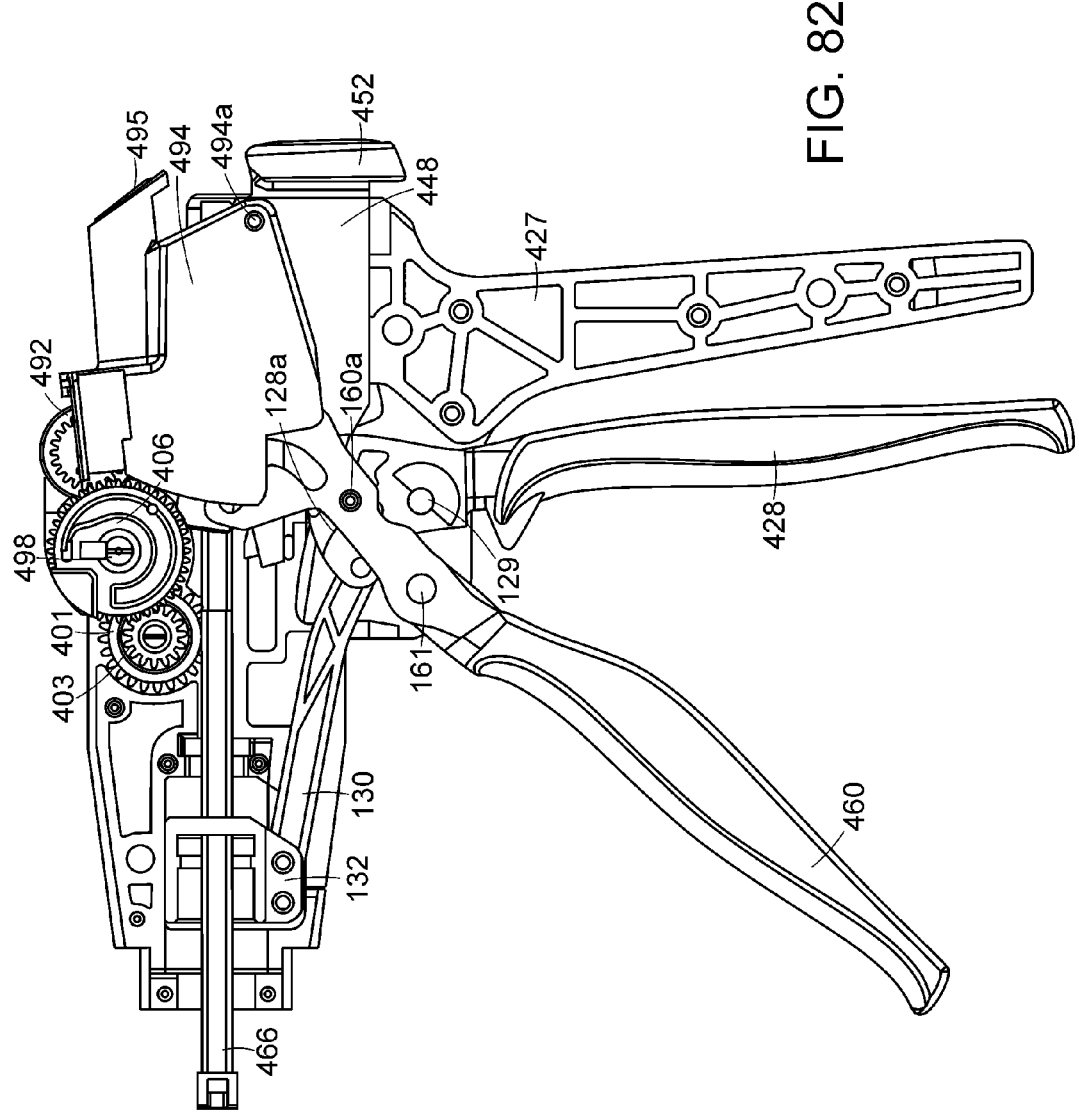
FIG. 82 is an elevational view of the return carriage of the surgical instrument of FIG. 68 in an actuated position and the reversing mechanism operably engaged with the firing member.
Figure 83:
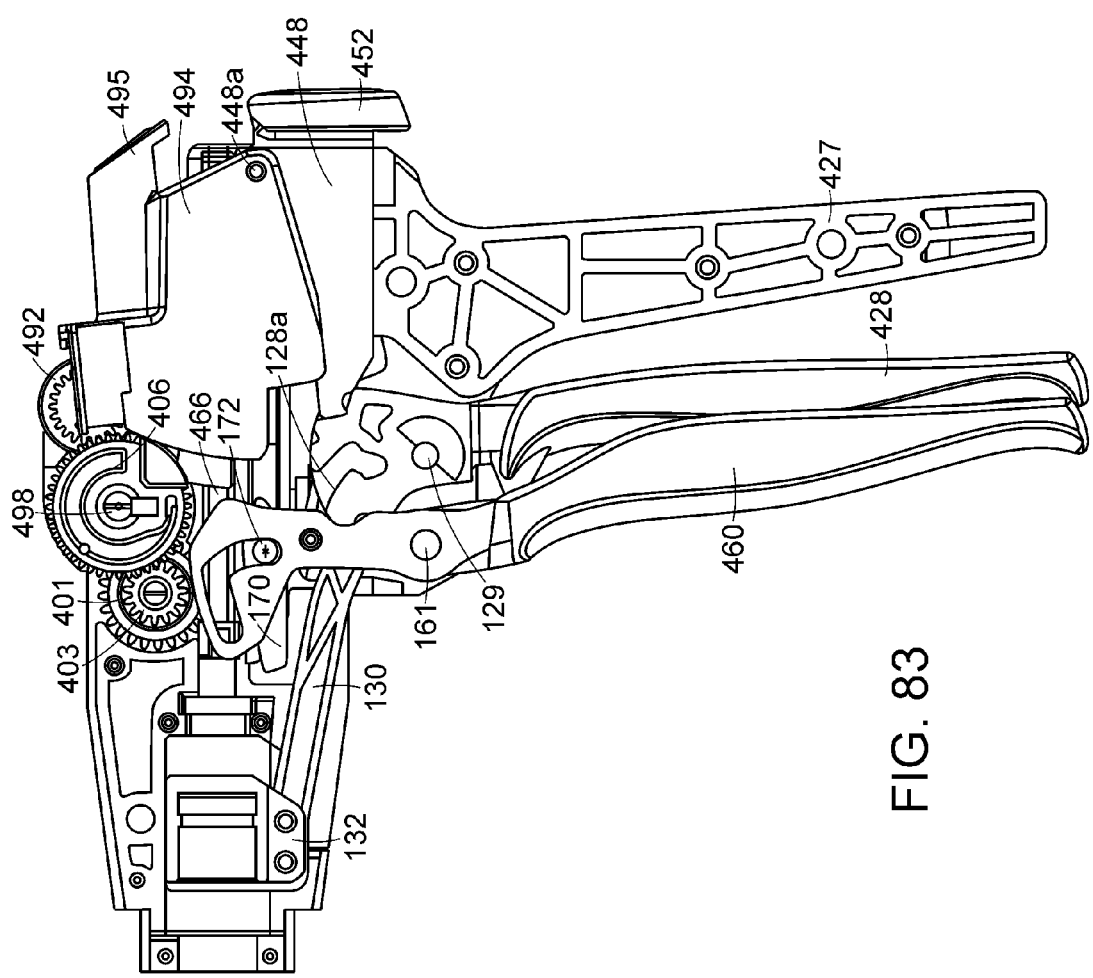
FIG. 83 is an elevational view of the surgical instrument of FIG. 68 illustrating the firing trigger in an actuated position after a fourth actuation which has retracted the firing member.
Figure 101:
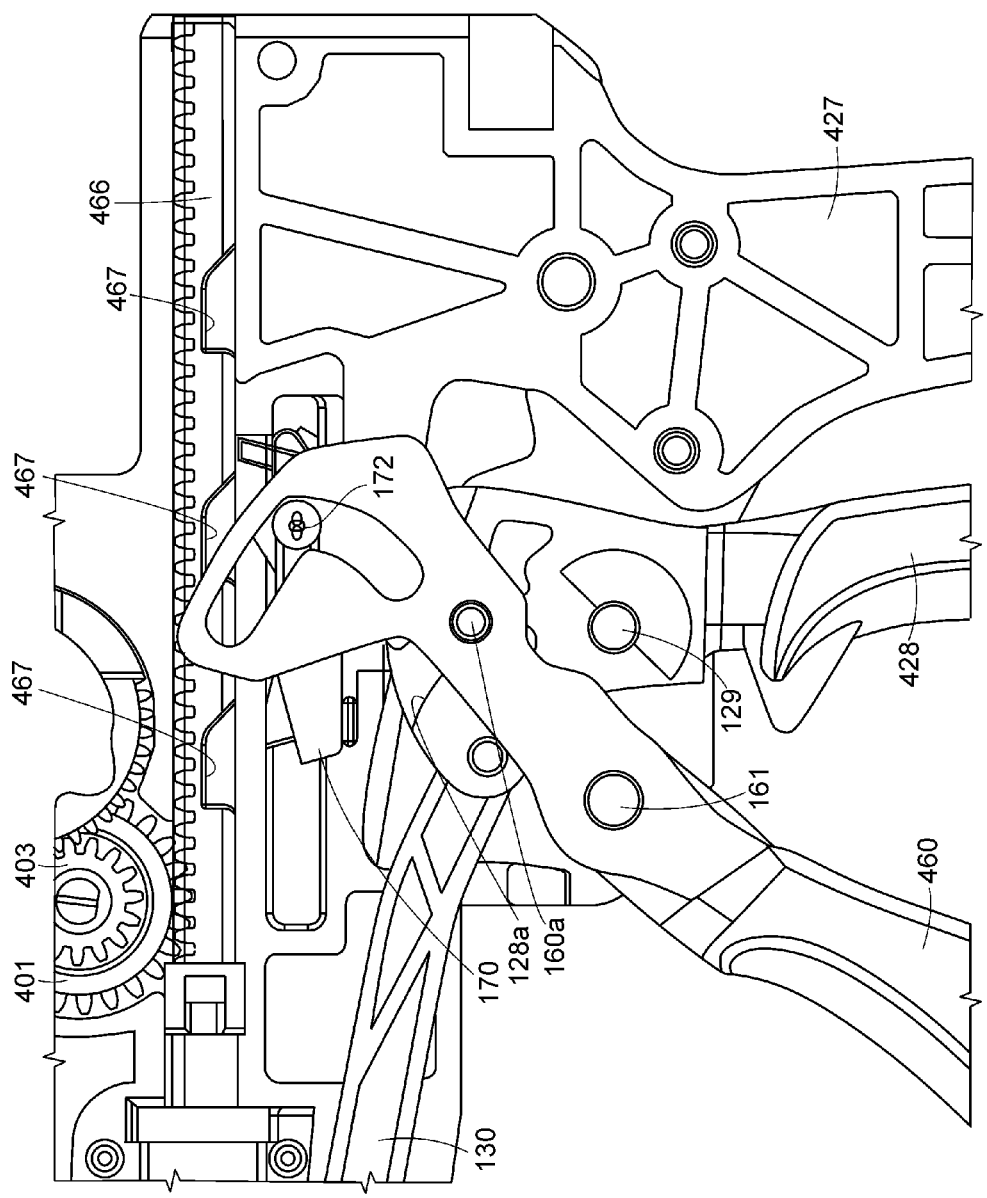
FIG. 101 is an elevational view of a surgical instrument in accordance with an alternative embodiment of the present invention including the firing drive and the reversing drive of the surgical instrument of FIG. 68 with some components of the surgical instrument removed wherein the pawl of the firing drive is illustrated as it would appear when it is withdrawn relative to the firing member.
Figure 102:
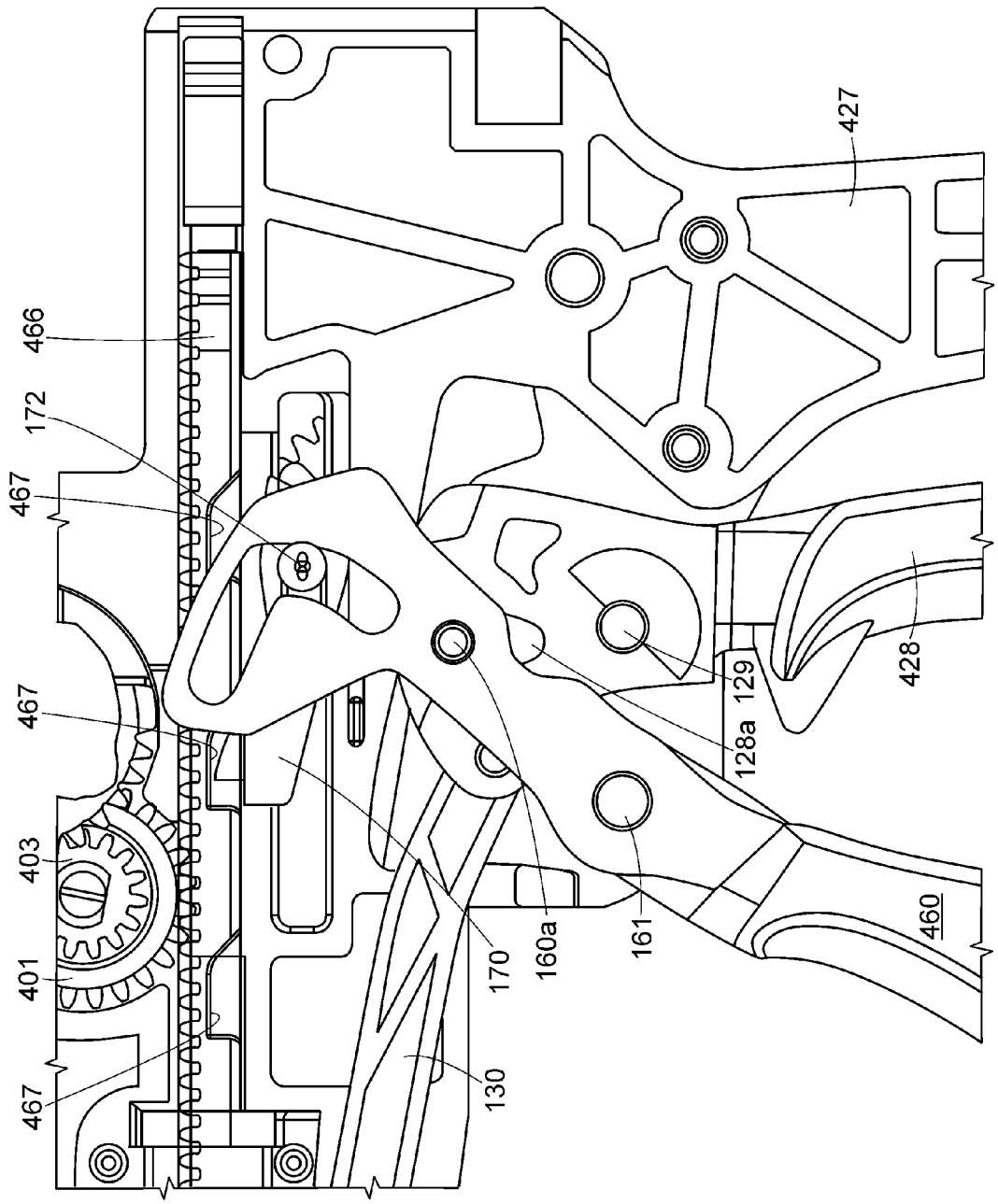
FIG. 102 is an elevational view of the surgical instrument of FIG. 101 illustrating the pawl operably engaged with the firing member.

In various embodiments, referring to FIGS. 101 and 102, firing member 466 can include a plurality of recesses 467 which can each receive at least a portion of pawl 170 such that pawl 170 can serially engage the recesses 467 in order to advance firing member 466 a plurality of times as described above. More particularly, in at least one embodiment, firing member 466 can include three recesses 467 which can allow firing member 466 to be advanced at least three times by trigger 460. By way of example, FIG. 73 illustrates the firing drive upon a second actuation of trigger 460, FIG. 74 illustrates the firing drive after trigger 460 has been returned to its unactuated position after its second actuation, FIG. 75 illustrates the firing drive upon a third actuation of trigger 460, and FIG. 82 illustrates the firing drive after trigger 460 has been returned to its unactuated position after its third actuation. At such point, as described in greater detail below, the firing drive can be disengaged from firing member 466 and the reversing drive can be operably engaged with firing member 466 such that, in various embodiments, firing member 466 can be retracted relative to the end effector and the surgical instrument can be reset. Although firing trigger 460 is actuated three times in order to fully advance firing member 466 in the illustrated exemplary embodiment, other embodiments are envisioned which can utilize more than, or less than, three strokes or actuations of the firing trigger.

In various embodiments, as outlined above, surgical instrument 400 can further include a gear-driven reversing drive, or mechanism, which can be configured to retract firing member 466, the cutting member, and/or the staple driver relative to the end effector of the surgical instrument. In at least one embodiment, the reversing mechanism can be operably engaged with firing member 466, or any other suitable portion of the firing drive, to move firing member 466 proximally. In at least one such embodiment, referring to FIG. 71, the reversing drive can include a gear train comprising trigger gear 496, key gear 406, pinion gear 401, intermediate gear 403, and spur gear 416, for example. In various embodiments, referring to FIG. 84, the reversing drive can further include gear portion 158 extending from firing trigger 460 which can be configured such that, when firing trigger 460 is rotated about pin 161, similar to the above, gear portion 158 can rotate trigger gear 496 about an axis defined by return pin 498. In at least one embodiment, gear portion 158 and trigger gear 496 can include teeth and/or recesses which can be configured to cooperate and transmit rotational motion therebetween.

Figure 77:
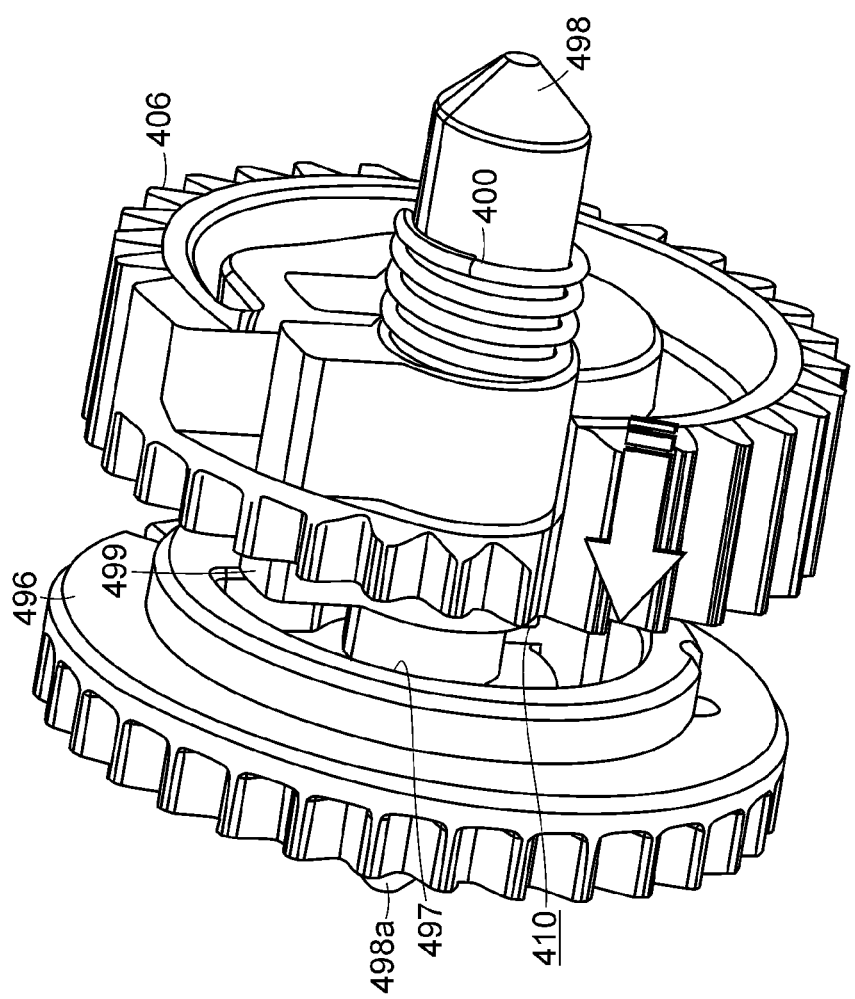
FIG. 77 is a perspective view of a trigger gear, key gear, and a return pin of the gear train of the reversing mechanism of FIG. 71.
Figure 78:
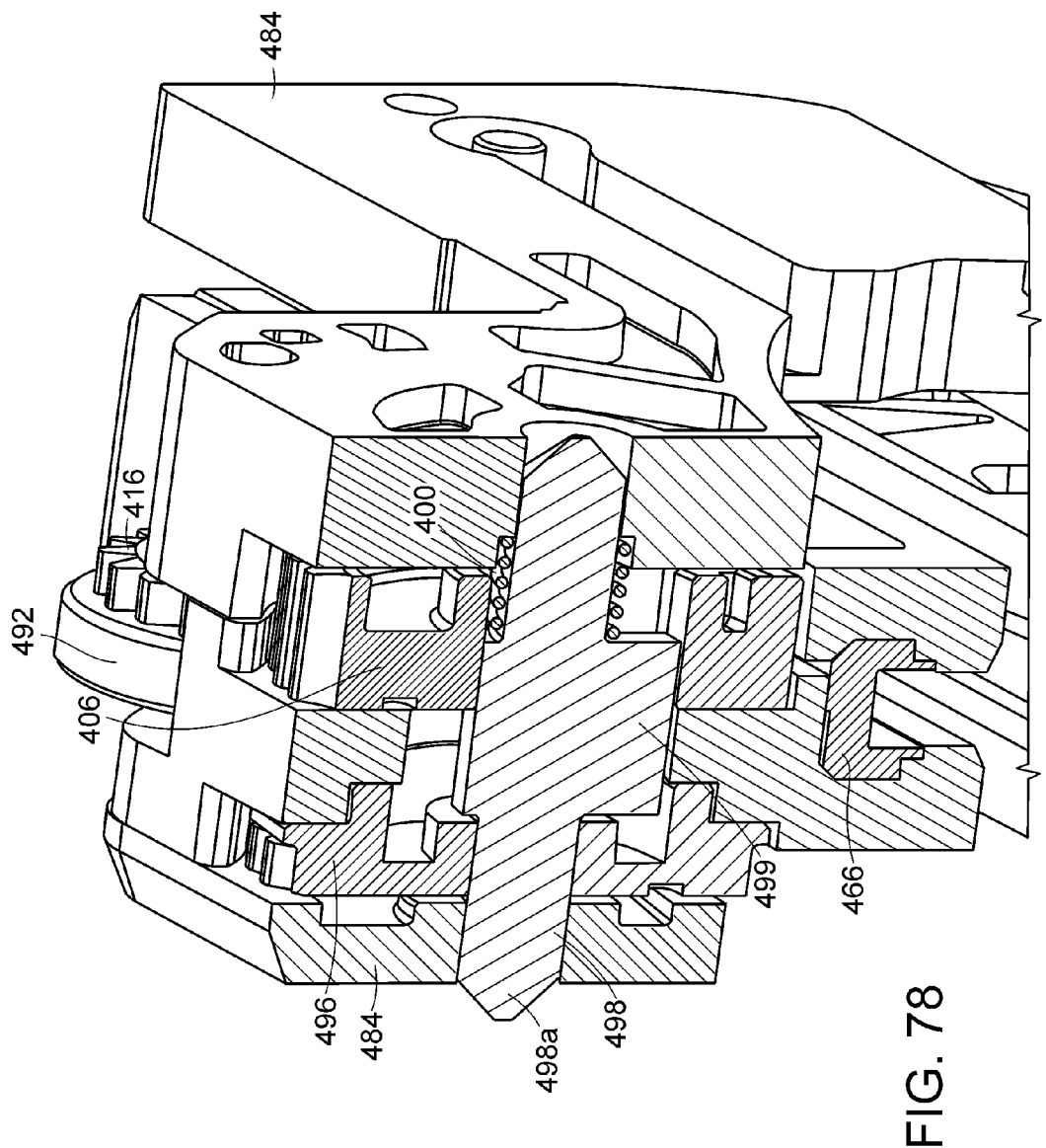
FIG. 78 is a cross-sectional view of the surgical instrument of FIG. 68 illustrating the return pin of FIG. 77 operatively engaged with the trigger gear and the key gear of the reversing mechanism of FIG. 71.
Figure 79:
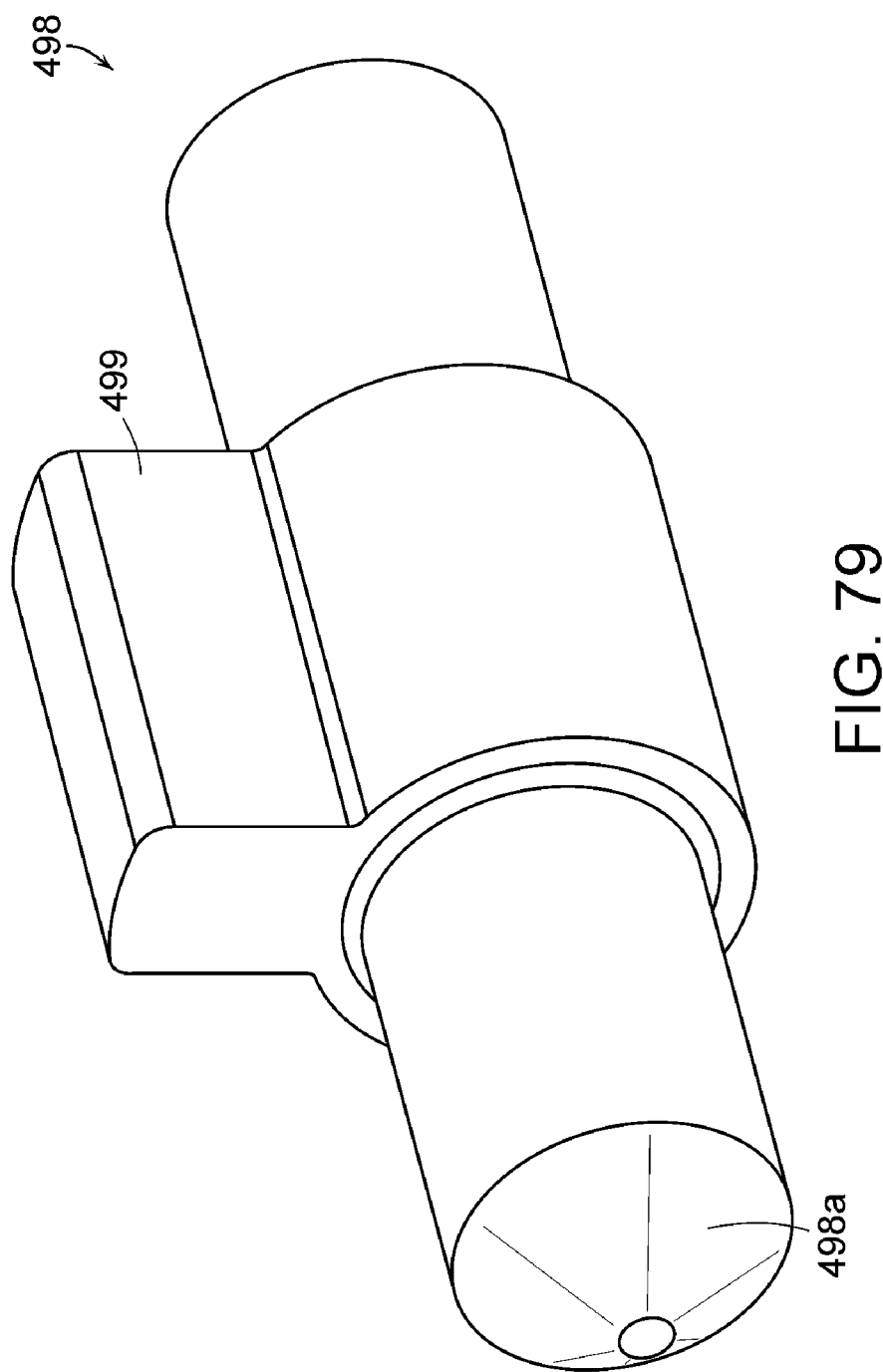
FIG. 79 is a perspective view of the return pin of FIG. 77.
Figure 80:
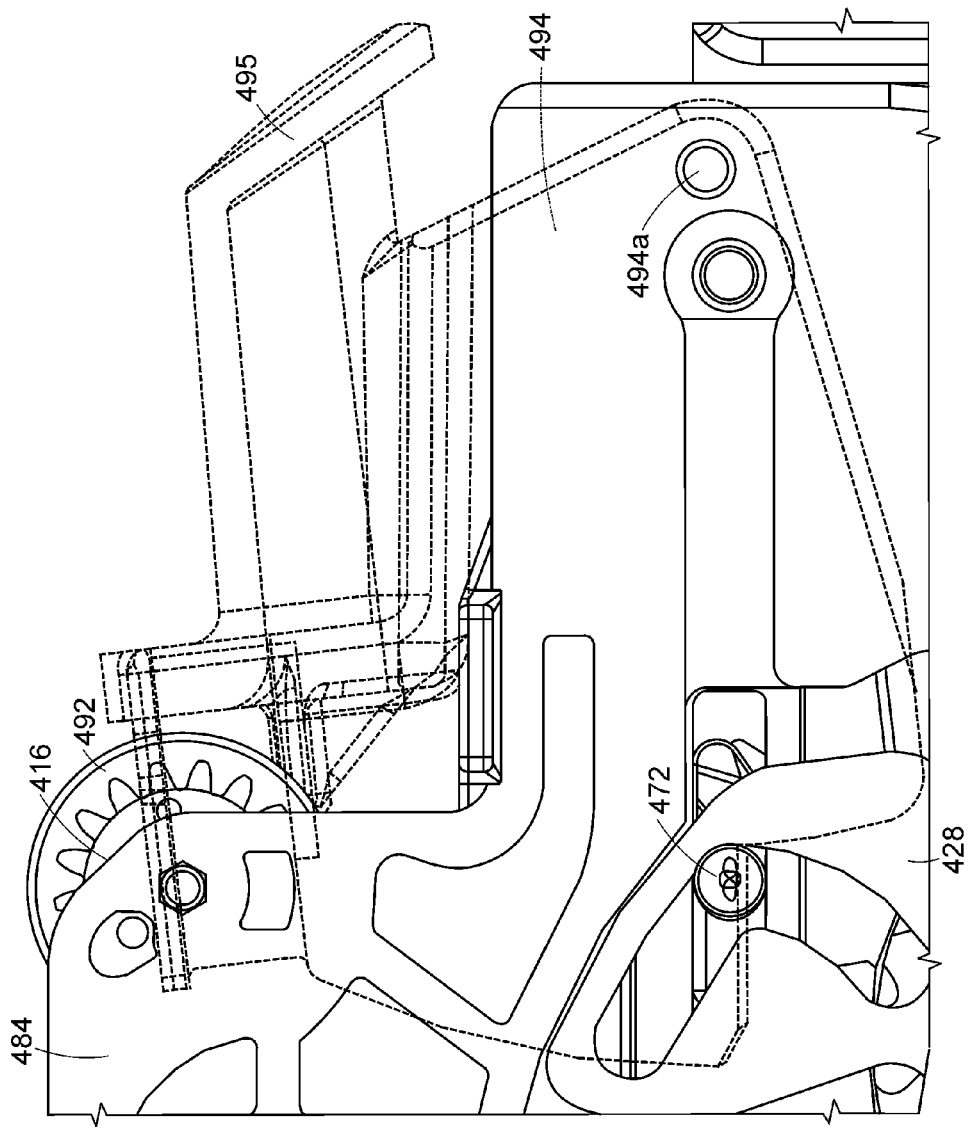
FIG. 80 is another elevational view of the return carriage of FIG. 76 in an actuated position.
Figure 81:
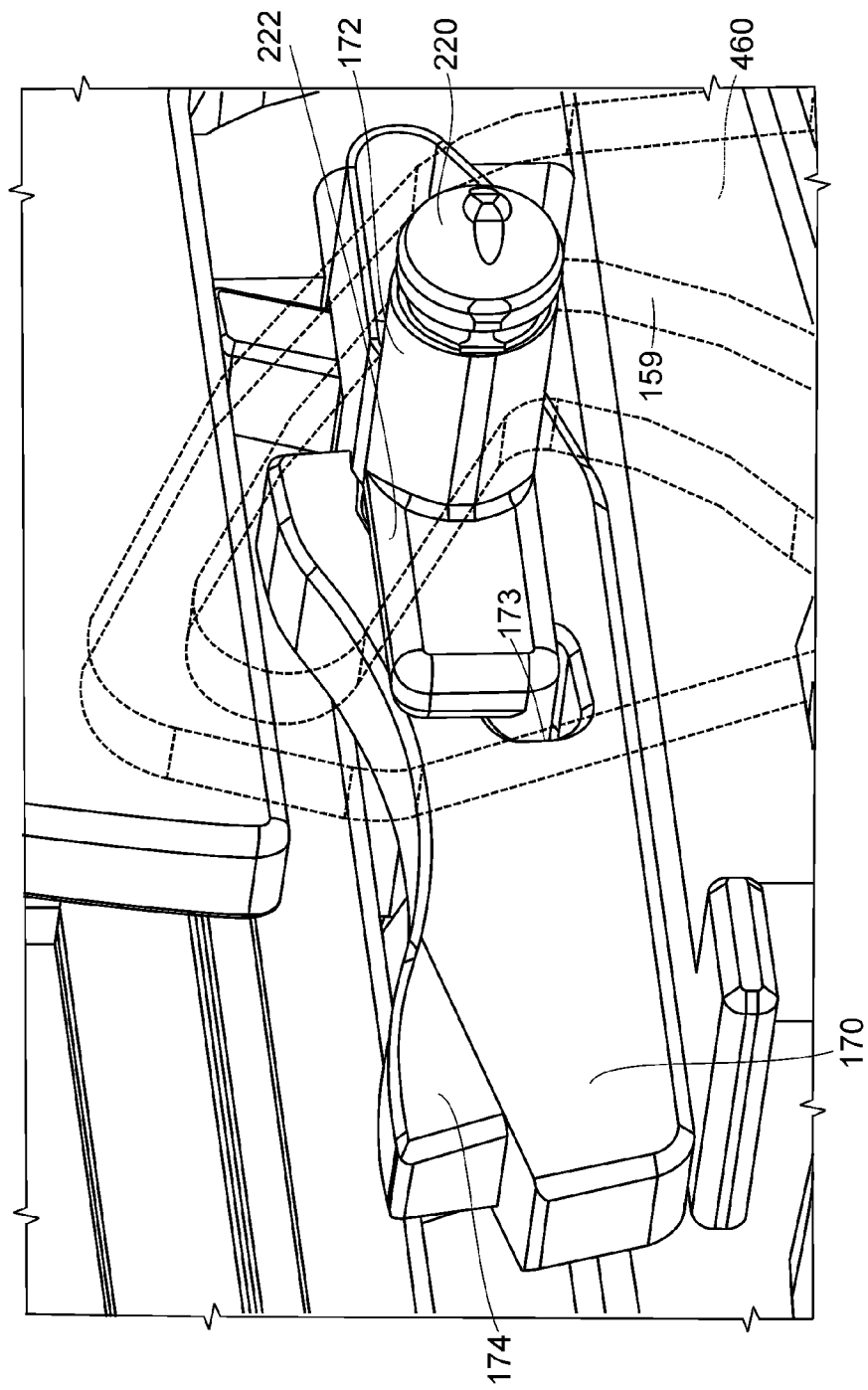
FIG. 81 is a perspective view of a firing pin engaged with a pawl of the firing drive of the surgical instrument of FIG. 68.

Referring to FIG. 77, also similar to the above, trigger gear 496 and return pin 498 can be configured such that they can be selectively engaged and disengaged with one another. In at least one such embodiment, trigger gear 496 can be operably disengaged with return pin 498 when firing member 466 is advanced by the firing drive. Stated another way, trigger gear 496 can be configured such that it does not transmit, or at least substantially transmit, rotational motion to return pin 498 when firing member 466 is being advanced by the firing drive as described above. Furthermore, in at least one such embodiment, referring to FIGS. 77 and 79, return pin 498 can include key 499 extending therefrom wherein key 499 can be held out of operative engagement with D-shaped cavity 497 in trigger gear 496 until the reversing drive is operatively engaged with firing member 466 as described in greater detail below. In order to hold key 499 out of operative engagement with trigger gear 496, referring to FIG. 84, return pin 498 can include end 498a which can be displaced, and/or held in position, by return carriage 494 such that key 499 is positioned outside of D-shaped cavity 497.

Figure 71:
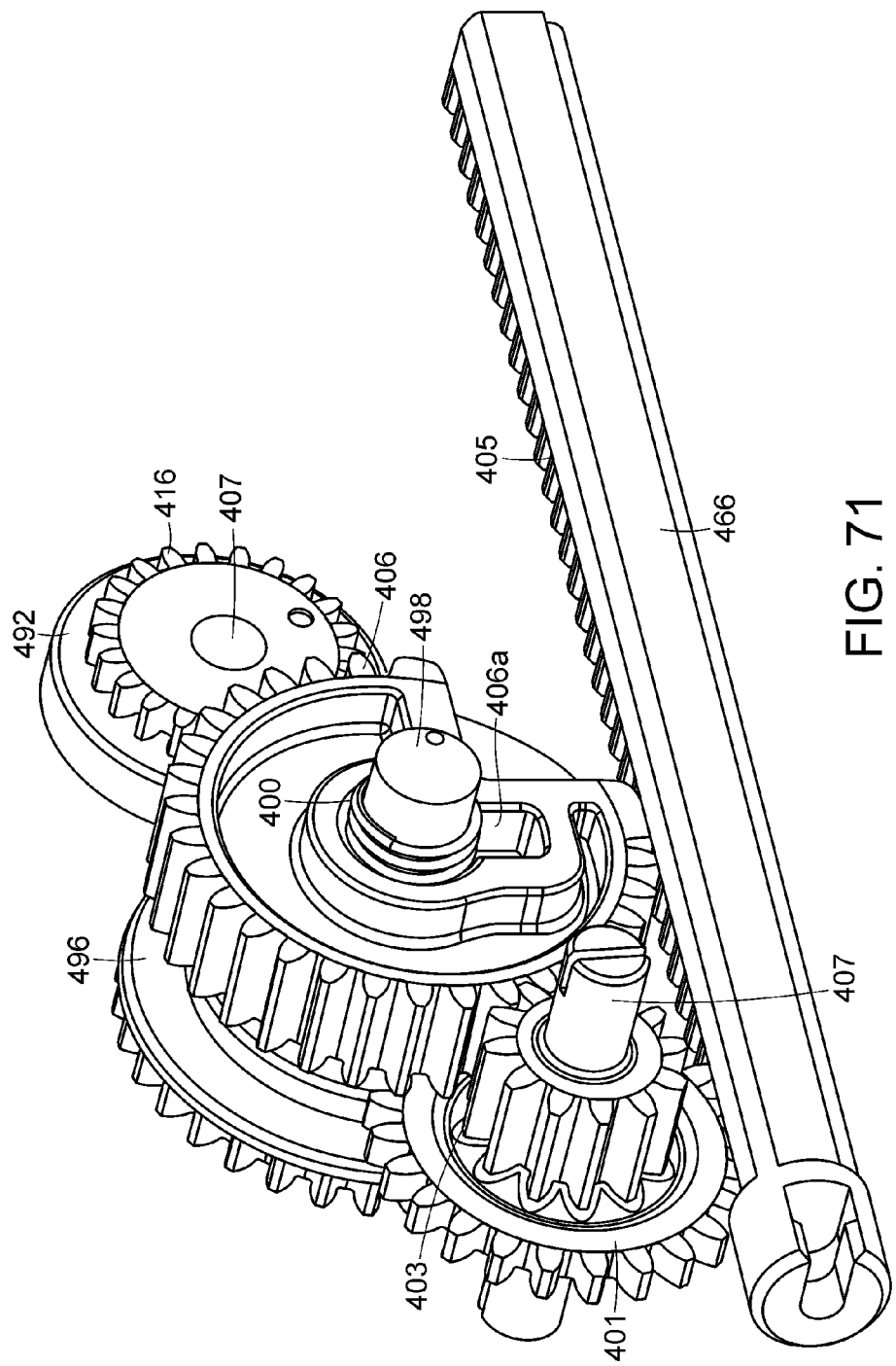
FIG. 71 is a perspective view of a gear train of a reversing mechanism of the surgical instrument of FIG. 68 for retracting a firing member.
Figure 72:
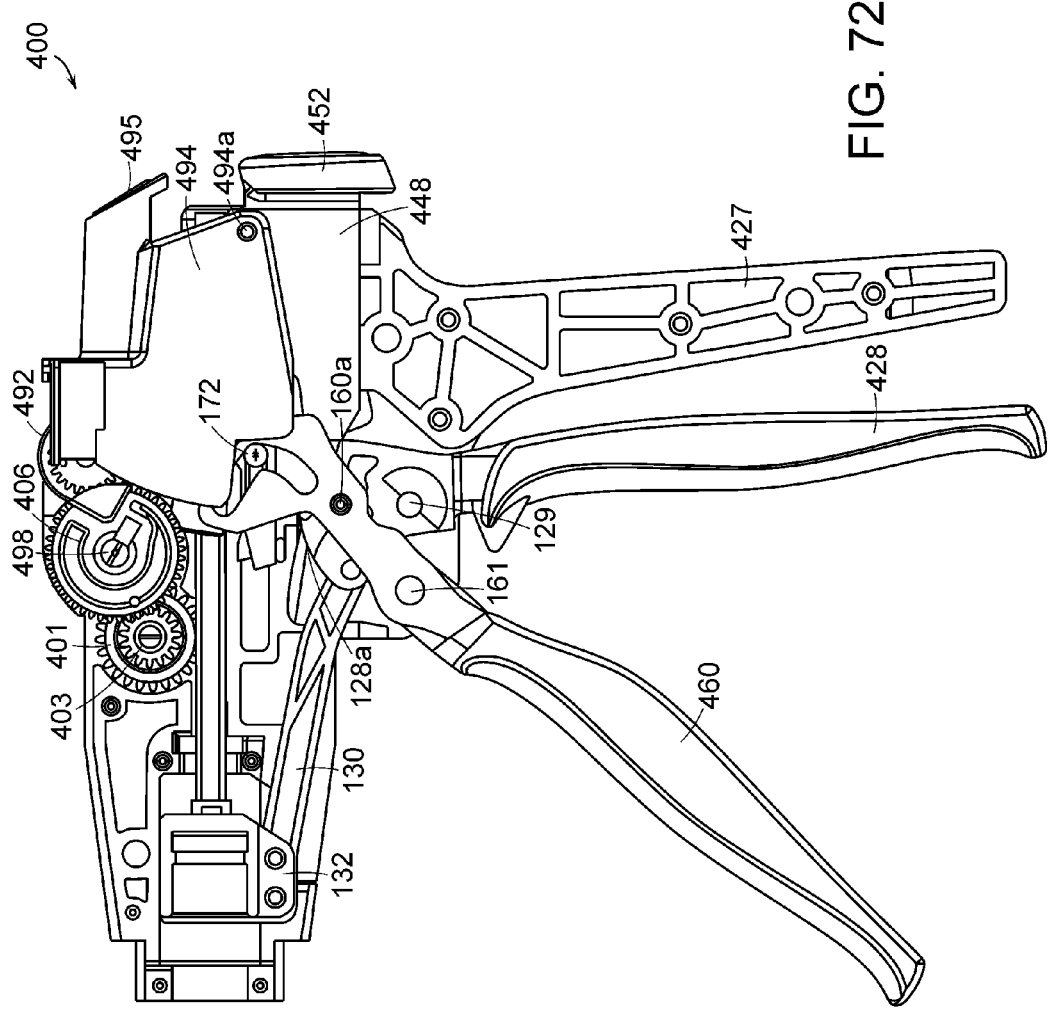
FIG. 72 is an elevational view of the surgical instrument of FIG. 68 illustrating the firing trigger in an unactuated position after it has been released from its first actuation.

Before trigger gear 496 and return pin 498 are operatively engaged as mentioned above, pinion gear 401 of the reversing drive, referring to FIG. 71, can be operatively engaged with rack portion 405 of firing member 466 such that, when firing member 466 is advanced distally by the firing drive as described above, rack portion 405 can rotate pinion gear 401 about an axis defined by axle 407. In various embodiments, rack 405 can include a plurality of teeth and/or grooves which can be configured to convert translational movement of firing member 466 into rotational movement of pinion gear 401. In various embodiments, intermediate gear 403 can be mounted to or integrally formed with pinion gear 401 such that the translation of firing member 466 can rotate intermediate gear 403 as well. In at least one embodiment, intermediate gear 403 and key gear 406 can include teeth and/or recesses which can be configured to cooperate and transmit rotational motion therebetween. Similarly, spur gear 416 can include teeth and/or recesses which can be configured to cooperate with the teeth and/or recesses of key gear 406 and transmit rotational motion therebetween. Thus, in view of the above, the advancement of firing member 466 can rotate gears 401, 403, 406, and 416 of the gear train.

Figure 84:
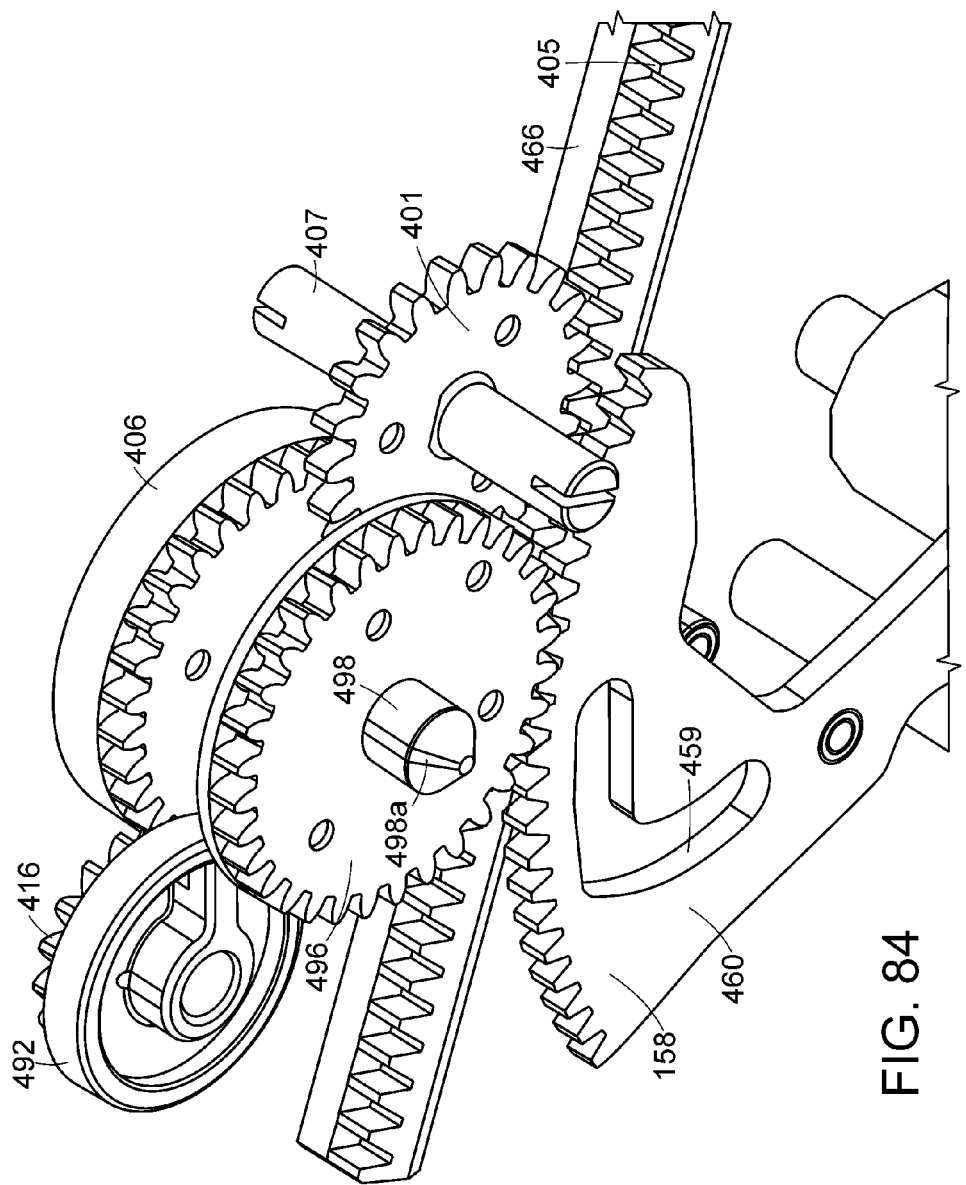
FIG. 84 is a perspective view of the reversing mechanism of FIG. 76 with some components removed.
Figure 85:
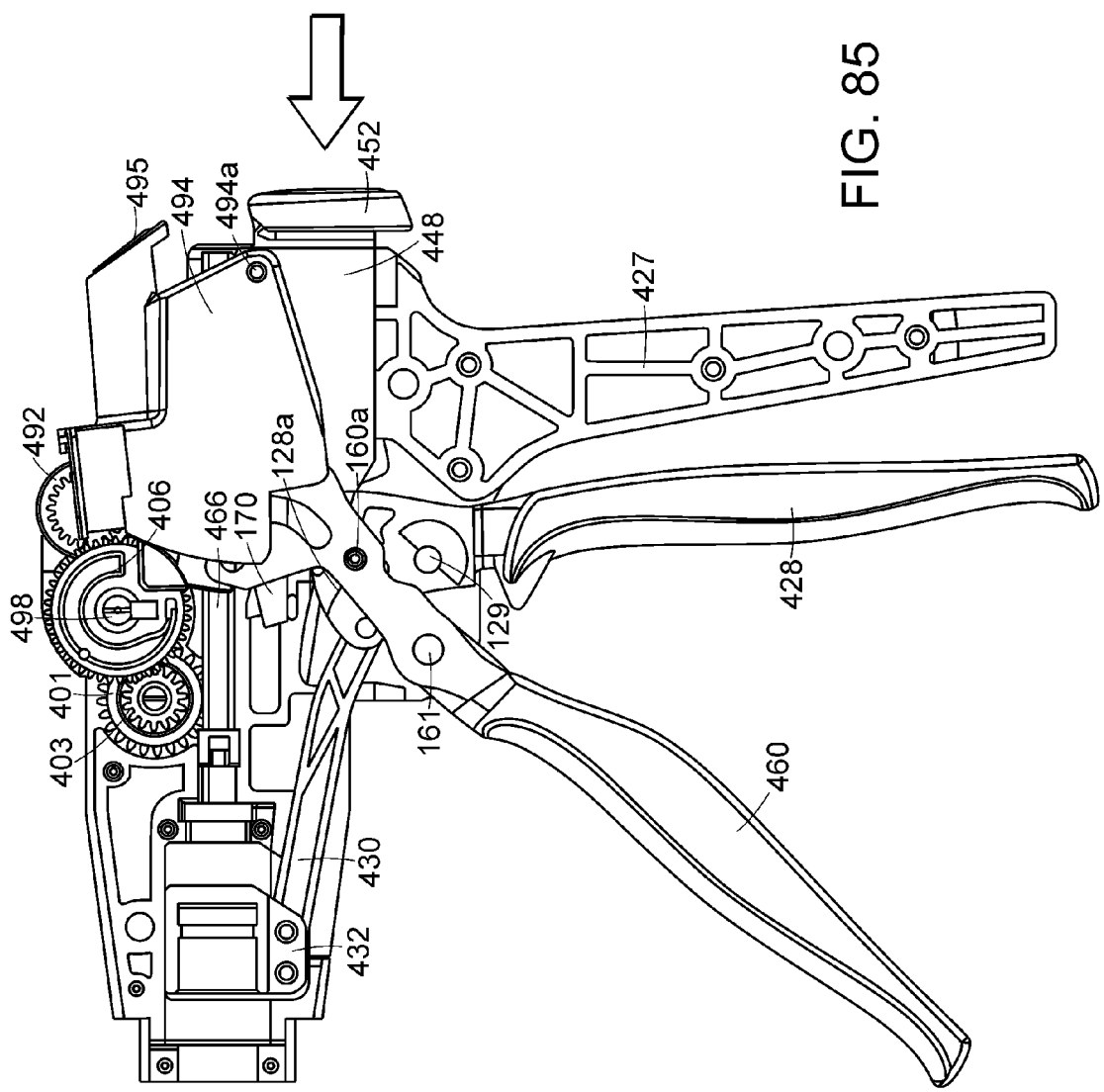
FIG. 85 is an elevational view of the surgical instrument of FIG. 68 illustrating the firing trigger in an unactuated position after it has been released from its fourth actuation.
Figure 86:
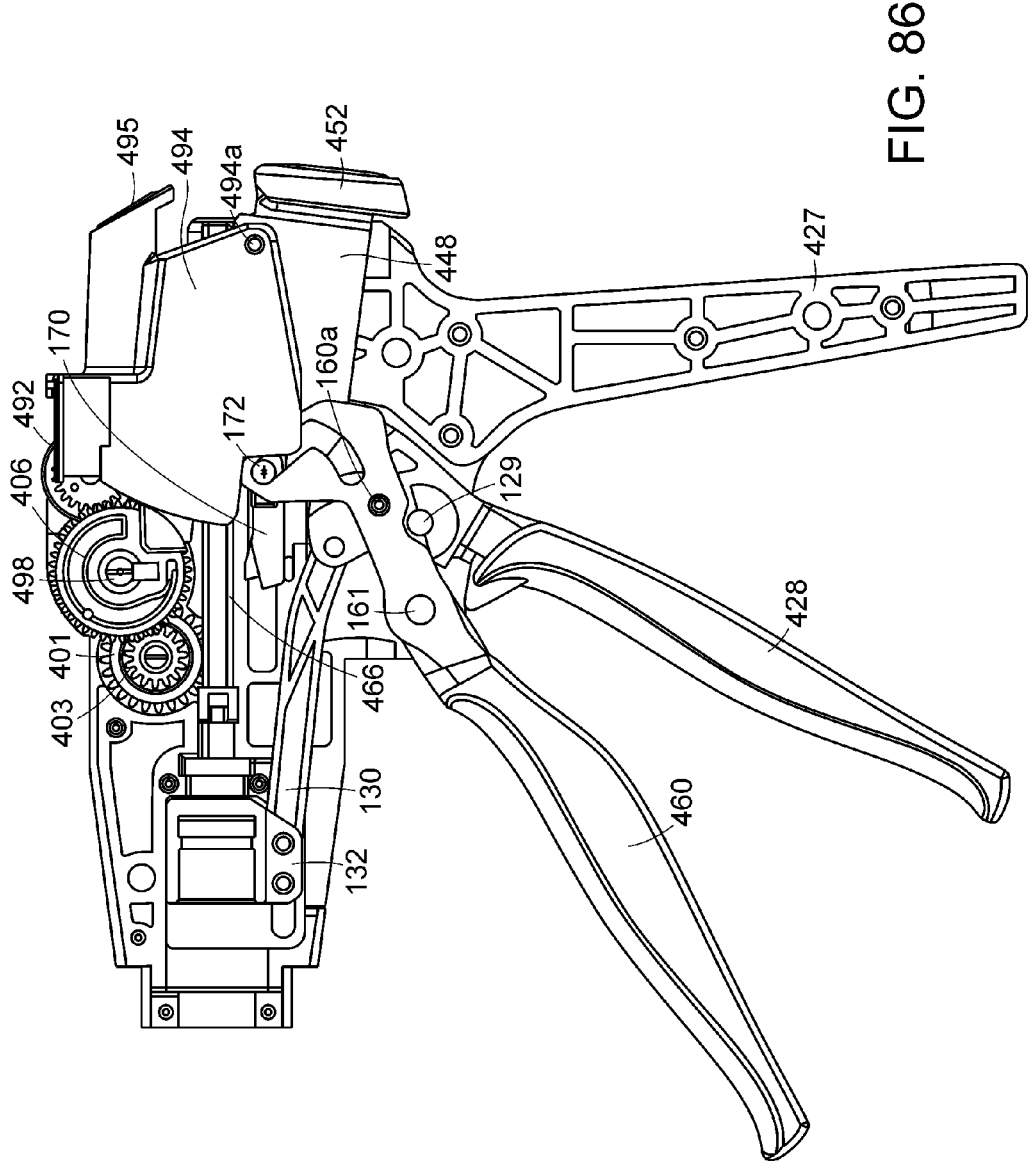
FIG. 86 is an elevational view of the surgical instrument of FIG. 68 illustrating the return carriage of FIG. 76 rotated upwardly into an unactuated position and also illustrating the closure trigger in its unactuated position.
Figure 87:
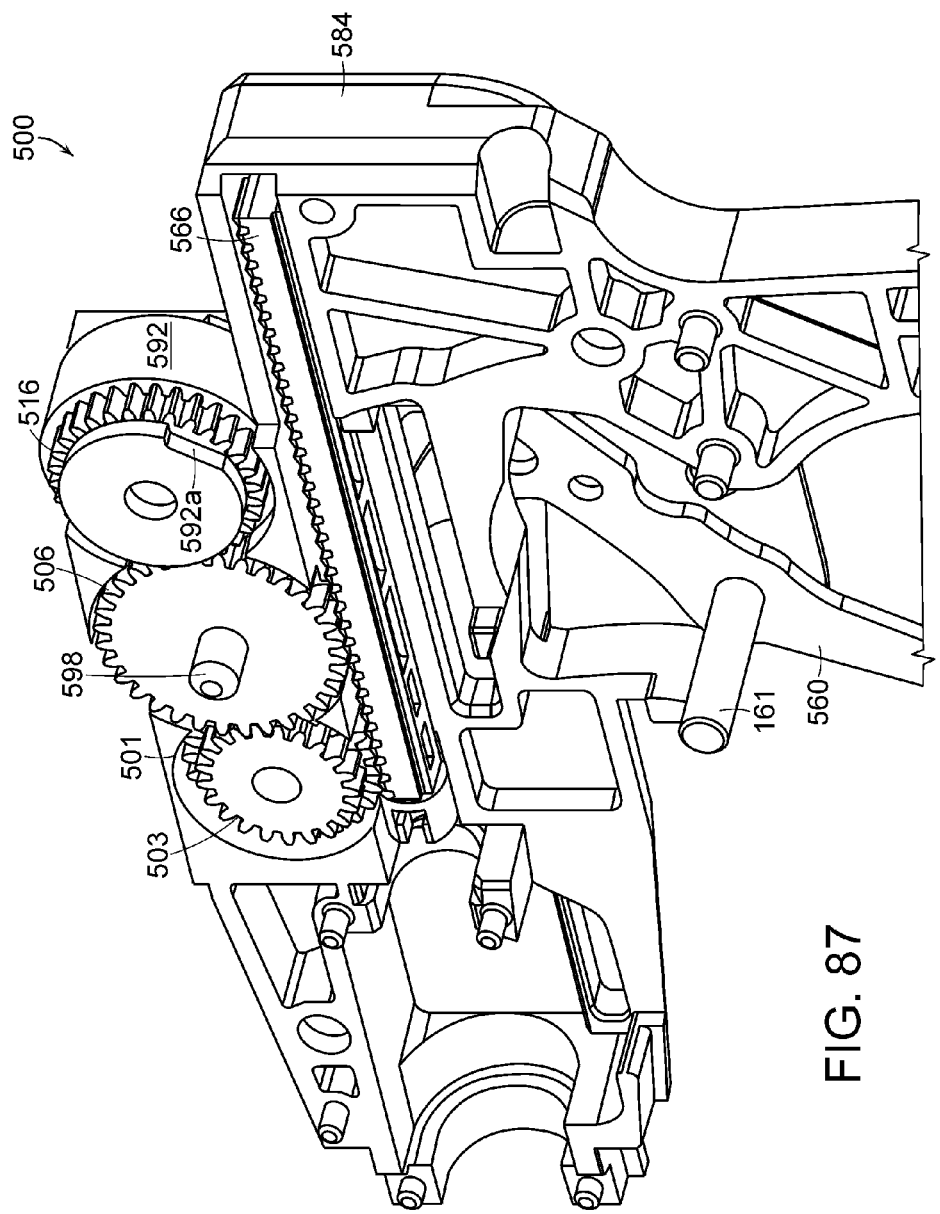
FIG. 87 is a perspective view of a surgical instrument in accordance with an alternative embodiment of the present invention with some components of the surgical instrument removed.

In at least one embodiment, referring to FIGS. 71 and 84, spur gear 416 can be mounted to or integrally-formed with indicator gear 492 such that, when spur gear 416 is rotated by key gear 406 as outlined above, indicator gear 492 can be rotated by spur gear 416. Thus, in at least one such embodiment, the forward advancement of firing member 466 can rotate indicator gear 492 about an axis defined by aperture 407. In various embodiments, indicator gear 492 can include at least one indicium thereon, such as letters, numbers, and/or any other suitable symbols, for example, for displaying the number of times that firing trigger 460 has been actuated, for example. In at least one such embodiment, the housing of the surgical instrument can include a window or aperture therein wherein a numeral "1", for example, on indicator gear 492 can be aligned with the window after a first actuation of firing trigger 460. Similarly, a numeral "2", for example, on indicator gear 492 can be aligned with the window after a second actuation of firing trigger and, correspondingly, a numeral "3", for example, can be aligned with the window after a third actuation. Alternatively, in at least one embodiment, indicator gear 492 can include indicia thereon which can correspond to the number of remaining actuations which are necessary to fully advance firing member 466, the cutting member, and/or the staple driver relative to the end effector.

Figure 76:
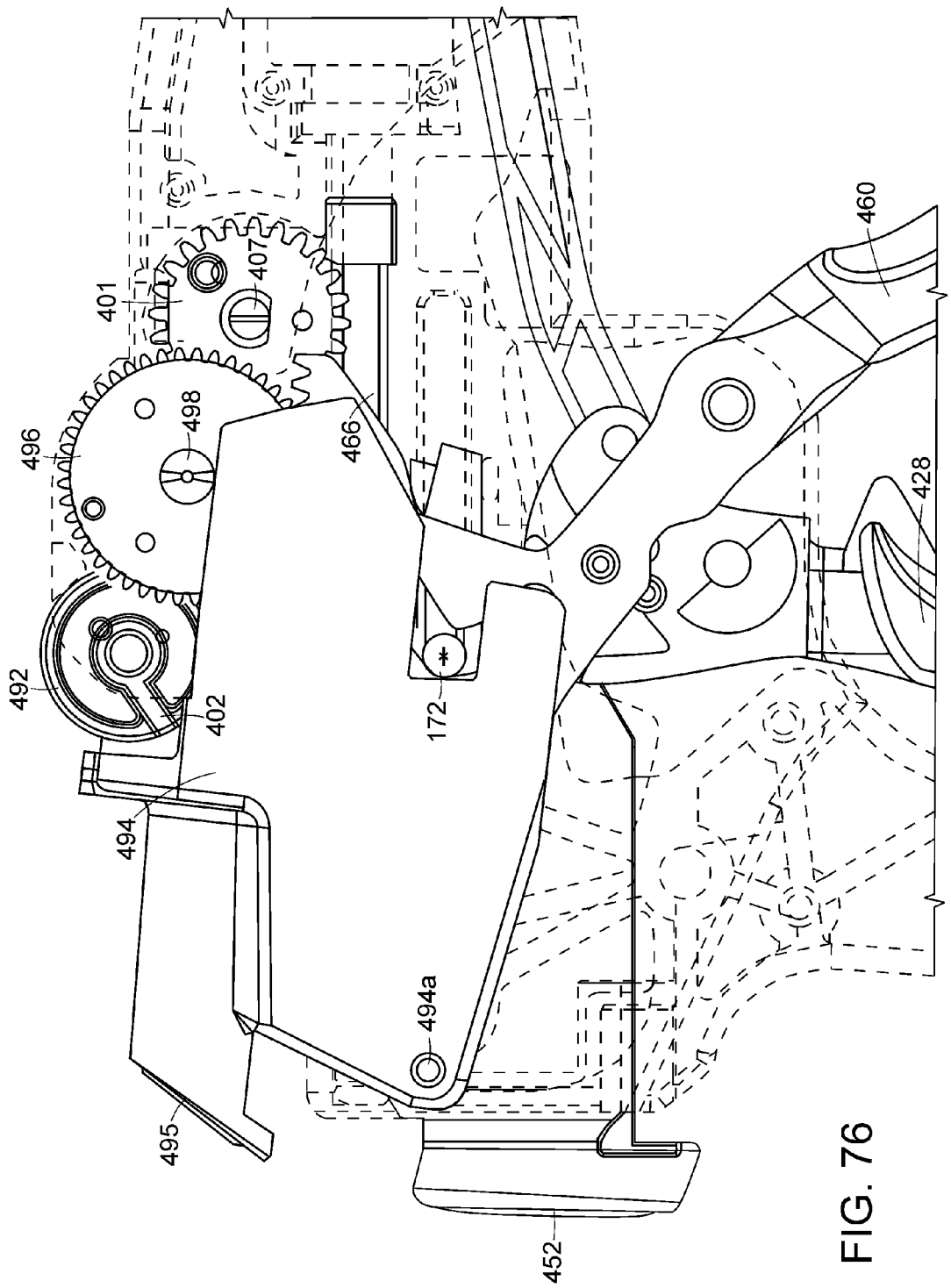
FIG. 76 is another elevational view of the surgical instrument of FIG. 68 illustrating a return carriage of the reversing mechanism after it has been rotated downwardly into an actuated position.

After firing member 466 has been fully advanced relative to the end effector, or at least suitably advanced, return carriage 494 can be rotated downwardly, referring to FIGS. 76 and 82, in order to operably couple the reversing drive, firing trigger 460, and firing member 466. In various embodiments, return carriage 494 can be rotated about pin 494a such that return carriage 494 no longer contacts, or at least substantially contacts, return pin 498. Thereafter, referring to FIGS. 77 and 78, spring 400 can slide or displace return pin 498 toward trigger gear 496 and position at least a portion of key 499 within cavity 497. In at least one such embodiment, referring to FIG. 78, spring 400 can be positioned intermediate frame 484 and key 499 of return pin 498 such that, when return carriage 494 no longer contacts end 498a, spring 400 can expand and displace key 499 into cavity 497. In various embodiments, referring to FIG. 80, return carriage 494 can also operably disengage the firing drive from firing member 466 when return carriage 494 is rotated downwardly as described above. More particularly, referring to FIG. 81, return carriage 494 can contact end 220 of firing pin 172 such that firing pin 172 can be slid toward pawl 170 and, as also described above, firing pin 172 can include key 222 extending therefrom which can engage recess 173 in pawl 170 to prevent pawl 170 from being pivoted upwardly to engage firing member 466. Thus, when pawl 170 is prevented from operably engaging firing member 466, the firing drive may no longer engage firing member 466 and the reversing drive can retract firing member 466 without interference from the firing drive.

Further to the above, in various embodiments, return carriage 494 can be rotated downwardly manually by a surgeon or by another clinician, for example. In various embodiments, referring generally to FIGS. 68 and 82, the surgeon can apply a force to button portion 495 such that return carriage 494 can be pivoted downwardly about an axis defined by pin 494a. Such a force can be applied after a predetermined amount of actuations of the firing trigger although, in various embodiments, such a force can be applied before the predetermined amount of actuations of the firing trigger is reached. In addition to or in lieu of the above, at least one of the gears of the reversing mechanism can be configured to contact return carriage 494 after a predetermined number of actuations of firing trigger 460. In various embodiments, referring to FIG. 76, indicator gear 492 can include cam 402 which can be configured to contact a portion of return carriage 494 and apply a force thereto upon the third actuation of firing trigger 460. In at least one such embodiment, the advancement of firing member 466 can rotate indicator gear 492 a predetermined amount upon each actuation of trigger 460 such that cam 402 can contact carriage 494 upon the third, or final, stroke of trigger 460 which advances firing member 466. In effect, indicator gear 492, or any other suitable gear of the reversing mechanism, can be configured to be rotated a predetermined amount before switching the surgical instrument from an 'advancing' operating mode to a 'reversing' operating mode.

Once return pin 498 has been operably engaged with trigger gear 496 and firing pin 172 has been engaged with pawl 170 in order to prevent pawl 170 from operably engaging firing member 466 as described above, firing trigger 460 can be actuated once again in order to retract firing member 466. In at least one such embodiment, the subsequent actuation of firing trigger 466 can rotate trigger gear 492 and, owing to the operative engagement between trigger gear 492 and return pin 498, trigger gear 492 can rotate key gear 406. More particularly, referring to FIGS. 71, 77, and 78, return pin key 499 can be operatively engaged with drive surface 410 of trigger gear 492 in addition to a sidewall of cavity 406a within key gear 406 such that the rotation of trigger gear 496 is transmitted to key gear 406 via return pin 498. In various embodiments, referring again to FIG. 71, the rotation of key gear 406 can rotate intermediate gear 403 and pinion gear 401 in order to drive, or retract, firing member 466 proximally. In effect, when trigger 460 is operably engaged with the reversing drive, pinion gear 401 can be rotated in a direction which is opposite the direction in which it is rotated when firing trigger 460 is operably engaged with the firing drive. In various embodiments, the size, or pitch radius, of gears 401, 403, 406, 492, 496 and gear portion 158 of trigger gear 460, for example, can be selected such that firing member 466 can be returned by one actuation of trigger 460, although other embodiments are envisioned in which more or less than one actuation of trigger 460 can be utilized.

After firing member 466 has been retracted, return carriage 494 can be pivoted upwardly into it its unactuated position in order to reset the surgical instrument. In various embodiments, referring to FIGS. 85 and 86, the surgeon or clinician can apply a force to button portion 452 of trigger lock 448 such that trigger lock 448 can rotate upwardly and abut return carriage 494. In such circumstances, trigger lock 448 can rotate return carriage 494 upwardly as well and position carriage 494 in its unactuated position. In doing so, return carriage 494 can engage end 221 of firing pin 172 in order to slide firing pin 172 away from pawl 170 and disengage key 222 from recess 173 in pawl 170 thereby allowing pawl 170 to re-engage firing member 466 upon a subsequent actuation of firing trigger 460. Return carriage 494 can also re-engage end 498a of return pin 498 when it is rotated upwardly so as to slide key 499 away from trigger gear 496, thereby operably disengaging return pin 498 from trigger gear 496 and, correspondingly, operably disengaging the reversing drive from firing member 466. Thereafter, the spent staple cartridge can be detached from the surgical instrument and replaced with a new staple cartridge such that the surgical instrument can be used once again.

In various alternative embodiments, a surgical instrument can include a clutch configured to operably engage and disengage a reversing drive with a firing member. In at least one embodiment, referring to FIGS. 87-94, surgical instrument 500, similar to surgical instrument 400, can include firing trigger 560 which can be configured to drive a firing pin and a pawl of a firing drive, for example, so as to advance firing member 566, a cutting member, and/or staple driver relative to an end effector. In various embodiments, also similar to the above, the surgical instrument can further include a reversing drive comprising pinion gear 501, intermediate gear 503, key gear 506, and spur gear 516. In at least one such embodiment, owing to the operative engagement between rack portion 505 of firing member 496 and pinion gear 501, the advancement of firing member 466 can rotate gears 501, 503, 506 and 516 as described in greater detail below. In various embodiments, return, or key, pin 598 can be mounted to or integrally formed with key gear 506 such that rotational motion is transmitted therebetween. In at least one such embodiment, referring to FIG. 89, at least a portion of return pin 598 can include a non-circular cross-section including flat portion 598b, for example, which can, referring to FIG. 92, be slidingly received within a correspondingly-shaped aperture 506b in key gear 506. Also similar to the above, firing trigger 560 can include gear portion 558 which can be operatively engaged with trigger gear 596 such that gear portion 558 can rotate trigger gear 596 about an axis defined by key pin 598, as described in greater detail below.

Figure 88:
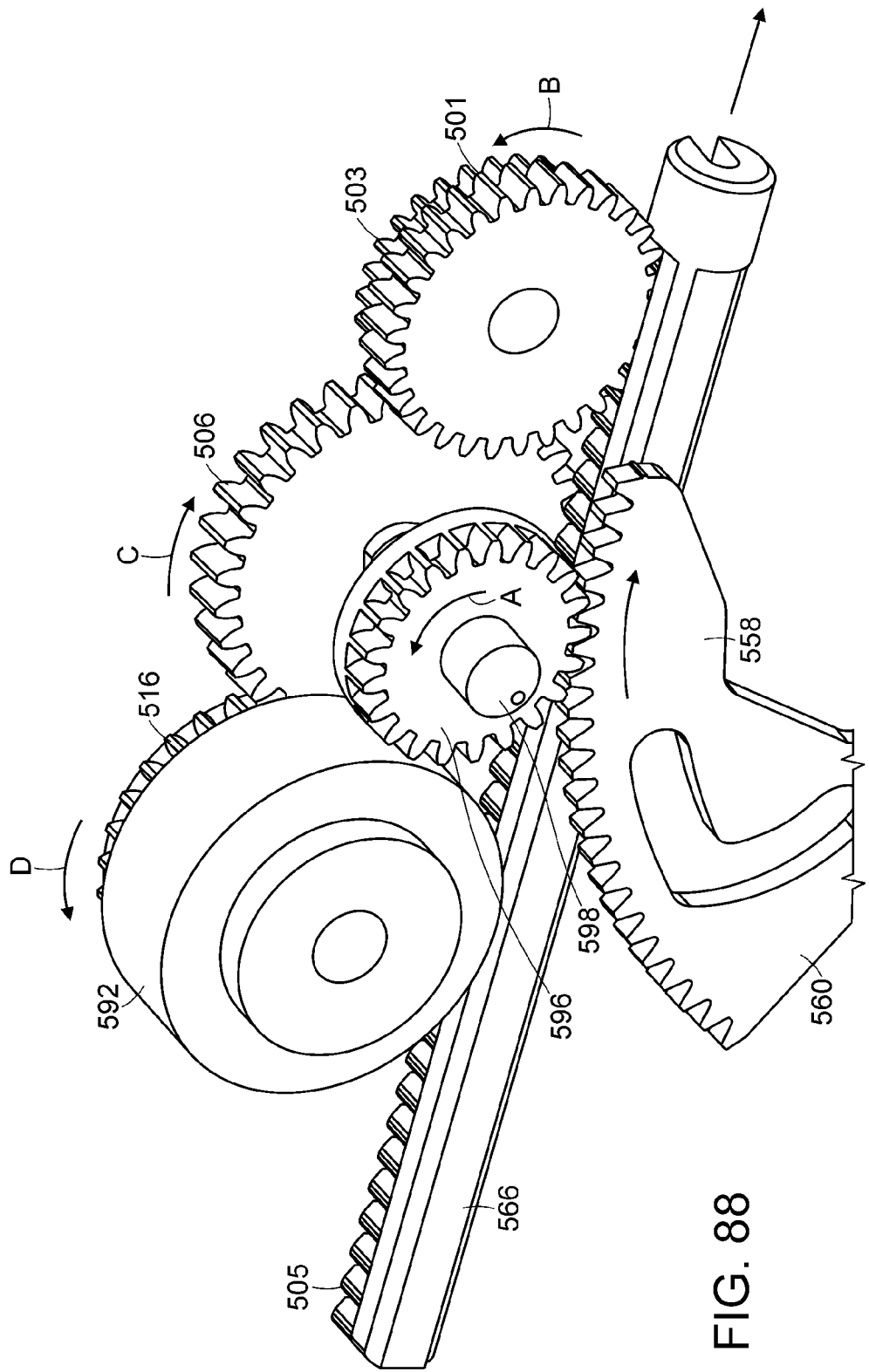
FIG. 88 is a perspective view of a reversing mechanism of the surgical instrument of FIG. 87 including a gear train illustrating the directions in which the gears of the gear train can rotate when a firing member of the surgical instrument is advanced.
Figure 89:
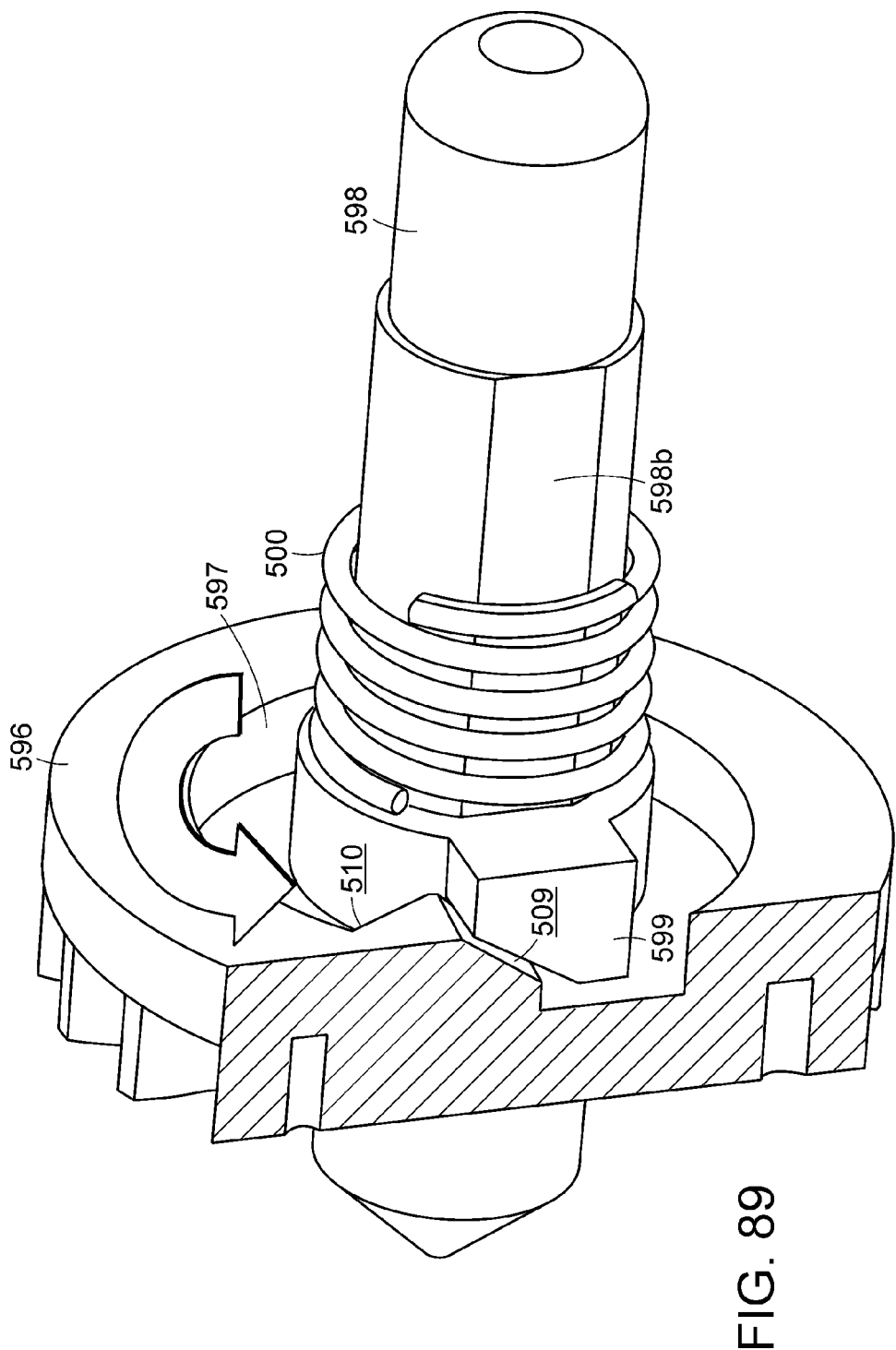
FIG. 89 is a perspective view of a trigger gear and a return pin of the reversing mechanism of FIG. 88 illustrating the trigger gear in cross-section.
Figure 90:
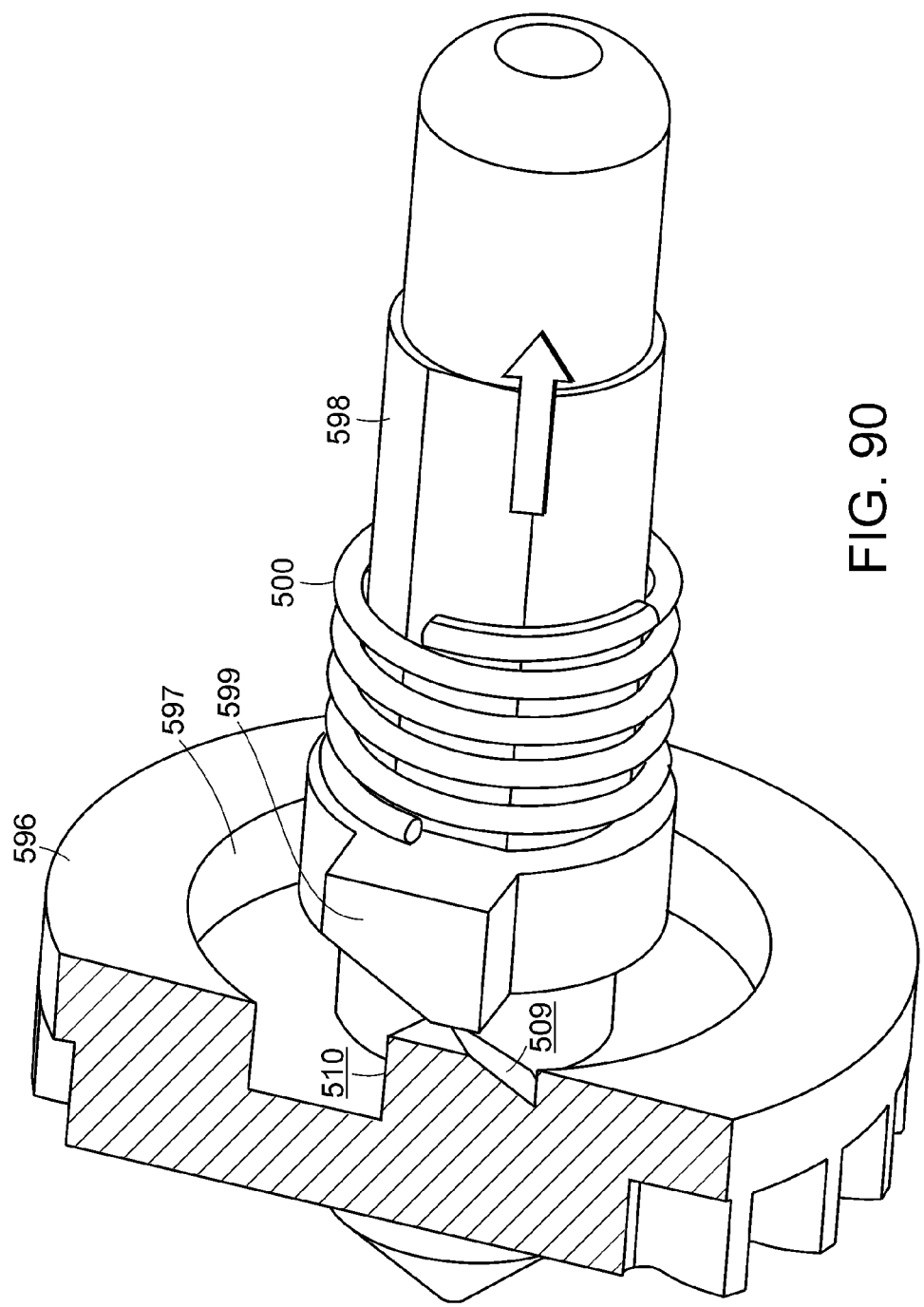
FIG. 90 is another perspective view of the trigger gear and return pin of FIG. 89 illustrating the return pin out of operative engagement with the trigger gear.
Figure 91:
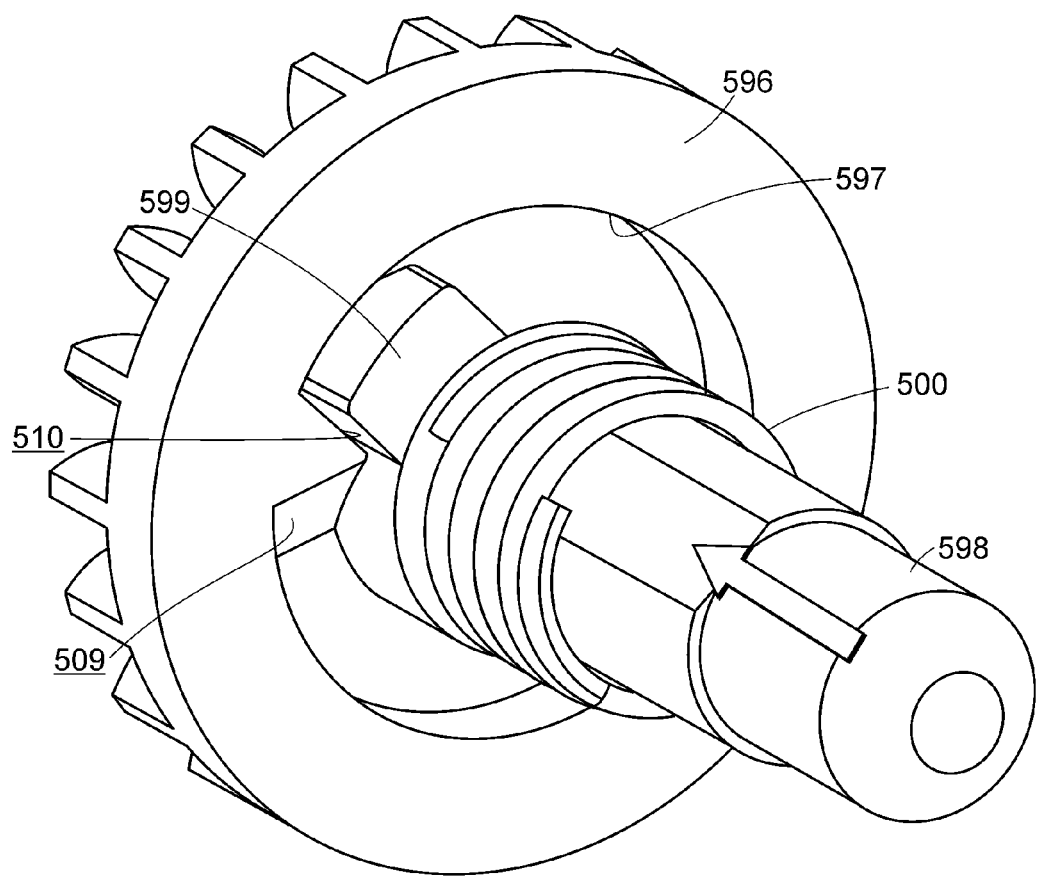
FIG. 91 is a perspective view of the trigger gear and return pin of FIG. 89 illustrating the return pin re-engaged with the trigger gear.

In use, upon the first actuation of firing trigger 560, firing trigger 560 can, similar to the above, rotate trigger gear 596 about key pin 598 without directly transmitting rotational movement to key pin 598 via trigger gear 596. Referring to FIG. 88, the first actuation of firing trigger 560 can rotate trigger gear 596 in a direction indicated by arrow "A", i.e., clockwise for the purposes of this discussion. Also upon the first actuation of firing trigger 560, firing member 566 can rotate pinion gear 501 and intermediate gear 503 in a direction indicated by arrow "B", key gear 506 in a direction indicated by arrow "C", and spur gear 516 and indicator gear 592 in a direction indicated by arrow "D". In various embodiments, as illustrated in FIG. 88, trigger gear 596 and key gear 506 can be rotated in opposite directions during the first actuation of trigger 560 and may not operably engaged with each other until after the first actuation of trigger 560 as described further below. When trigger 560 is released or returned to its unactuated position after its first actuation, the pawl of the firing drive, for example, can be disengaged from the firing member 566 such that pinion gear 501 and key gear 506, for example, are not rotated, or at least substantially rotated, when trigger 560 is returned to its starting, or unactuated, position. Trigger gear 596, however, can be rotated by firing trigger 560 when trigger 560 is returned to its unactuated position and, as a result, trigger gear 596 can be rotated relative to key gear 506 as illustrated in FIG. 89. As trigger 560 is returned to its unactuated position, as described above, inclined surface 509 of trigger gear 596 can contact clutch dog 599 of key pin 598 and displace key pin 598 away from trigger gear 596 as illustrated in FIG. 90. Thereafter, trigger gear 596 can be further rotated by firing trigger 560 until inclined surface 509 has entirely passed by clutch dog 599 and spring 500 can bias clutch dog 599 into a position behind drive surface 510 as illustrated in FIG. 91. At such point, firing trigger 560 may be in its unactuated position.

Figure 92:
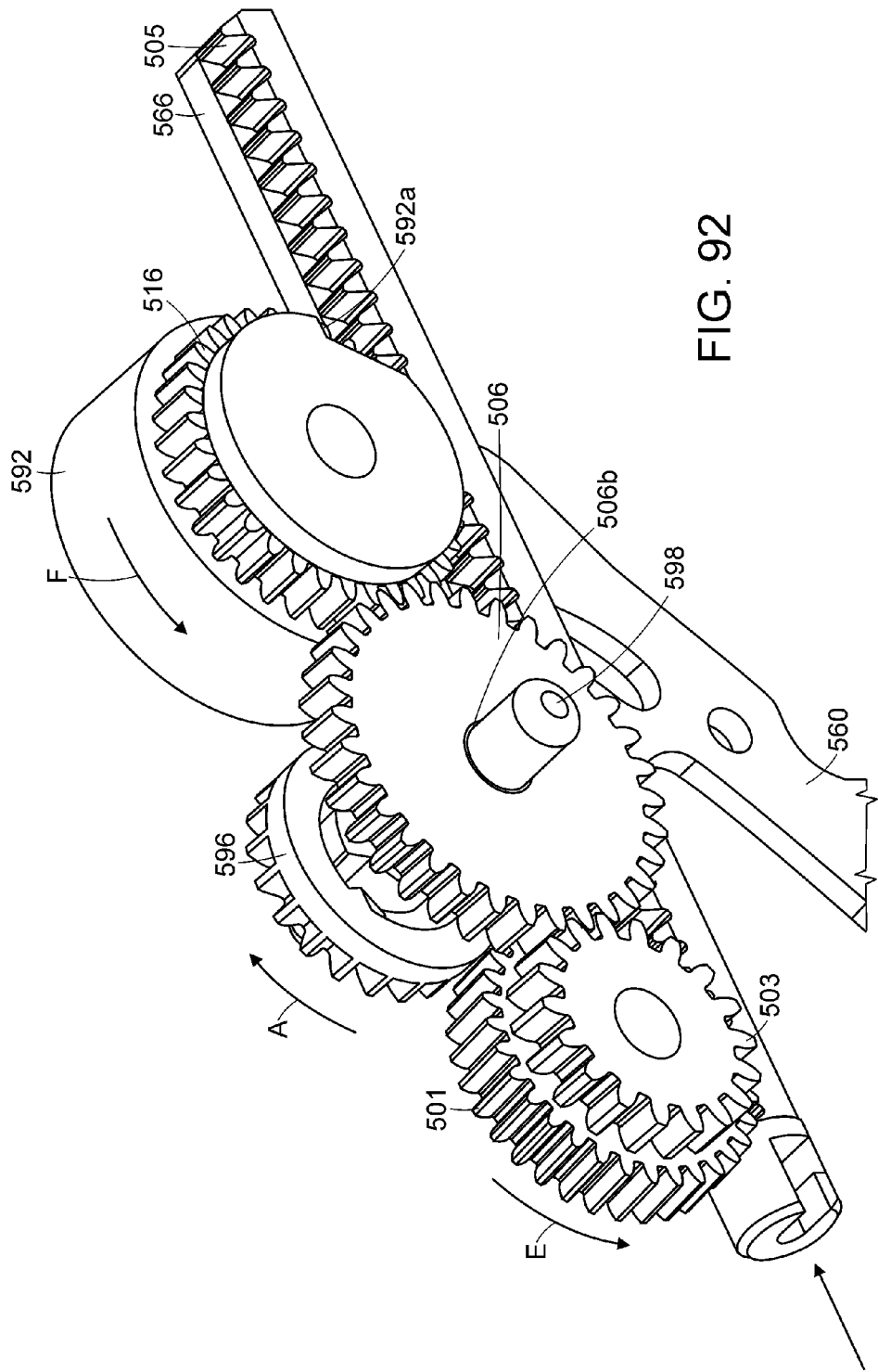
FIG. 92 is a perspective view of the reversing mechanism of FIG. 88 illustrating the directions in which the gears of the gear train rotate when the firing member is retracted.
Figure 93:
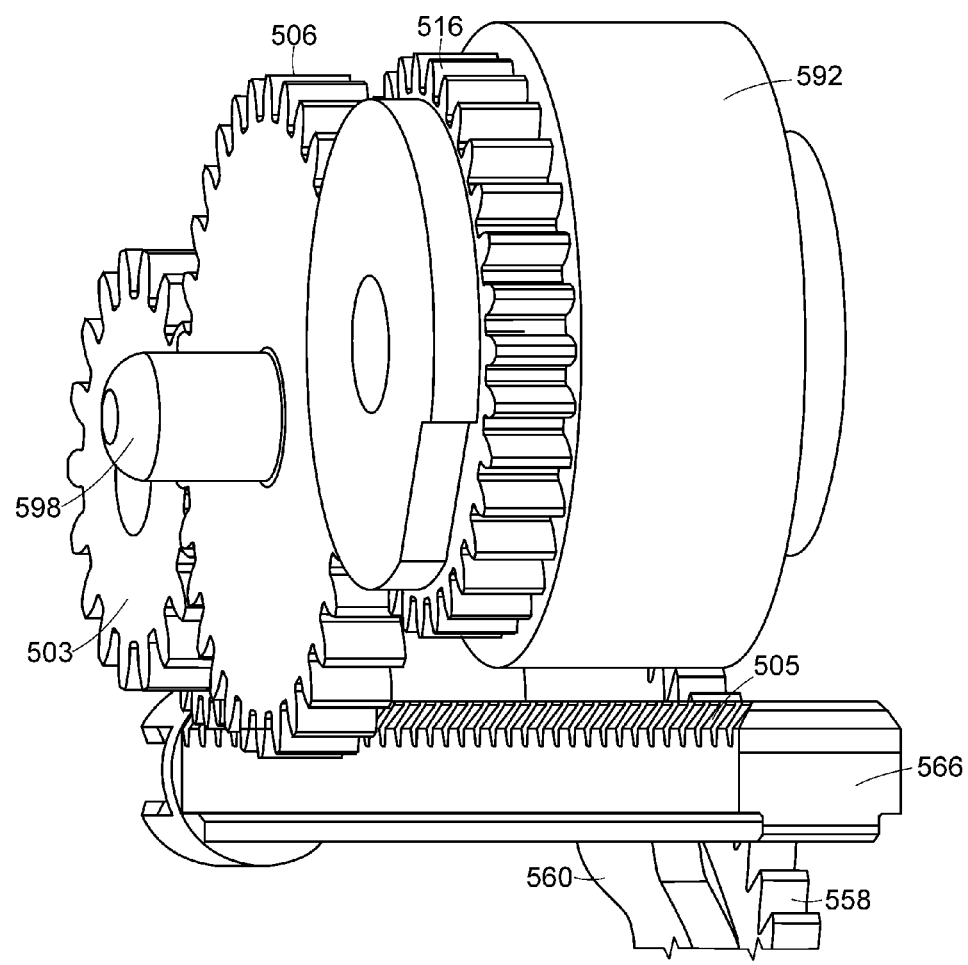
FIG. 93 is a further perspective view of the reversing mechanism of FIG. 88.

Upon a second actuation of firing trigger 560, the pawl of the firing drive can remain disengaged from firing member 566 although the second actuation of firing trigger 560 can once again rotate trigger gear 596 in a direction indicated by arrow A, referring to FIG. 92. Owing to the position of dog 599 behind drive surface 510 of trigger gear 596, the rotation of trigger gear 596 can cause key pin 598 and key gear 506 to rotate in a clockwise direction indicated by arrow A as well, i.e., in a direction opposite of arrow C. Correspondingly, key gear 506 can rotate pinion gear 501 and intermediate gear 503 in a direction indicated by arrow E, i.e., a direction opposite of arrow B, and also rotate indicator gear 592 in a direction indicated by arrow F, i.e., a direction opposite of arrow D. Owing to the rotation of pinion gear 501 in an opposite direction during the second actuation of trigger 560, pinion gear 501 can retract firing member 566 relative to the end effector and reposition, or at least substantially reposition, firing member 566 in its starting, or unactuated, position. Thereafter, firing trigger 566 can be released and returned to its unactuated position. In such circumstances, drive surface 510 of trigger gear 596 can be rotated away from clutch dog 599 and, whereas the pawl of the firing drive can still be operatively disengaged from firing member 566, key pin 598 and key gear 596 can remain in position. In order to reset the surgical instrument, the pawl of the firing drive can be released such that it can re-engage firing member 566 upon the next actuation of trigger 560. In such embodiments, the spent staple cartridge can be replaced such that the surgical instrument can be used once again.

Figure 94:
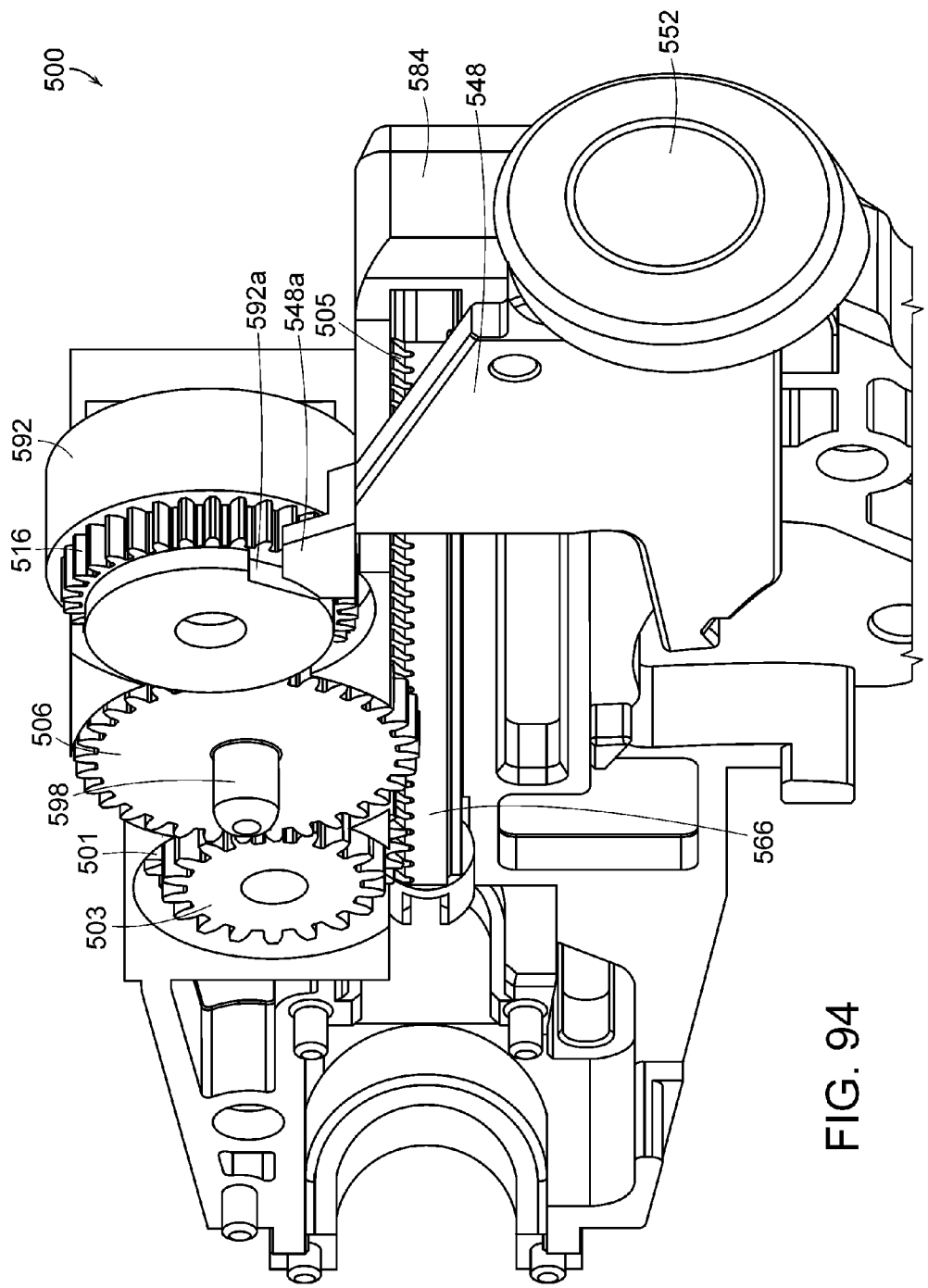
FIG. 94 is a perspective view of the surgical instrument of FIG. 87 illustrating a trigger lock which is configured to engage a gear of the reversing mechanism of FIG. 88 in addition to the trigger.

In various embodiments, referring to FIG. 94, surgical instrument 500 can further include trigger lock 548 which, similar to trigger lock 148 described above, can be utilized to hold a closure trigger in position. In at least one embodiment, trigger lock 548 can be rotated between actuated and unactuated positions to lock and unlock, respectively, a closure trigger such as closure trigger 428 (FIG. 68), for example. In at least one such embodiment, when trigger lock 548 is in its unactuated position, portion 548a of trigger lock 548 can be positioned within recess 592a of indicator 592 to prevent, or at least substantially prevent, the gear train and firing member 566 from being unintentionally motivated. Stated another way, when portion 548a is positioned within recess 592a, the firing and reversing drives described above can be rendered substantially inoperative and, as a result, firing member 566 cannot be substantially moved. When trigger lock 548 is moved into its actuated position to hold or lock the closure trigger in place, portion 548a of trigger lock 548 can be moved, or rotated, out of recess 592a such that the firing and reversing drives described above can be operated.

In various alternative embodiments, a surgical instrument can include a ratchet configured to operably engage and disengage a reversing drive with a firing member. In at least one embodiment, referring to FIGS. 95-100, surgical instrument 600 can include firing trigger 660 which can be configured to drive a firing pin and a pawl of a firing drive, for example, so as to advance firing member 666, a cutting member, and/or staple driver relative to an end effector, similar to the above. In various embodiments, also similar to the above, the surgical instrument can further include a reversing mechanism comprising pinion gear 601, key gear 606, and spur gear 616 where the advancement of firing member 666 can rotate gears 601, 606 and 616 owing to the operative engagement between rack portion 605 of firing member 696 and pinion gear 601. In various embodiments, return, or key, pin 698 can be mounted to or integrally formed with key gear 606 such that rotational motion can be transmitted therebetween. Also similar to the above, firing trigger 660 can include gear portion 658 which can be operatively engaged with trigger gear 696 such that gear portion 658 can rotate trigger gear 696 about an axis defined by key pin 698.

In use, upon the first actuation of firing trigger 660, firing trigger 660 can rotate trigger gear 696 about key pin 698 without directly transmitting rotational movement to key pin 698 and key gear 606. More particularly, referring to FIG. 97, trigger gear 696 can include aperture 696a which can be configured such that there is a clearance fit between key pin 698 and the sidewalls of aperture 696a and, as a result, key pin 698 can rotate therein. Furthermore, referring to FIG. 96, key gear 606 can include ratchet face 606c and trigger gear 696 can include ratchet face 696c which, when firing member 666 is being advanced by the firing drive, can be operably disengaged, or separated, from one another such that rotational movement is also not transmitted therebetween. After firing member 666 has been sufficiently advanced, similar to the above, return carriage 694 can be rotated downwardly about pin 694a, for example, such that return carriage 694, referring to FIG. 99, can be disengaged from end 698a of return pin 698. In such circumstances, as described in greater detail below, return pin 698 can be operatively engaged with trigger gear 696 and firing member 666 can be retracted.

Figure 95:
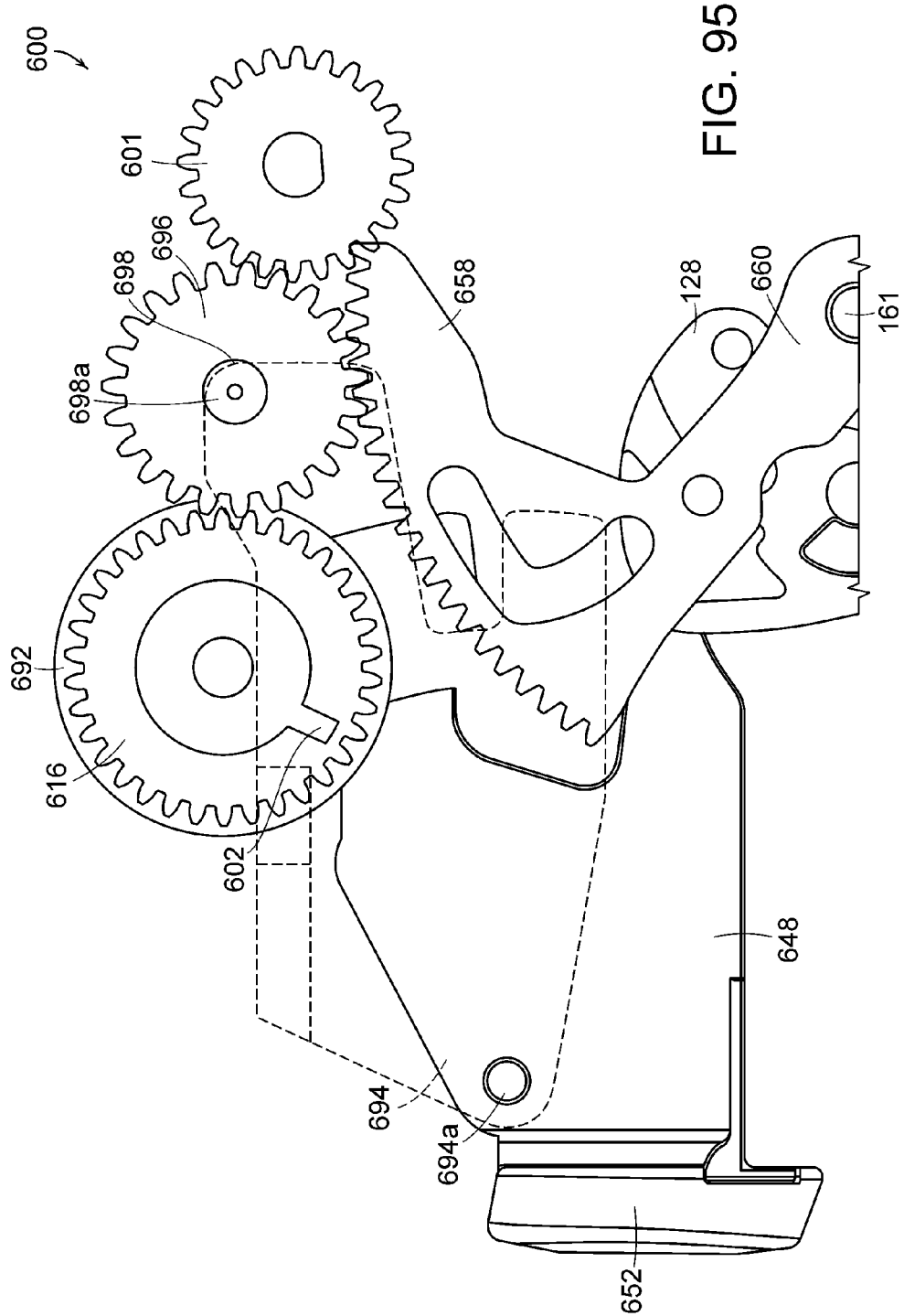
FIG. 95 is an elevational view of a reversing mechanism of a surgical instrument in accordance with an alternative embodiment of the present invention illustrating a return carriage in an unactuated position with some components of the surgical instrument removed.
Figure 96:
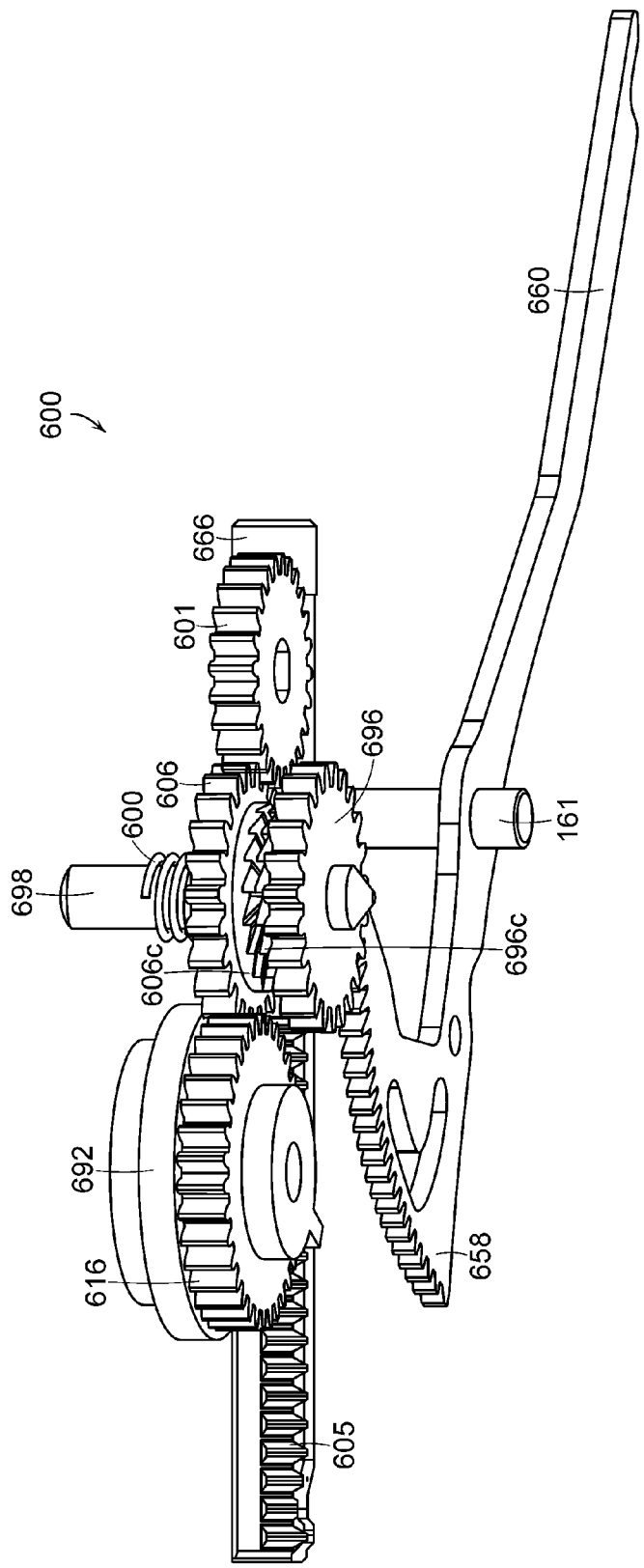
FIG. 96 is a perspective view of the reversing mechanism of FIG. 95 illustrating a trigger gear having a ratchet face and, in addition, a key gear having a ratchet face with some additional components of the surgical instrument removed.
Figure 98:
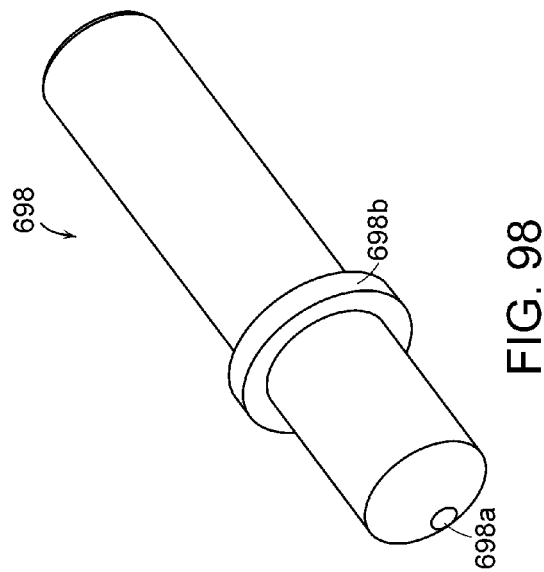
FIG. 98 is a perspective view of a return pin of the reversing mechanism of FIG. 95.
Figure 97:
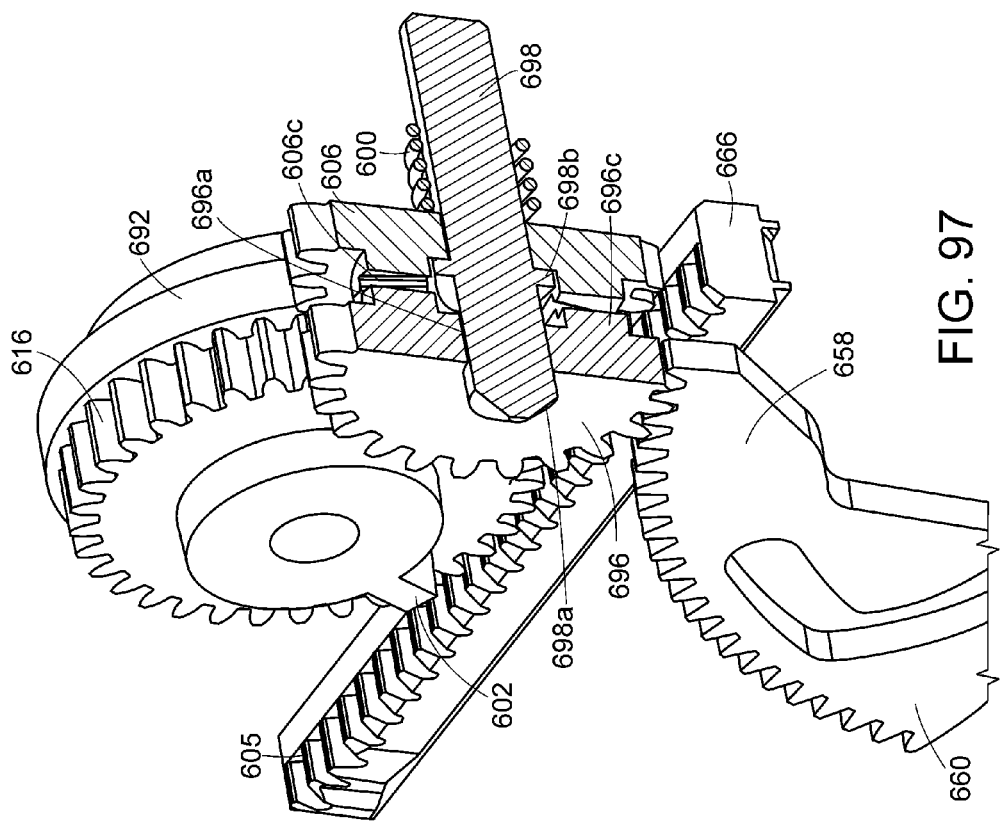
FIG. 97 is a cross-sectional view of the reversing mechanism of FIG. 95 illustrated in the configuration of FIG. 96.

In various embodiments, further to the above, return carriage 694 can be manually moved between its unactuated position illustrated in FIG. 95 to its actuated position illustrated in FIG. 99, similar to return carriage 494. In addition to or in lieu of the above, at least one of the gears in the gear train, such as indicator gear 692, for example, can include a cam, such as cam 602, for example, which can contact return carriage 694 and rotate it downwardly after a predetermined amount of actuations of firing trigger 660. Thereafter, in either event, key gear 606 can be slid toward trigger gear 696 by spring 600. More particularly, referring to FIG. 100, spring 600, which can be positioned, or compressed, intermediate key gear 606 and a frame of the surgical instrument, for example, such that, once return carriage 694 has been disengaged from end 698a of return pin 698, spring 600 can expand to slide key gear 606 toward trigger gear 696. Furthermore, in at least one embodiment, return pin 698 can be mounted to or integrally formed with key gear 606 such that return pin 698 can be slid toward trigger gear 696 with key gear 606. In at least one embodiment, referring to FIG. 97, return pin 698 can include collar 698b in which key gear 606 can abut and push return pin 698 toward trigger gear 696.

Figure 100:
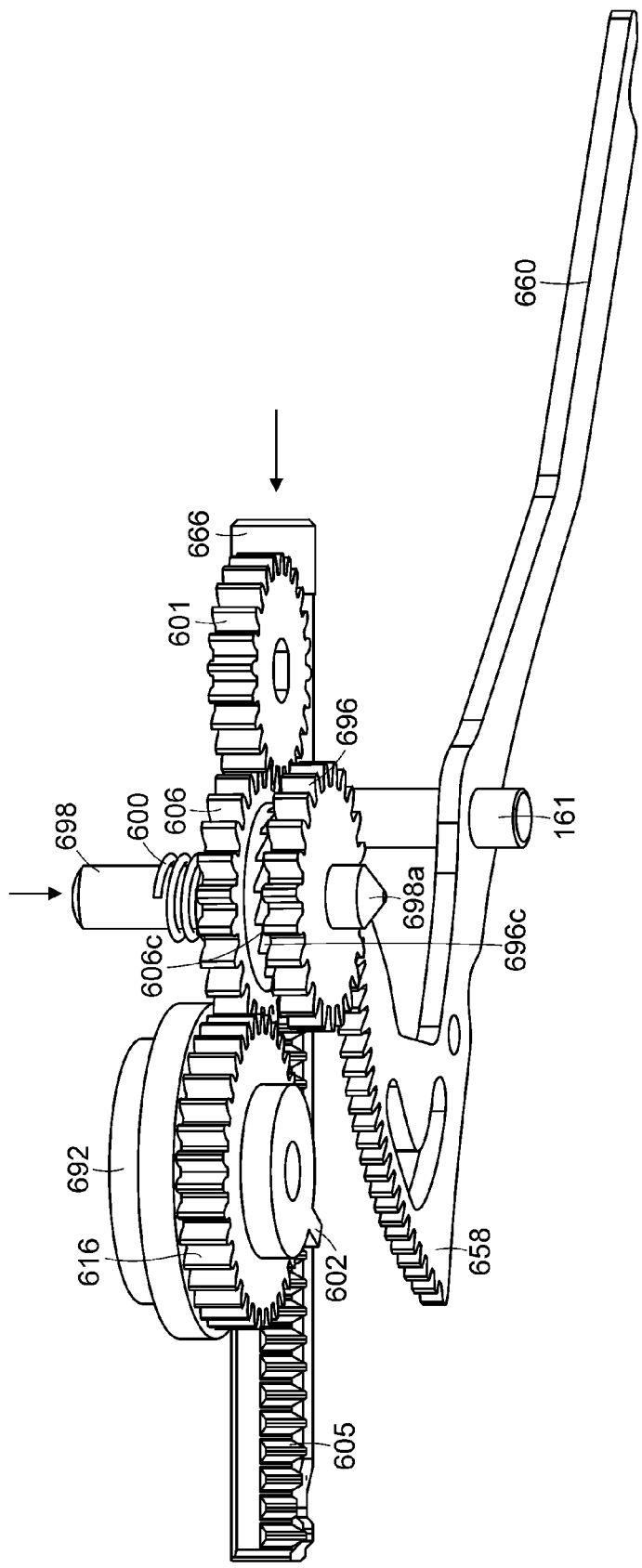
FIG. 100 is a perspective view of the reversing mechanism of FIG. 95 wherein the ratchet faces of the trigger and key gears are engaged with one another.

In various embodiments, as a result of the above, ratchet faces 606c and 696c can be positioned against one another by spring 600 when return carriage 694 is rotated downwardly into its actuated position as illustrated in FIG. 100. In at least one embodiment, referring to FIG. 97, ratchet faces 606c and 696c can each include teeth extending therefrom which can cooperate to transmit rotational movement therebetween. In use, upon a subsequent actuation of firing trigger 660, firing trigger 660 can rotate trigger gear 696, and key gear 606, in a clockwise direction indicated by arrow A, referring to FIG. 99, wherein key gear 606 can rotate pinion gear 601 in a direction indicated by arrow E. As a result of the operative engagement between pinion gear 601 and rack portion 605 of firing member 666, for example, pinion gear 601 can retract firing member 666, the cutting member, and/or the staple driver relative to the end effector, similar to the above. In at least one embodiment, gears 601, 606, and 696 and gear portion 658 can be configured such that firing member 666 can be fully retracted with one actuation of trigger 460.

Thereafter, firing trigger 460 can be released and/or returned to its unactuated position. In at least one such embodiment, ratchet faces 606c and 696c can include beveled surfaces which can allow ratchet faces 606c and 696c to rotate relative thereto when trigger 660 is returned to its unactuated position. In such circumstances, trigger gear 696 can be rotated in a counterclockwise direction, i.e., in a direction opposite of that indicated by arrow A. In at least one embodiment, ratchet faces 606c and 696c can rotate relative to each other even though the ratchet faces are in contact with one another. Thereafter, return carriage 694 can be rotated upwardly such that it can contact end 698a of return pin 698 and slide return pin 698 and key gear 606 away from trigger gear 696. In such circumstances, as a result, ratchet face 606c can be disengaged from ratchet face 696c such that they are no longer operably engaged with one another. In at least one such embodiment, return carriage 694 can apply a force to end 698a of return pin 698, wherein the force can be transmitted to key gear 606 via collar 698b in order to displace key gear 606 away from trigger gear 696.

Figure 103:
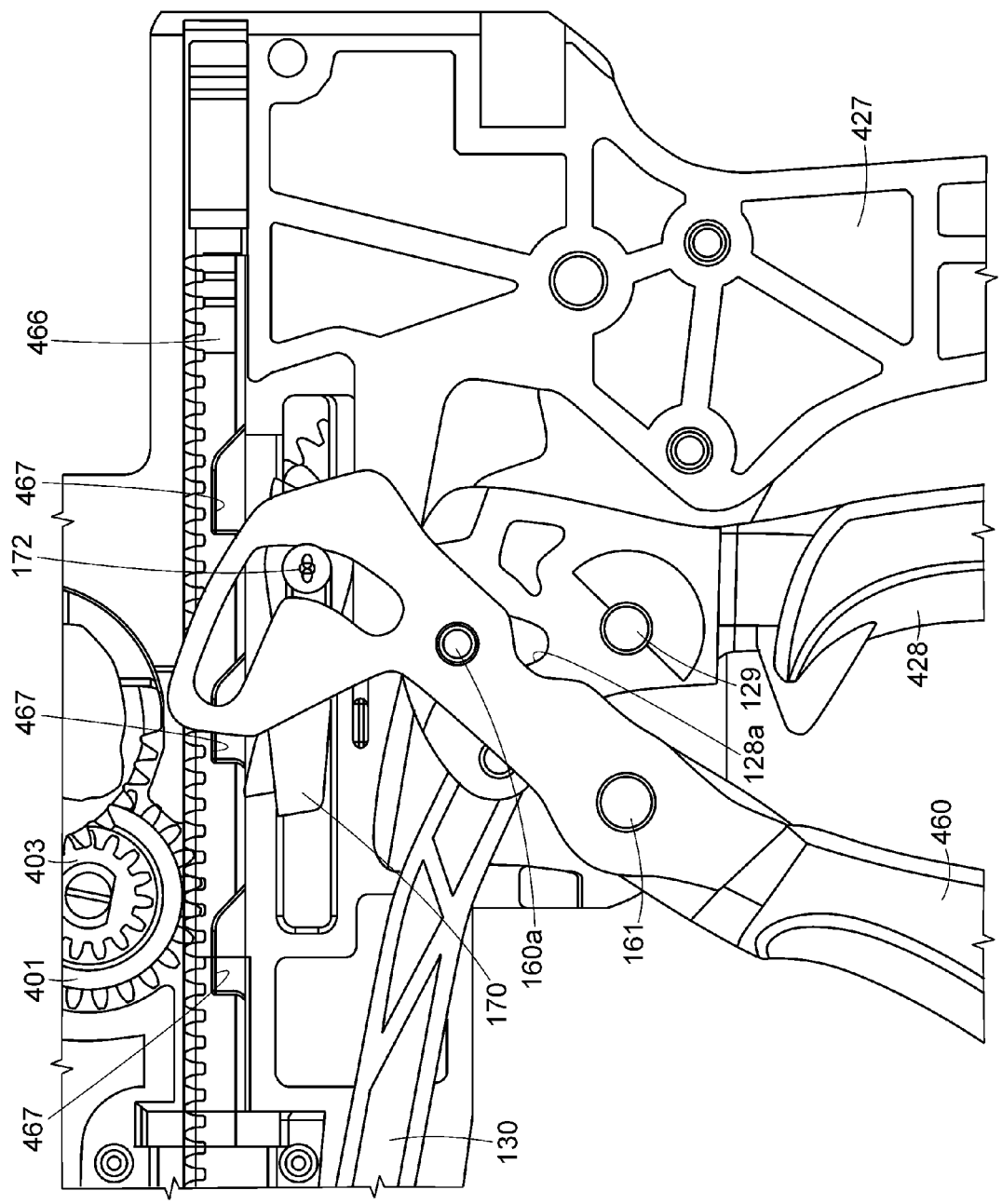
FIG. 103 is an elevational view of the surgical instrument of FIG. 101 illustrating misalignment between the pawl and a recess in the firing member when the firing member unintentionally backs-up relative to its intended position.

As described above, surgical instruments in accordance with the present invention can include a firing drive having a pawl which can be configured to advance a firing member relative to an end effector. In various embodiments, as described above, pawl 170 can be pivoted upwardly to engage a recess 467 in firing member 466, for example, and advance firing member 466 distally. Thereafter, referring once again to FIGS. 101 and 102, pawl 170 can be pivoted downwardly and retracted proximally relative to firing member 466 so as to reposition pawl 170 such that pawl 170 can be pivoted upwardly once again to engage another recess 467 and further advance firing member 466. In various circumstances, though, pawl 170 may not be able to engage a recess 467 when it is pivoted upwardly as illustrated in FIG. 103. Such circumstances may arise when firing member 466, for example, is unintentionally moved by forces or energy transmitted through and/or stored within the various mechanisms of the surgical instrument. If the pawl is unable to re-engage the firing member, the surgical instrument may be rendered inoperable and, as a result, the surgical instrument may have to be manually reset. In order to ameliorate this condition, surgical instruments in accordance with various embodiments of the present invention can include an anti-backup mechanism which can retain, or at least substantially retain, the firing member in position.

Figure 104:
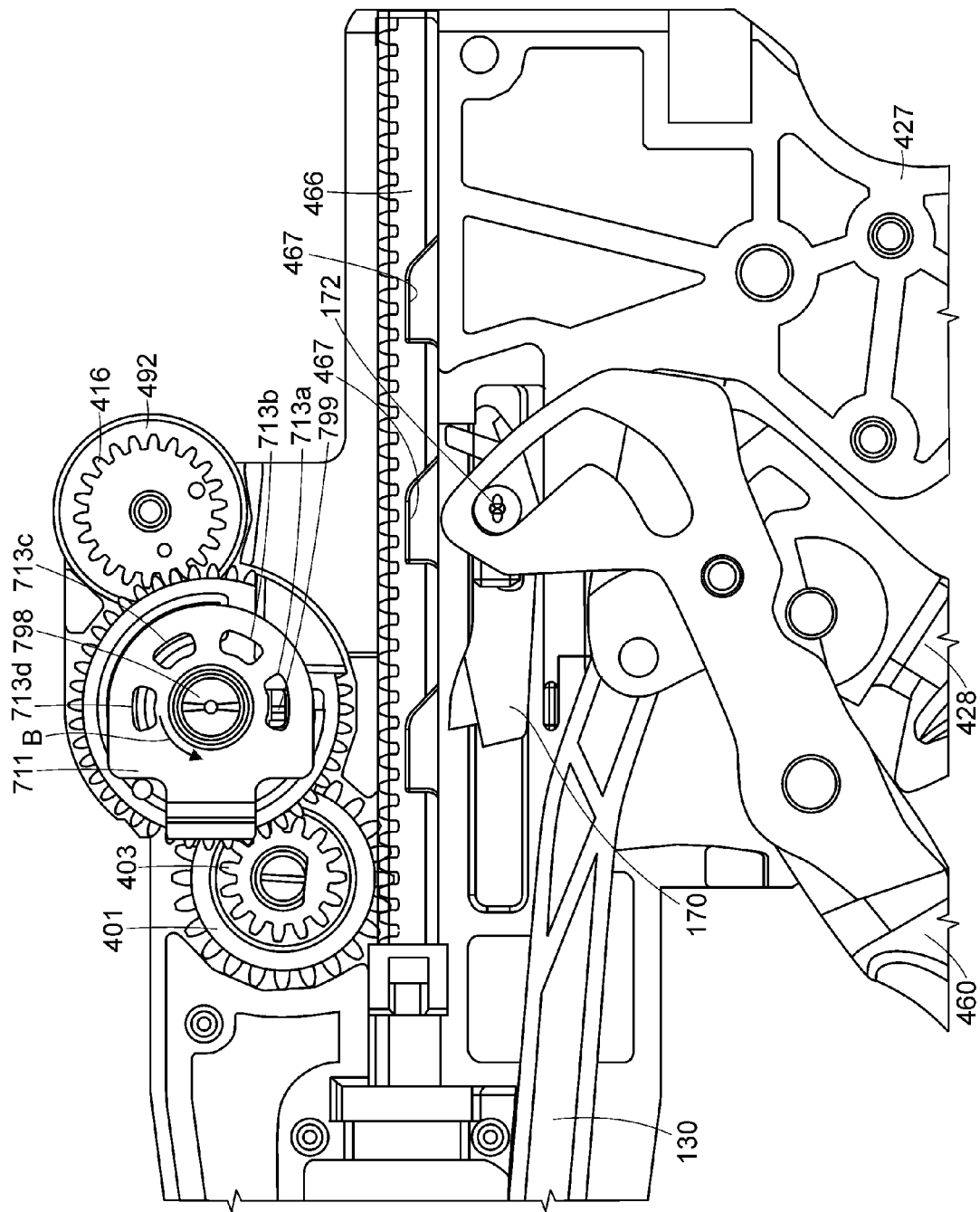
FIG. 104 is an elevational view of a surgical instrument in accordance with an alternative embodiment of the present invention including an anti-backup mechanism with some components of the surgical instrument removed.

In various embodiments, referring to FIG. 104, an anti-backup mechanism can be configured to hold at least a portion of a firing drive and/or reversing drive in position while pawl 170 is retracted relative to firing member 466, for example. In at least one embodiment, an anti-backup mechanism can include indexing mechanism, or plate, 711 which can be configured to permit return pin 798 to rotate in a counterclockwise direction indicated by arrow B when firing member 466 is advanced, as described above, yet prohibit, or at least substantially prohibit, return pin 798 from rotating in a clockwise direction, i.e., in a direction opposite of arrow B. In effect, as return pin 798 is rotatably engaged with key gear 406, and key gear 406 is operably engaged with firing member 466 via intermediate gear 403 and pinion gear 401, indexing mechanism 711 can also prevent, or at least substantially prevent, firing member 466 from being retracted proximally. Furthermore, as described in greater detail below, indexing mechanism 711 can also inhibit firing member 466 from being unintentionally advanced distally as well.

Figure 106:
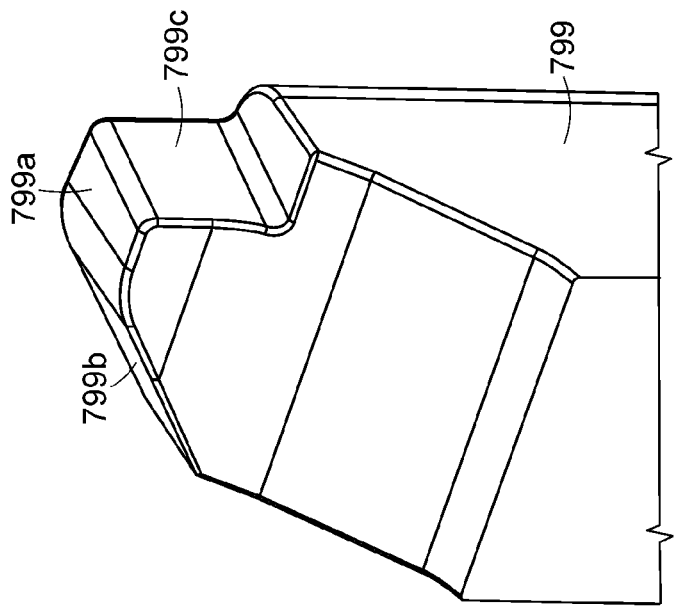
FIG. 106 is a detail view of a key extending from the return pin of FIG. 105.
Figure 105:
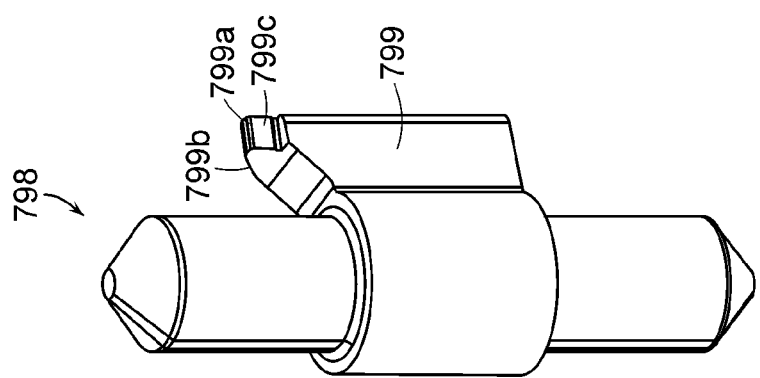
FIG. 105 is a perspective view of a return pin of the anti-backup mechanism of FIG. 104.
Figure 107:
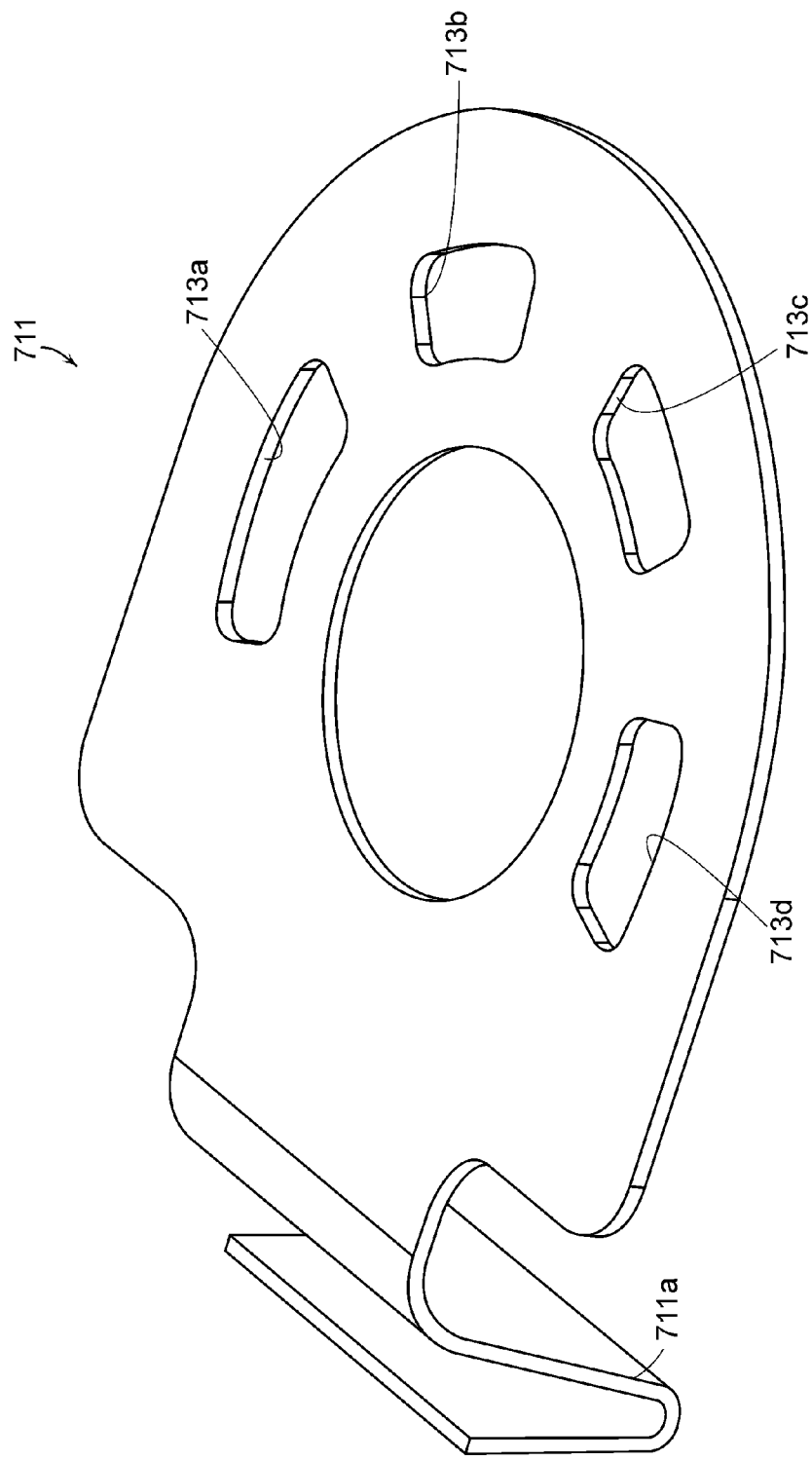
FIG. 107 is a perspective view of an indexing element of the anti-backup mechanism of FIG. 104.
Figure 108:
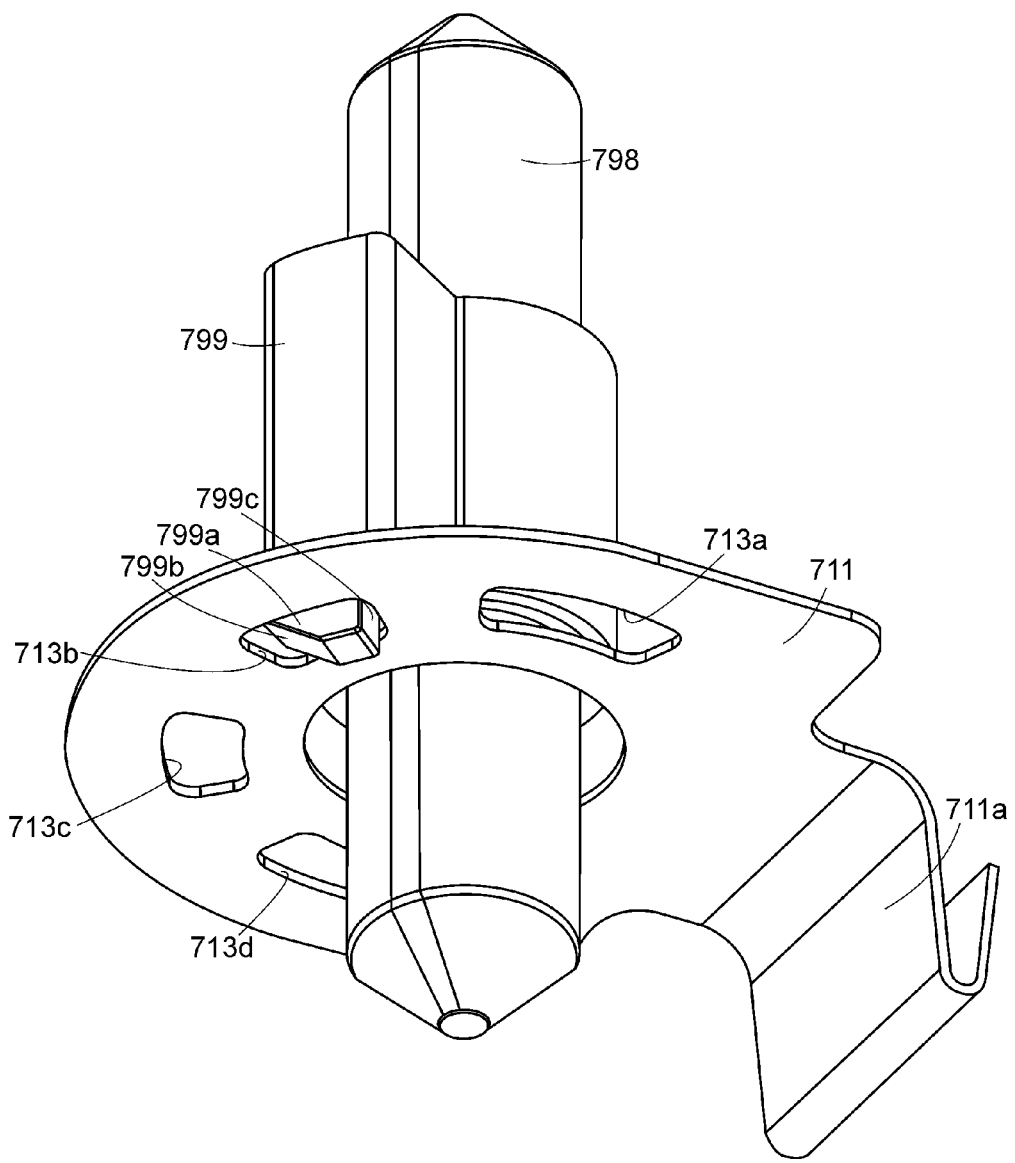
FIG. 108 is a perspective view of the return pin of FIG. 105 operably engaged with the indexing element of FIG. 107.
Figure 111:
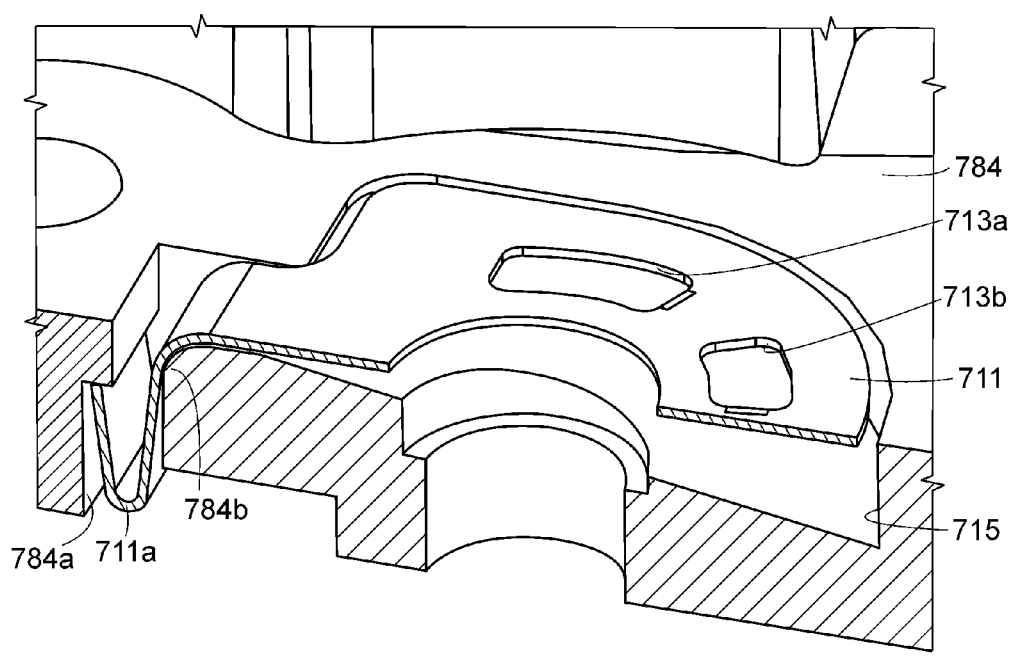
FIG. 111 is a cross-sectional view of the indexing element of FIG. 107.

In order to prevent return pin 798 from unintentionally rotating as outlined above, indexing element 711 can include one or more recesses and/or apertures therein for holding or retaining return pin 798 in position. In various embodiments, referring to FIGS. 104, 107, and 111, indexing mechanism 711 can comprise a leaf spring including clip end 711a which can be retained within recess 784a of frame 784 such that indexing mechanism 711 can flex and/or rotate relative to fulcrum 784b of frame 784. In at least one embodiment, referring to FIGS. 105 and 106, return pin 798 can include key 799 extending therefrom wherein key 799 can be configured to engage indexing mechanism 711. More particularly, in at least one such embodiment, indexing mechanism 711 can include a plurality of recesses, or apertures, 713a-d, referring to FIGS. 107 and 108, which can each be configured to retain projection 799a extending from key 799 therein and thereby hold return pin 798 in position as described in greater detail below.

Figure 109:
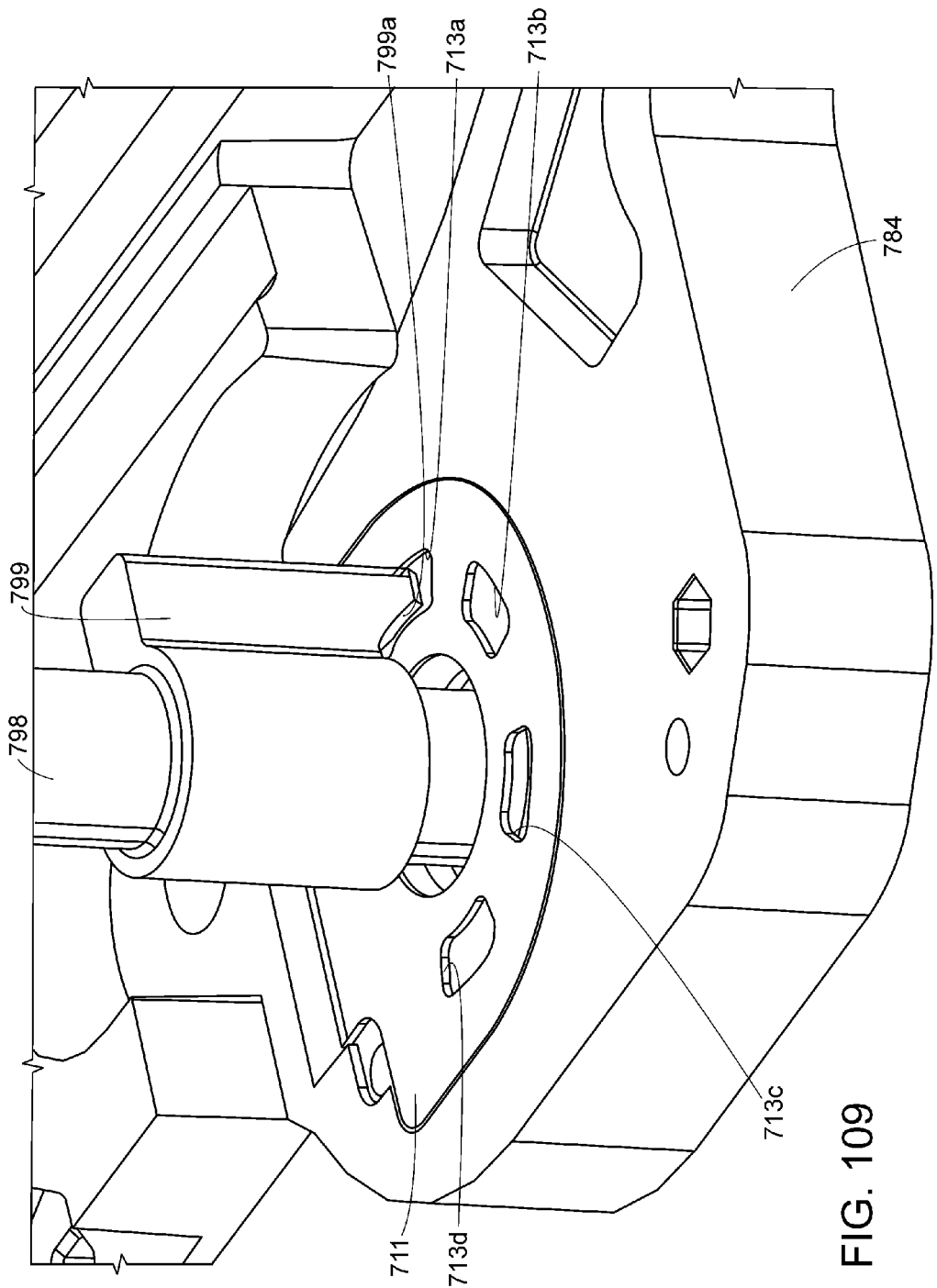
FIG. 109 is a perspective view of the return pin and the indexing element illustrating the key of the return pin positioned within a first aperture in the indexing element.
Figure 110B:
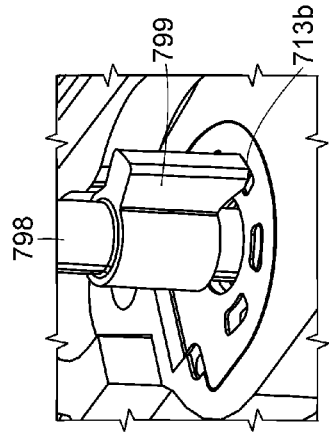
FIG. 110b is a perspective view of the return pin key depressing the indexing element when the return pin key is moved from the first aperture to a second aperture of the indexing element.

In use, an end effector of the surgical instrument can be closed onto the soft tissue of a patient, for example and, thereafter, as outlined above, a firing member of the surgical instrument can be advanced by a firing drive. Prior to the advancement of the firing member, projection 799a of return pin 798 can be received within first aperture 713a of indexing element 711 as illustrated in FIG. 110a. In various embodiments, referring to FIGS. 106 and 109, key 799 can further include inclined or beveled surface 799b which can be configured such that, when return pin 798 is rotated in a direction indicated by arrow B by firing member 466, pinion gear 401, intermediate gear 403, and key gear 406 upon the first actuation of trigger 460, beveled surface 799b can contact the edge of aperture 713a and deflect and/or rotate indexing mechanism 711 downwardly as illustrated in FIG. 110b. Notably, a certain amount of force may be required to deflect and/or rotate indexing mechanism 711 and, as a result, the possibility of return pin 798 being unintentionally displaced from recesses 713 can be reduced. More particularly, absent a large pulling force applied to firing member 766, for example, the recesses in the indexing element may be able to hold key 799 of return pin 798 therein and, correspondingly, the possibility that firing member 466 may be unintentionally advanced can also be reduced.

Figure 110C:
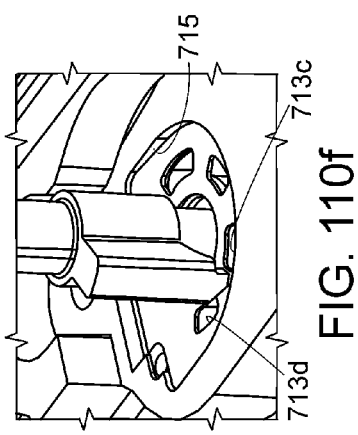
FIG. 110c is a perspective view of the key portion of the return pin positioned within the second aperture of the indexing element.
Figure 110A:
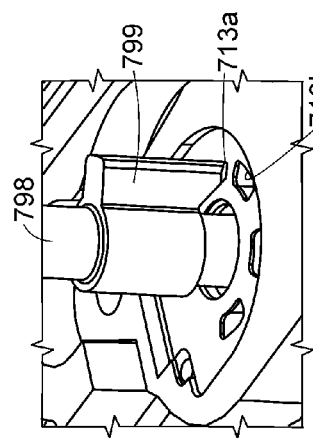
FIG. 110a is another perspective view of the return pin key and the indexing element of FIG. 109.

By the end of the first actuation of firing trigger 460, key 799 can be positioned within second aperture 713b of indexing mechanism 711 as illustrated in FIG. 110c. In such a position, key 799 can be prevented from moving backward into aperture 713a owing to stop surface 799c. More particularly, referring to FIG. 108, key 799 can further include stop surface 799*c* which can be configured to abut the perimeter of aperture 713*b*, for example, and, owing to the configuration of stop surface 799*c*, aperture 713*b* and stop surface 799*c* can be configured to prevent key 799 from deflecting or rotating indexing mechanism 711 downwardly within recess 715 (FIG. 111) and allowing return pin 798 to be rotated in a direction opposite of arrow B. In at least one such embodiment, stop surface 799*c* and the perimeter of aperture 713*b* can include surfaces which are parallel to one another. In other various embodiments, the abutting surfaces can include at least partially beveled portions which can be configured such that, when stop surface 799*c* is forced against the edge of aperture 713*b*, key 799 can be further drawn into aperture 713*b* as opposed to being lifted out of the same. In either event, owing to the operative relationship between return pin 798, the gears of the gear train, and firing member 466 as described above, firing member 466 can be prevented, or at least substantially prevented, from unintentionally retracting proximally by indexing member 711. In such embodiments, as a result, the possibility that pawl 170 may be misaligned relative to the recesses 467 within firing member 466 when pawl 170 is retracted relative to firing member 466, for example, can be reduced.

Figure 110E:
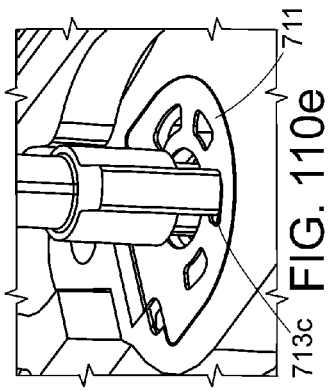
FIG. 110e is a perspective view of the key portion of the return pin positioned within the third aperture of the indexing element.
Figure 110G:
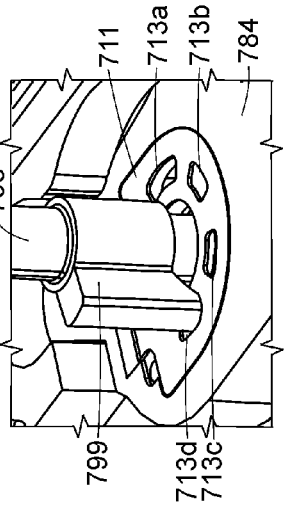
FIG. 110g is a perspective view of the key portion of the return pin positioned within the fourth aperture of the indexing element.
Figure 110D:
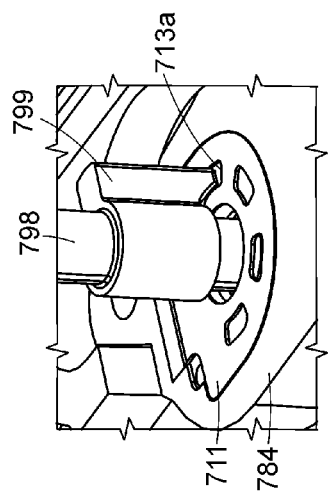
FIG. 110d is a perspective view of the return pin key depressing the indexing element when the return pin key is moved from the second aperture to a third aperture of the indexing element.
Figure 110F:
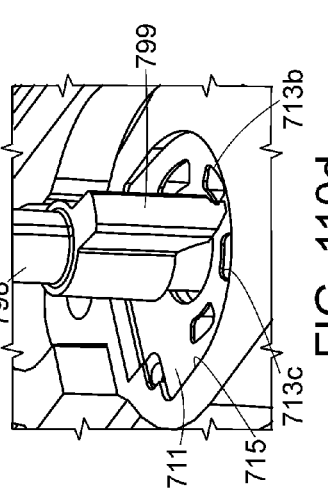
FIG. 110f is a perspective view of the return pin key depressing the indexing element when the return pin key is moved from the third aperture to a fourth aperture of the indexing element.

Upon a second actuation of firing trigger 460, firing member 466 can once again rotate gears 401, 403, and 406 such that return pin 798 is rotated in a direction indicated by arrow B. In various embodiments, as a result, beveled surface 799*b* can contact the edge of second aperture 713*b* and deflect and/or rotate indexing mechanism 711 downwardly as illustrated in FIG. 110*d*. By the end of the second actuation of firing trigger 460, key 799 can be positioned within third aperture 713*c* of indexing mechanism 711 as illustrated in FIG. 110*e*. In such a position, key 799 can be prevented from moving backward into second aperture 713*b* owing to stop surface 799*c*, similar to the above. Furthermore, upon a third actuation of firing trigger 460, firing member 466 can once again rotate return pin 798 in a direction indicated by arrow B and, as a result, beveled surface 799*b* can contact the edge of third aperture 713*c* and deflect and/or rotate indexing mechanism 711 downwardly as illustrated in FIG. 110*f*. By the end of the third actuation of firing trigger 460, key 799 can be positioned within fourth aperture 713*d* of indexing mechanism 711 as illustrated in FIG. 110*g*. In such a position, similar to the above, key 799 can be prevented from moving backward into third aperture 713*c* owing to stop surface 799*c*.

At such point, in order to operably engage the reversing drive with the firing member, similar to the above, return pin 798 and key 799 can be moved toward trigger gear 496 in order to operably engage key gear 406 with trigger gear 496. In various embodiments, as a result, projection 799*a* can be moved away from indexing member 711 and out of fourth aperture 713*d*. Thereafter, upon the return stroke of firing trigger 460, firing member 466 can be retracted and return pin 798 can be rotated in a clockwise direction, i.e., in a direction opposite arrow B. At such point, firing member 466 and pawl 170 will have both been returned to their starting positions, return pin 798 will have been rotated such that it is realigned with first aperture 713*a*, and return pin 798 can be disengaged from trigger gear 496 such that key 499 is slid into engagement with first aperture 713*a*. Thereafter, as a result, the surgical instrument can be used once again.

Figure 112:
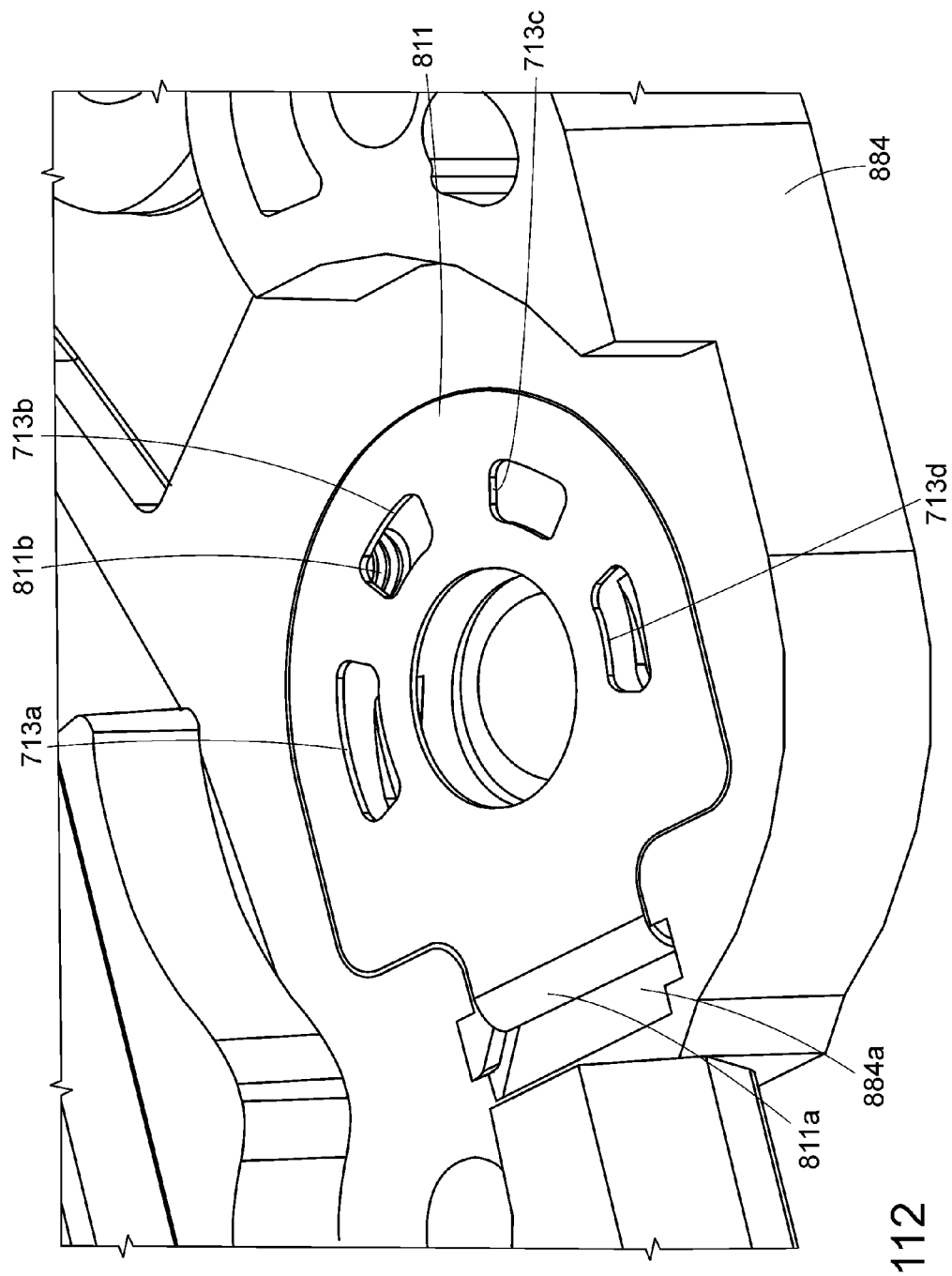
FIG. 112 is a perspective view of an indexing element in accordance with an alternative embodiment of the present invention and a return spring operatively engaged with the indexing element.
Figure 113:
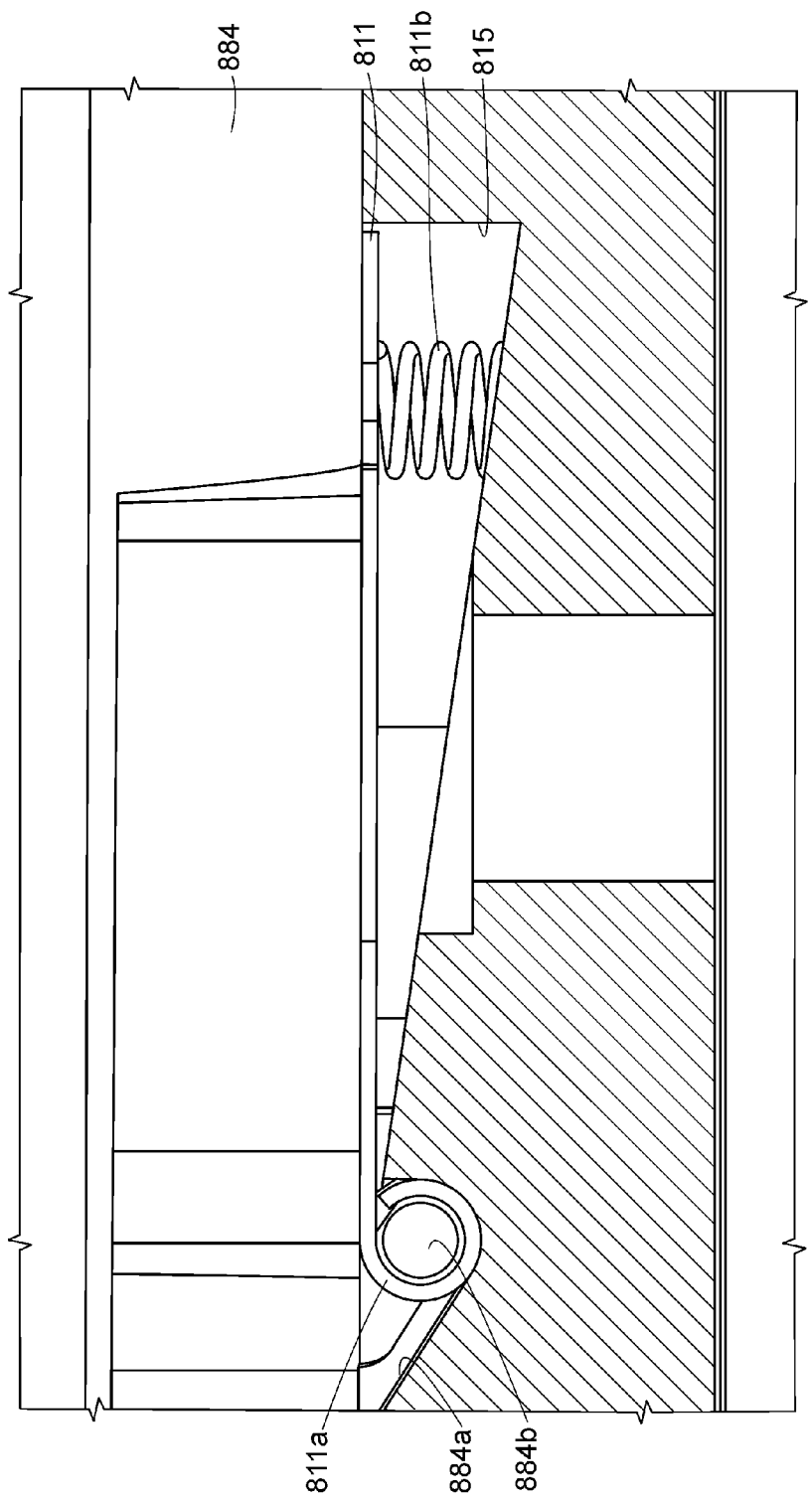
Figure 114:
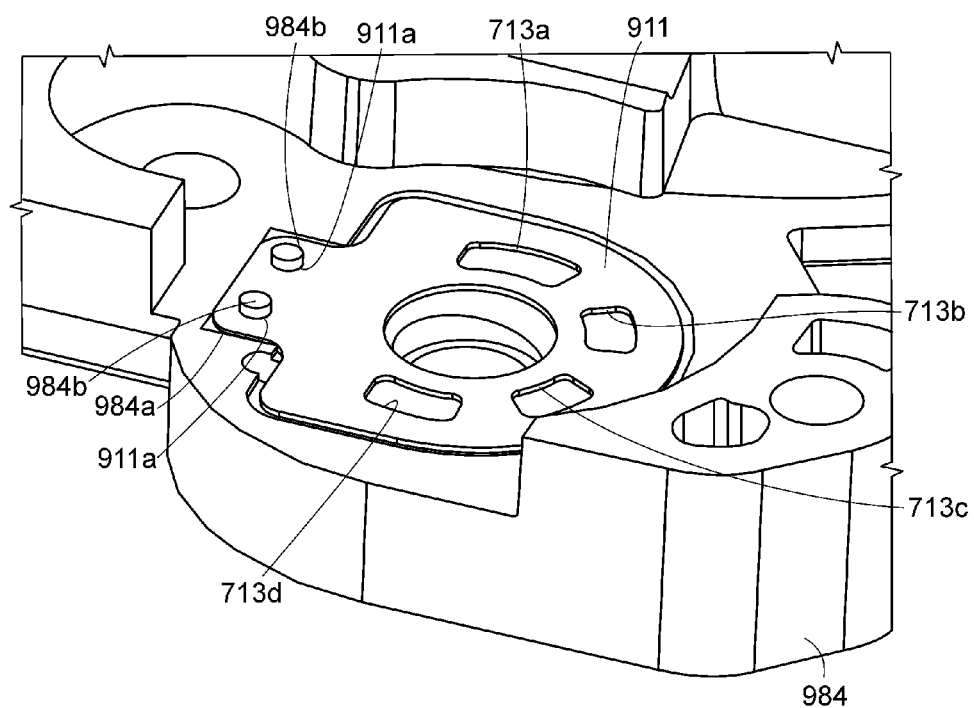

In various alternative embodiments, referring to FIGS. 112 and 113, an anti-backup mechanism can include indexing element, or plate, 811 which can be rotatably mounted within recess 884*a* of frame 884 such that hinge end 811*a* can be rotatably mounted to pin portion 884*b*. In at least one embodiment, similar to the above, indexing element 811 can be rotated and/or deflected relative to pin 811*b*. In various embodiments, the anti-backup mechanism can further include at least one spring element, or return spring, 811*b* within recess 815 which can be configured to bias indexing member 811 into the position illustrated in FIGS. 112 and 113. Similarly, return spring 811*b* can be further configured to restore indexing element to such a position after it has been deflected by key 799 as outlined above. In various embodiments, the at least one return spring can be positioned intermediate indexing element 811 and a sidewall of recess 815, for example. In various alternative embodiments, referring to FIG. 114, an anti-backup mechanism can include indexing element 911 which, similar to the above, can be mounted within recess 984*a* of frame 984. In at least one such embodiment, frame 984 can further include mounting projections 984*b* which can be configured to be press-fit within apertures 911*a* in indexing element 911 such that indexing element 911 can be flexed and/or rotated relative to frame 984.

In various alternative embodiments, an anti-backup mechanism in accordance with at least one embodiment of the present invention can include a ratchet mechanism for preventing, or at least limiting, undesirable movement of the firing member and/or gear train. In various embodiments, referring to FIGS. 115-118, the ratchet mechanism can include a pawl which can be configured to allow the gears of the gear train, such as indicator gear 492 and spur gear 416, for example, to rotate in a first direction when they are driven by the firing member, such as firing member 466, for example, yet prohibit, or at least limit, the gears from rotating in an opposite direction when the pawl of the firing drive, such as pawl 170, for example, is retracted relative to the firing member. In at least one embodiment, referring to FIG. 116, the ratchet mechanism can include leaf spring, or pawl, 1011 which can limit the rotation of spur gear 416 as described in greater detail below.

Further to the above, when firing member 466, for example, is advanced by firing trigger 460, for example, firing member 466 can rotate spur gear 416 in a direction indicated by arrow D (FIG. 116) owing to the operative engagement of pinion gear 401, intermediate gear 403, key gear 406, and spur gear 416 as described above. When spur gear 416 is rotated in direction D, in at least one embodiment, gear teeth 416*a* of gear 416 can be configured to contact and deflect pawl 1011 such that gear teeth 416*a* can pass thereby. However, in the event that firing member 466 is unintentionally retracted and/or spur gear 416 is rotated in a direction indicated by arrow H, pawl 1011 can be configured such that at least a portion thereof can be positioned intermediate two adjacent gear teeth 416*a* and prevent, or at least limit, spur gear 416 from rotating in direction H. In various embodiments, referring to FIG. 116, at least a portion of pawl 1011 can be wedged between gear teeth 416*a* or 'bite' into gear 416 such that gear 416 cannot substantially rotate in direction H, at least not until the reversing drive of the surgical instrument is operably engaged with the firing member as described in greater detail below.

Figure 115:
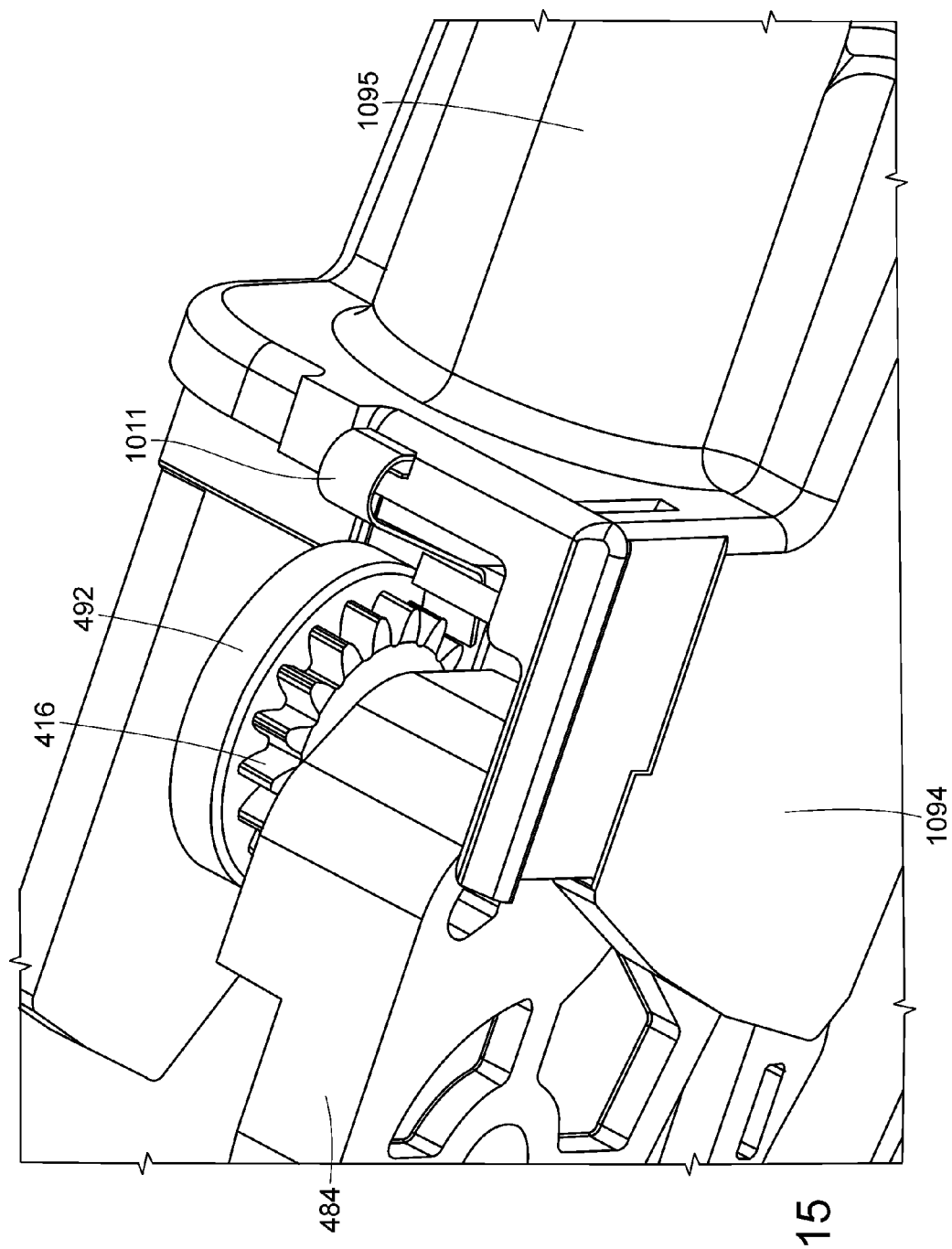
Figure 116:
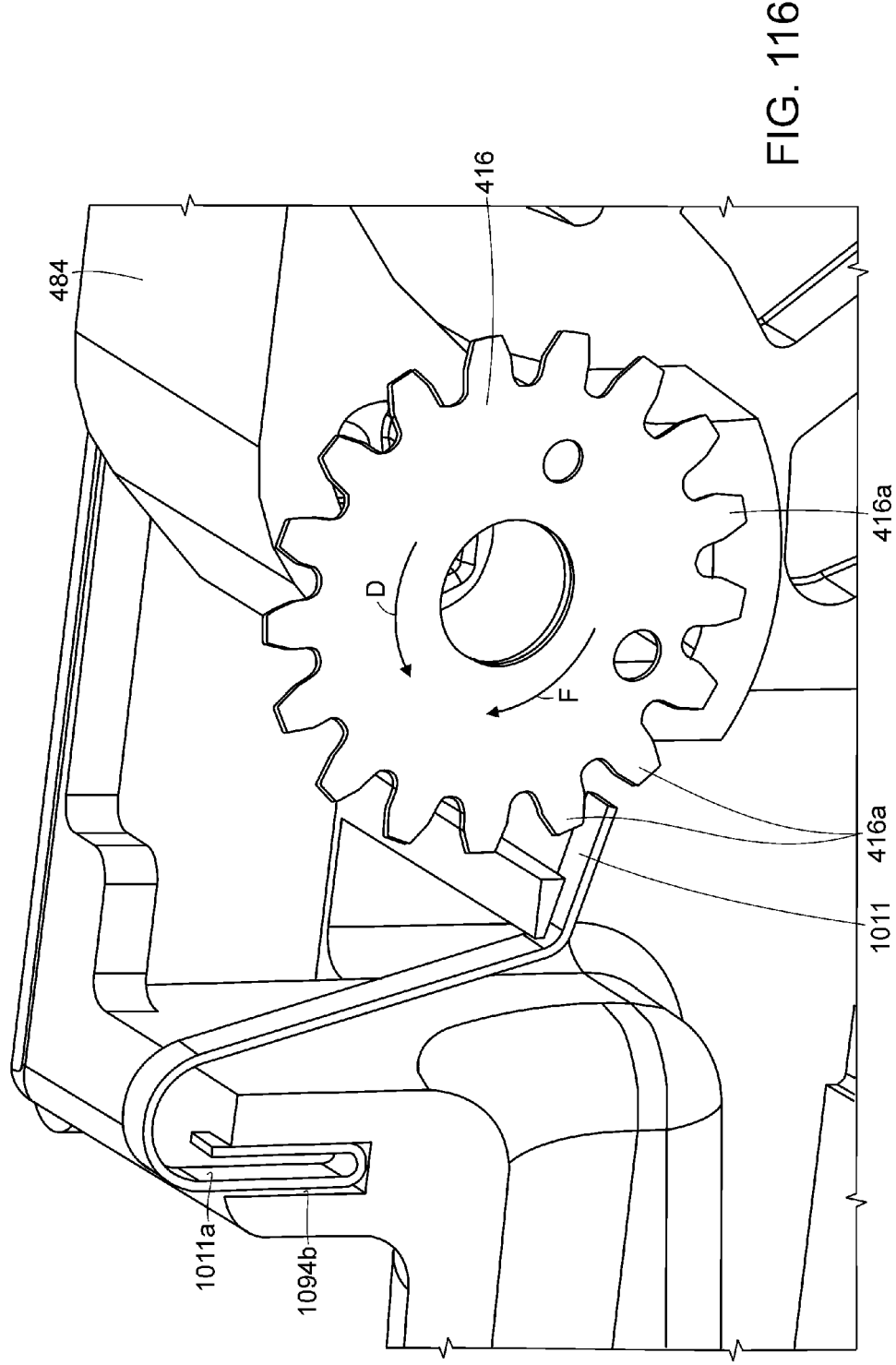
Figure 117:
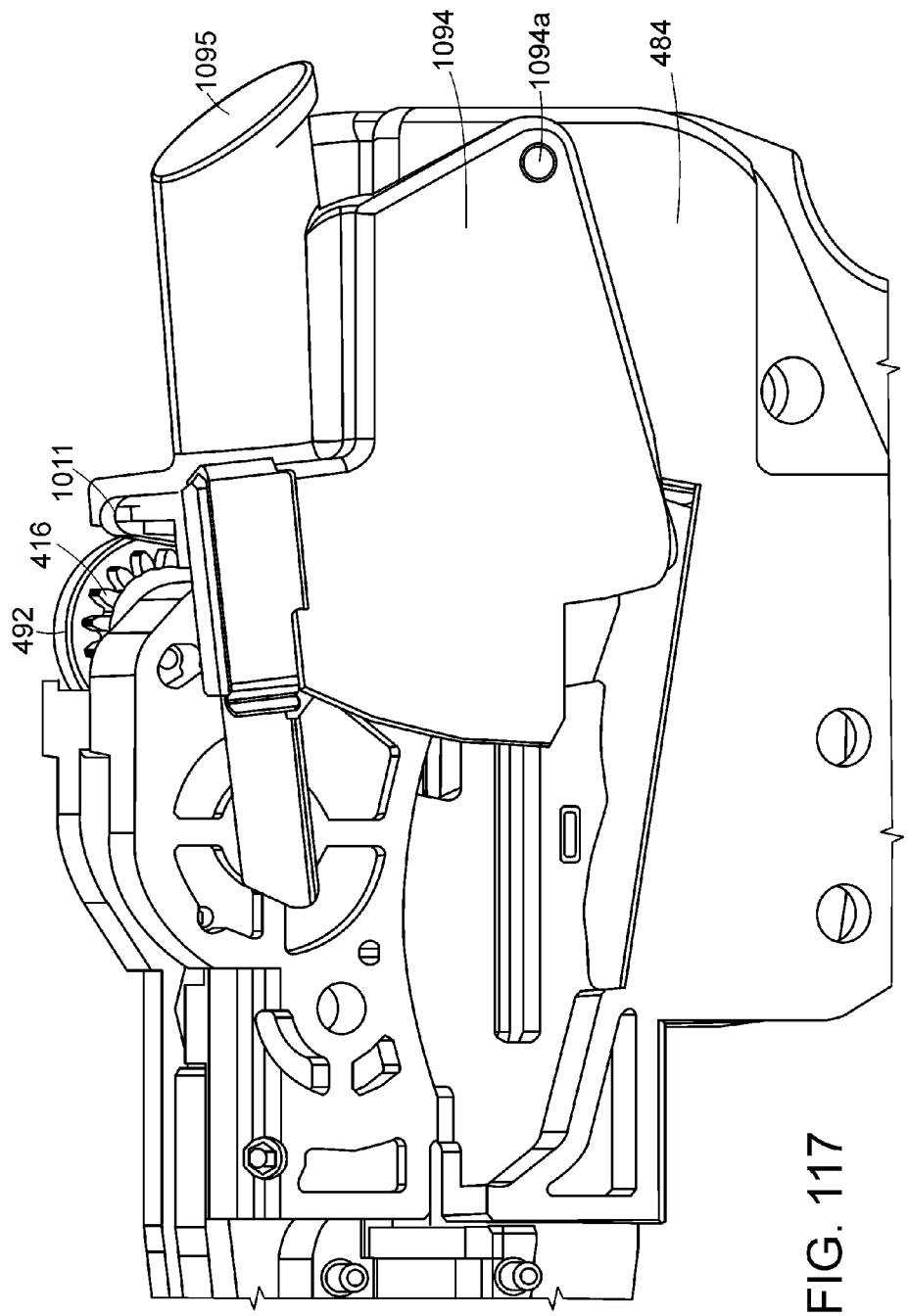
Figure 118:
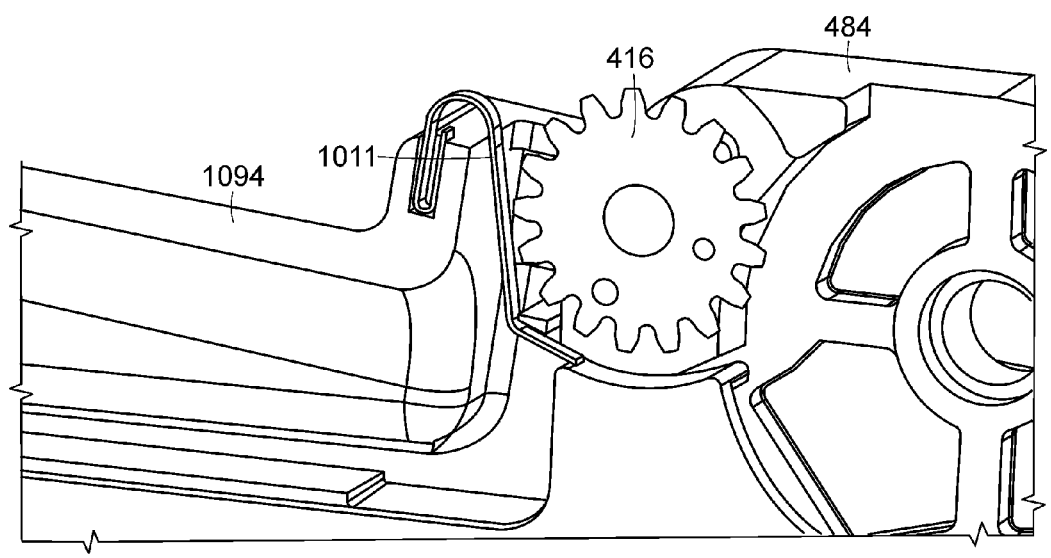

In various embodiments, the surgical instrument can include a return carriage which can be moved between an unactuated position as illustrated in FIGS. 115 and 116 and an actuated position as illustrated in FIGS. 117 and 118 to place the surgical instrument in its reversing or retracting mode of operation. Similar to return carriage 494, in at least one embodiment, return carriage 1094 can be rotated relative to frame 484 about pin 1094*a*. In various embodiments, referring to FIG. 118, pawl 1011 can be mounted to return carriage 1094 such that, when return carriage 1094 is rotated downwardly into its actuated position, pawl 1011 can be moved out of operative engagement with spur gear 416. In such circumstances, spur gear 416 can be permitted to rotate in a direction indicated by arrow H when the surgical instrument is placed in its reversing mode. When spur gear 416 is permitted to rotate in direction H, the gear train can be permitted to rotate without interference, or at least substantial interference, from the anti-backup mechanism such that the firing member can be retracted as outlined above. After the firing member has been sufficiently retracted, return carriage 1094 can be rotated upwardly into its unactuated position and pawl 1011 can be operably re-engaged with spur gear 416.

In various circumstances, a reversing drive of a surgical instrument may be prevented from being properly engaged with a firing member of the surgical instrument. In at least one embodiment, the return carriage of a reversing drive, such as return carriages 494 and 1094, for example, may not be able to properly contact and motivate firing pin 172 and/or return pin 498, for example. More particularly, the return carriage may fail to properly displace firing pin 172 and/or return pin 498 such that key gear 406 is operably engaged with trigger 496 and, furthermore, such that pawl 170 is prevented from operably engaging firing member 466. In various embodiments, as outlined above, a return carriage can include a button portion which can be configured to manually rotate the return carriage downwardly when a force is applied thereto. In various circumstances, however, this force may have insufficient leverage to move the return carriage, especially if the return carriage and/or one of pins 172 and 498 is stuck in position, for example.

In various embodiments of the present invention, a surgical instrument can include a switch which can be better configured to manually engage the reversing drive of the surgical instrument with the firing member. In at least one embodiment, referring to FIG. 119, the switch can include first and second portions, wherein first portion 1194 can be movably connected relative to frame 1184, for example, and wherein second portion 1118 can also be movably connected relative to frame 1184 as well. In various embodiments, first switch portion 1194 can be pivotably connected to frame 1184 such that, when first switch portion 1194 is pivoted downwardly by a cam, similar to cam 402, for example, first portion 1194 can be configured to disengage return pin 498 and allow key portion 499 of return pin 498 to engage trigger gear 496 as described above. In various embodiments, although not illustrated in FIG. 119, return carriage 1194 can include arm 1194d extending therefrom which can be moved away from end 498a of return pin 498 such that a spring, for example, can bias return pin 498 into operative engagement with trigger gear 496.

In addition to the above, first switch portion 1194, when pivoted downwardly, can be configured to contact return pin 172 and operably engage key 222 of return pin 172 with pawl 170 such that pawl 170 cannot be pivoted upwardly, as also described above. In effect, in at least one such embodiment, first switch portion 1194 can comprise a cam which can be actuated to operably disengage the firing drive from, and operably engage the reversing drive with, the firing member. In various circumstances, only the operation of first portion 1194 may be needed in order to switch the surgical instrument between its advancing and reversing operating modes. In the event, however, that the cam of the reversing drive, such as cam 402, for example, cannot properly position, or actuate, first switch portion 1194, second portion 1118 of the switch may be utilized to actuate first switch portion 1194 as described in greater detail below.

Further to the above, second switch portion 1118 can be actuated in order to actuate first switch portion 1194. In various embodiments, referring again to FIG. 119, second switch portion 1118 can include handle 1118b which can be configured to be grasped by a surgeon, for example, such that the surgeon can apply a force thereto and rotate switch portion 1118 about pivot 1118a. In at least one embodiment, second switch portion 1118 can be configured to contact first switch portion 1184 and move first portion 1184 between its unactuated position illustrated in FIG. 119 and its actuated position as described above. In various embodiments, in effect, second switch portion 1118 can comprise a cam which can contact first portion 1194 and drive first portion 1194 downwardly such that first portion 1194 contacts firing pin 172 and return pin 498. In at least one such embodiment, referring to FIG. 119, second switch portion 1118 can include contact surface 1118c which can be configured to contact surface 1194c of first switch portion 1194. In various embodiments, contact surface 1118c can be positioned directly above contact surface 1194c such that surfaces 1118c and 1194c can be aligned and the possibility of second switch portion 1118 not contacting first switch portion 1194 can be reduced.

Figure 119:
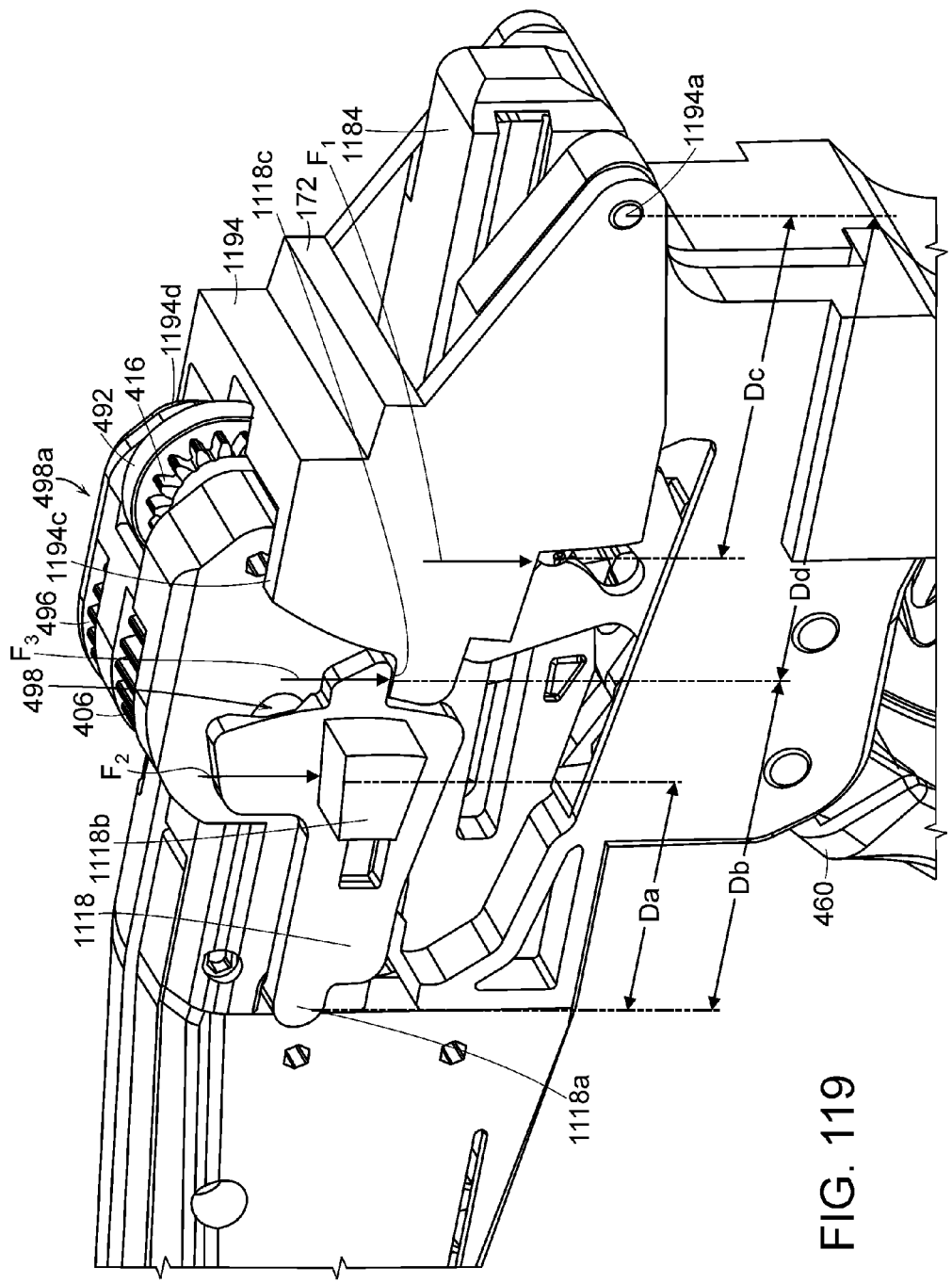

In various embodiments, further to the above, contact surfaces 1118c and 1194c can be positioned and arranged such that a force, $F_2$, applied to handle 1198b has sufficient mechanical advantage to move first switch portion 1194 into its actuated position. In at least one embodiment, handle force $F_2$ can be transmitted through the body of second switch portion 1118 and to first switch portion 1194 via contact surfaces 1118c and 1194c as transmission force $F_3$. Notably, in various embodiments, transmission force $F_3$ can be different than handle force $F_2$ Further to this point, referring to FIG. 119, the torques associated with handle force $F_2$ and transmission force $F_3$ in order to initially move first switch portion 1194 can be substantially the same, i.e., the product of distance Da and force $F_2$ can substantially equal the product of distance Db and force $F_3$, wherein distance Da can represent the distance between pivot 1118a and the application of force $F_2$, and wherein distance Db can represent the distance between pivot 1118a and the transmission of force $F_3$. Thus, when distance Da is smaller than distance Db, as illustrated in FIG. 119, force $F_2$ can be larger than force $F_3$. Accordingly, in order for force $F_3$ to be substantially equal to force $F_2$, handle 1118b would have to be positioned substantially above surfaces 1118c and 1194c when force $F_2$ is applied to handle 1118b.

In various embodiments, further to the above, transmission force $F_3$ can be transmitted through the body of first switch portion 1194 to firing pin 172 as displacement force $F_1$. Similar to the above, displacement force $F_1$ can be different than transmission force $F_3$. Further to this point, referring again to FIG. 119, the torques associated with displacement force $F_1$ and transmission force $F_3$ in order to initially displace firing pin 172 toward pawl 170, as outlined above, can be substantially the same, i.e., the product of distance Dc and force $F_1$ can substantially equal the product of distance Dd and force $F_3$, wherein distance Dc can represent the distance between pivot 1194a and the application of force $F_3$, and wherein distance Dd can represent the distance between pivot 1194a and the transmission of force $F_3$. Thus, when distance Dc is smaller than distance Dd, as illustrated in FIG. 119, force $F_1$ can be larger than force $F_3$. In effect, the smaller transmission force $F_3$ can be utilized to apply a larger displacement force $F_1$ to firing pin 172, depending on the selection of distances Da, Db, Dc, and Dd. In various embodiments, as a result, the first and second portions of the switch can be configured such that force $F_2$ supplied by the surgeon, for example, can be sufficient to manually position the first portion of the switch in its actuated position via the second portion of the switch and thereby manipulate the surgical instrument from an advancing operating mode to a reversing operating mode, as outlined further above. In order to return the surgical instrument to its advancing operating mode, first switch portion 1194, for example can be rotated upwardly such that second switch portion 1118 can also rotated upwardly, thereby resetting the switch assembly.

Figure 120:
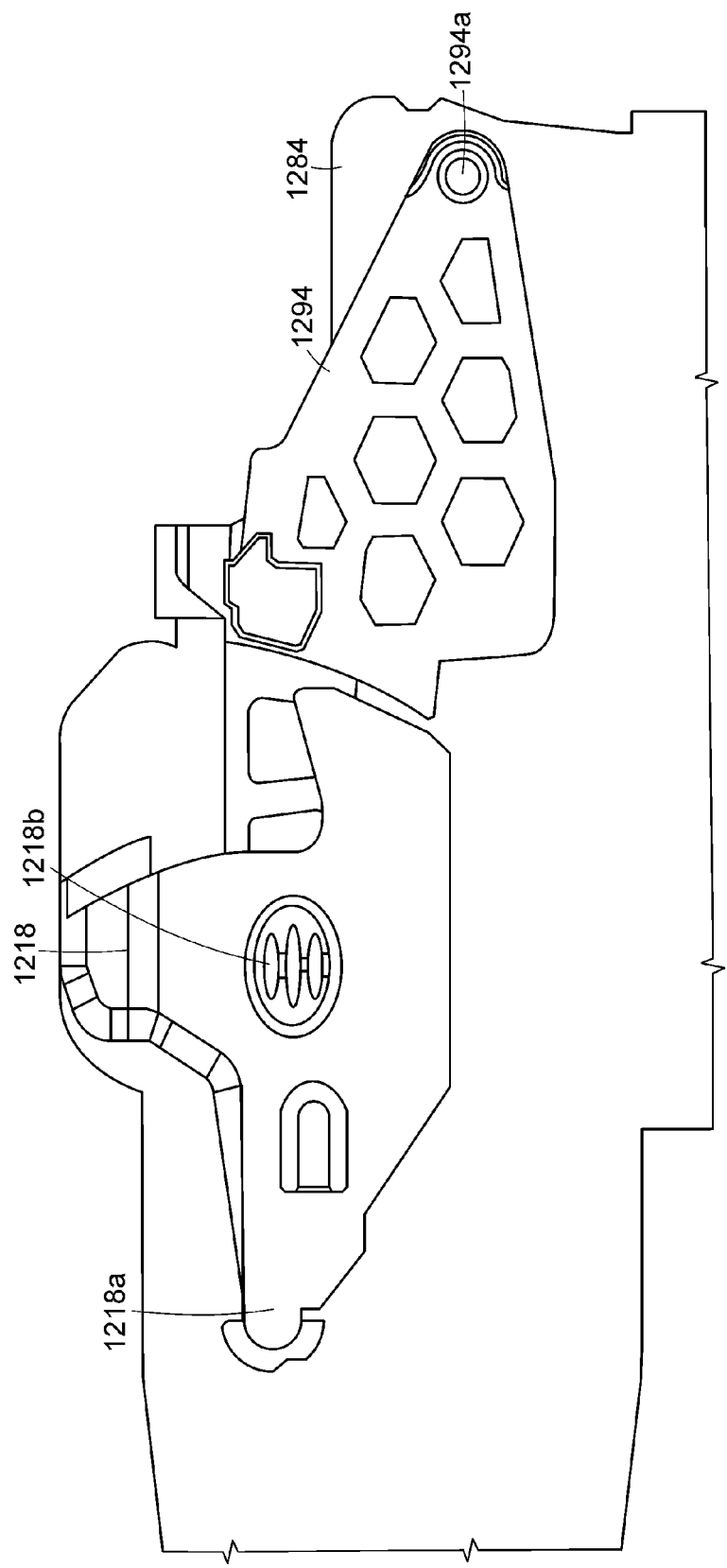
Figure 121:
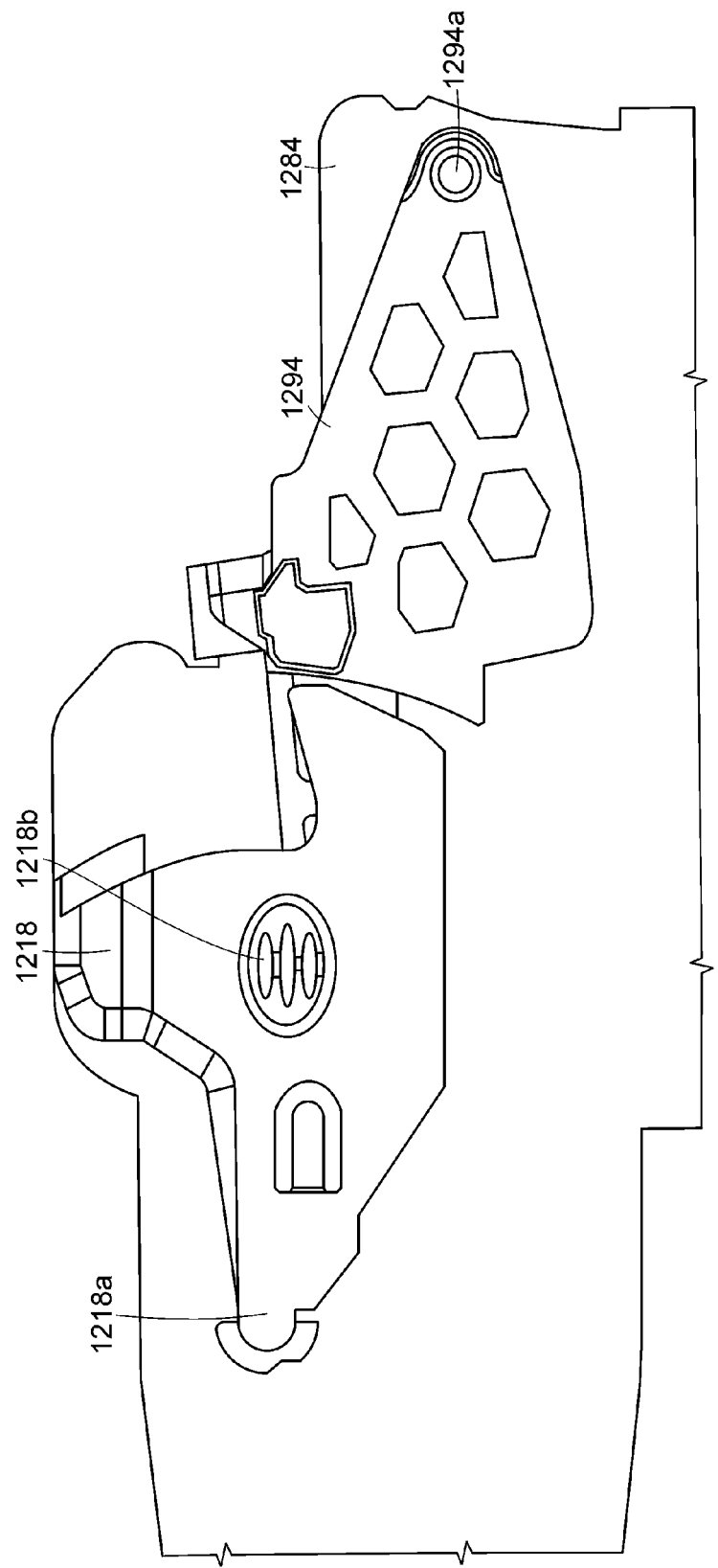
Figure 122:
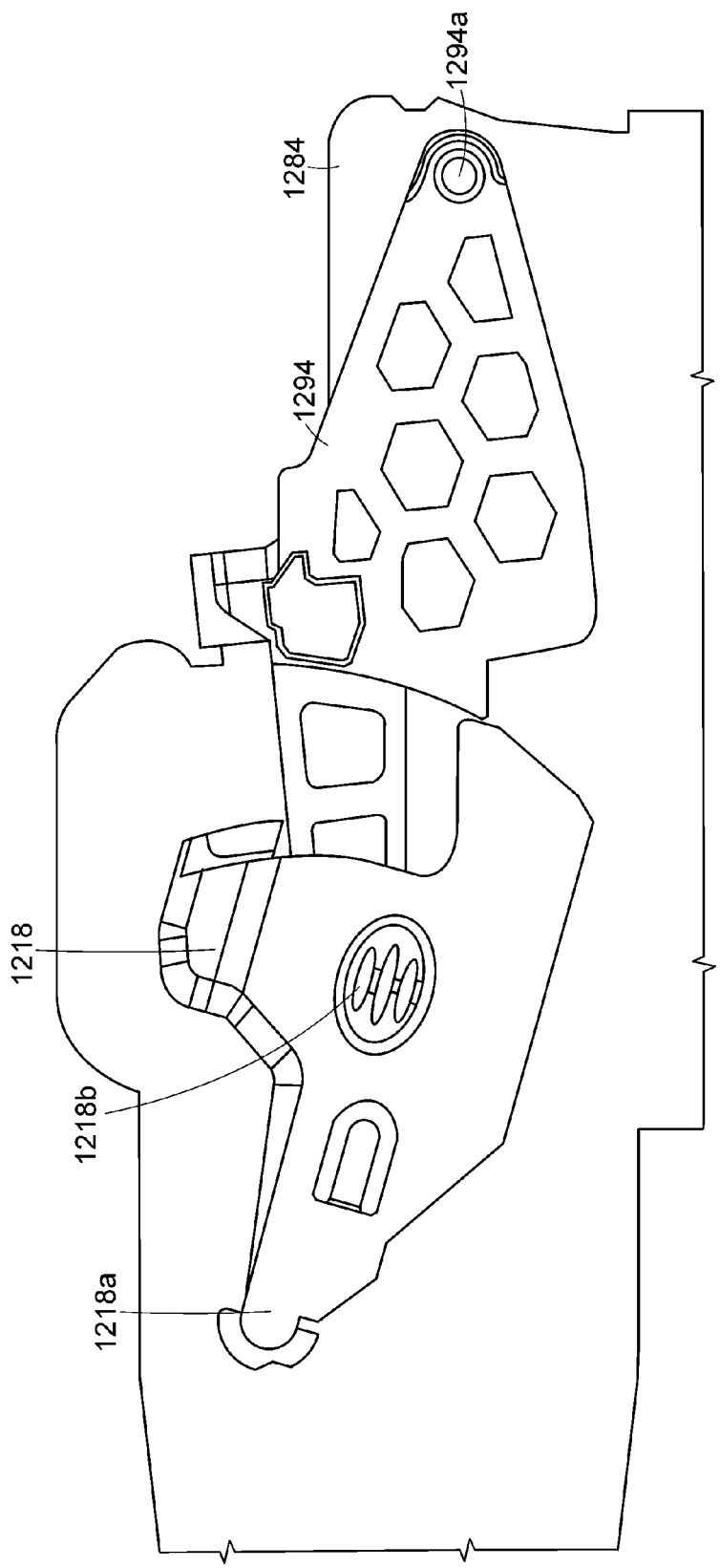

In a further exemplary embodiment, referring to FIGS. 120-122, a surgical instrument can include a switch assembly comprising first portion 1294 which can be pivotably mounted to frame 1284 about pin 1294*a* and, in addition, a second portion 1218 which can be pivotably mounted to frame 1284 about pivot 1218*a*. Although the first and second switch portions can be pivotably mounted to frame 1284, the switch portions can be pivotably mounted to any other suitable portion of the surgical instrument. In various embodiments, similar to the above, first switch portion 1294 can be operated to switch the surgical instrument between advancing and reversing operated modes. In at least one embodiment, first switch portion 1294 can be rotated between its unactuated position illustrated in FIG. 120 and its actuated position illustrated in FIG. 121. Similar to the above, second switch portion 1218 can be moved downwardly by a force applied to handle 1218*b* in order to move first portion 1294 downwardly into its actuated position.

In various embodiments, second switch portion 1218, for example, and the firing trigger of the surgical instrument, such as firing trigger 460, for example, can be configured such that second portion 1218 can be prevented, or at least substantially prevented, from being rotated downwardly unless the firing trigger is in its unactuated position. By requiring that the firing trigger be in its unactuated position before allowing the switch to be operated, first switch portion 1294 of the reversing mechanism may be properly aligned with the firing pin of the firing drive, such as firing pin 172, for example, when first portion 1294 is rotated downwardly. In various embodiments, the surgical instrument can be configured such that the firing pin is positioned within a predetermined range such that the firing pin can be contacted by first switch portion 1294 and slid into engagement with the pawl of the firing drive, such as pawl 170, for example.

Figure 50:
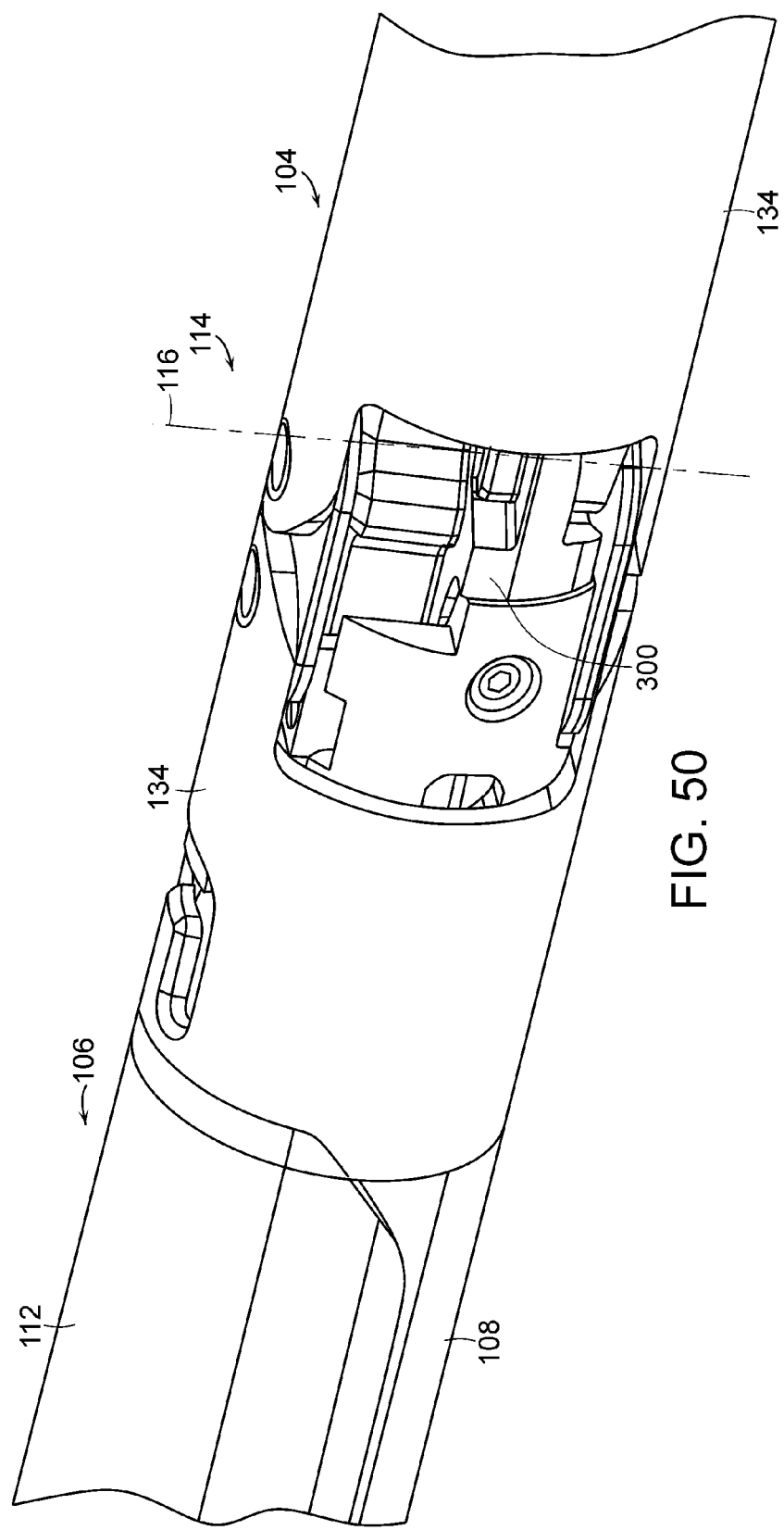
FIG. 50 is a perspective view of the articulation joint of FIG. 5.

In various embodiments, referring to FIG. 50, surgical instrument 100 can include end effector 106 and elongate shaft assembly 104, where end effector 106 and shaft assembly 104 can be pivotably connected by articulation joint 114. As outlined above, articulation joint 114 can allow end effector 106 to be moved, or articulated, relative to shaft assembly 106 about axis 116. In various circumstances, a surgeon can articulate end effector 106 to more easily access a surgical site within a patient's body. More particularly, a surgeon may insert end effector 106 and shaft assembly 104 through a cannula at least partially inserted into the patient's body and, once end effector 106 has passed through the cannula, end effector 106 can be pivoted, or articulated, in order to position end effector 106 relative to soft tissue, for example, in the surgical site that is to be stapled and/or incised. Once end effector 106 has been positioned, the relative relationship between end effector 106 and shaft assembly 104 can be fixed, or locked, by a locking mechanism as described in greater detail further below.

Figure 51:
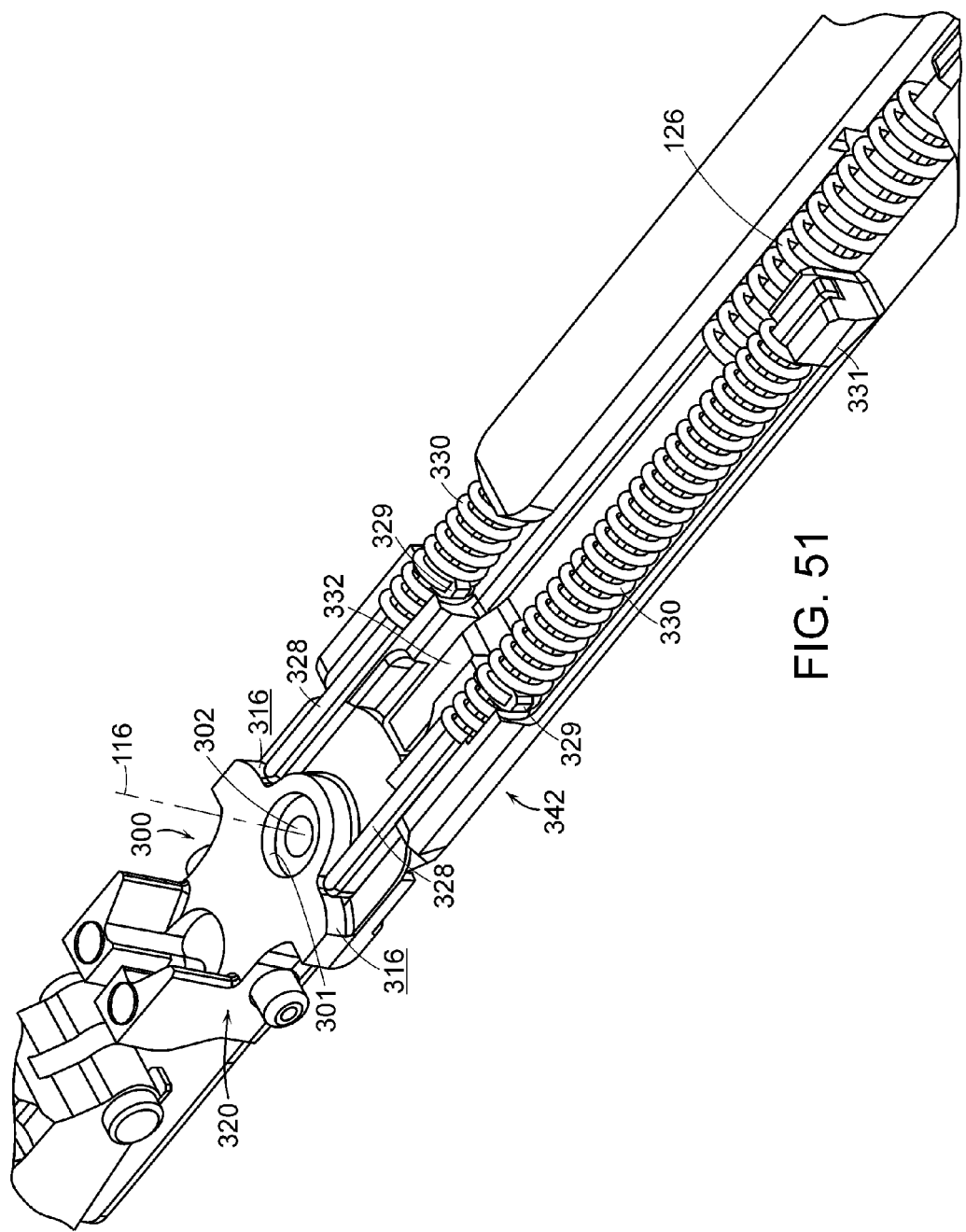
FIG. 51 is a perspective view of the articulation joint of FIG. 5 with some components of the surgical instrument removed.
Figure 52:
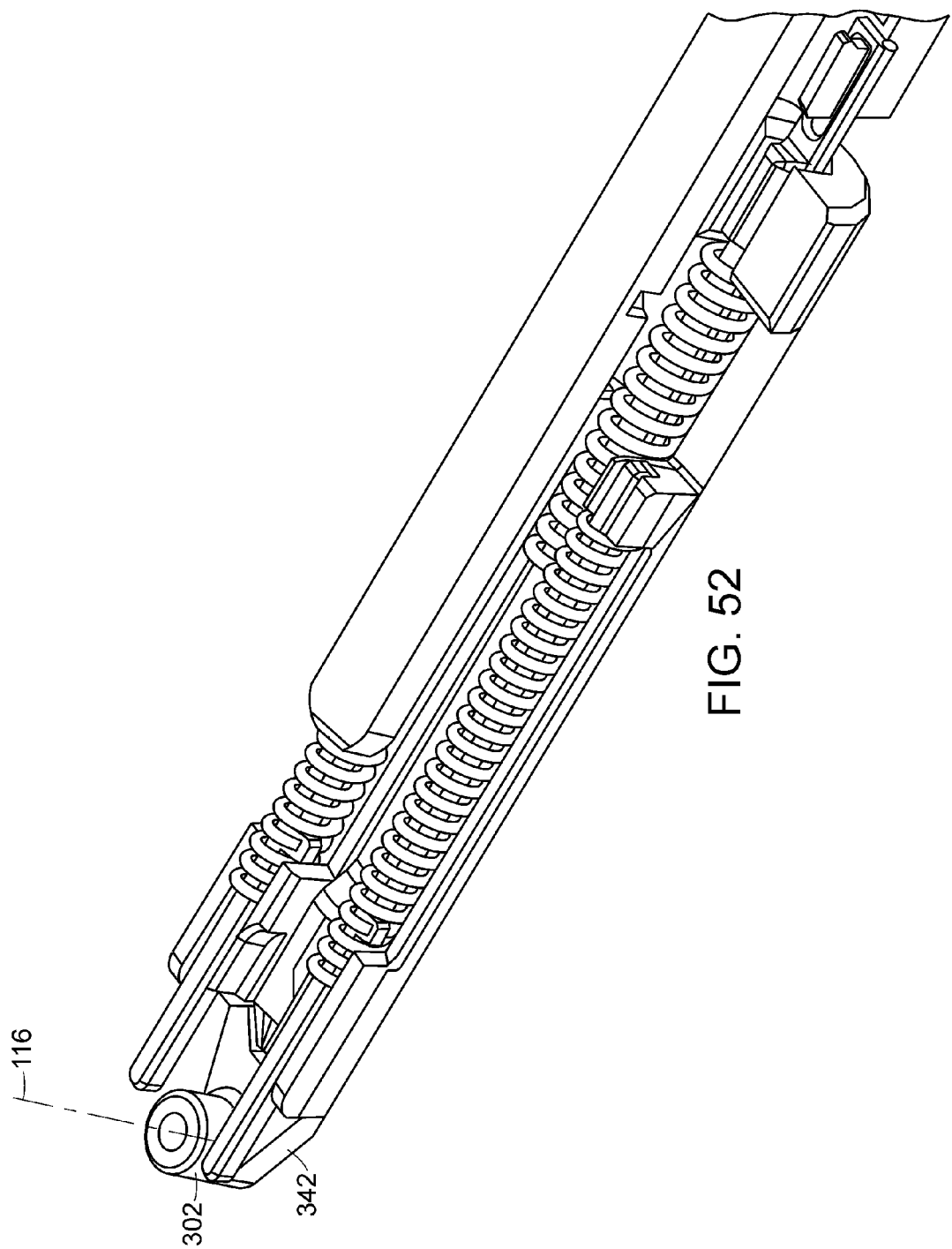
FIG. 52 is a perspective view of the articulation joint of FIG. 5 with additional components of the surgical instrument removed.
Figure 53:
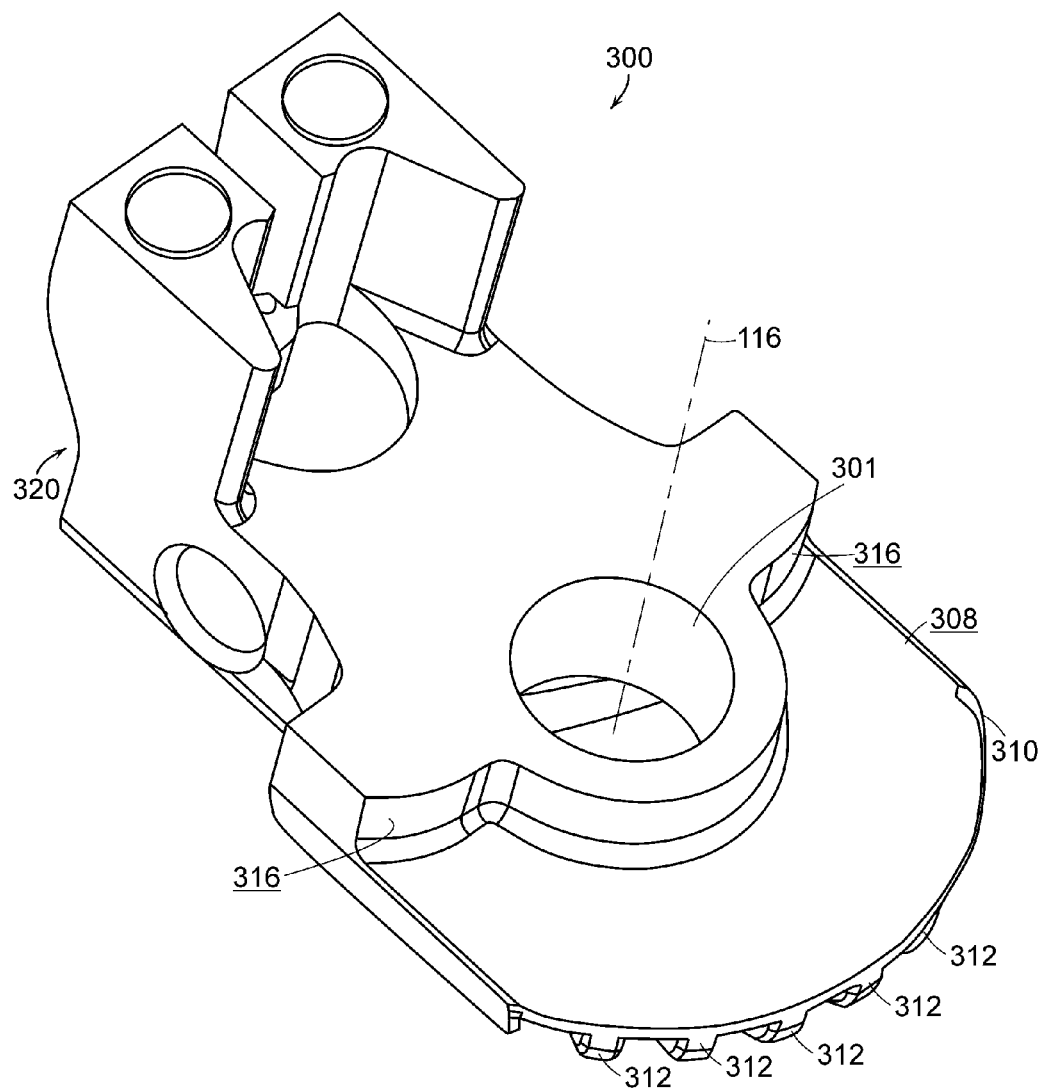
FIG. 53 is a perspective view of a lock member of the end effector of FIG. 3.
Figure 54:
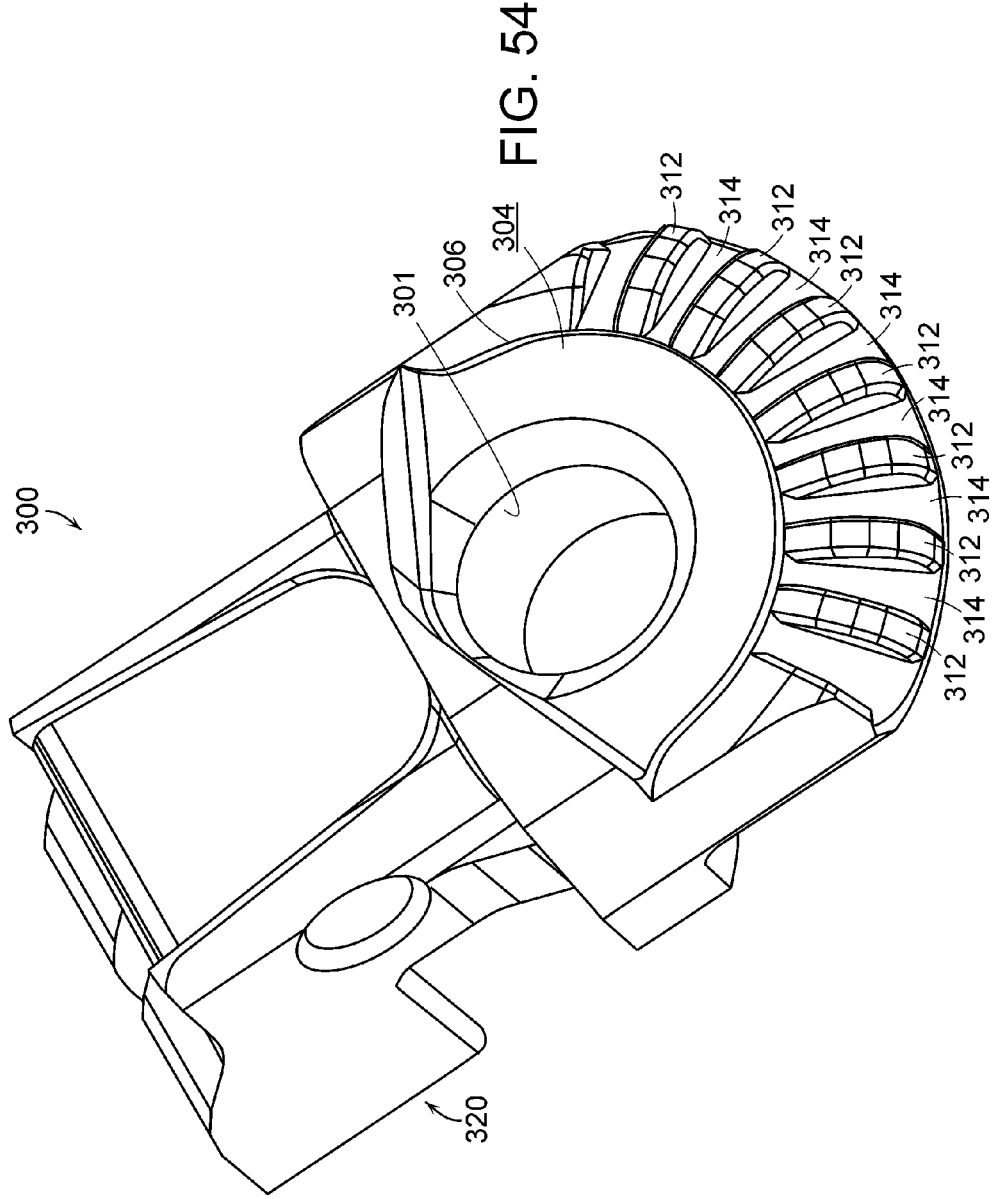
FIG. 54 is another perspective view of the end effector lock member of FIG. 53.
Figure 55:
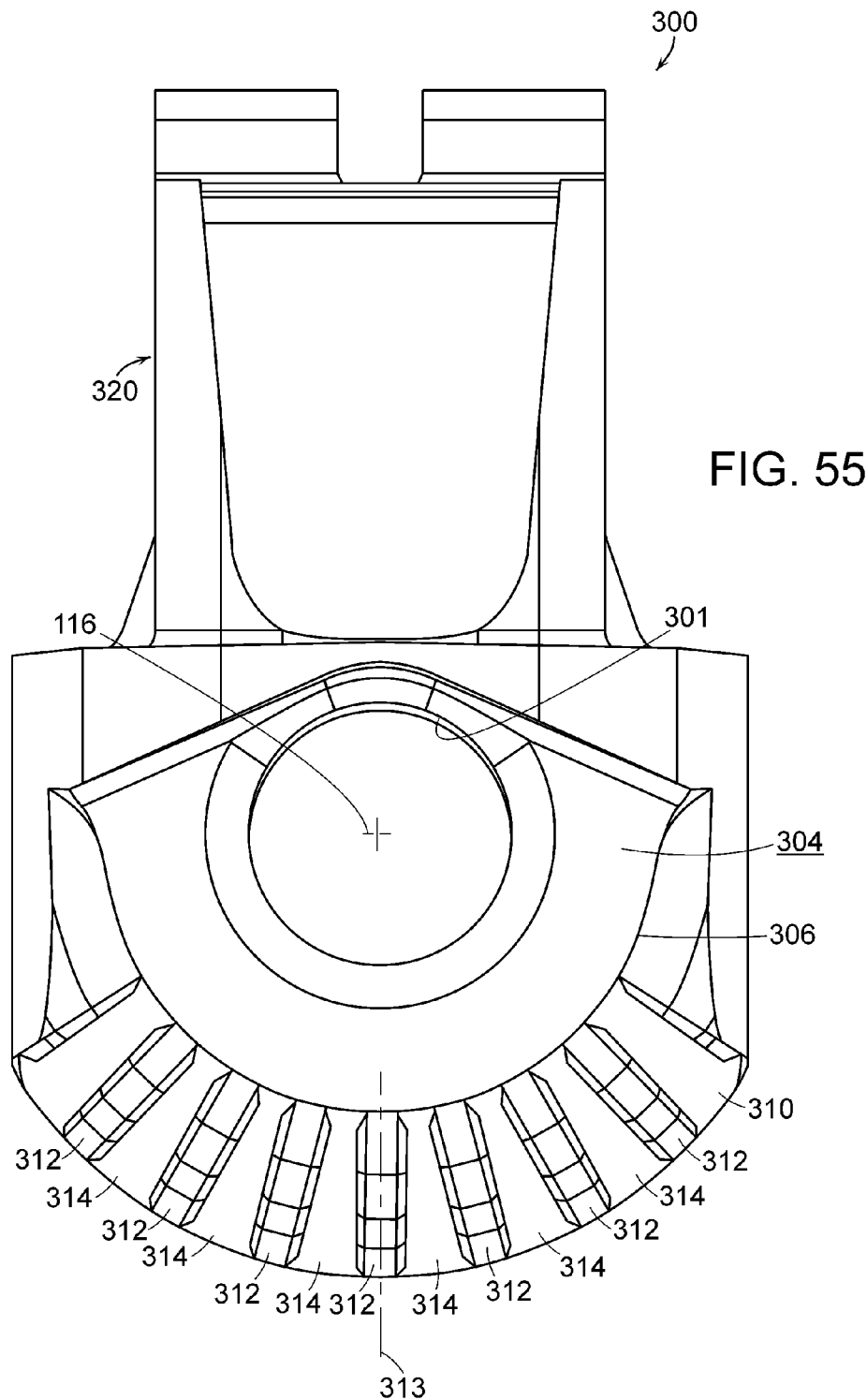
FIG. 55 is a bottom view of the end effector lock member of FIG. 53.
Figure 56:
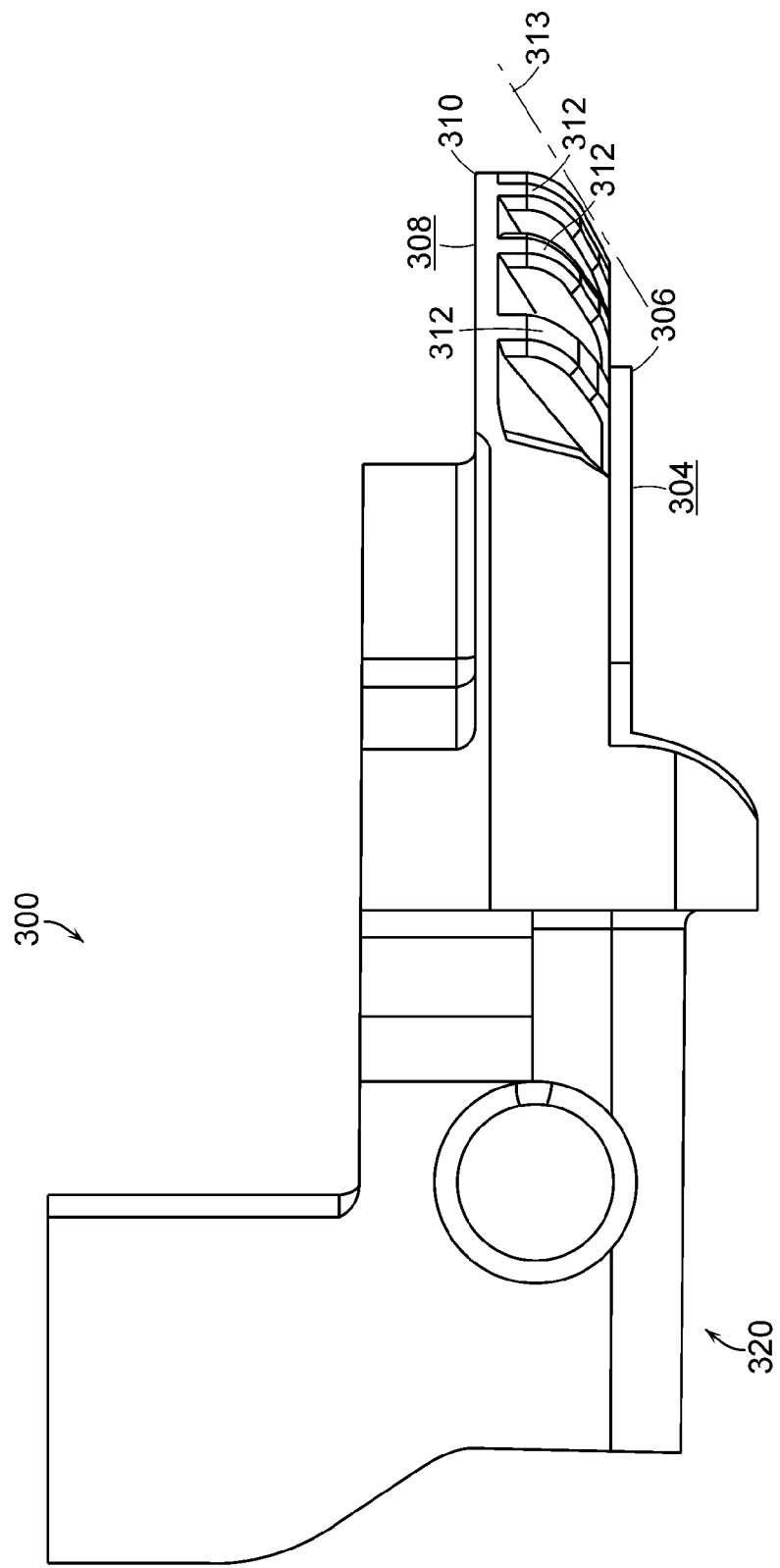
FIG. 56 is an elevational view of the end effector lock member of FIG. 53.

In at least one embodiment, referring to FIGS. 51 and 52, articulation joint 114 can include end effector lock member 300 and pivot 302. In various embodiments, referring to FIGS. 53-56, end effector lock member 300 can include connector portion 320 which can secure lock member 300 to end effector 106 and, referring to FIG. 52, shaft assembly 104 can include pivot connector 342, where pivot connector 342 can include pivot 302 extending therefrom. In various embodiments, lock member 300 can include aperture 301 which can be sized and configured to receive at least a portion of pivot 302 therein. In at least one embodiment, pivot 302 and aperture 301 can be configured such that end effector 106 can rotate freely about axis 116. In other various embodiments, pivot 302 and aperture 301 can be configured such that friction between pivot 302 and aperture 301 can resist, although permit, relative movement between end effector 106 and shaft assembly 104. Although not illustrated, articulation joint 114 can include more than one axis, or pivot, about which end effector 106 can be rotated.

In various embodiments, a surgeon can articulate end effector 106 relative to shaft assembly 104 by pushing end effector 106 against a cavity side wall surrounding a surgical site, for example, and applying a force to shaft assembly 104 such that end effector 106 pivots about axis 116. Thereafter, if the surgeon desires to re-center end effector 106, i.e., orient end effector 106 and shaft assembly 104 along a line, the surgeon can place end effector 106 against a cavity side wall once again, for example, and a apply a force to shaft assembly 104 as described above. In various embodiments, referring to FIGS. 51 and 52, surgical instrument 100 can include a re-centering mechanism which can automatically re-center, or at least substantially re-center, end effector 106 relative to shaft assembly 104. In various embodiments, end effector lock member 300 can include centering surfaces 316 and elongate shaft assembly 104 can include centering shafts 328 and biasing members 330, where biasing members 330 can be configured to bias centering shafts 328 against centering surfaces 316. In at least one such embodiment, centering surfaces 316 can be disposed on substantially opposite sides of axis 116 such that centering shafts 328 can apply a substantially equal torque, or moment, to lock member 300 and, absent an additional motivating force, hold end effector 106 in a substantially centered position. When end effector 106 is articulated by such a motivating force, as described above, lock member 300 can be configured to displace one of centering shafts 328 proximally and compress the biasing member 330 operably engaged therewith. More particularly, the biasing member 330 can be positioned between a guide 331 and at least one projection 329 extending from centering shaft 328 such that, when projection 329 is moved proximally by shaft 328, biasing member 330 is compressed therebetween. After the motivating force is removed, the compressed biasing member 330 can expand and rotate lock member 300 to its center position via centering shaft 328, or to a position where the torque applied by biasing members 330 is substantially balanced. Although biasing member 330 is illustrated as a coil spring, biasing member 330 can include any suitable elastic member.

In various embodiments, a locking mechanism can be used to hold end effector 106 in its articulated position even after the motivating force has been removed. In at least one embodiment, referring to FIGS. 53-56, end effector lock member 300 can include a first portion having first surface 308, a second portion having second surface 304, teeth 312, and recesses 314 defined between teeth 312 where, as described in greater detail further below, teeth 312 and recesses 314 can be configured to be operably engaged with a shaft assembly locking member in order to fix, or lock, the relative relationship between end effector 106 and shaft assembly 104. In various embodiments, teeth 312 and recesses 314 can be positioned intermediate first surface 308 and second surface 304. In at least one embodiment, first surface 308 can extend from aperture 301 to first perimeter 310, and second surface 304 can extend from aperture 301 to second perimeter 306. In various embodiments, first perimeter 310 can define a first plane and second perimeter 306 can define a second plane where teeth 312 and recesses 314 can be positioned intermediate the first and second planes. In embodiments where first perimeter 310 is different than second perimeter 306, teeth 312 can extend at an angle, or bevel, therebetween. In various embodiments, a tooth 312 can intersect first perimeter 310 at a point further away from axis 116 than a point at which the tooth 312 intersects second perimeter 306. In at least one embodiment, at least one of the teeth 312 can define a first axis 313 which can extend between first surface 308 and second surface 304 in a direction which is not perpendicular to first surface 308 and/or axis of rotation 116. In such embodiments, teeth 312 can slide over soft tissue, for example, which is positioned adjacent to articulation joint 114. Stated another way, owing to the angled, or beveled, surfaces of teeth 112, the probability of teeth 112 catching on, or impinging upon, the soft tissue surrounding articulation joint 114 when end effector 106 is articulated can be reduced. In at least one embodiment, teeth 312 may not extend beyond first perimeter 310 such that, in the event that at least a portion of first perimeter 310 is in contact with soft tissue, for example, first perimeter 310 and teeth 312 can, as above, easily slide relative to the soft tissue.

Figure 57:
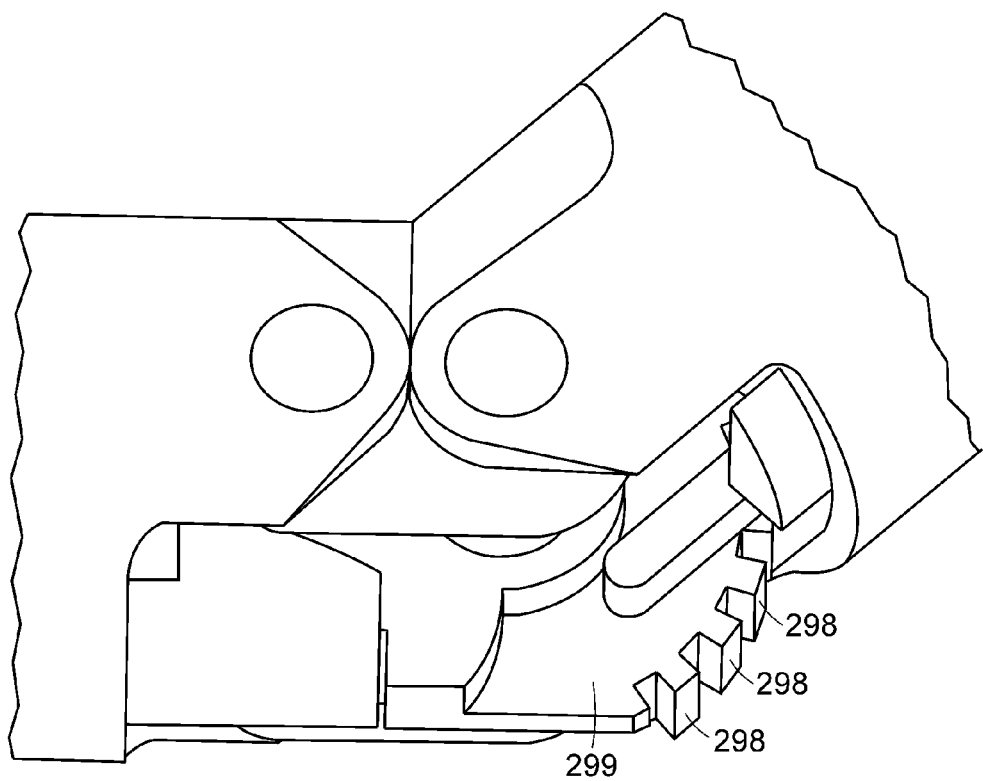
FIG. 57 is a partial perspective view of an articulation joint of a previous surgical instrument.
Figure 58:
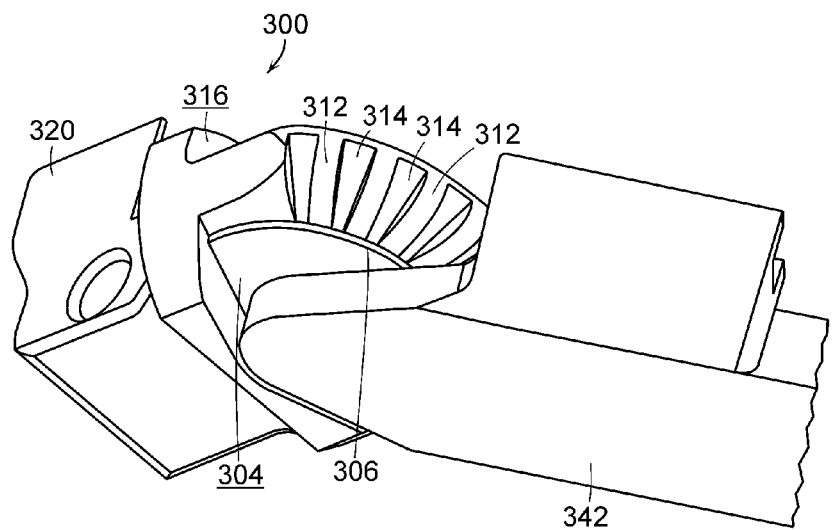
FIG. 58 is a perspective view of the articulation joint of FIG. 5 with some components of the end effector and elongate shaft assembly removed.
Figure 59:
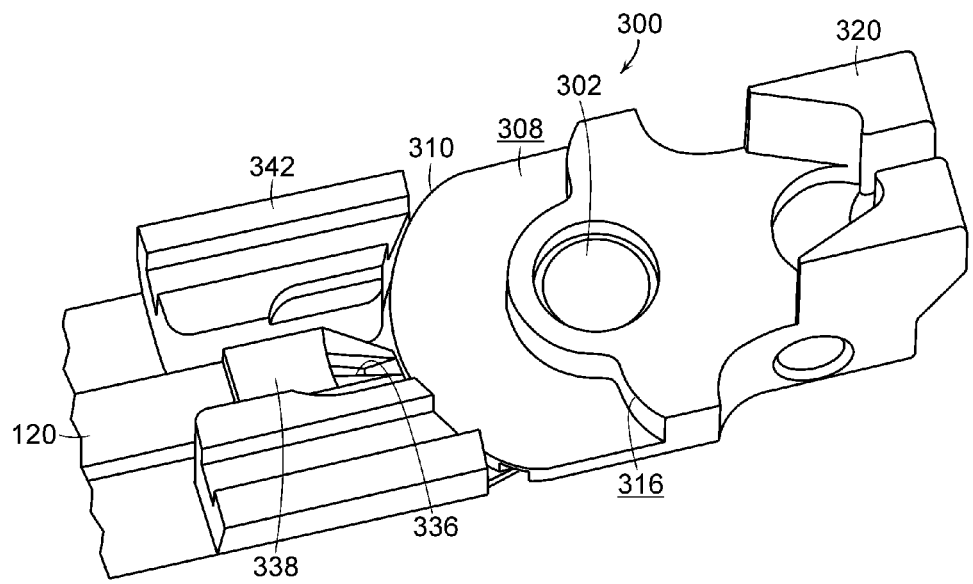
FIG. 59 is another perspective view of the articulation joint of FIG. 5 with some components of the end effector and elongate shaft assembly removed.
Figure 60:
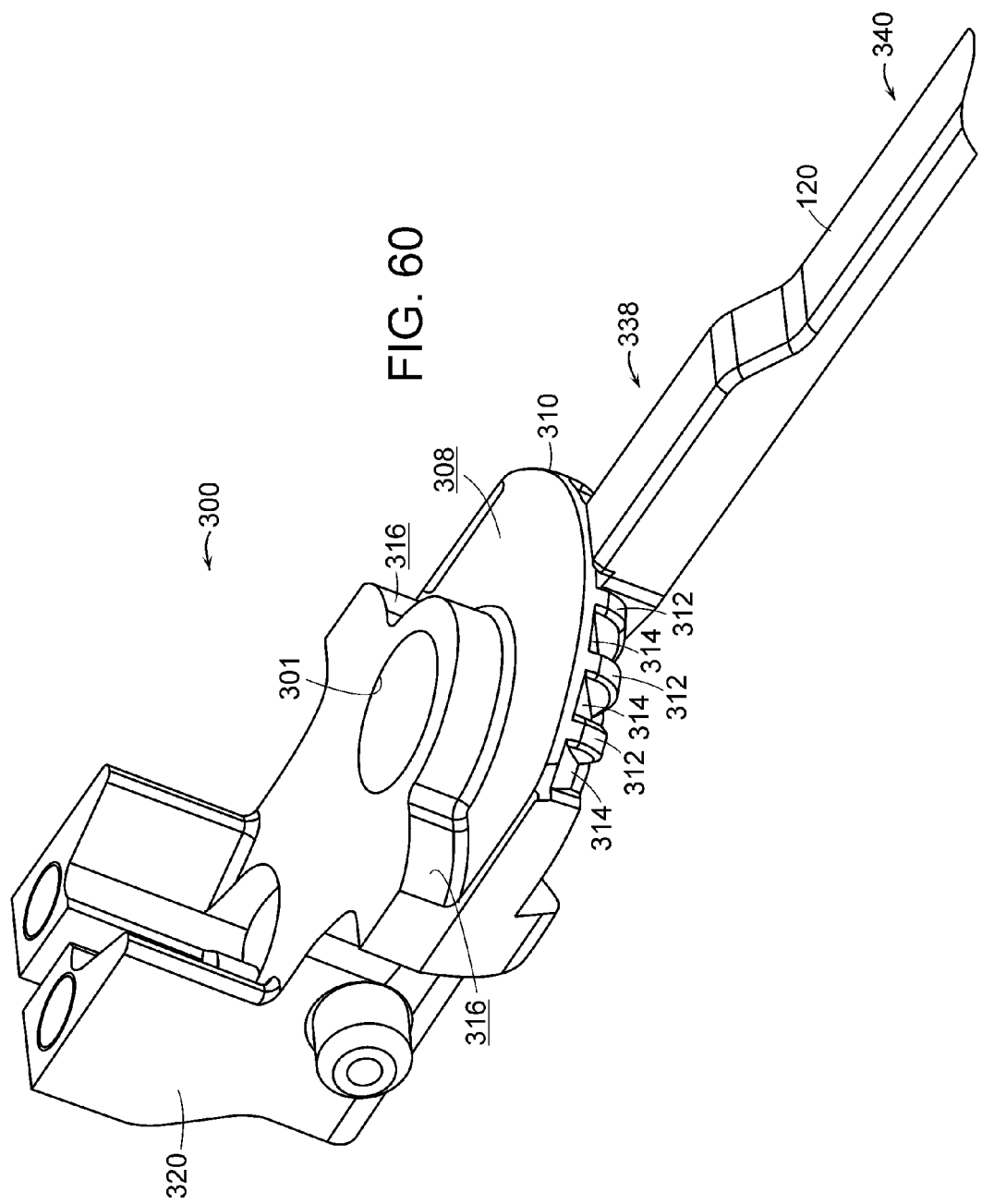
FIG. 60 is a perspective view of the end effector lock member of FIG. 53 operably engaged with a lock member of the elongate shaft assembly.
Figure 61:
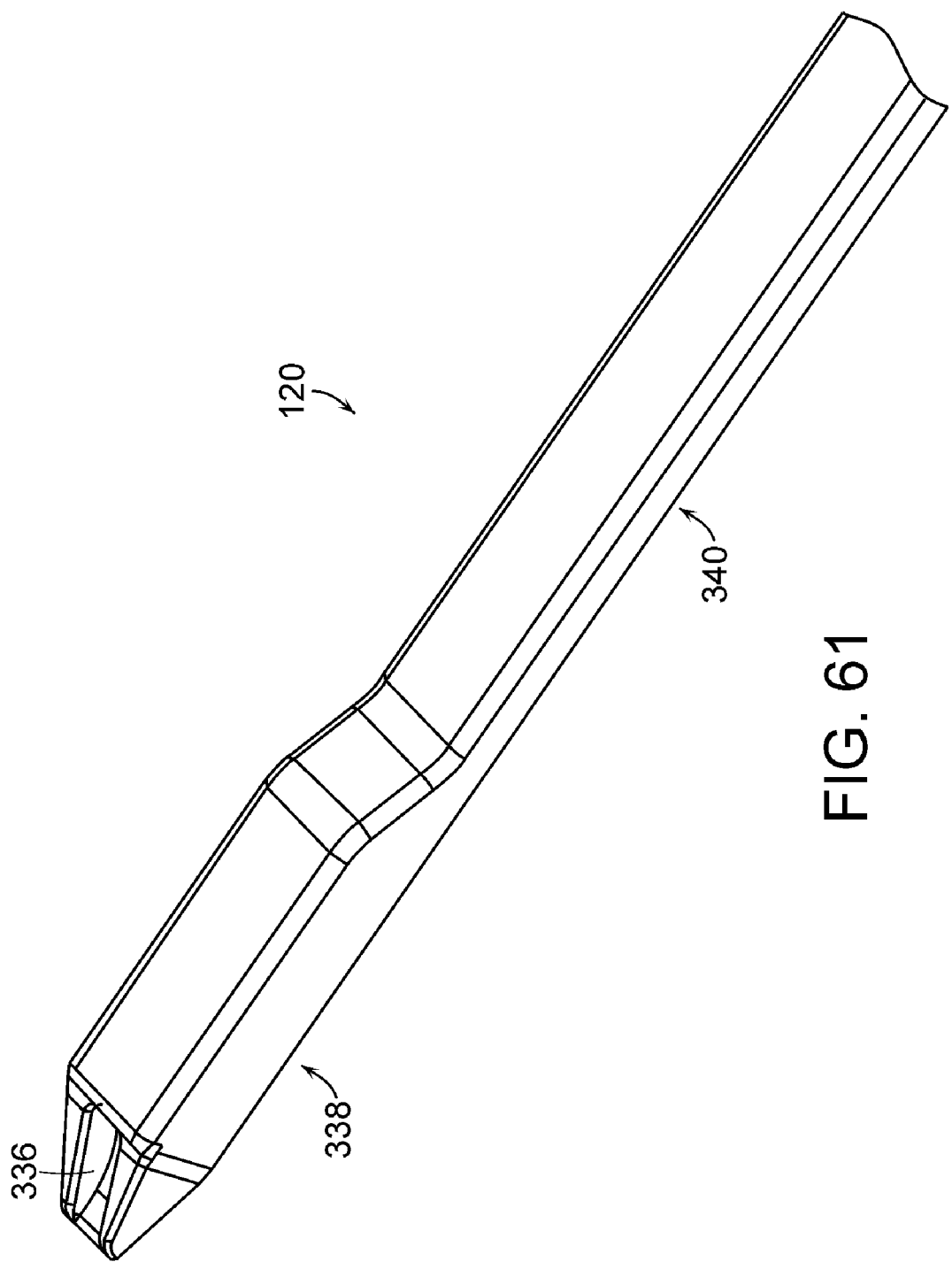
FIG. 61 is a perspective view of the shaft assembly lock member of FIG. 60.
Figure 62:
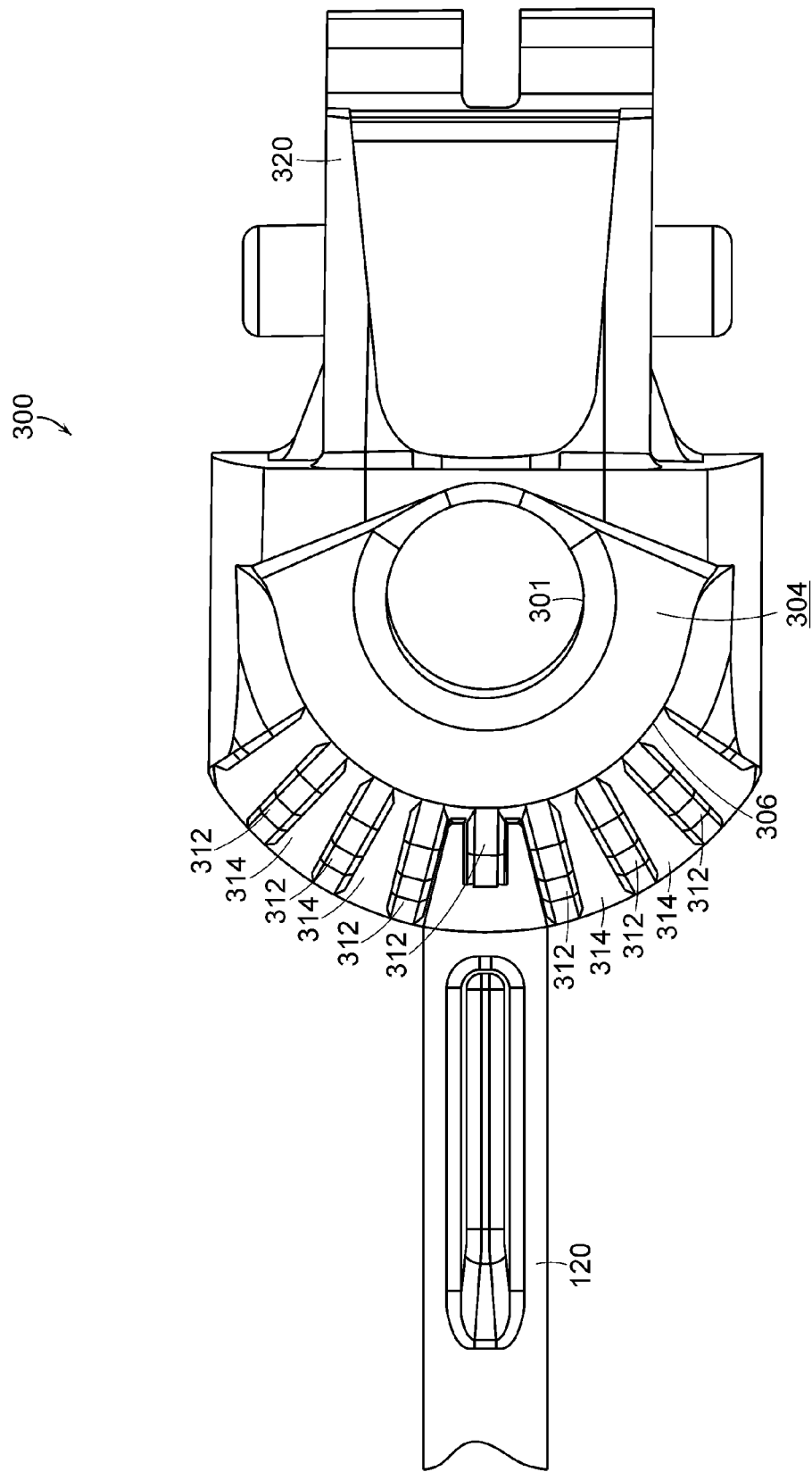
FIG. 62 is a bottom view of end effector lock member of FIG. 53 operably engaged with the shaft assembly lock member of FIG. 60.
Figure 63:
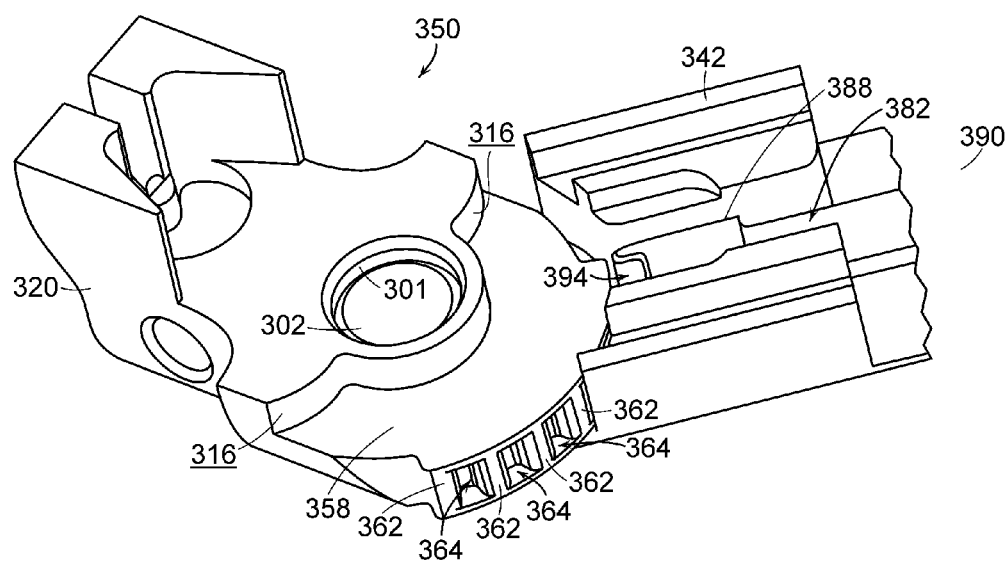
FIG. 63 is a perspective view of an articulation joint of a surgical instrument in accordance with an alternative embodiment of the present invention with some components of the surgical instrument removed.
Figure 64:
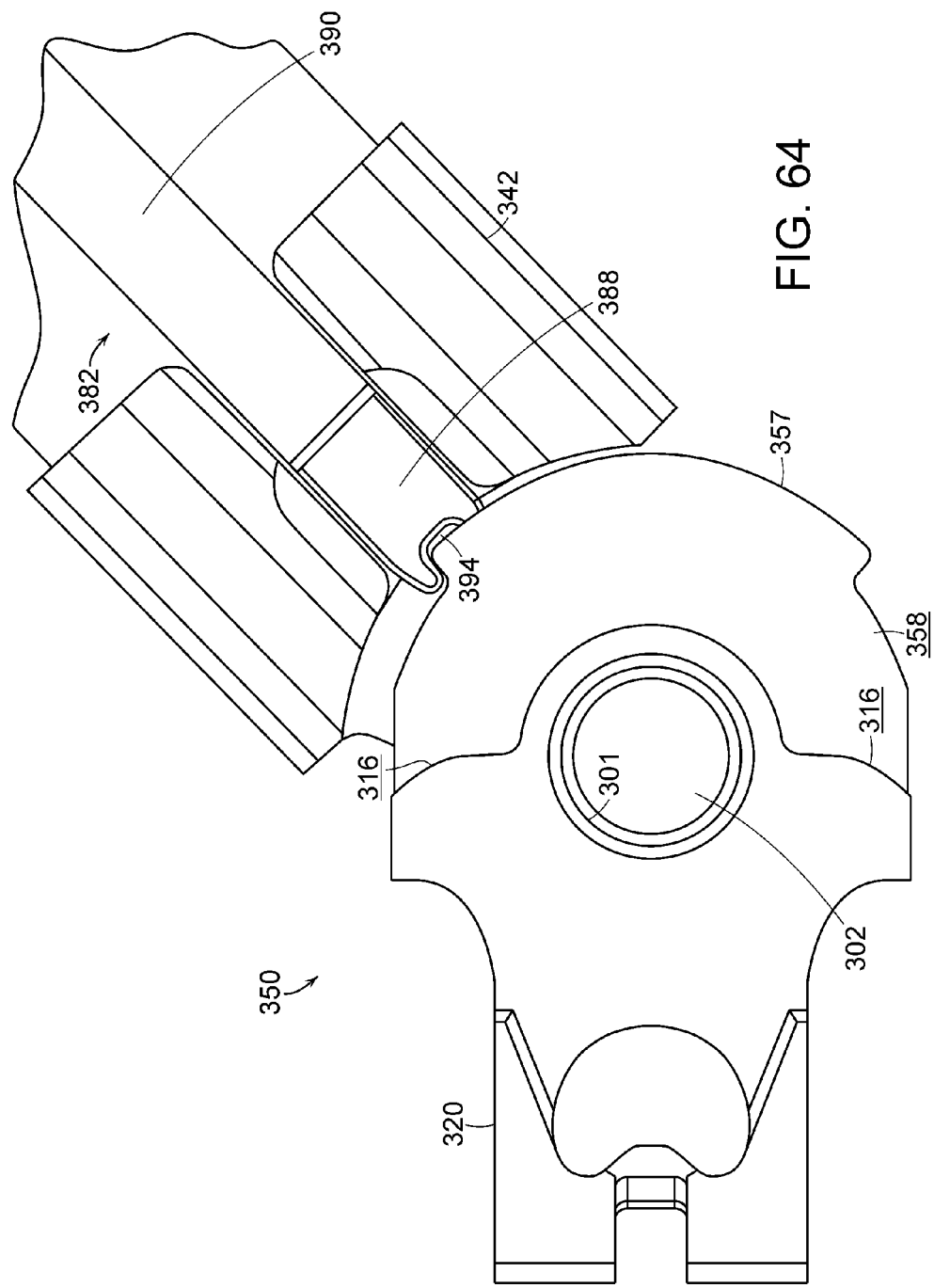
FIG. 64 is a top view of an end effector lock member operably engaged with a shaft assembly lock member of the surgical instrument of FIG. 63.
Figure 65:
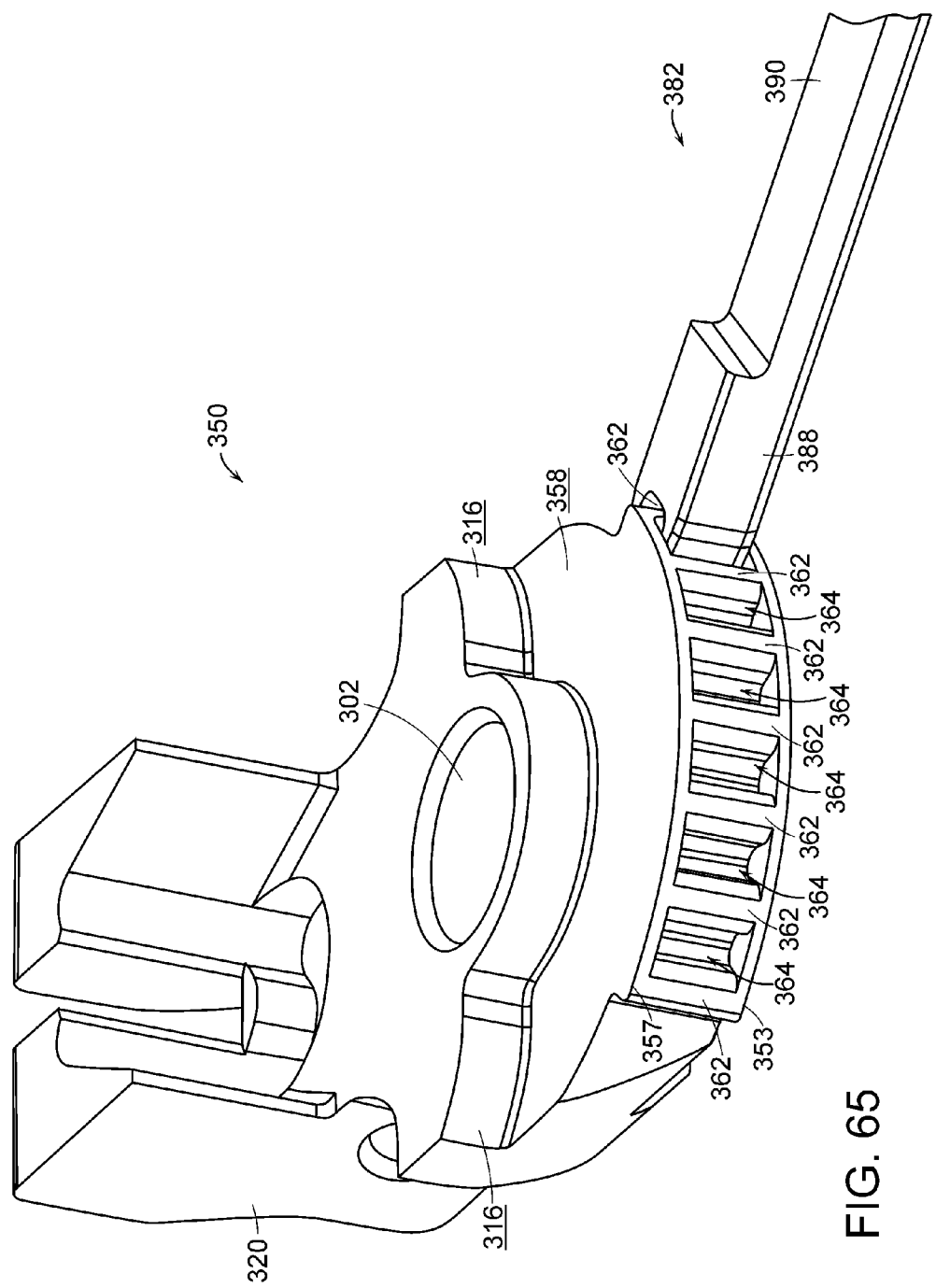
FIG. 65 is a perspective view of the end effector lock member operably engaged with the shaft assembly lock member of FIG. 64.
Figure 66:
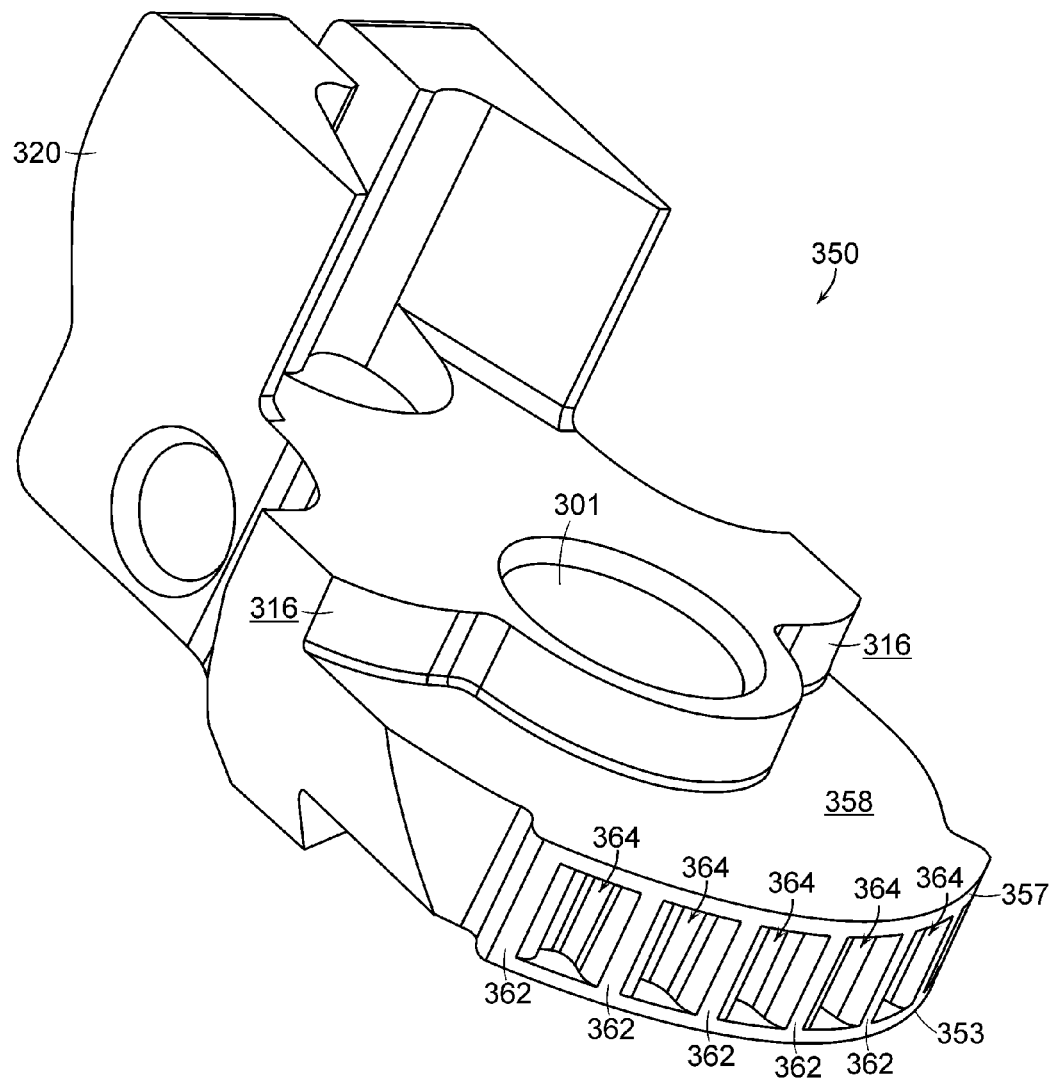
FIG. 66 is a perspective view of the end effector lock member of FIG. 64.
Figure 67:
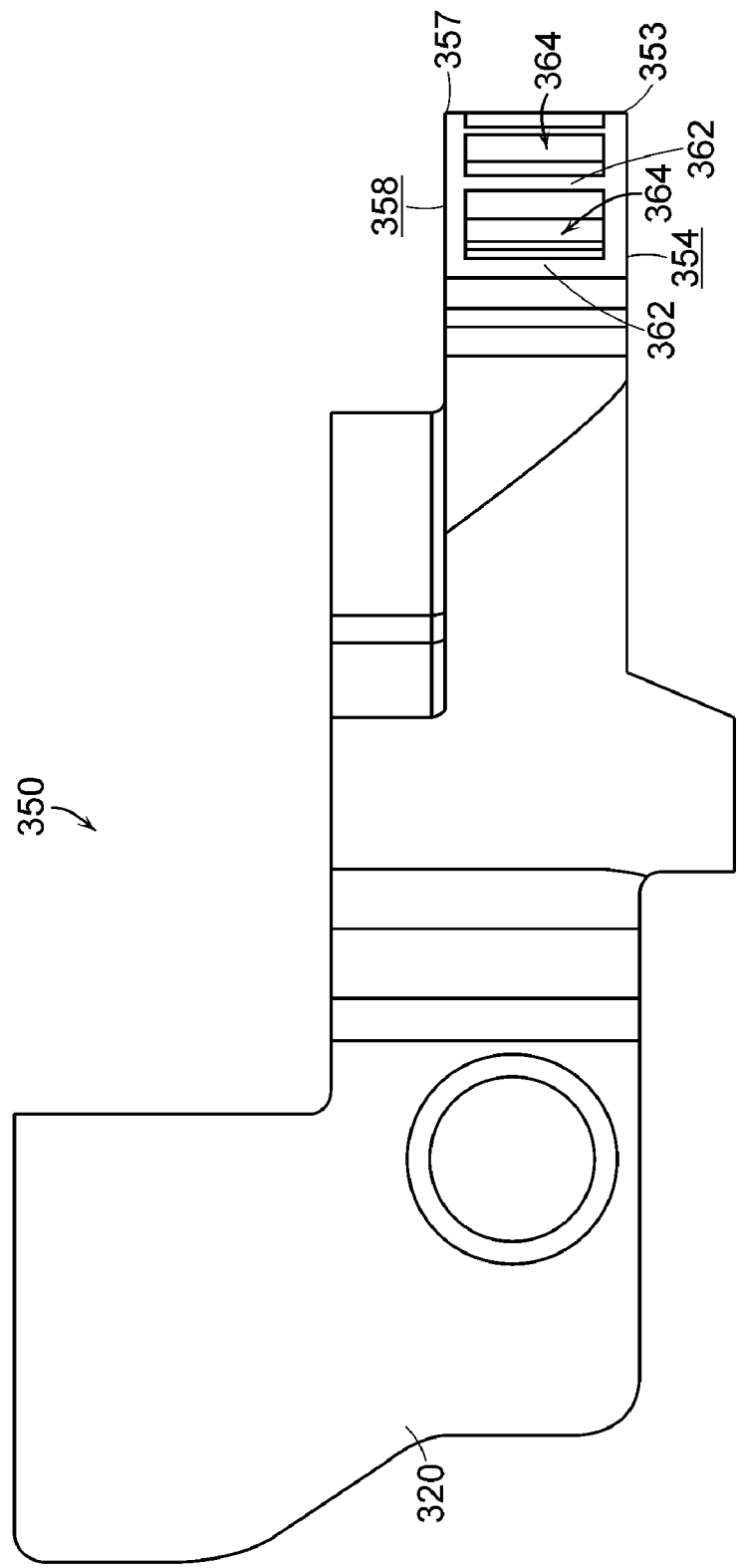
FIG. 67 is an elevational view of the end effector lock member of FIG. 64.

Further to the above, embodiments of the present invention can provide significant advantages over previous surgical instruments. More particularly, referring to FIG. 57, the articulation joints of previous end effectors have included lock members, such as lock member 299, for example, which include teeth 298 that extend outwardly from the perimeter of the lock member. As a result, when the end effector is articulated relative to the shaft assembly of the surgical instrument, teeth 298 can catch on, or impinge upon, the surrounding soft tissue and potentially cause trauma thereto. In various circumstances, tissue can be caught between adjacent teeth 298 such that, when the end effector is articulated, the soft tissue can be pulled into the articulation joint and can be pinched by the relatively moving components of the joint. In embodiments of the present invention in which the teeth of the lock member are angled, or beveled, as outlined above and illustrated in FIG. 58, the soft tissue can more easily flow over the teeth and reduce the possibility that the soft tissue can be pulled into the articulation joint.

As outlined above, referring to FIGS. 59-62, surgical instrument 100 can further include locking member 120 which can be slid relative to end effector 106 and can be operably engaged with end effector 106 to prevent, or at least limit, relative movement between shaft assembly 104 and end effector 106. In at least one embodiment, lock member 120 can be configured to engage at least one of teeth 312 such that end effector 106 is prevented from moving relative to lock member 120. More particularly, lock member 120 can include end portion 338 and shaft portion 340, where end portion 338 can include recess 336 which can be configured to receive a tooth 312 of lock member 300 in a close-fit, or even interference-fit, relationship. In various alternative embodiments, locking portion 338 can be received within at least one of recesses 314 in a close-fit, or interference-fit, relationship similar to the above. In either event, surgical instrument 100 can further include spring 126 which can be configured to bias lock member 120 into engagement with end effector lock member 300. In the event that recess 336 is not aligned with a tooth 312, in at least one embodiment, the biasing force applied to lock member 120 by spring 126 can cause lock member 120 to contact and rotate end effector lock member 300 about axis 116 until one of teeth 312 is aligned with recess 336. In various embodiments, spring 126 can comprise any suitable biasing member including a helical spring, leaf spring, or other biasing material.

In various alternative embodiments, referring to FIGS. 63-67, a surgical instrument can include end effector lock member 350 comprising aperture 301, a first portion including first surface 358, a second portion including second surface 354 (FIG. 67), and connector portion 320. End effector lock member 350 can also comprise teeth 362 and recesses 364 defined between teeth 362 where, in at least one embodiment, teeth 362 and recesses 364 can be positioned intermediate first surface 358 and second surface 354. In various embodiments, referring to FIGS. 65-67, teeth 362 may not extend beyond first perimeter 357 of first surface 358 and/or second perimeter 353 of second surface 354. In at least one such embodiment, teeth 362 may be completely positioned, or contained, between first surface 358 and second surface 354. In at least one alternative embodiment, teeth 362 may partially extend from first perimeter 357 and/or second perimeter 353. In various embodiments, first perimeter 357 and second perimeter 353 can define an outer surface therebetween where recesses 364 can be defined in the outer surface. As a result of the above-described features, end effector lock member 350 can slide relative to soft tissue positioned adjacent to the articulation joint without impinging on the soft tissue. In various embodiments, teeth 362 may be blunted or rounded to further facilitate the relative sliding described above. In at least one embodiment, referring to FIGS. 63-65, a locking mechanism can be configured to engage at least one of teeth 362 and recesses 364 and can include lock member 382 comprising end portion 388 and shaft portion 390. In at least one embodiment, similar to the above, end portion 388 can include recess 394 which can be configured to engage at least one of teeth 362, for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical instrument, comprising:
   an end effector;
   a firing member;
   a trigger;
   a firing drive selectively engageable with said firing member, wherein said firing drive comprises;
      a rack, and wherein said rack comprises:
         a first drive portion, wherein said firing drive is configured to engage said first drive portion and advance said firing member relative to said end effector upon a first actuation of said trigger; and
         a second drive portion, wherein said firing drive is configured to engage said second drive portion and advance said firing member relative to said end effector upon a second actuation of said trigger; and
      a rotatable portion configured to be rotated a first amount during said first actuation of said trigger and a second amount during said second actuation of said trigger, wherein said rotatable portion comprises a key positionable in an initial position, and wherein said rotatable portion may be configurable in an activated configuration and a deactivated configuration;
   a reversing drive selectively engageable with said rack, wherein said reversing drive is configured to retract said rack and said firing member relative to said end effector upon a subsequent actuation of said trigger, and wherein said subsequent actuation is subsequent to said second actuation; and
   an indexing member, said indexing member comprising:
      a first stop, wherein said key is configured to rotate past said first stop into a first position during said first actuation of said trigger, and wherein said first stop is configured to prevent said key from returning to said initial position when said rotatable portion is in said activated configuration; and
      a second stop, wherein said key is configured to rotate past said second stop into a second position during said second actuation of said trigger, wherein said second stop is configured to prevent said key from returning to said first position when said rotatable portion is in said activated configuration, and wherein said key is configured to rotate past said second stop and said first stop when said rotatable portion is in said deactivated configuration and said key is returned to said initial position.

2. The surgical instrument of claim 1, further comprising a frame, wherein said indexing member is mounted to said frame, and wherein said indexing member is configured to rotate relative to said frame when said key is moved from said initial position to said first position and from said first position to said second position.

3. The surgical instrument of claim 2, wherein said frame comprises a recess, and wherein said indexing member is movably positioned in said recess.

4. The surgical instrument of claim 2, wherein said indexing member comprises a spring mounted to said frame.

5. The surgical instrument of claim 4, wherein said spring is configured to be deflected by said key when said rotatable portion is moved from said initial position to said first position and from said first position to said second position.

6. The surgical instrument of claim 1, wherein said indexing member comprises a plate, a first aperture, and a second aperture, wherein said key is positioned within said first aperture when said key is in said first position, and wherein said key is positioned within said second aperture when said key is in said second position.

7. The surgical instrument of claim 6, wherein a sidewall of said first aperture defines said first stop and a sidewall of said second aperture defines said second stop.

8. The surgical instrument of claim 6, further comprising a frame, wherein said plate comprises a cantilever including a fixed end mounted to said frame and a movable end movable relative to said fixed end.

9. The surgical instrument of claim 1, further comprising:
   a frame, wherein said indexing member comprises a plate mounted to said frame; and
   at least one spring positioned between said plate and said frame, wherein said spring is configured to bias said plate toward said key.

10. The surgical instrument of claim 1, wherein said rack comprises a third drive portion, wherein said firing drive is configured to engage said third drive portion and advance said firing member relative to said end effector upon a third actuation of said trigger, wherein said subsequent actuation is subsequent to said third actuation, wherein said indexing member comprises a third stop, wherein said key is configured to rotate past said third stop into a third position during said third actuation of said trigger, wherein said third stop is configured to prevent said key from returning to said second position when said rotatable portion is in said activated configuration, and wherein said key is configured to rotate past said third stop when said rotatable portion is in said deactivated configuration and said key is returned toward said initial position.

11. A surgical instrument, comprising:
    a shaft comprising a distal end;
    a firing member;
    a trigger;
    a firing drive selectively engageable with said firing member, wherein said firing drive comprises:
       a first drive portion, wherein said firing drive is configured to engage said first drive portion and advance said firing member relative to said distal end upon a first actuation of said trigger;
       a second drive portion, wherein said firing drive is configured to engage said second drive portion and advance said firing member relative to said distal end upon a second actuation of said trigger; and
       a rotatable portion configured to be rotated a first amount during said first actuation of said trigger and a second amount during said second actuation of said trigger, wherein said rotatable portion comprises a key positionable in an initial position;
    a reversing drive selectively engageable with said firing member, wherein said reversing drive is configured to retract said firing member relative to said distal end upon a subsequent actuation of said trigger, and wherein said subsequent actuation is subsequent to said second actuation; and
    a holding member, comprising:
       a first backstop, wherein said key is configured to rotate past said first backstop into a first position during said first actuation of said trigger, and wherein said first backstop is configured to prevent said key from returning to said initial position prior to said reversing drive being engaged with said firing member; and a second backstop, wherein said key is configured to rotate past said second backstop into a second position during said second actuation of said trigger, wherein said second backstop is configured to prevent said key from returning to said first position prior to said reversing drive being engaged with said firing member, and wherein said reversing drive is configured to disengage said key from said holding member when said reversing drive is engaged with said firing member.

12. The surgical instrument of claim 11, further comprising a frame, wherein said holding member is mounted to said frame, and wherein said holding member is configured to rotate relative to said frame when said key is moved from said initial position to said first position and from said first position to said second position.

13. The surgical instrument of claim 12, wherein said holding member comprises a spring mounted to said frame.

14. The surgical instrument of claim 13, wherein said spring is configured to be deflected by said key when said rotatable portion is moved from said initial position to said first position and from said first position to said second position.

15. The surgical instrument of claim 11, wherein said holding member comprises a plate, a first aperture, and a second aperture, wherein said key is positioned within said first aperture when said key is in said first position, and wherein key is positioned within said second aperture when said key is in said second position.

16. The surgical instrument of claim 15, wherein a sidewall of said first aperture defines said first backstop and a sidewall of said second aperture defines said second backstop.

17. The surgical instrument of claim 11, wherein said firing drive comprises a third drive portion, wherein said firing drive is configured to engage said third drive portion and advance said firing member relative to said distal end upon a third actuation of said trigger, wherein said subsequent actuation is subsequent to said third actuation, wherein said holding member comprises a third backstop, wherein said key is configured to rotate past said third backstop into a third position during said third actuation of said trigger, and wherein said third backstop is configured to prevent said key from returning to said second position prior to said reversing drive being engaged with said firing member.

18. A surgical instrument comprising:
 a distal end;
 a firing member, wherein said firing member is configured to move toward said distal end during a plurality of firing strokes, and wherein said plurality of firing strokes comprises a first firing stroke and a second firing stroke;
 a firing drive, wherein said firing drive is configured to selectively engage said firing member and to actuate said plurality of firing strokes;
 a key positionable in an initial configuration, wherein said key is configured to rotate into a first position during said first firing stroke, and wherein said key is configured to rotate into a second position during said second firing stroke; and
 a holding member comprising:
  a first stop, wherein said first stop is configured to prevent said key from rotating to said initial position from said first position when said firing drive is engaged with said firing member; and
  a second stop, wherein said second stop is configured to prevent said key from rotating to said first position from said second position when said firing drive is engaged with said firing member;
 wherein said key is configured to overcome said first and second stops and return to said initial position when said firing drive is disengaged from said firing member.

19. The surgical instrument of claim 18, further comprising a frame, wherein said holding member is mounted to said frame, and wherein said holding member is deflectable relative to said frame when said key is moved from said initial position to said first position and from said first position to said second position.

20. The surgical instrument of claim 19, wherein said holding member comprises a spring mounted to said frame.

21. The surgical instrument of claim 20, wherein said spring is configured to be deformed when said key is rotated from said initial position to said first position and from said first position to said second position.

22. The surgical instrument of claim 18, wherein said holding member comprises a plate, a first aperture, and a second aperture, wherein said key is positioned within said first aperture when said key is in said first position, and wherein said key is positioned within said second aperture when said key is in said second position.

23. The surgical instrument of claim 22, wherein a sidewall of said first aperture defines said first stop and a sidewall of said second aperture defines said second stop.

24. The surgical instrument of claim 18, wherein said plurality of firing strokes comprises a third firing stroke, wherein said key is configured to rotate into a third position during said third firing stroke, wherein said holding member comprises a third stop, wherein said third stop is configured to prevent said key from rotating to said second position from said third position when said firing drive is engaged with said firing member, and wherein said key is configured to overcome said third stop when said firing drive is disengaged from said firing member.

25. A surgical instrument comprising:
 a distal end;
 a firing member, wherein said firing member is configured to move toward said distal end during a plurality of firing strokes, and wherein said plurality of firing strokes comprises a first firing stroke and a second firing stroke;
 a key positionable in an initial configuration, wherein said key is configured to rotate into a first position during said first firing stroke, and wherein said key is configured to rotate into a second position during said second firing stroke; and
 a holding member, wherein said key is configured to selectively engage said holding member, and wherein said holding member comprises:
  a first stop, wherein said first stop is configured to prevent said key from rotating to said initial position from said first position when said key is engaged with said holding member; and
  a second stop, wherein said second stop is configured to prevent said key from rotating to said first position from said second position when said key is engaged with said holding member;
 wherein said key is configured to overcome said first and second stops and return to said initial position when said key is disengaged from said holding member.

26. The surgical instrument of claim 25, further comprising a frame, wherein said holding member is mounted to said frame, and wherein said holding member is deflectable relative to said frame when said key is moved from said initial position to said first position and from said first position to said second position.

27. The surgical instrument of claim 26, wherein said holding member comprises a spring mounted to said frame.

28. The surgical instrument of claim 27, wherein said spring is configured to be deformed when said key is rotated from said initial position to said first position and from said first position to said second position.

29. The surgical instrument of claim 25, wherein said holding member comprises a plate, a first aperture, and a second aperture, wherein said key is positioned within said first aperture when said key is in said first position, and wherein said key is positioned within said second aperture when said key is in said second position.

30. The surgical instrument of claim 29, wherein a sidewall of said first aperture defines said first stop and a sidewall of said second aperture defines said second stop.

31. The surgical instrument of claim 25, wherein said plurality of firing strokes comprises a third firing stroke, wherein said key is configured to rotate into a third position during said third firing stroke, wherein said holding member comprises a third stop, wherein said third stop is configured to prevent said key from rotating to said second position from said third position when said key is engaged with said holding member, and wherein said key is configured to overcome said third when said key is disengaged from said holding member.

* * * * *